(12) United States Patent
Osaka et al.

(10) Patent No.: US 8,614,334 B2
(45) Date of Patent: Dec. 24, 2013

(54) ORGANIC COMPOUND, LIGHT-EMITTING ELEMENT, LIGHT-EMITTING DEVICE, ELECTRONIC DEVICE, AND LIGHTING DEVICE

(75) Inventors: Harue Osaka, Kanagawa (JP); Takako Takasu, Kanagawa (JP); Hiroshi Kadoma, Kanagawa (JP); Yuko Kawata, Kanagawa (JP); Satoko Shitagaki, Kanagawa (JP); Hiromi Nowatari, Kanagawa (JP); Tsunenori Suzuki, Kanagawa (JP); Nobuharu Ohsawa, Kanagawa (JP); Satoshi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 13/241,313

(22) Filed: Sep. 23, 2011

(65) Prior Publication Data
US 2012/0077987 A1 Mar. 29, 2012

(30) Foreign Application Priority Data
Sep. 27, 2010 (JP) ................... 2010-215856

(51) Int. Cl.
C07D 209/86 (2006.01)
(52) U.S. Cl.
USPC .......................................... 548/445; 428/917
(58) Field of Classification Search
None
See application file for complete search history.

(56) References Cited

U.S. PATENT DOCUMENTS

| | | | |
|---|---|---|---|
| 7,709,101 B2 | 5/2010 | Seo et al. | |
| 2005/0146268 A1 | 7/2005 | Seo et al. | |
| 2005/0260442 A1 | 11/2005 | Yu et al. | |
| 2007/0075632 A1 | 4/2007 | Kawakami et al. | |
| 2007/0152572 A1 | 7/2007 | Kawakami et al. | |
| 2007/0202355 A1 | 8/2007 | Kim et al. | |
| 2007/0247063 A1 | 10/2007 | Murase et al. | |
| 2007/0267969 A1 | 11/2007 | Nakashima et al. | |
| 2008/0111478 A1 | 5/2008 | Lyu et al. | |
| 2008/0268284 A1 | 10/2008 | Kawakami et al. | |
| 2009/0174321 A1 | 7/2009 | Osaka et al. | |
| 2009/0317539 A1* | 12/2009 | Shitagaki et al. | 427/66 |
| 2010/0069647 A1 | 3/2010 | Suzuki et al. | |
| 2010/0301383 A1* | 12/2010 | Shitagaki et al. | 257/103 |
| 2011/0037056 A1 | 2/2011 | Dubois et al. | |
| 2011/0057178 A1* | 3/2011 | Shitagaki et al. | 257/40 |
| 2011/0057179 A1* | 3/2011 | Nowatari et al. | 257/40 |
| 2011/0101379 A1* | 5/2011 | Sugisawa et al. | 257/79 |
| 2011/0127510 A1* | 6/2011 | Seo et al. | 257/40 |
| 2011/0172441 A1* | 7/2011 | Osaka | 548/440 |
| 2011/0215714 A1* | 9/2011 | Seo et al. | 313/504 |
| 2011/0240971 A1* | 10/2011 | Nowatari et al. | 257/40 |
| 2011/0240972 A1* | 10/2011 | Nowatari et al. | 257/40 |
| 2011/0315968 A1* | 12/2011 | Nowatari et al. | 257/40 |

FOREIGN PATENT DOCUMENTS

| | | |
|---|---|---|
| CN | 1638573 | 7/2005 |
| EP | 1 553 155 A1 | 7/2005 |
| JP | 09-310066 | 12/1997 |
| JP | 2005-170809 | 6/2005 |
| JP | 2007-131722 | 5/2007 |
| JP | 2008-088083 | 4/2008 |
| JP | 2009120582 A * | 6/2009 |
| JP | 2009-167175 | 7/2009 |
| JP | 2009-209127 | 9/2009 |
| JP | 2009-221442 | 10/2009 |
| JP | 2010-100593 | 5/2010 |
| KR | 2009052697 A * | 5/2009 |
| KR | 2011006129 A * | 1/2011 |
| KR | 2011-0041729 | 4/2011 |
| KR | 2011-0043270 | 4/2011 |
| TW | 201016664 | 5/2010 |
| TW | 201033327 | 9/2010 |

(Continued)

OTHER PUBLICATIONS

Shi.J et al., "Anthracene Derivatives for Stable Blue-Emitting Organic Electroluminescence Devices,", Applied Physics Letters, Apr. 29, 2002, vol. 80, No. 17, pp. 3201-3203.
Sasabe.H et al., "m-Terphenyl-modified carbazole host material for highly efficient blue and green PHOLEDS,", Chemical Communications, 2009, pp. 6655-6657.
"European Search Report (Application No. 11181231.9;EP14055) Dated Dec. 28, 2011,".
Taiwanese Office Action (Application No. 100134616) dated May 7, 2013.

*Primary Examiner* — Nyeemah A Grazier
(74) *Attorney, Agent, or Firm* — Nixon Peabody LLP; Jeffrey L. Costellia

(57) ABSTRACT

A novel substance with which an increase in life and emission efficiency of a light-emitting element can be achieved is provided. A carbazole compound having a structure represented by General Formula (G1) is provided. Note that a substituent which makes the HOMO level and the LUMO level of a compound in which a bond of the substituent is substituted with hydrogen deep and shallow, respectively is used as each of substituents in General Formula (G1) ($R^1$, $R^2$, $Ar^3$, and $\alpha^3$). Further, a substituent which makes the band gap (Bg) and the T1 level of a compound in which a bond of the substituent is substituted with hydrogen wide and high is used as each of the substituents in General Formula (G1) ($R^1$, $R^2$, $Ar^3$, and $\alpha^3$).

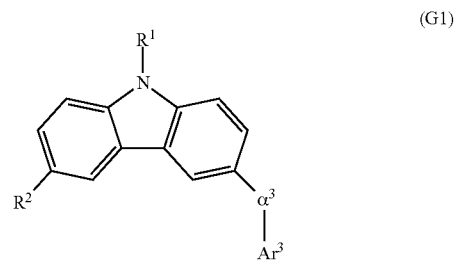

(G1)

19 Claims, 68 Drawing Sheets

(56) References Cited

FOREIGN PATENT DOCUMENTS

| WO | WO 2005-113531 A1 | 12/2005 |
| WO | WO 2006-104221 A1 | 10/2006 |
| WO | WO 2007-013537 A1 | 2/2007 |
| WO | WO 2009081800 A1 * | 7/2009 |
| WO | WO-2010/005066 A1 | 1/2010 |
| WO | WO-2010/068865 | 6/2010 |
| WO | WO 2011027653 A1 * | 3/2011 |
| WO | WO-2011/081423 A2 | 7/2011 |

* cited by examiner

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a carbazole compound and a light-emitting element using the carbazole compound. The present invention also relates to a light-emitting device, an electronic device, and a lighting device each including the light-emitting element.

2. Description of the Related Art

In recent years, research and development of light-emitting elements using electroluminescence (EL) have been actively conducted. In a basic structure of such a light-emitting element, a layer containing a light-emitting substance is interposed between a pair of electrodes. By voltage application to this element, light emission can be obtained from the light-emitting substance.

Such a light-emitting element is of self-luminous type, and thus has advantages over a liquid crystal display in that visibility of pixels is high, backlight is not needed, and so on. Therefore, such a light-emitting element is probably suitable as a flat panel display element. Besides, such a light-emitting element has advantages in that it can be manufactured to be thin and lightweight and has very fast response speed.

Further, since such a light-emitting element can be manufactured to have a film shape, surface light emission can be easily obtained. Therefore, a large-area element using the surface light emission can be formed. This is a feature that is difficult to obtain with point light sources typified by an incandescent lamp and an LED or linear light sources typified by a fluorescent lamp. Therefore, the light-emitting element is extremely effective for use as a surface light source applicable to lighting and the like.

Light-emitting elements utilizing electroluminescence are broadly classified according to whether they use an organic compound or an inorganic compound as a light-emitting substance. In the case where an organic compound is used as a light-emitting substance, by application of voltage to a light-emitting element, electrons and holes are injected into a layer containing the light-emitting organic compound from a pair of electrodes, whereby current flows. Then, these carriers (i.e., electrons and holes) are recombined, whereby the light-emitting organic compound is excited. The light-emitting organic compound returns to the ground state from the excited state, thereby emitting light. Note that the excited state of an organic compound can be a singlet excited state or a triplet excited state, and light emission from the singlet excited state is referred to as fluorescence, and light emission from the triplet excited state is referred to as phosphorescence.

There are many problems which depend on a substance in improving element characteristics of such a light-emitting element. In order to solve the problems, improvement in an element structure, development of a substance, and the like have been conducted. For example, Patent Document 1 discloses a light-emitting element in which a compound having an anthracene skeleton and a carbazole skeleton is used as a light-emitting material. However, it cannot be said that the light-emitting element has sufficiently high reliability.

Further, Patent Document 2 discloses a light-emitting element in which a compound which has an anthracene skeleton including a substituted or unsubstituted phenyl group and a carbazole skeleton and has an excellent carrier-transport property is used. The light-emitting element has low drive voltage and has high reliability.

[Reference]
[Patent Document 1] PCT International Publication No. WO 2005/113531
[Patent Document 2] Japanese Published Patent Application No. 2009-167175

SUMMARY OF THE INVENTION

In the case where the compound described in Patent Document 2 is used in an element including a phosphorescent substance, the excitation energy of the phosphorescent substance might be quenched due to an insufficient T1 level (triplet excitation energy) of the anthracene skeleton in the compound, which might make it difficult to obtain high emission efficiency. In addition, in the case where the compound is used in an element including a blue fluorescent substance, higher efficiency is demanded though high emission efficiency can be obtained.

In view of the foregoing problems, an object of one embodiment of the present invention is to provide a novel substance with which the lifetime and emission efficiency of a light-emitting element can be increased. Specifically, an object of one embodiment of the present invention is to provide a novel carbazole compound which can be used in a light-emitting element.

One embodiment of the present invention is a carbazole compound represented by General Formula (G1).

[1]

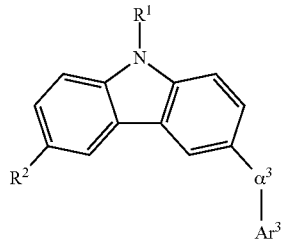

(G1)

Note that in General Formula (G1), $R^1$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, and a substituent represented by General Formula (G1-1). In General Formula (G1), $R^2$ represents any one of hydrogen, an alkyl group having 1 to 12 carbon atoms, a substituted or unsubstituted phenyl group, a substituted or unsubstituted biphenyl group, and a substituent represented by General Formula (G1-2).

In General Formula (G1), $\alpha^3$ represents either a substituted or unsubstituted phenylene group or a substituted or unsubstituted biphenyldiyl group. In General Formula (G1), $Ar^3$ represents any one of a substituted or unsubstituted naphthyl group, a substituted or unsubstituted phenanthryl group, and a substituted or unsubstituted triphenylenyl group.

[2]

$n = 0$ or $1$ (G1-1)

Note that in General Formula (G1-1), $Ar^1$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-1), $\alpha^1$ represents either a substituted or unsubstituted phenylene group or a substituted or unsubstituted biphenyldiyl group. In General Formula (G1-1), n represents 0 or 1.

[3]

(G1-2)

Note that in General Formula (G1-2), $Ar^2$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-2), $\alpha^2$ represents either a substituted or unsubstituted phenylene group or a substituted or unsubstituted biphenyldiyl group.

Further, $R^1$ in General Formula (G1) may be any one of structures represented by Structural Formulae (S-1) to (S-5) and General Formula (G1-1).

[4]

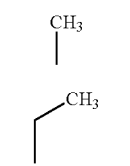
(S-1)

(S-2)

(S-3)

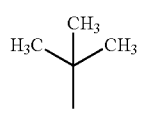
(S-4)

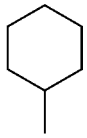
(S-5)

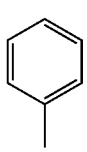
(G1-1)

$n = 0$ or $1$

Note that in General Formula (G1-1), $Ar^1$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-1), $\alpha^1$ represents either a substituted or unsubstituted phenylene group or a substituted or unsubstituted biphenyldiyl group. In General Formula (G1-1), n represents 0 or 1.

Further, $R^2$ in General Formula (G1) may be any one of structures represented by Structural Formulae (S-11) to (S-16) and General Formula (G1-2).

[5]

(S-11)

(S-12)

(S-13)

(S-14)

(S-15)

(S-16)

(G1-2)

Note that in General Formula (G1-2), $Ar^2$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-2), $\alpha^2$ represents either a substituted or unsubstituted phenylene group or a substituted or unsubstituted biphenyldiyl group.

Further, $\alpha^3$ in General Formula (G1), $\alpha^1$ in General Formula (G1-1), and $\alpha^2$ in General Formula (G1-2) may be separately any one of structures represented by Structural Formulae ($\alpha$-1) to ($\alpha$-7).

[6]
(α-1)
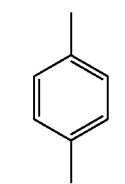
(α-2)
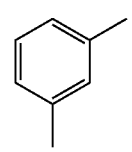
(α-3)
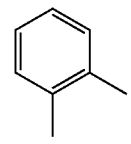
(α-4)
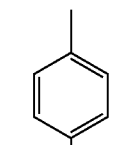
(α-5)
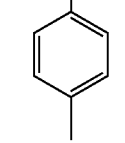
(α-6)
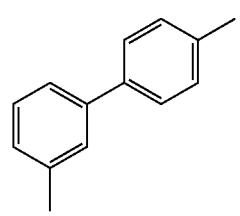
(α-7)
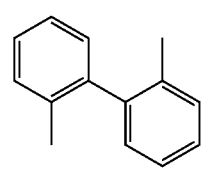
Further, Ar$^1$ in General Formula (G1-1) and Ar$^2$ in General Formula (G1-2) may be separately any one of structures represented by Structural Formulae (Ar-1) to (Ar-10).
[7]
 (Ar-1)
 (Ar-2)
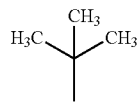 (Ar-3)
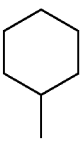 (Ar-4)
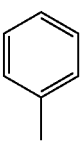 (Ar-5)
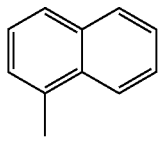 (Ar-6)
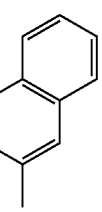 (Ar-7)
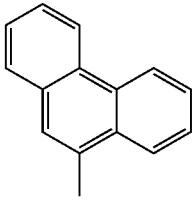 (Ar-8)
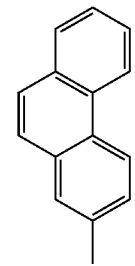 (Ar-9)

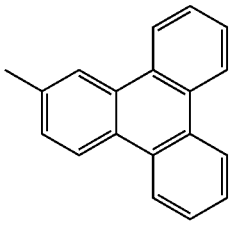
(Ar-10)

Further, Ar³ in General Formula (G1) may be any one of structures represented by Structural Formulae (Ar-11) to (Ar-15).

[8]

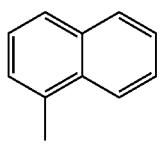
(Ar-11)

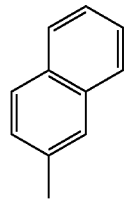
(Ar-12)

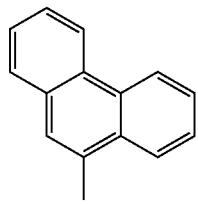
(Ar-13)

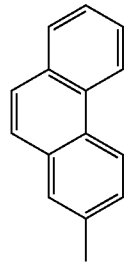
(Ar-14)

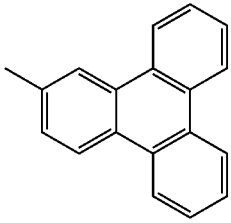
(Ar-15)

One embodiment of the present invention is a light-emitting element using the carbazole compound.

One embodiment of the present invention is a light-emitting device including the light-emitting element.

One embodiment of the present invention is a lighting device including the light-emitting device.

One embodiment of the present invention is an electronic device including the light-emitting device.

Note that the light-emitting device in this specification includes, in its category, an image display device and, a light-emitting device, and a light source. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

According to one embodiment of the present invention, a novel carbazole compound can be provided. The carbazole compound has a wide band gap and is useful as a material of a light-emitting element. Further, the carbazole compound has a high T1 level and is useful as a material of a light-emitting element. Further, the carbazole compound has a high carrier-transport property and is useful as a material of a light-emitting element.

According to one embodiment of the present invention, a light-emitting element that has high emission efficiency and long lifetime can be provided. Moreover, according to one embodiment of the present invention, highly reliable light-emitting device, lighting device, and electronic device in each of which the light-emitting element is used can be provided.

DETAILED DESCRIPTION OF THE INVENTION

Figure 1A:
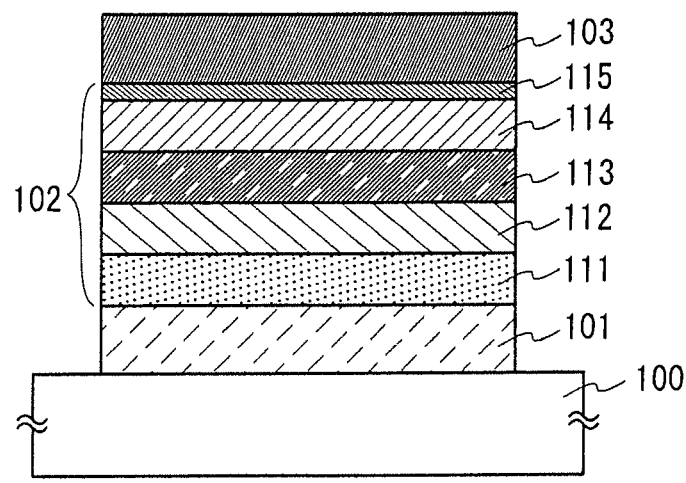
FIGS. 1A and 1B each illustrate a light-emitting element of one embodiment of the present invention.

Hereinafter, embodiments and examples will be described in detail with reference to the drawings. Note that the present invention is not limited to the description below, and it is easily understood by those skilled in the art that various changes and modifications can be made without departing from the spirit and scope of the present invention. Therefore, the present invention should not be construed as being limited to the description in the embodiments and examples.

(Embodiment 1)

In this embodiment, a carbazole compound according to one embodiment of the present invention will be described.

The carbazole compound according to one embodiment of the present invention is a carbazole compound represented by General Formula (G1).

[9]

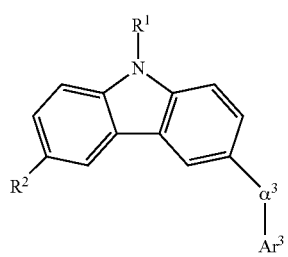
(G1)

Note that in General Formula (G1), $R^1$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, and a substituent represented by General Formula (G1-1). In General Formula (G1), $R^2$ represents any one of hydrogen, an alkyl group having 1 to 12 carbon atoms, a substituted or unsubstituted phenyl group, a substituted or unsubstituted biphenyl group, and a substituent represented by General Formula (G1-2). In General Formula (G1), $\alpha^3$ represents either a substituted or unsubstituted phenylene group or a substituted or unsubstituted biphenyldiyl group. In General Formula (G1), $Ar^3$ represents any one of a substituted or unsubstituted naphthyl group, a substituted or unsubstituted phenanthryl group, and a substituted or unsubstituted triphenylenyl group.

[10]

(G1-1)

n = 0 or 1

Note that in General Formula (G1-1), $Ar^1$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-1), $\alpha^1$ represents either a substituted or unsubstituted phenylene group or a substituted or unsubstituted biphenyldiyl group. In General Formula (G1-1), n represents 0 or 1.

[11]

(G1-2)

Note that in General Formula (G1-2), $Ar^2$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-2), $\alpha^2$ represents either a substituted or unsubstituted phenylene group or a substituted or unsubstituted biphenyldiyl group.

Note that a substituent which makes the HOMO level of a compound in which a bond of the substituent is substituted with hydrogen deep (absolute value is large) is used as each of the substituents in General Formula (G1) (specifically, $R^1$, $R^2$, $Ar^3$, and $\alpha^3$). Specifically, it is preferable that the HOMO level of the compound in which the bond of the substituent in General Formula (G1) is substituted with hydrogen be less than or equal to −5.5 eV. Accordingly, the carbazole compound of this embodiment that is represented by General Formula (G1) can have a deep HOMO level.

Further, a substituent which makes the band gap (Bg) and the T1 level of a compound in which a bond of the substituent is substituted with hydrogen wide and high is used as each of the substituents in General Formula (G1) (specifically, $R^1$, $R^2$, $Ar^3$, and $\alpha^3$). Specifically, it is preferable that the band gap of the compound in which the bond of the substituent in General Formula (G1) is substituted with hydrogen be greater than or equal to 2.7 eV (greater than or equal to the energy of blue fluorescence, preferably greater than or equal to 3.0 eV) and that the T1 level of the compound be greater than or equal to 1.8 eV (greater than or equal to the energy of red phosphorescence). Accordingly, the carbazole compound of this embodiment that is represented by General Formula (G1) can have a wide band gap and a high T1 level. Therefore, when the carbazole compound of this embodiment is used as a host material of a light-emitting layer or a layer adjacent to the light-emitting layer, a light-emitting element is probably able to emit light more efficiently without taking excitation energy away from a light-emitting substance with high excitation energy. Further, in the case where the carbazole compound of this embodiment is used as a light-emitting substance, light with a short wavelength (blue violet to blue) can be obtained.

Even if a material has a deep HOMO level, the material can maintain a shallow LUMO level as long as it has a wide band gap. Therefore, when the carbazole compound of this embodiment is used for a hole-transport layer of a light-emitting element, electrons are probably able to be prevented from passing through an adjacent light-emitting layer, and recombination of carriers in the light-emitting layer is probably able to be performed efficiently.

For the above reason, a substituent which makes the LUMO level of a compound in which a bond of the substituent is substituted with hydrogen shallow (absolute value is small) is used as each of the substituents in General Formula (G1) (specifically, $R^1$, $R^2$, $Ar^3$, and $\alpha^3$). Specifically, it is preferable that the LUMO level of the compound in which the bond of the substituent in General Formula (G1) is substituted with hydrogen be greater than or equal to −2.5 eV.

In the case where $R^1$, $R^2$, $\alpha^3$, and $Ar^3$ further have substituents, the substituents are separately preferably any of an alkyl group having 1 to 12 carbon atoms, a phenyl group, a biphenyl group, a naphthyl group, a phenanthryl group, and a triphenylenyl group in consideration of the HOMO level, the LUMO level, and the band gap.

In particular, $Ar^3$ ($Ar^2$) that is a part of the substituent connected to the 3-position (6-position) of a carbazole skeleton is preferably a condensed ring such as a naphthyl group, a phenanthryl group, and a triphenylenyl group because such a condensed ring has an excellent carrier-transport property. In particular, $Ar^3$ ($Ar^2$) is preferably a naphthyl group or a phenanthryl group. Further, $Ar^3$ ($Ar^2$) is preferably a phenanthryl group or a triphenylenyl group in terms of a high molecular weight and an improvement in thermophysical property. Note that naphthalene is a bicyclic condensed ring, and thus has a wide band gap and a high T1 level. Although phenanthrylene or triphenylene is a condensed ring having three or more rings, phenanthrylene or triphenylene has a wider band gap and a higher T1 level than anthracene that is a tricyclic condensed ring or tetracene that is a tetracyclic condensed ring because phenanthrylene or triphenylene does not have a polyacene structure (the condensed ring is not straight) but has a structure in which helicene structures are combined (a condensed ring is twisted).

Further, arylene represented by $\alpha^3$ ($\alpha^2$) is preferably interposed between the carbazole skeleton and $Ar^3$ ($Ar^2$), in which case conjugation hardly extends from the carbazole skeleton to $Ar^3$ ($Ar^2$). In particular, arylene is preferably bonded to the meta-position or the ortho-position (e.g., the 1-position and the 3-position of phenylene, and 1-position and the 2-position of phenylene), in which case extension of conjugation is probably suppressed more and the band gap is probably increased. In the case where arylene is bonded to the para-position, an excellent thermophysical property (high Tg) and an excellent carrier-transport property are probably obtained. Further, a phenyl skeleton or a biphenyl skeleton, for example, is used so that $\alpha^3$ ($\alpha^2$) is an arylene group with small conjugation in order to prevent $\alpha^3$ ($\alpha^2$) itself from causing extension of conjugation.

A substituent connected to each of the substituents $Ar^1$, $Ar^2$, and $Ar^3$ in General Formula (G1) is preferably an alkyl group, in which case the carbazole compound is easily dissolved in a solvent. In particular, a methyl group or a tert-butyl group is preferable because of its excellent solubility. In the case where the substituents $Ar^1$, $Ar^2$, and $Ar^3$ in General Formula (G1) have substituents such as an alkyl group or an aryl group, the structure of the carbazole compound of this embodiment becomes more steric. As a result, it is likely that crystallization does not occur easily and concentration quenching due to stacked molecules, can be suppressed.

Further, in the case where the substituent $R^2$ in General Formula (G1) is a group other than hydrogen, the substituent $R^2$ and the substituent $\alpha^3$-$Ar^3$ are preferably the same, in which case synthesis is performed more easily. The substituent $R^2$ and the substituent $\alpha^3$-$Ar^3$ are preferably the same, in which case the molecular weight is increased, which results in an improvement in the thermophysical property. Note that the substituent $R^2$ is preferably hydrogen, in which case the band gap is wider and the T1 level is higher than those in the case where the substituent $R^2$ is a group other than hydrogen.

Specific examples of the substituent to be used will be described below.

As specific examples of the substituent represented by $R^1$ in General Formula (G1), Structural Formulae (S-1) to (S-5), General Formula (G1-1), and the like are given.

[12]

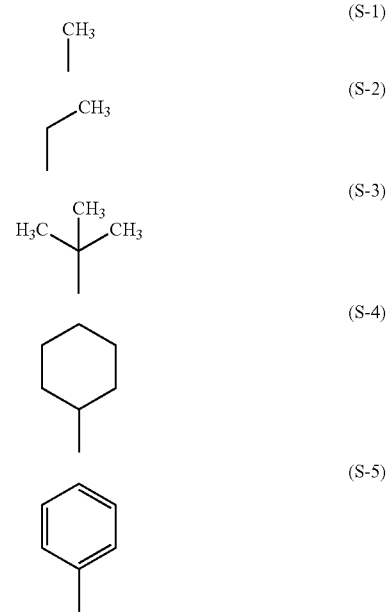

(G1-1)

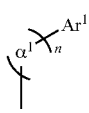

n = 0 or 1

Note that in General Formula (G1-1), Ar$^1$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-1), α$^1$ represents either a substituted or unsubstituted phenylene group or a substituted or unsubstituted biphenyldiyl group. In General Formula (G1-1), n represents 0 or 1.

As specific examples of the substituent represented by R$^2$ in General Formula (G1), Structural Formulae (S-11) to (S-16), General Formula (G1-2), and the like are given.

[13]

(S-11)

(S-12)

(S-13)
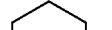

(S-14)

(S-15)
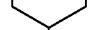

(S-16)
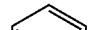

(G1-2)
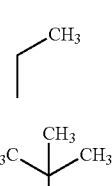

Note that in General Formula (G1-2), Ar$^2$ represents any one of an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. In General Formula (G1-2), α$^2$ represents either a substituted or unsubstituted phenylene group or a substituted or unsubstituted biphenyldiyl group.

As specific examples of the substituent represented by α$^3$ in General Formula (G1), α$^1$ in General Formula (G1-1), or α$^2$ in General Formula (G1-2), Structural Formulae (α-1) to (α-7) and the like are given.

[14]

(α-1)
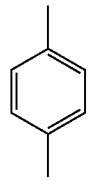

(α-2)
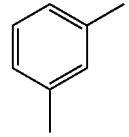

(α-3)
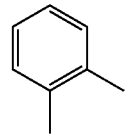

(α-4)
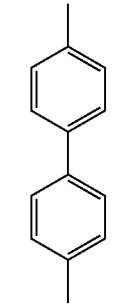

(α-5)
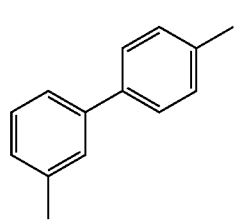

(α-6)
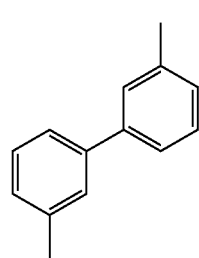

(α-7)
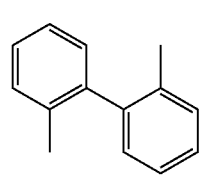

As specific examples of the substituent represented by Ar¹ in General Formula (G1-1) or Ar² in General Formula (G1-2), Structural Formulae (Ar-1) to (Ar-10) and the like are given.

[15]

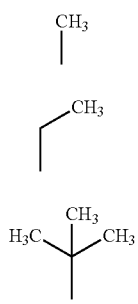
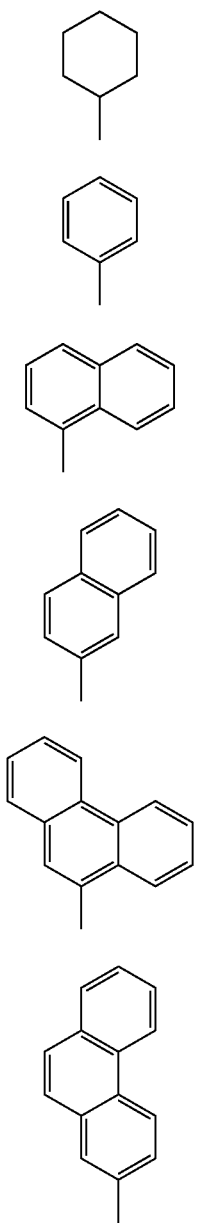

(Ar-1)
(Ar-2)
(Ar-3)
(Ar-4)
(Ar-5)
(Ar-6)
(Ar-7)
(Ar-8)
(Ar-9)

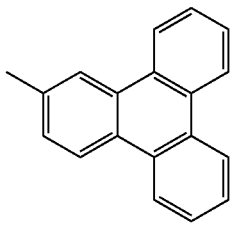

(Ar-10)

As specific examples of the substituent represented by Ar³ in General Formula (G1), Structural Formulae (Ar-11) to (Ar-15) and the like are given.

[16]

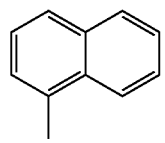

(Ar-11)

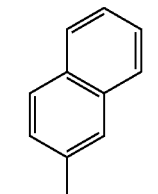

(Ar-12)

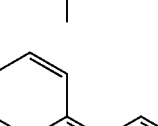

(Ar-13)

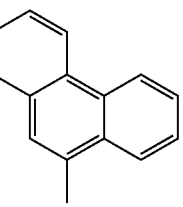

(Ar-14)

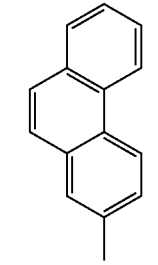

(Ar-15)

As specific examples of the carbazole compound represented by General Formula (G1), carbazole compounds represented by Structural Formulae (100) to (131), (140) to (151), (160) to (183), and (190) to (197) can be given. However, the present invention is not limited to these.

[17]
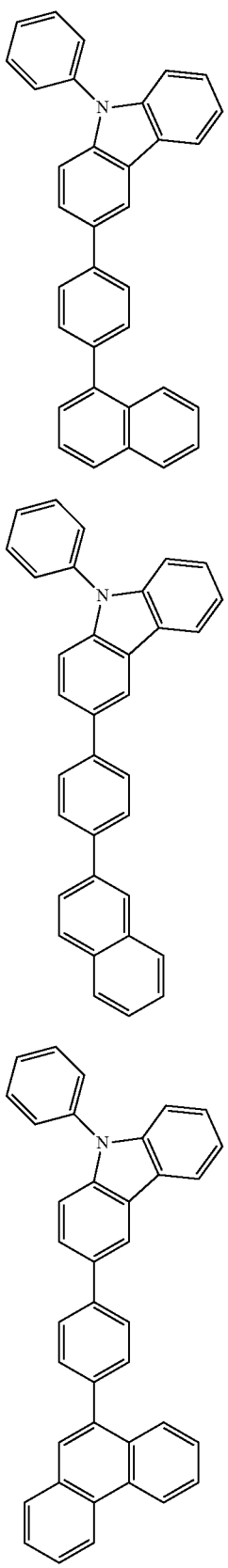

(105)
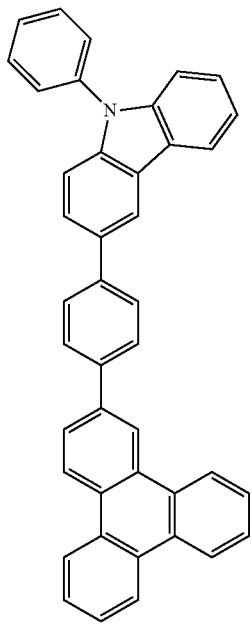
(106)
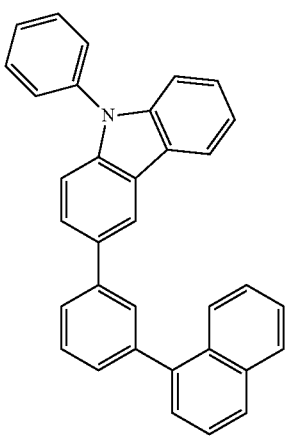
(107)
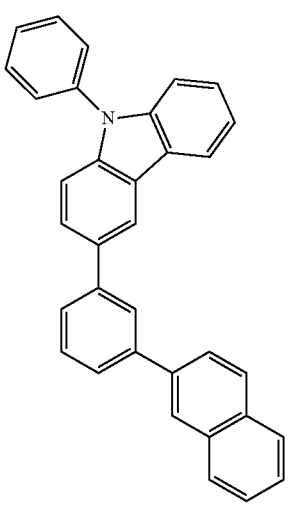
(108)
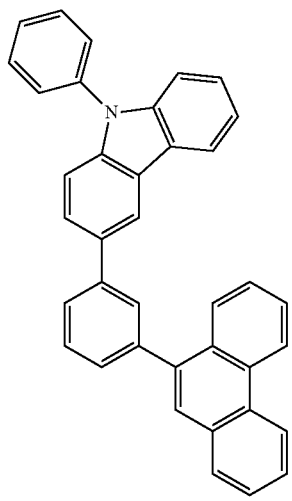
(109)
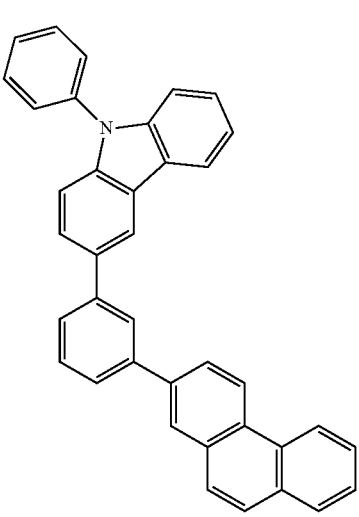
(110)
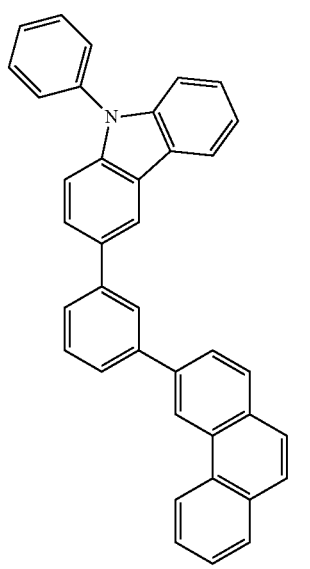

(111)
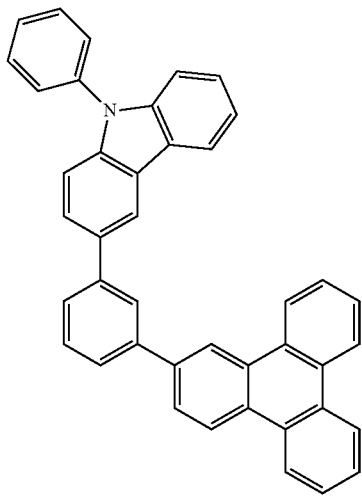
(112)
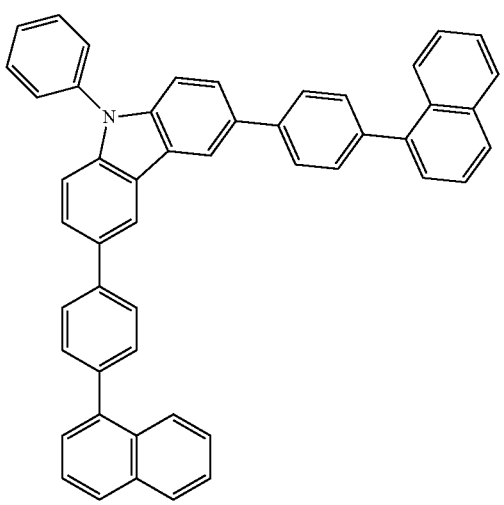
(113)
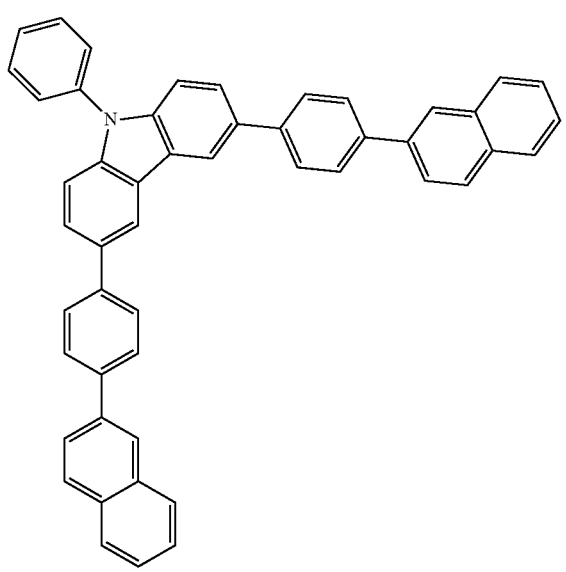
(114)
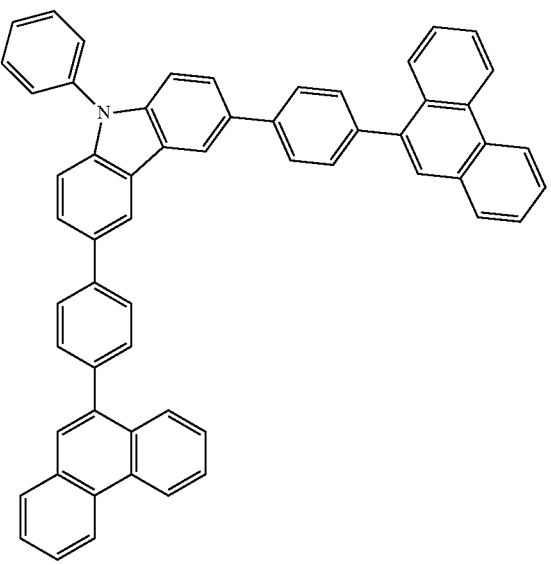
(115)

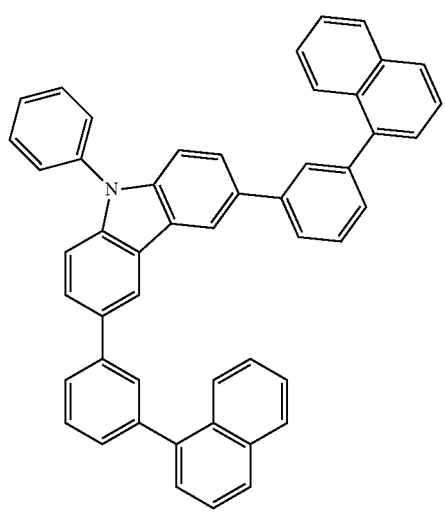
(116)
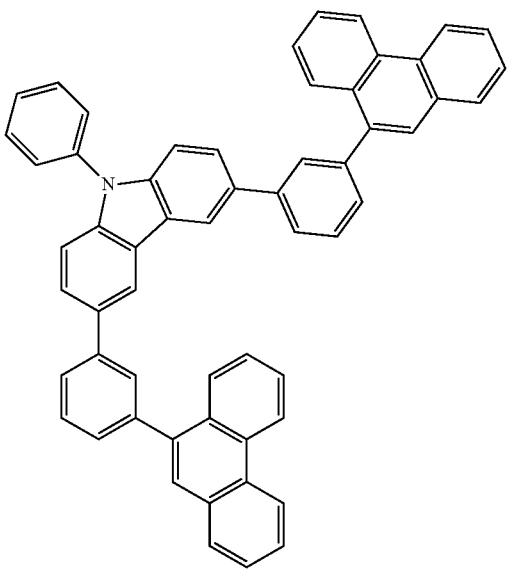
(118)
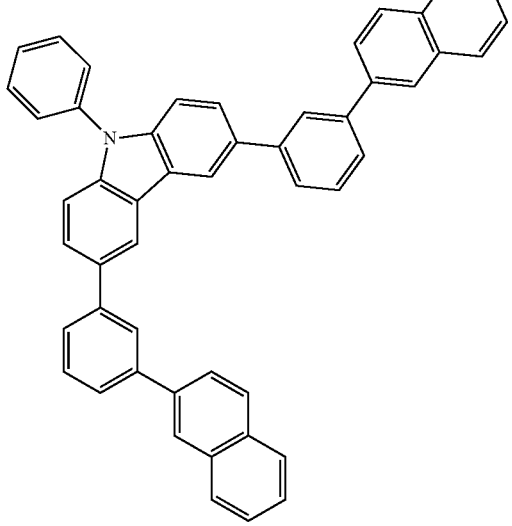
(117)
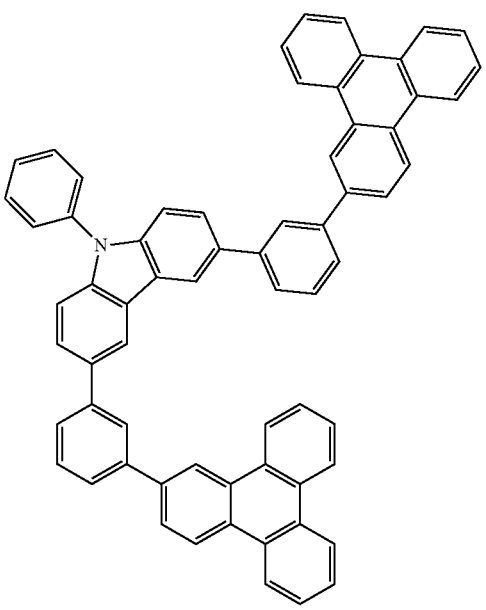
(119)

(120)
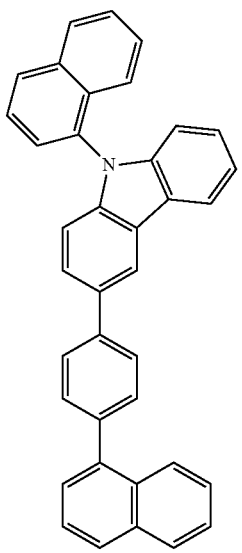
(121)
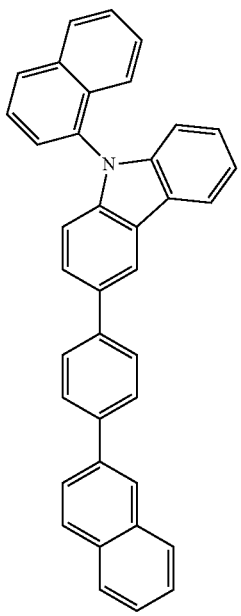
(122)
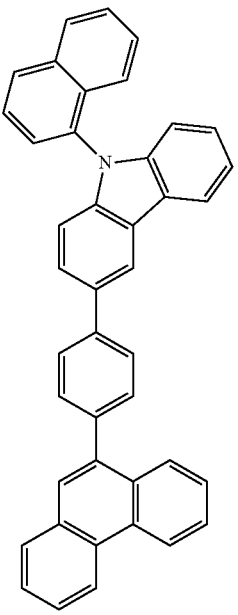
(123)
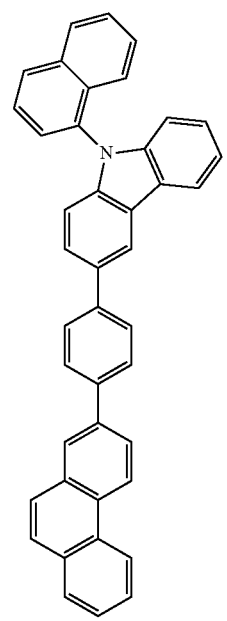

[22]
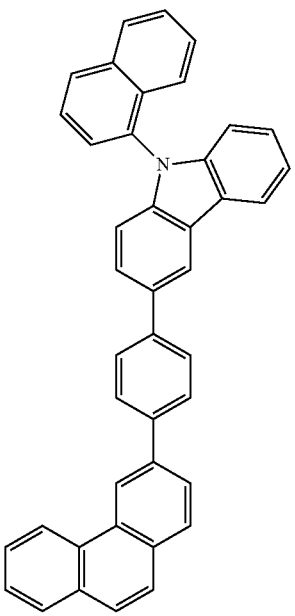
(124)
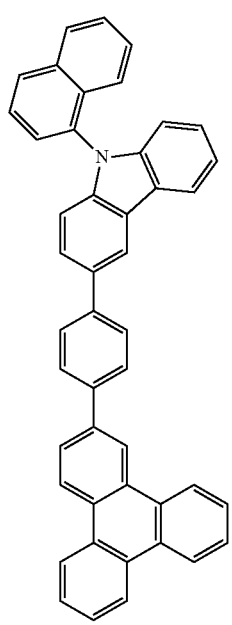
(125)
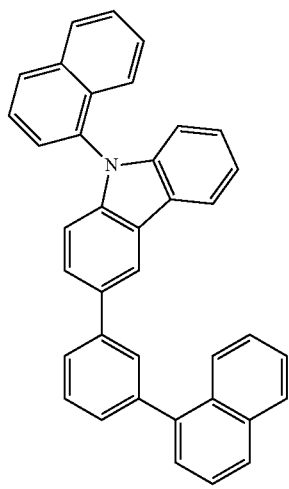
(126)
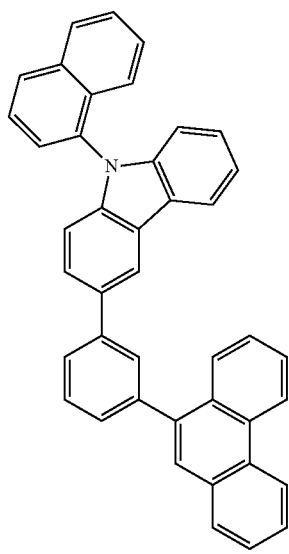
(127)
(128)

(129)
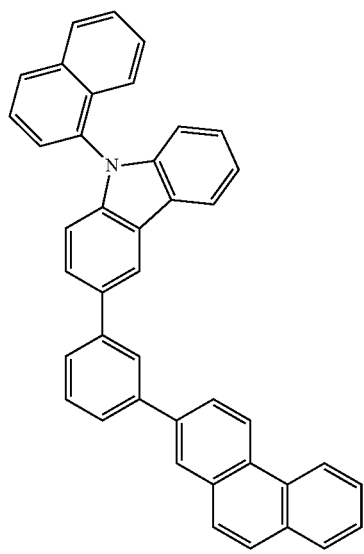
(131)
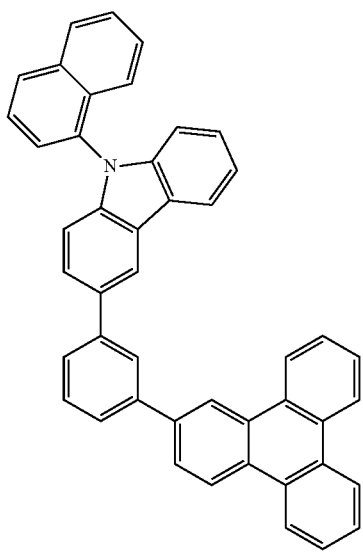
(130)
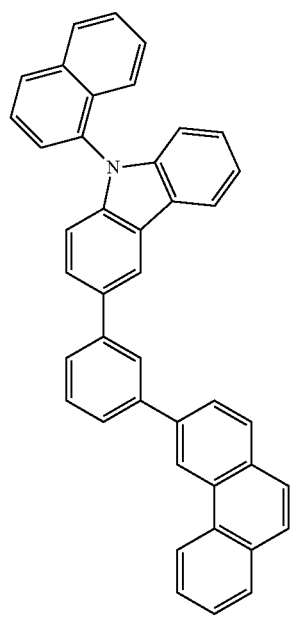
(140)
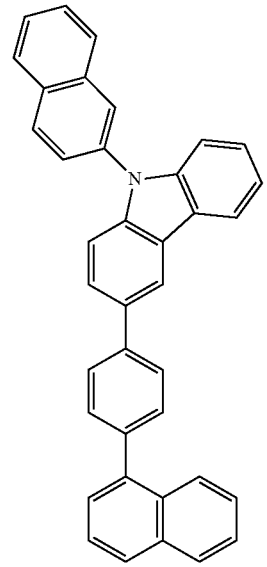

(141)
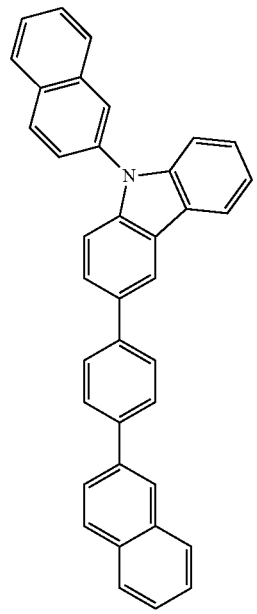
(142)
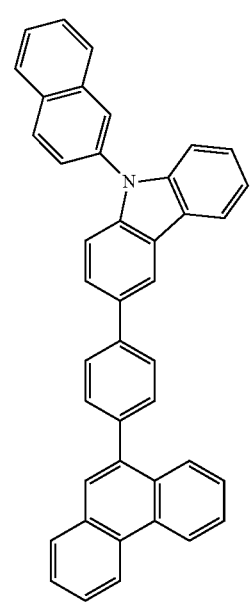
(143)
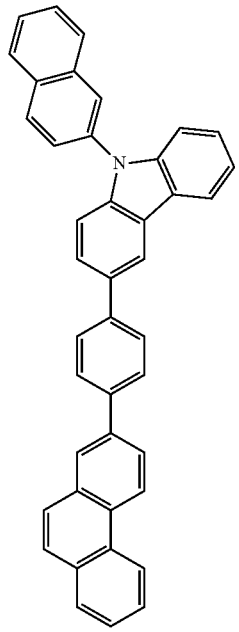
(144)
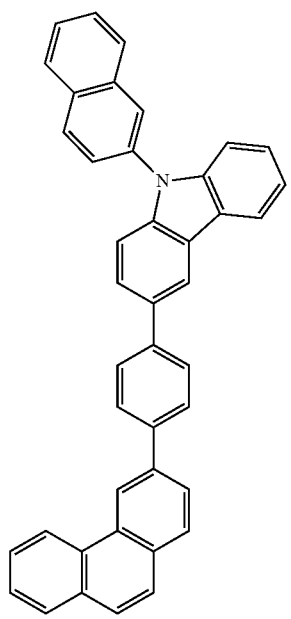

(145)
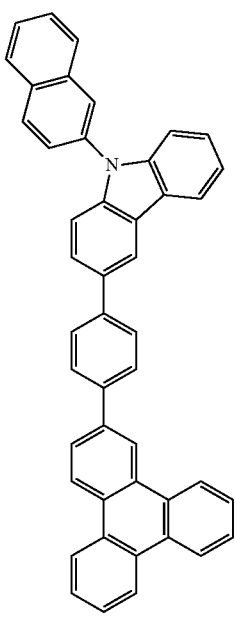
(147)
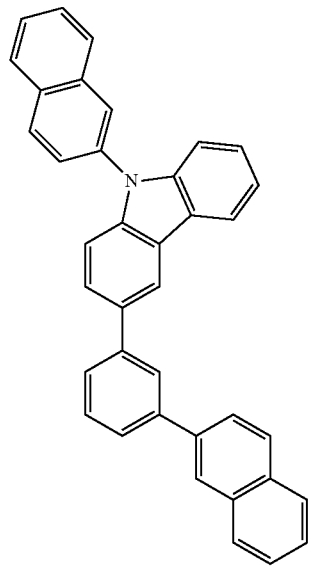
[24]
(146)
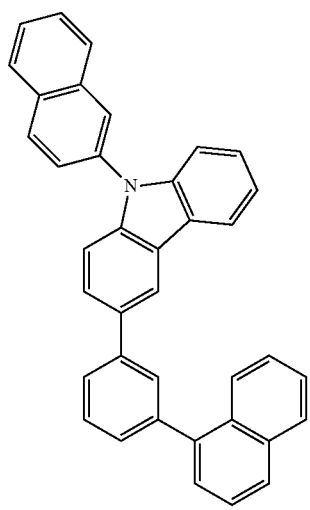
(148)
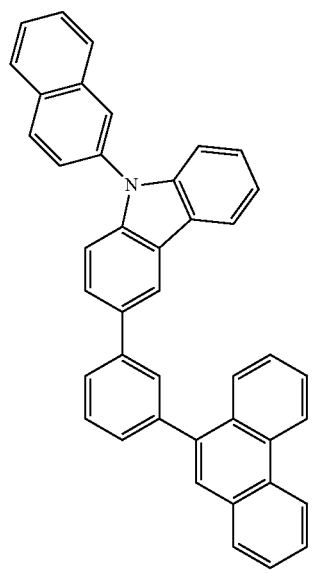

(149)
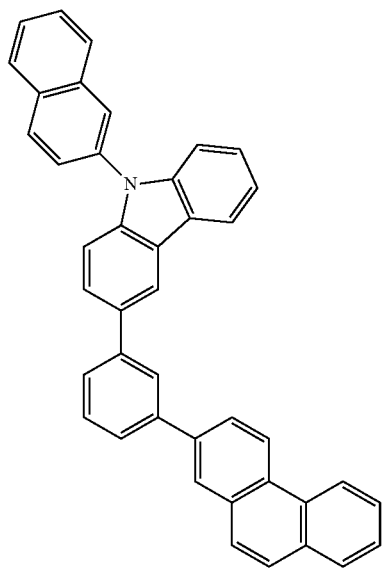
(150)
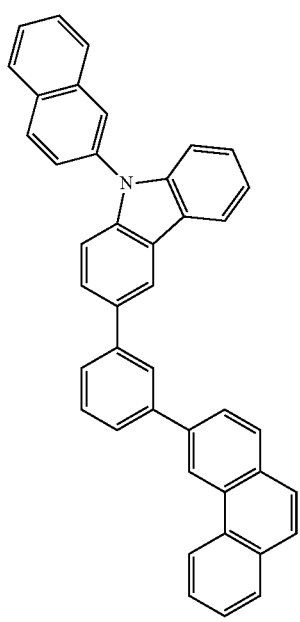
(151)
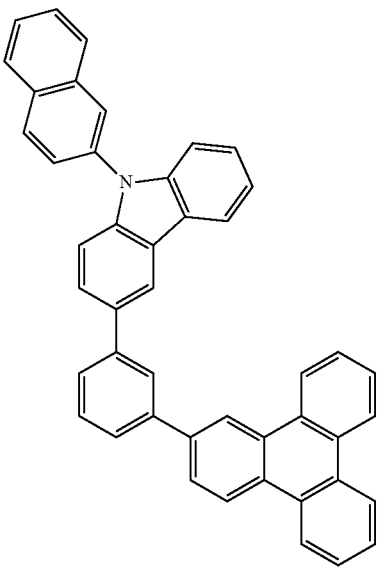
(160)
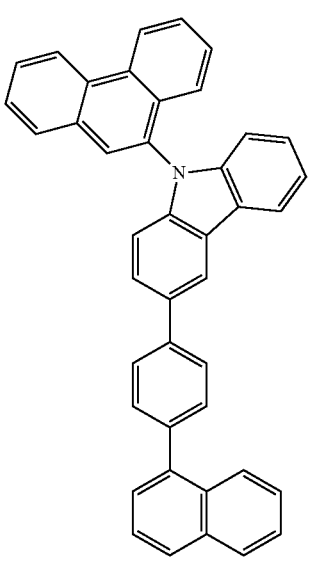

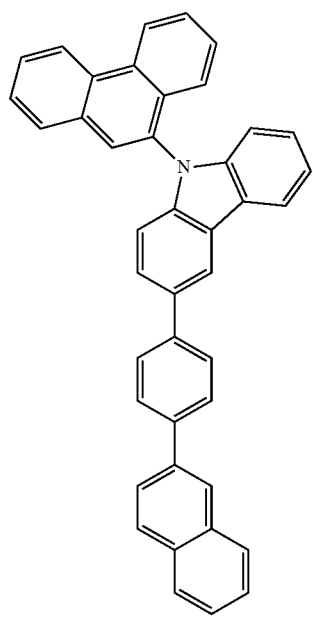
(161)
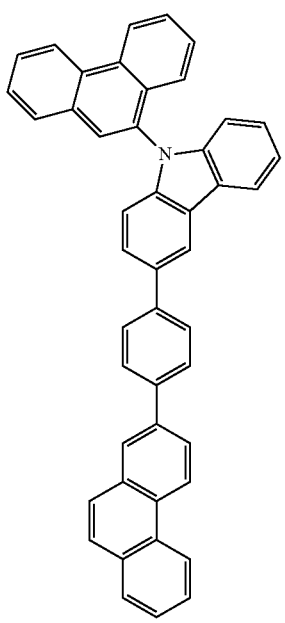
(163)
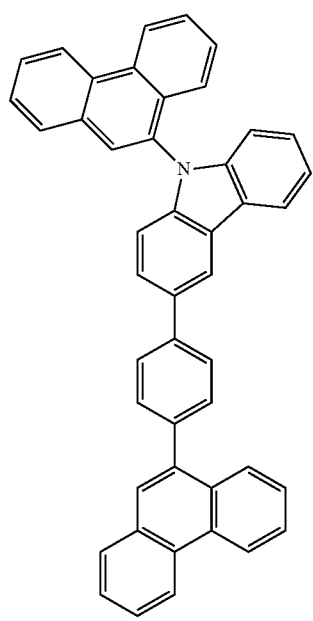
(162)
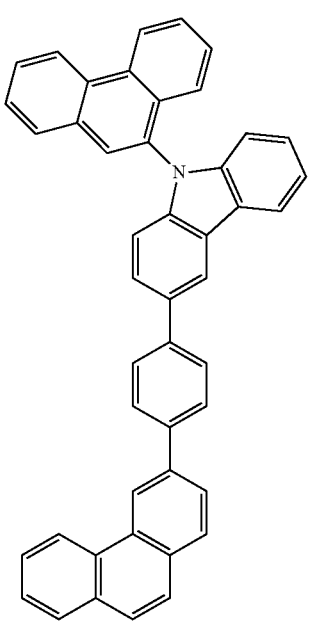
(164)

(165)
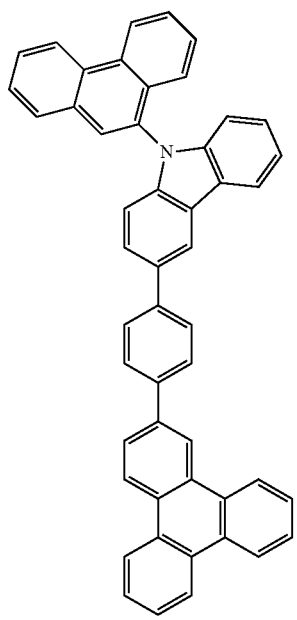
(166)
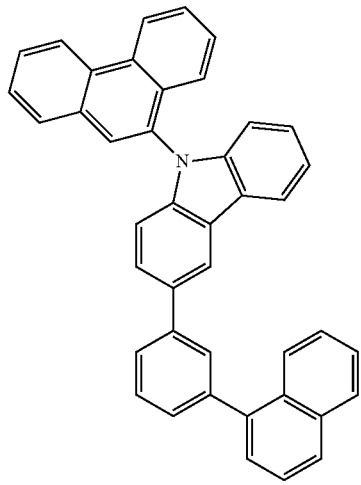
(167)
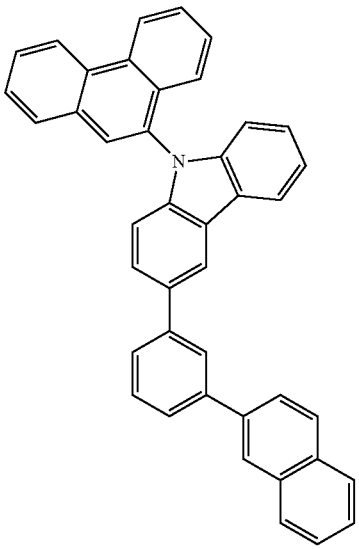
(168)
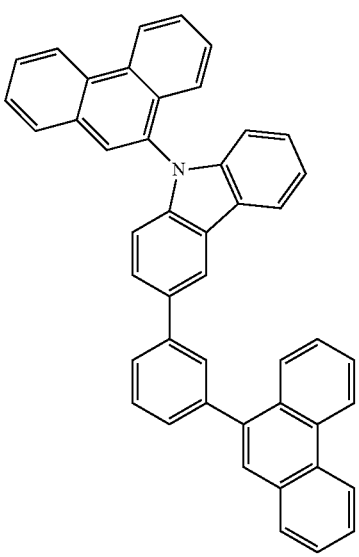
(169)
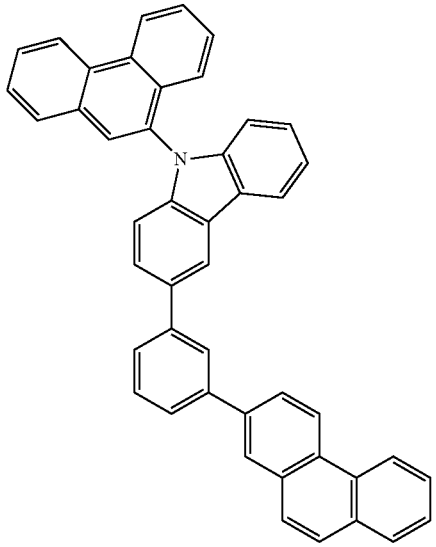

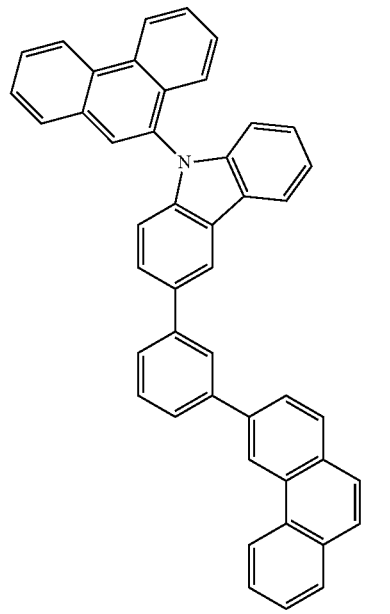
(170)
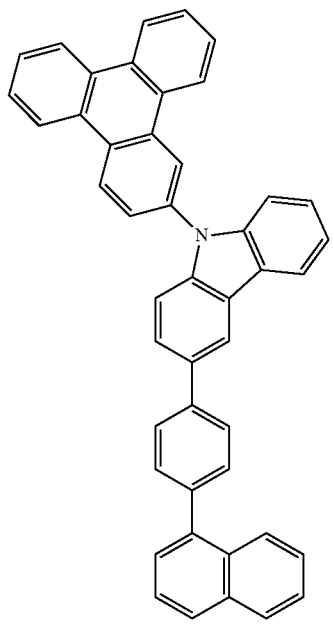
(172)
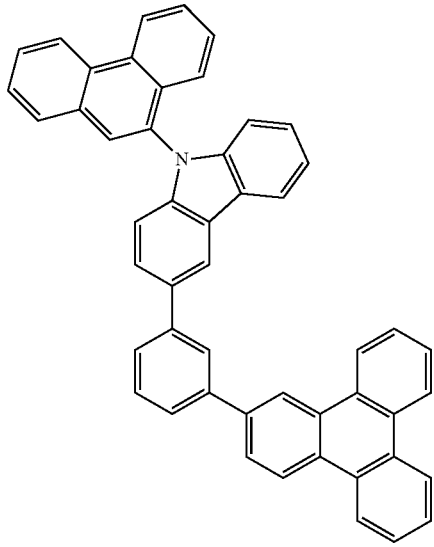
(171)
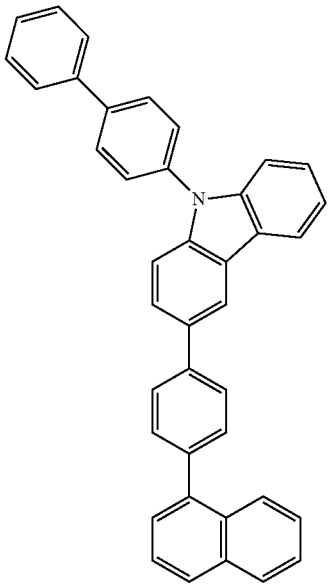
(173)

(174)
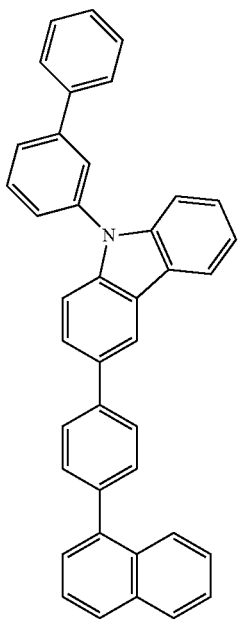
(175)
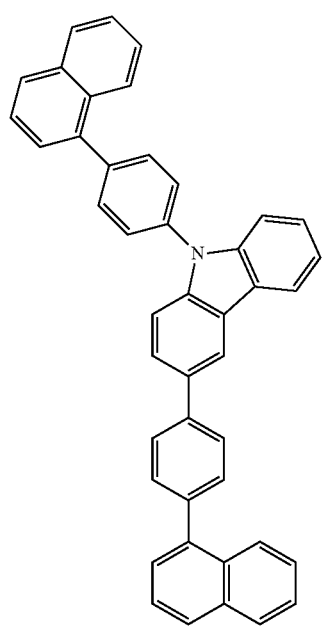
(176)
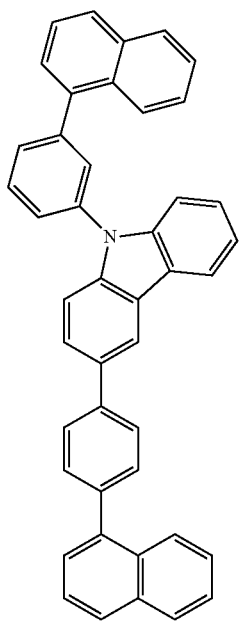
(177)
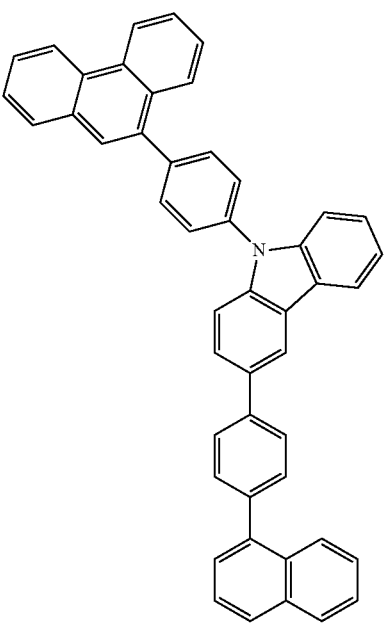
(178)
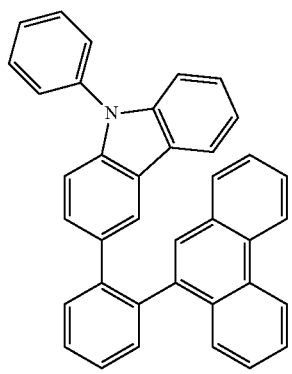

(179)
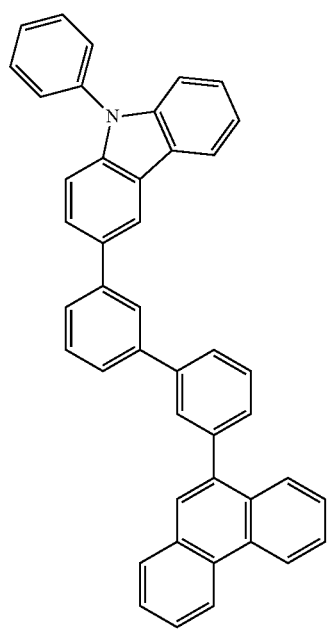
(180)
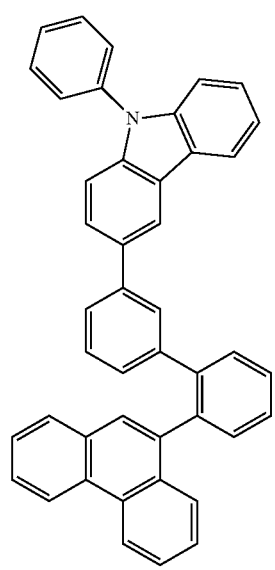
(181)
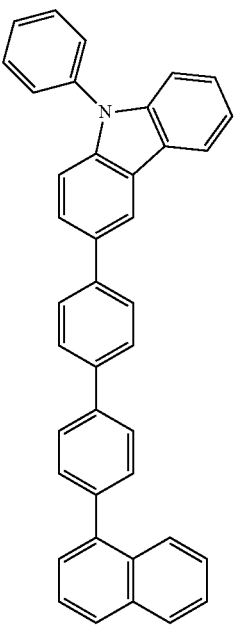
(182)
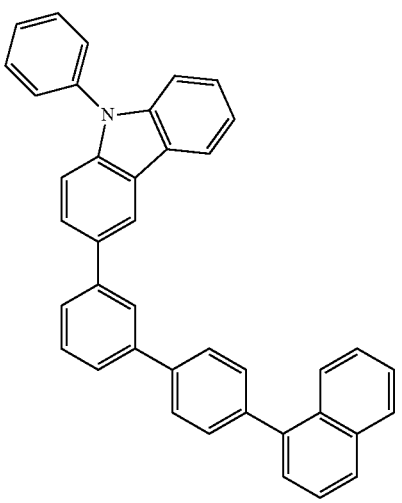
(183)
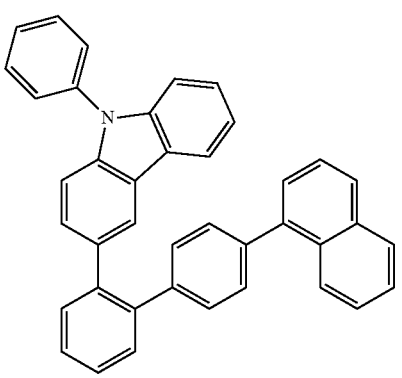

[29]
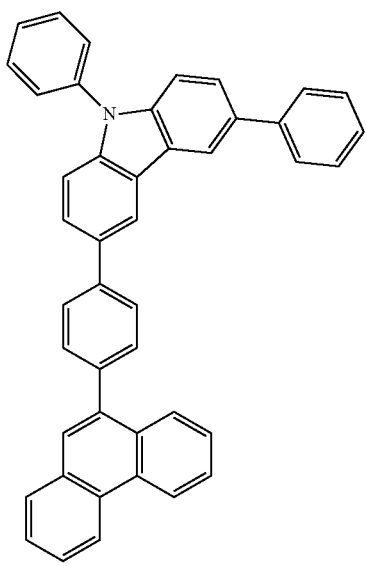
(190)
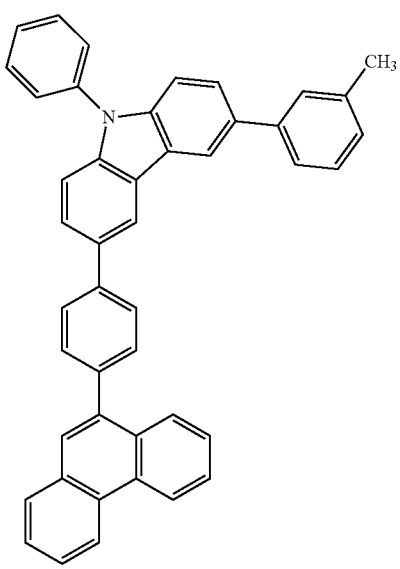
(191)
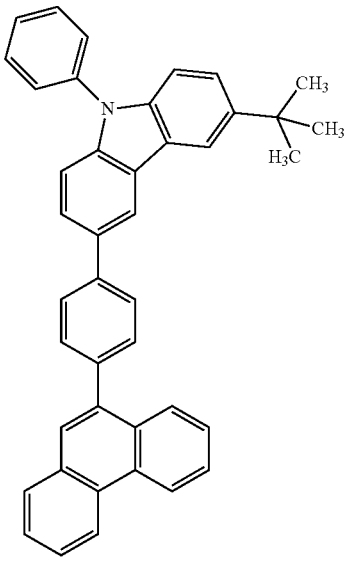
(192)
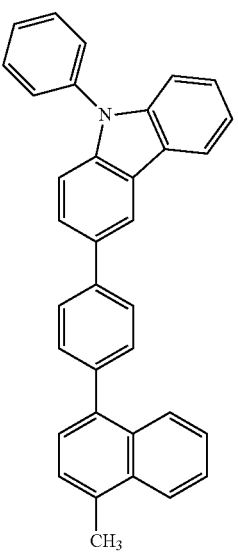
(193)
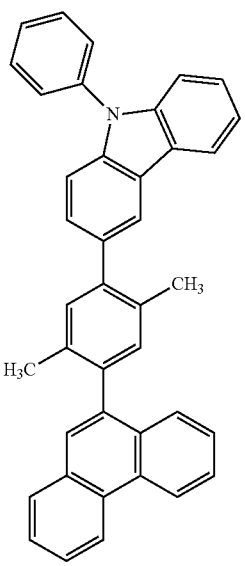
(194)

-continued

[30]

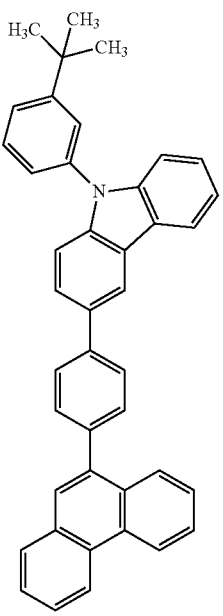

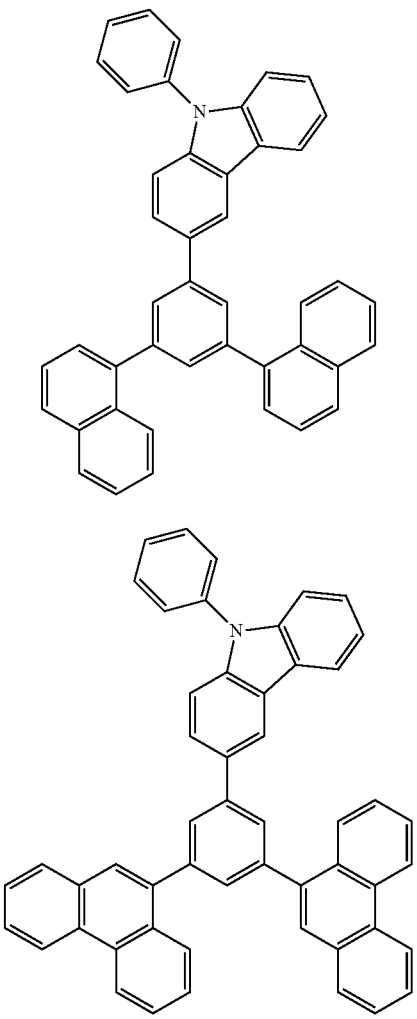

A variety of reactions can be applied to a synthesis method of the carbazole compound of this embodiment. For example, the carbazole compound of this embodiment can be synthesized by any of the synthesis reactions described in Synthesis Methods 1 to 3. Note that in reaction schemes described below, the description of General Formula (G1) can be referred to for reference numerals that are not particularly explained (i.e., $R^1$, $R^2$, $α^3$, and $Ar^3$).

<Synthesis Method 1>

First, as shown in Reaction Scheme (A-1), a carbazole compound (a3) is synthesized by coupling of a halogenated carbazole compound (a1) and an arylboron compound (a2).

[31]

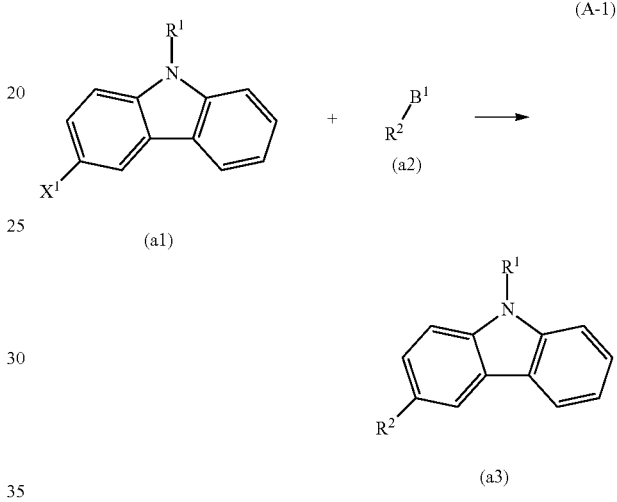

Note that $X^1$ represents halogen. $X^1$ preferably represents bromine, more preferably iodine, which have high reactivity. $B^1$ represents boronic acid or dialkoxyboron.

Note that a variety of reaction conditions can be employed for the coupling reaction in Reaction Scheme (A-1). As an example thereof, a synthesis method using a metal catalyst in the presence of a base can be employed.

The case of using the Suzuki-Miyaura Reaction in Reaction Scheme (A-1) will be described. A palladium catalyst can be used as the metal catalyst, and a mixture of a palladium complex and a ligand thereof can be used as the palladium catalyst. As examples of the palladium complex, palladium (II) acetate, tetrakis(triphenylphosphine)palladium(0), bis (triphenylphosphine)palladium(II)dichloride, and the like are given. As examples of the ligand, tri(ortho-tolyl)phosphine, triphenylphosphine, tricyclohexylphosphine, and the like are given. In addition, as examples of the substance that can be used as the base, an organic base such as sodium tert-butoxide, an inorganic base such as potassium carbonate, and the like are given. The reaction is preferably performed in a solution. As examples of the solvent that can be used, the following are given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of ethers such as ethyleneglycoldimethylether and water; and the like. However, the catalyst, ligand, base, and solvent that can be used are not limited thereto. Further, in Reaction Scheme (A-1), an aryl aluminum compound, an aryl zirconium compound, an aryl zinc compound, an aryl tin compound, or the like may be used instead of the arylboronic compound (a2). In addition, the reaction is preferably performed in an inert atmosphere of nitrogen, argon, or the like.

In Reaction Scheme (A-1), the case where the halogen group $X^1$ of the compound (a1) and the boron compound group $B^1$ of the compound (a2) are reacted with each other is shown. However, the carbazole compound (a3) can be obtained even by coupling the compound (a1) as a boron compound and the compound (a2) as a halide (with reaction groups $X^1$ and $B^1$ replaced with each other).

Next, as shown in Reaction Scheme (A-2), a halogenated carbazole compound (a4) is synthesized by halogenating the carbazole compound (a3).

[32]

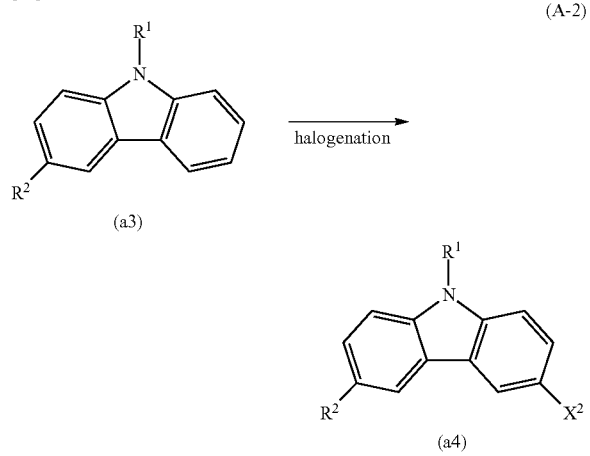

(A-2)

Note that $X^2$ represents halogen. $X^2$ preferably represents bromine, more preferably iodine, which have high reactivity.

A variety of reaction conditions can be employed for a halogenation reaction in Reaction Scheme (A-2). For example, a reaction in which a halogenating agent is used in the presence of a polar solvent can be used. As the halogenating agent, N-bromosuccinimide (abbreviation: NBS), N-iodosuccinimide (abbreviation: NIS), bromine, iodine, potassium iodide, or the like can be used. A bromide is preferably used as the halogenating agent, in which case synthesis can be performed at low cost. In addition, when an iodide is used as the halogenating agent, an iodine-substituted portion in a generated compound (i.e., an iodide) is highly active. Thus, a reaction using the generated compound (i.e., the iodide) as a raw material is preferably performed, in which case the reaction proceeds more easily.

Next, as shown in Reaction Scheme (A-3), a carbazolyl boron compound (a5) is synthesized by reacting the compound activated by reaction of the halogenated carbazole compound (a4) with the metal catalyst with a boron compound.

[33]

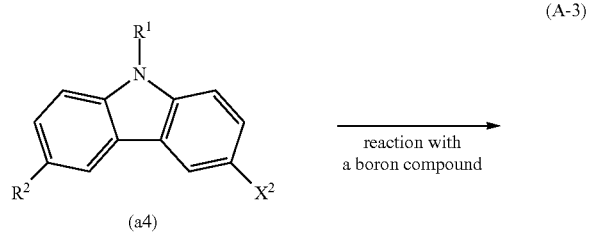

(A-3)

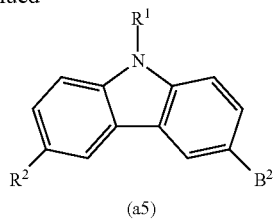

(a5)

Note that $X^2$ represents halogen. $X^2$ preferably represents bromine, more preferably iodine, which have high reactivity. In addition, $B^2$ represents boronic acid or dialkoxyboron.

In Reaction Scheme (A-3), as an example of the activation of the halogenated carbazole compound (a4), a lithiation reaction with an alkyl lithium reagent can be used. As examples of the alkyl lithium reagent, n-butyllithium, tert-butyllithium, methyllithium, and the like are given. As acid, hydrochloric acid or the like can be used. As a dehydrating solvent, an ether such as diethyl ether or tetrahydrofuran (THF) can be used. As examples of the boron compound that can be used, trimethyl borate, triethyl borate, and the like are given.

Next, as shown in Reaction Scheme (A-4), a halogenated carbazole compound (a7) can be obtained by coupling a carbazolyl boron compound (a5) and a dihalogenated aryl compound (a6).

[34]

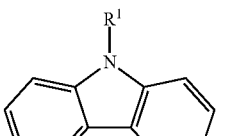

(A-4)

Note that $X^3$ and $X^4$ each represent halogen. Each of $X^3$ and $X^4$ preferably represents bromine, more preferably iodine, which have high reactivity. In the case where $B^2$ and $X^3$ are specifically reacted, halogen which has higher reactivity than $X^4$ is preferably used as $X^3$. Note that in halogen, bromine has higher reactivity than chlorine and iodine has higher reactivity than bromine. $B^2$ represents boronic acid or dialkoxyboron.

A variety of reaction conditions can be employed for the coupling reaction in Reaction Scheme (A-4). As an example thereof, a synthesis method using a metal catalyst in the presence of a base can be employed. Specifically, the coupling reaction can be performed in a manner similar to that in Reaction Scheme (A-1); therefore, the description given above can be referred to.

In Reaction Scheme (A-4), the case where the halogen group $X^3$ of the compound (a6) and the boron compound group $B^2$ of the compound (a5) are reacted with each other is shown. However, the carbazole compound (a7) can be obtained even by coupling the compound (a5) as a boron compound and the compound (a6) as a halide (with reaction groups $X^3$ and $B^2$ replaced with each other). Note that in this case, a halogen group which has higher reactivity than the halogen group $X^4$ needs to be used as the halogen group $X^3$ in order to prevent reaction between the compounds (a6).

Next, as shown in Reaction Scheme (A-5), the carbazole compound represented by General Formula (G1) can be obtained by coupling the halogenated carbazole compound (a7) and an aryl boron compound (a8).

[35]

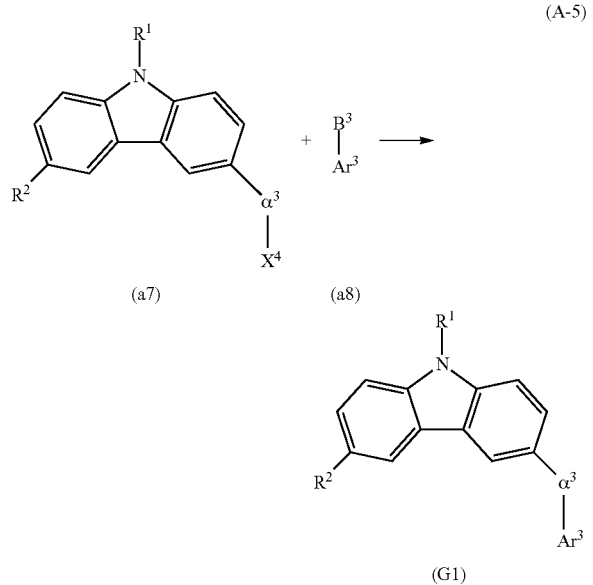

(A-5)

(a7)  (a8)

(G1)

Note that $X^4$ represents halogen. $X^4$ preferably represents bromine, more preferably iodine, which have high reactivity. $B^3$ represents boronic acid or dialkoxyboron.

A variety of reaction conditions can be employed for the coupling reaction in Reaction Scheme (A-5). As an example thereof, a synthesis method using a metal catalyst in the presence of a base can be employed. Specifically, the coupling reaction can be performed in a manner similar to that in Reaction Scheme (A-1); therefore, the description given above can be referred to.

In Reaction Scheme (A-5), the case where the halogenated group $X^4$ of the compound (a7) and the boron compound group $B^3$ of the compound (a8) are reacted with each other is shown. However, the carbazole compound represented by General Formula (G1) can be obtained even by coupling of the compound (a7) as a boron compound and the compound (a8) as a halide (with reaction groups $X^4$ and $B^3$ replaced with each other).

Further, in Reaction Schemes (A-1) to (A-5), the example in which the substituent-$R^2$ is combined with the 3-position of the carbazole skeleton, and then the substituent-$\alpha^3$-$Ar^3$ is combined with the 6-position of the carbazole skeleton is shown. However, the present invention is not limited to the above reaction. The carbazole compound represented by General Formula (G1) can be synthesized even by combining the substituent-$R^2$ after combining the substituent-$\alpha^3$-$Ar^3$.

Note that the substituent-$R^2$ and the substituent-$\alpha^3$-$Ar^3$ preferably have the same skeleton, in which case a reaction in which the substituent $R^2$ and the substituent $\alpha^3$-$Ar^3$ are combined with the 3-position and the 6-position of the carbazole skeleton, respectively, at the same time is performed easily.

Synthesis Method 2 will be described below as a synthesis method of the carbazole compound of this embodiment, which is different from Synthesis Method 1.

<Synthesis Method 2>

As shown in Reaction Scheme (B-1), the carbazole compound represented by general Formula (G1) can be synthesized by coupling the halogenated carbazole compound (a4) and an aryl boron compound (a9).

[36]

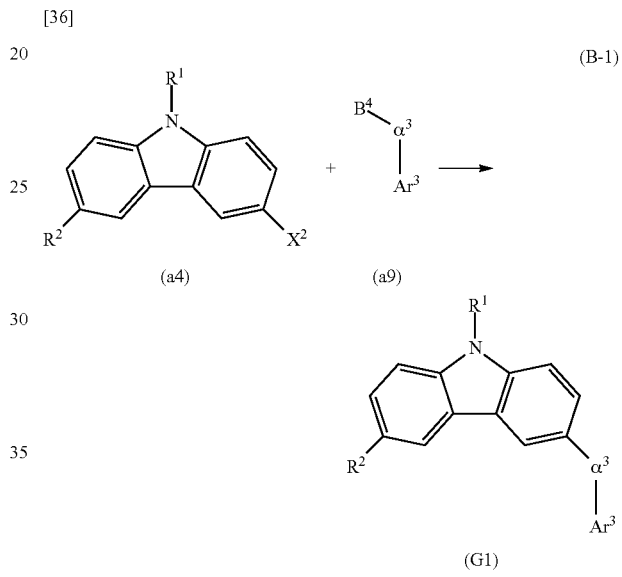

(B-1)

(a4)  (a9)

(G1)

Note that $X^2$ represents halogen. $X^2$ preferably represents bromine, more preferably iodine, which have high reactivity. $B^4$ represents boronic acid or dialkoxyboron.

A variety of reaction conditions can be employed for the coupling reaction in Reaction Scheme (B-1). As an example thereof, a synthesis method using a metal catalyst in the presence of a base can be employed. Specifically, the coupling reaction can be performed in a manner similar to that in Reaction Scheme (A-1); therefore, the description given above can be referred to.

In Reaction Scheme (B-1), the case where the halogenated group $X^2$ of the compound (a4) and the boron compound group $B^4$ of the compound (a9) are reacted with each other is shown. However, the carbazole compound represented by General Formula (G1) can be synthesized even by coupling the compound (a4) as a boron compound and the compound (a9) as a halide (with reaction groups $X^2$ and $B^4$ replaced with each other).

Further, in Reaction Scheme (B-1), the example in which the substituent-$R^2$ is combined with the 3-position of the carbazole skeleton, and then the substituent-$\alpha^3$-$Ar^3$ is combined with the 6-position of the carbazole skeleton is shown. However, the present invention is not limited to the above reaction. The carbazole compound represented by General Formula (G1) can be synthesized even by combining the substituent-$R^2$ after combining the substituent-$\alpha^3$-$Ar^3$.

Note that the substituent-$R^2$ and the substituent-$\alpha^3$-$Ar^3$ preferably have the same skeleton, in which case a reaction in which the substituent-$R^2$ and the substituent-$\alpha^3$-$Ar^3$ are combined with the 3-position and the 6-position of the carbazole skeleton, respectively, at the same time can be performed easily.

Synthesis Method 3 will be described below as a synthesis method of the carbazole compound of this embodiment, which is different from Synthesis Method 1 and Synthesis Method 2.

<Synthesis Method 3>

As shown in Reaction Scheme (C-1), the carbazole compound represented by general Formula (G1) can be synthesized by coupling a carbazole compound (a10) and a halogenated aryl compound (a11).

[37]

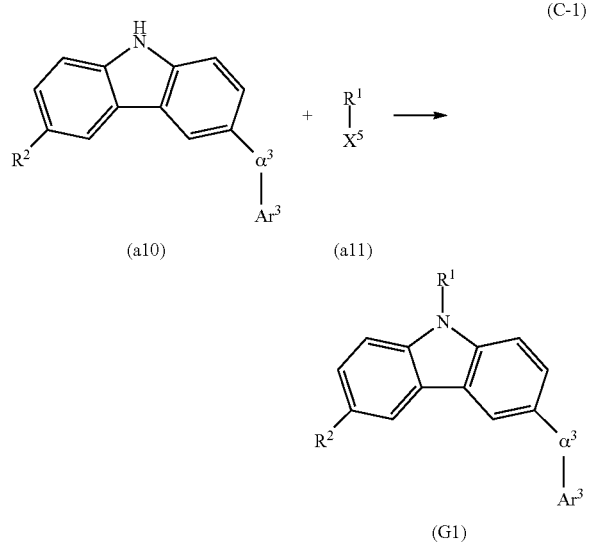

Note that $X^5$ represents halogen. $X^5$ preferably represents bromine, more preferably iodine, which have high reactivity.

A variety of reaction conditions can be employed for the coupling reaction in a coupling reaction of an aryl compound having a halogen group and the 9-position of carbazole in Reaction Scheme (C-1). As an example thereof, a synthesis method using a metal catalyst in the presence of a base can be employed.

The case where the Buchwald-Hartwig reaction is performed in Reaction Scheme (C-1) will be described. A palladium catalyst can be used as the metal catalyst, and a mixture of a palladium complex and a ligand thereof can be used as the palladium catalyst. As examples of the palladium catalyst, bis(dibenzylideneacetone)palladium(0), palladium(II) acetate, and the like are given. As examples of the ligand, tri(tert-butyl)phosphine, tri(n-hexyl)phosphine, tricyclohexylphosphine, 1,1-bis(diphenylphosphino)ferrocene (abbreviation: DPPF), and the like are given. As a substance that can be used as the base, an organic base such as sodium tert-butoxide, an inorganic base such as potassium carbonate, and the like are given. In addition, this reaction is preferably performed in a solution. As examples of the solvent that can be used, toluene, xylene, benzene, and the like are given. However, the catalyst, ligand, base, and solvent that can be used are not limited thereto. Note that this reaction is preferably performed in an inert atmosphere of nitrogen, argon, or the like.

The case where the Ullmann reaction is performed in Reaction Scheme (C-1) is will be described. A copper catalyst can be used as a metal catalyst, and copper(I) iodide and copper (II) acetate are given as examples of the copper catalyst. As examples of the substance that can be used as a base, inorganic bases such as potassium carbonate are given. The above reaction is preferably performed in a solution, and 1,3-dimethyl-3,4,5,6-tetrahydro-2(1H)-pyrimidinone (abbreviation: DMPU), toluene, xylene, benzene, and the like are given as examples of the solvent that can be used. However, the catalyst, ligand, base, and solvent that can be used are not limited thereto. In addition, this reaction is preferably performed under an inert atmosphere of nitrogen, argon, or the like.

Note that a solvent having a high boiling point such as DMPU or xylene is preferably used because, by the Ullmann reaction, an object can be obtained in a shorter time and in a higher yield when the reaction temperature is higher than or equal to 100° C. In particular, DMPU is more preferable because the reaction temperature is more preferably greater than or equal to 150° C.

Note that a reaction in which a substituent-$R^2$ and a substituent-$\alpha^3$-$Ar^3$ are combined with the 3-position and the 6-position of a carbazole skeleton can be performed in a manner similar to that in Reaction Schemes (A-1) to (A-5) or Reaction Scheme (B-1). Therefore, the above description can be referred to for the detail.

In the above manner, the carbazole compound of this embodiment can be synthesized.

The carbazole compound of this embodiment has a deep HOMO level (i.e., the absolute value is large), and thus has an excellent property of injecting holes into a light-emitting layer. In addition, the carbazole compound of this embodiment is electrochemically stable to oxidation. For these reasons, the carbazole compound of this embodiment can be favorably used as a material of a hole-transport layer of a light-emitting element. Further, a composite material in which the carbazole compound of this embodiment (an electron donor) and an electron acceptor are mixed can be used for a hole-injection layer of a light-emitting element. Note that the electron acceptor and the electron donor are at least capable of donating and accepting electrons with the assistance of an electric field.

Further, the carbazole compound of this embodiment has a shallow LUMO level (i.e., the absolute value is small); thus, transfer of electrons to an anode can be blocked by using the carbazole compound as a material of a hole-transport layer of a light-emitting element. Thus, the efficiency of the light-emitting element in which the carbazole compound of this embodiment is used can be increased.

Further, the carbazole compound of this embodiment has a wide band gap; thus, energy transfer from a light-emitting layer can be suppressed even in the case where the carbazole compound is used for a hole-transport layer adjacent to a light-emitting layer. Thus, the lifetime as well as the efficiency of the light-emitting element in which the carbazole compound of this embodiment is used can be increased.

Further, the carbazole compound of this embodiment emits fluorescence, and thus can emit light with a short wavelength. Thus, the use of the carbazole compound of this embodiment as a light-emitting material, light of blue-violet to blue can be obtained.

Further, the carbazole compound of this embodiment is also preferable as a host material of a light-emitting layer in a light-emitting element. In other words, when a light-emitting substance (hereinafter, also referred to as a "dopant") having a narrower band gap than the carbazole compound of this embodiment is added to a layer formed of the carbazole compound, light can be emitted from the dopant. At this time, even if a fluorescent dopant which emits light with a relatively short wavelength, such as blue light, is used, light can be emitted efficiently from the dopant because the carbazole compound of this embodiment has a wide band gap. In other words, the carbazole compound of this embodiment can be used as a host material of a compound which emits fluorescence in the visible region. Further, in the case where a dopant is a phosphorescent compound, a substance which has a higher T1 level than the dopant is preferably used as a host material. The carbazole compound of this embodiment has a high T1 level, and thus can be used as a host material of a compound which emits phosphorescence in the visible region with a wavelength longer than that of at least green light.

Further, the carbazole compound of this embodiment has weak absorption of light in the visible region (approximately 380 nm to 750 nm), the transmittance of visible light is high when a thin film is formed using the carbazole compound. Thus, the carbazole compound of this embodiment does not easily absorb emission energy even when used in a light-emitting element, which allows the light-emitting element to have a high external quantum yield.

This embodiment can be implemented in combination with any of the other embodiments as appropriate.

(Embodiment 2)

In this embodiment, as one embodiment of the present invention, a light-emitting element in which the carbazole compound described in Embodiment 1 is used will be described with reference to FIGS. 1A and 1B.

In the light-emitting element of this embodiment, an EL layer including at least a light-emitting layer is interposed between a pair of electrodes. The EL layer may have a plurality of layers in addition to the light-emitting layer. The plurality of layers are stacked in combination of layers formed of substances having a high carrier-injection property and a high carrier-transport property so that a light-emitting region is formed away from the electrodes, that is, carriers are recombined in a portion away from the electrodes. As the plurality of layers, for example, a hole-injection layer, a hole-transport layer, an electron-transport layer, an electron-injection layer, and the like may be included.

In the light-emitting element of this embodiment illustrated in FIG. 1A, an EL layer 102 is provided between a pair of electrodes, a first electrode 101 and a second electrode 103. In addition, the EL layer 102 includes a hole-injection layer 111, a hole-transport layer 112, a light-emitting layer 113, an electron-transport layer 114, and an electron-injection layer 115. Note that, in the light-emitting element described in this embodiment, the first electrode 101 provided over a substrate 100 functions as an anode and the second electrode 103 functions as a cathode.

A substrate 100 is used as a support of the light-emitting element. For example, glass, quartz, plastic, or the like can be used for the substrate 100. A flexible substrate may be used. A flexible substrate is a substrate that can be bent (is flexible). As examples of the flexible substrate, plastic substrates made of polycarbonate, polyarylate, and polyether sulfone, and the like are given. A film (made of polypropylene, polyester, vinyl, polyvinyl fluoride, vinyl chloride, or the like), an inorganic film formed by evaporation, or the like can be used. Note that other materials may also be used as long as they function as a support in a manufacturing process of the light-emitting element.

For the first electrode 101, a metal, an alloy, an electrically conductive compound, a mixture thereof, or the like which has a high work function (specifically, a work function of 4.0 eV or more) is preferably used. Specifically, for example, indium oxide-tin oxide (ITO: indium tin oxide), indium oxide-tin oxide including silicon or silicon oxide, indium oxide-zinc oxide (IZO: indium zinc oxide), indium oxide including tungsten oxide and zinc oxide (IWZO), and the like are given. Films of these conductive metal oxides are usually formed by sputtering, but may be formed by application of a sol-gel method or the like. For example, indium zinc oxide (IZO) can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Besides, gold, platinum, nickel, tungsten, chromium, molybdenum, iron, cobalt, copper, palladium, nitride of a metal material (e.g., titanium nitride), and the like are given.

Note that, in the EL layer 102, when a layer in contact with the first electrode 101 is formed using a composite material of an organic compound and an electron acceptor (acceptor) described later, the first electrode 101 can be formed using any of a variety of metals, alloys, and electrically conductive compounds, a mixture thereof, and the like regardless of the work function. For example, aluminum, silver, an alloy containing aluminum (e.g., Al—Si), or the like can be used.

In the EL layer 102 formed over the first electrode 101, at least any of the hole-injection layer 111, the hole-transport layer 112, and the light-emitting layer 113 contain the carbazole compound that is one embodiment of the present invention. A known substance can be used for part of the EL layer 102, and either a low molecular compound or a high molecular compound can be used. Note that the substance used for forming the EL layer 102 may have not only a structure formed of only an organic compound but also a structure in which an inorganic compound is partially contained.

The hole-injection layer 111 is a layer that contains a substance having a high hole-injection property. As the substance having a high hole-injection property, for example, metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. A phthalocyanine-based compound such as phthalocyanine (abbreviation: $H_2Pc$), or copper(II) phthalocyanine (abbreviation: CuPc) can also be used.

Other examples of a substance that can be used are aromatic amine compounds which are low molecular organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Further, any of high molecular compounds (e.g., oligomers, dendrimers, or polymers) can be used. As examples of the high molecular compounds, the following are given: poly (N-vinylcarbazole) (abbreviation: PVK), poly(-vinyltriphenylamine) (abbreviation: PVTPA), poly[N-(4-{N'-[4-(4-diphenylamino)phenyl]phenyl-N'-phenylamino}phenyl)

methacrylamide] (abbreviation: PTPDMA), poly[N,N'-bis(4-butylphenyl)-N,N'-bis(phenyl)benzidine] (abbreviation: Poly-TPD), and the like. A high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can also be used.

A composite material in which an organic compound and an electron acceptor (acceptor) are mixed may be used for the hole-injection layer 111. Such a composite material is excellent in a hole-injection property and a hole-transport property because holes are generated in the organic compound by the electron acceptor. In this case, the organic compound is preferably a material excellent in transporting the generated holes (a substance having a high hole-transport property).

As the organic compound for the composite material, any of a variety of compounds such as aromatic amine compounds, carbazole derivatives, aromatic hydrocarbons, and high molecular compounds (e.g., oligomer, dendrimer, and polymer) can be used. The organic compound used for the composite material is preferably an organic compound having a high hole-transport property. Specifically, a substance having a hole mobility of $10^{-6}$ cm$^2$/Vs or higher is preferably used. Note that any other substances may also be used as long as the hole-transport property thereof is higher than the electron-transport property thereof. The organic compounds that can be used for the composite material will be specifically given below.

The carbazole compound of one embodiment of the present invention is an organic compound having a high hole-transport property, and thus can be used favorably for a composite material. Besides, as the organic compound that can be used for the composite material, the following can be used, for example: aromatic amine compounds such as TDATA, MTDATA, DPAB, DNTPD, DPA3B, PCzPCA1, PCzPCA2, PCzPCN1,4,4'-bis[N-(1-naphthyl)-N-phenylamino]biphenyl (abbreviation: NPB or a-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole compounds such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Any of the following aromatic hydrocarbon compounds can be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, and the like.

Any of the following aromatic hydrocarbon compounds can be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

As examples of the electron acceptor, organic compounds such as 7,7,8,8-tetracyano-2,3,5,6-tetrafluoroquinodimethane (abbreviation: F$_4$-TCNQ) and chloranil; and transition metal oxides can be given. Oxides of metals belonging to Groups 4 to 8 in the periodic table can be also given. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is particularly preferable because it is stable in the air, has a low hygroscopic property, and is easily handled.

Note that the composite material may be formed using the above-described electron acceptor and the above high molecular compound such as PVK, PVTPA, PTPDMA, or Poly-TPD and may be used for the hole-injection layer 111.

The hole-transport layer 112 is a layer that contains a substance having a high hole-transport property. The carbazole compound of one embodiment of the present invention is a substance having a high hole-transport property, and thus can be favorably used as a material of the hole-transport layer 112.

The light-emitting layer 113 is a layer that contains a light-emitting substance. As the light-emitting substance, for example, a fluorescent compound which emits fluorescence or a phosphorescent compound which emits phosphorescence can be used.

The carbazole compound of one embodiment of the present invention is a material which exhibits fluorescence of blue-violet to blue, and thus can also be used as a light-emitting substance.

Besides, as the fluorescent compound that can be used for the light-emitting layer 113, a material for blue light emission, a material for green light emission, a material for yellow light emission, and a material for red light emission are given. As examples of the material for blue light emission, the following are given:
N,N'-bis[4-(9H-carbazol-9-yl)phenyl]-N, N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. As examples of the material for green light emission, the following are given: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. As examples of the material for yellow light emission, rubrene, 5,12-bis(1,1'-biphenyl-4-yl)-6,11-diphenyltetracene (abbreviation: BPT), and the like are given. As examples of the material for red light emission, N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-d iamine (abbreviation: p-mPhAFD), and the like are given.

As the phosphorescent compound that can be used for the light-emitting layer 703, a material for blue light emission, a material for green light emission, a material for yellow light emission, a material for orange light emission, and a material for red light emission are given. As examples of the material for blue light emission, the following are given: bis[2-(4',6'-difluorophenyl)pyridinato-N,C$^{2'}$]iridium(III)tetrakis(1-pyrazolyl)borate (abbreviation: FIr6); bis[2-(4',6'-difluorophenyl)pyridinato-N,C$^{2'}$]iridium(III)picolinate (abbreviation: FIrpic); bis{2-[3',5'-bis(trifluoro methyl)phenyl]pyridinato-N,C$^{2'}$}iridium(III) picolinate (abbreviation: Ir(CF$_3$ppy)$_2$(pic)); bis[2-(4',6'-difluorophenyl)pyridinato-N,C$^{2'}$]iridium(III)acetylacetonate (abbreviation: FIr(acac)); and the like. As examples of the material for green light emission, the following are given: tris(2-phenylpyridinato-N,C$^{2'}$)iridium(III) (abbreviation: Ir(ppy)$_3$), bis[2-phenylpyridinato-N,C$^{2'}$]iridium(III)acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), tris(benzo[h]quinolinato)iridium(III) (abbreviation: Ir(bzq)$_3$), and the like. As examples of the material for yellow light emission, the following are given: bis(2,4-diphenyl-1,3-oxazolato-N,C$^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetyl acetonate (abbreviation: Ir(bt)$_2$(acac)) (acetylacetonato)bis[2,3-bis(4-fluorophenyl)-5-methylpyrazinato]iridium(III) (abbreviation: Ir(Fdppr-Me)$_2$(acac)), (acetylacetonato)bis {2-(4-methoxyphenyl)-3,5-dimethylpyrazinato}iridium(III) (abbreviation: Ir(dmmoppr)$_2$(acac)), and the like. As examples of the material for orange light emission, the following are given: tris(2-phenylquinolinato-N,C$^{2'}$)iridium (III) (abbreviation: Ir(pq)$_3$), bis(2-phenylquinolinato-N,C$^{2'}$)iridium(III)acetylacetonate (abbreviation: Ir(pq)$_2$(acac)), (acetylacetonato)bis(3,5-dimethyl-2-phenylpyrazinato)iridium(III) (abbreviation [Ir(mppr-Me)$_2$(acac)]), (acetylacetonato)bis(5-isopropyl-3-methyl-2-phenylpyrazinato)iridium (III) (abbreviation: Ir(mppr-iPr)$_2$(acac)), and the like. As examples of the material for red light emission, organometallic complexes such as bis[2-(2'-benzo[4,5-α]thienyl)pyridinato-N,C$^{3'}$)iridium(III)acetylacetonate (abbreviation: [Ir(btp)$_2$(acac)]), bis(1-phenylisoquinolinato-N,C$^{2'}$)iridium(III)acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), (dipivaloylmethanato)bis(2,3,5-triphenylpyrazinato)iridium(III) (abbreviation: [Ir(tppr)$_2$(dpm)]), and (2,3,7,8,12,13,17,18-octaethyl-21H,23H-porphyrin)platinum(II) (abbreviation: PtOEP). In addition, rare-earth metal complexes, such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)), exhibit light emission from rare-earth metal ions (electron transition between different multiplicities), and thus can be used as phosphorescent compounds.

A high molecular compound can be used as the light-emitting substance. Specifically, a material for blue light emission, a material for green light emission, and a material for orange to red light emission are given. As examples of the material for blue light emission, the following are given: poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. As examples of the material for green light emission, the following are given: poly(p-phenylenevinylene) (abbreviation: PPV), poly[(9,9-dihexylfluorene-2,7-diyl)-alt-co-(benzo[2,1,3]thiadiazol-4,7-diyl)] (abbreviation: PFBT), poly[(9,9-dioctyl-2,7-divinylenfluorenylene)-alt-co-(2-methoxy-5-(2-ethylhexyloxy)-1,4-phenylene)], and the like. As examples of the material for orange to red light emission, the following are given: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-d]hexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

Note that the light-emitting layer 113 may have a structure in which the above light-emitting substance (a guest material) is dispersed in another substance (a host material). As a host material, a variety of kinds of materials can be used, and it is preferable to use a substance which has a higher lowest unoccupied molecular orbital level (LUMO level) than the light-emitting material and has a lower highest occupied molecular orbital level (HOMO level) than the light-emitting material.

The carbazole compound of one embodiment of the present invention has a wide band gap (the S1 level is high), and thus can also be used favorably as a host material of the light-emitting layer 113.

In the case where a light-emitting substance is a phosphorescent compound, a substance which has a higher T1 level than the light-emitting substance is preferably used as a host material of the light-emitting substance.

The carbazole compound of one embodiment of the present invention has a high T1 level, and thus can also be used favorably as a host material of a phosphorescent substance.

As specific examples of the host material that can be used in addition to the above, the following are given: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), and bathocuproine (BCP); condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl) diphenanthrene (abbreviation: DPNS2), 3,3',3''-(benzene-1,3,5-triyl)tripyrene (abbreviation: TPB3), 9,10-diphenylanthracene (abbreviation: DPAnth), and 6,12- dimethoxy-5,11-diphenylchrysene; aromatic amine compounds such as N,N-dipheyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and the like.

Plural kinds of materials can be used as the host material. For example, in order to suppress crystallization, a substance such as rubrene which suppresses crystallization may be further added. In addition, NPB, Alq, or the like may be further added in order to efficiently transfer energy to the guest material.

When the structure in which a guest material is dispersed in a host material is employed, crystallization of the light-emitting layer 113 can be suppressed. In addition, concentration quenching due to high concentration of the guest material can be suppressed.

The electron-transport layer 114 is a layer that contains a substance having a high electron-transport property. As examples of the substance having a high electron-transport property, the following are given: metal complexes having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), and bis(2-methyl-8-quinolinolato)(4-phenylphenolato)aluminum (abbreviation: BAlq). A metal complex or the like including an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can also be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones that have an electron mobility of $10^{-6}$ cm$^2$/V·s or higher. Note that the electron-transport layer is not limited to a single layer and may be a stack of two or more layers containing any of the above substances.

The electron-injection layer 115 is a layer that contains a substance having a high electron-injection property. For the electron-injection layer 115, an alkali metal, an alkaline earth metal, or a compound thereof, such as lithium, cesium, calcium, lithium fluoride, cesium fluoride, calcium fluoride, or lithium oxide, can be used. A rare earth metal compound such as erbium fluoride can also be used. Any of the above substances for forming the electron-transport layer 114 can also be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, the above-described materials for forming the electron-transport layer 114 (e.g., a metal complex or a heteroaromatic compound) can be used for example. As the electron donor, a substance exhibiting an electron-donating property to the organic compound may be used. It is preferable to use an alkali metal, an alkaline-earth metal, or a rare earth metal, such as lithium, cesium, magnesium, calcium, erbium, or ytterbium. In addition, it is preferable to use an alkali metal oxide or an alkaline-earth metal oxide, such as lithium oxide, calcium oxide, or barium oxide. Lewis base such as magnesium oxide can also be used. An organic compound such as tetrathiafulvalene (abbreviation: TTF) can also be used.

Note that the hole-injection layer 111, the hole-transport layer 112, the light-emitting layer 113, the electron-transport layer 114, and the electron-injection layer 115 which are described above can each be formed by a method such as an evaporation method (e.g., a vacuum evaporation method), an ink-jet method, or a coating method.

When the second electrode 103 functions as a cathode, it can be formed using a metal, an alloy, an electrically-conductive compound, a mixture thereof, or the like having a low work function (preferably, a work function of 3.8 eV or less). Specifically, any of the following can be used: aluminum or silver; an element belonging to Group 1 or Group 2 of the periodic table, that is, an alkali metal such as lithium or cesium or an alkaline earth metal such as magnesium, calcium, or strontium; an alloy of the above metals (e.g., Mg—Ag or Al—Li); a rare earth metal such as europium or ytterbium; an alloy of the above metals; or the like.

Note that, in the case where in the EL layer 102, a layer formed in contact with the second electrode 103 is formed using a composite material in which the organic compound and the electron donor, which are described above, are mixed, a variety of conductive materials such as aluminum, silver, ITO, and indium tin oxide containing silicon or silicon oxide can be used regardless of the work function.

Note that the second electrode 103 can be formed by a vacuum evaporation method or a sputtering method. In the case of using a silver paste or the like, a coating method, an inkjet method, or the like can be used.

In the above light-emitting element, current flows due to a potential difference generated between the first electrode 101 and the second electrode 103 and holes and electrons recombine in the EL layer 102, whereby light is emitted. Then, this emitted light is extracted through one or both of the first electrode 101 and the second electrode 103. Therefore, one or both of the first electrode 101 and the second electrode 103 is/are an electrode having a property of transmitting visible light.

Note that the structure of the layer provided between the first electrode 101 and the second electrode 103 is not limited to the above structure. A structure other than the above may also be employed as long as a light-emitting region in which holes and electrons recombine is provided in a portion away from the first electrode 101 and the second electrode 103 in order to prevent quenching due to proximity of the light-emitting region to a metal.

In other words, a stacked structure of the layer is not particularly limited, and a layer formed of a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer.

Figure 1B:
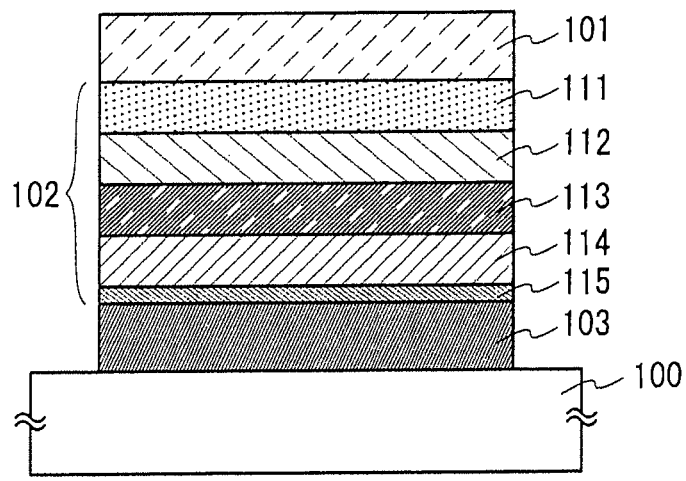

In a light-emitting element illustrated in FIG. 1B, the EL layer 102 is provided between the first electrode 101 and the second electrode 103 over the substrate 100. The EL layer 102 includes a hole-injection layer 111, a hole-transport layer 112, the light-emitting layer 113, an electron-transport layer 114, and an electron-injection layer 115. The light-emitting element in FIG. 1B includes: the second electrode 103 serving as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 serving as an anode over the hole-injection layer 111.

Further, the HOMO level of the carbazole compound of one embodiment of the present invention is deep and the LUMO level thereof is shallow. In addition, the carbazole compound has a wide band gap. For these reasons, the carbazole compound can be favorably used as a carrier-transport layer adjacent to a light-emitting layer (e.g., a hole-transport layer, an electron-transport layer, or a hole-blocking layer). The use of the carbazole compound allows an element with high efficiency to be obtained.

A specific manufacturing method of a light-emitting element will be described below.

The light-emitting element of this embodiment has a structure in which an EL layer is interposed between a pair of electrodes. The electrode (the first electrode or the second electrode) and the EL layer may be formed by a wet process such as a droplet discharging method (an ink-jet method), a spin coating method, or a printing method, or by a dry process such as a vacuum evaporation method, a CVD method, or a sputtering method. The use of a wet process enables formation at atmospheric pressure with a simple device and by a simple process, which gives effects of simplifying the process and improving productivity. In contrast, a dry process does not need dissolution of a material and enables use of a material that has low solubility in a solution, which expands the range of material choices.

All the thin films included in the light-emitting element may be formed by a wet method. In this case, the light-emitting element can be manufactured with only facilities needed for a wet process. Alternatively, formation of the stacked layers up to formation of the light-emitting layer may be performed by a wet process whereas the functional layer, the first electrode, and the like which are stacked over the light-emitting layer may be formed by a dry process. Further alternatively, the second electrode and the functional layer may be formed by a dry process before the formation of the light-emitting layer whereas the light-emitting layer, the functional layer stacked thereover, and the first electrode may be formed by a wet process. Needless to say, this embodiment is not limited to this, and the light-emitting element can be formed by appropriate selection from a wet method and a dry method depending on a material to be used, film thickness that is necessary, and the interface state.

As described above, the light-emitting element can be manufactured using the carbazole compound of one embodiment of the present invention. According to one embodiment of the present invention, a light-emitting element with high emission efficiency can be obtained. In addition, a light-emitting element with long lifetime can be obtained.

Further, a light-emitting device (such as an image display device) using the light-emitting element of one embodiment of the present invention, which is manufactured as described above, can have low power consumption.

Note that by use of a light-emitting element described in this embodiment, a passive matrix light-emitting device or an active matrix light-emitting device in which driving of the light-emitting element is controlled by a thin film transistor (TFT) can be manufactured.

This embodiment can be implemented in appropriate combination with any of the other embodiments.

(Embodiment 3)

In this embodiment, a mode of a light-emitting element having a structure in which a plurality of light-emitting units are stacked (hereinafter, referred to as a stacked-type element) will be described with reference to FIGS. 2A and 2B. This light-emitting element is a light-emitting element including a plurality of light-emitting units between a first electrode and a second electrode.

Figure 2A:
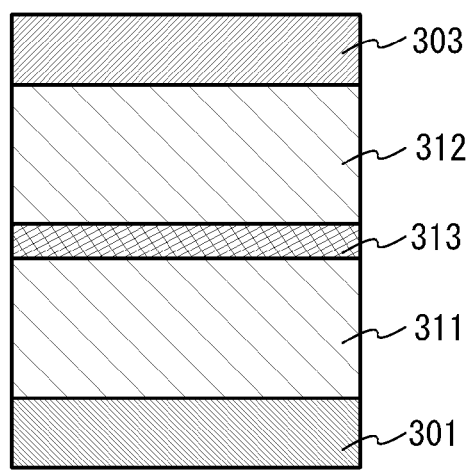
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. Further, the first light-emitting unit 311 and the second light-emitting unit 312 may have the same structure or different structures. The first light-emitting unit 311 and the second light-emitting unit 312 may have the same structure as in Embodiment 2, or either of the units may have a structure different from that in Embodiment 2.

Further, a charge generation layer 313 is provided between the first light-emitting unit 311 and the second light-emitting unit 312. The charge generation layer 313 functions so that electrons are injected into one light-emitting unit and holes are injected into the other light-emitting unit by application of voltage between the first electrode 301 and the second electrode 303. In this embodiment, when voltage is applied to the first electrode 301 so that the potential thereof is higher than that of the second electrode 303, the charge generation layer 313 injects electrons into the first light-emitting unit 311 and injects holes into the second light-emitting unit 312.

Note that the charge generation layer 313 preferably has a property of transmitting visible light in terms of light extraction efficiency. Further, the charge generation layer 313 functions even when it has lower conductivity than the first electrode 301 or the second electrode 303.

The charge generation layer 313 may have either a structure including an organic compound having a high hole-transport property and an electron acceptor or a structure including an organic compound having a high electron-transport property and an electron donor. Alternatively, both of these structures may be stacked. Note that the electron acceptor and the electron donor are at least capable of donating and accepting electrons with the assistance of an electric field.

In the case of a structure in which an electron acceptor is added to an organic compound having a high hole-transport property, as the organic compound having a high hole-transport property, the carbazole compound of one embodiment of the present invention can be used. Besides, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/V·s or higher. Note that substances other than the above substances may be used as long as they are organic compounds whose hole-transport properties are higher than the electron-transport properties.

As examples of the electron acceptor, 7,7,8,8-tetracyano-2,3,5,6-tetrafluoroquinodimethane (abbreviation: $F_4$-TCNQ), chloranil, and the like can be given. In addition, a transition metal oxide can be given. Oxides of metals belonging to Groups 4 to 8 in the periodic table can be also given. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is particularly preferable because it is stable in the air, has a low hygroscopic property, and is easily handled.

In contrast, in the case of the structure in which an electron donor is added to an organic compound having a high electron-transport property, as the organic compound having a high electron-transport property, a metal complex having a quinoline skeleton or a benzoquinoline skeleton, such as Alq, Almq$_3$, BeBq$_2$, or BAlq, or the like can be used, for example. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances mentioned here are mainly ones that have an electron mobility of $10^{-6}$ cm$^2$/V·s or higher. Note that substances other than the above substances may be used as long as they are organic compounds whose electron-transport properties are higher than the hole-transport properties.

Further, as the electron donor, an alkali metal, an alkaline earth metal, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that formation of the charge generation layer 313 using any of the above materials makes it possible to suppress an increase in drive voltage caused when the EL layers are stacked.

Figure 2B:
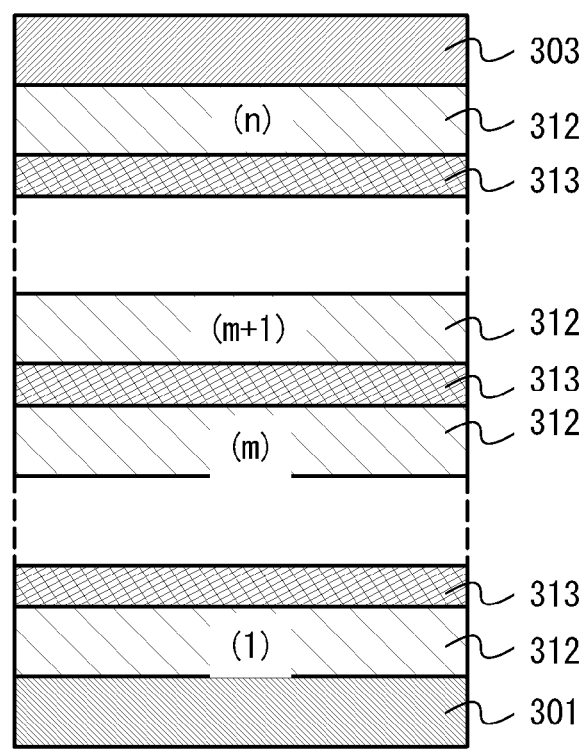

In this embodiment, the light-emitting element having two light-emitting units is described, and one embodiment of the present invention can be similarly applied to a light-emitting element having a stack of three or more light-emitting units as illustrated in FIG. 2B. A plurality of light-emitting units which are partitioned by a charge generation layer are arranged between a pair of electrodes, as in the light-emitting element according to this embodiment, whereby it is possible to provide a light-emitting element which has long lifetime and is able to emit light with luminance while current density is kept low.

Further, when emission colors of the light-emitting units are made different, light emission having a desired color can be obtained from the light-emitting element as a whole. For example, in the light-emitting element having two light-emitting units, when an emission color of the first light-emitting unit and an emission color of the second light-emitting unit are made to be complementary colors, it is possible to obtain a light-emitting element from which white light is emitted from the whole light-emitting element. Note that "complementary colors" refer to colors that can produce an achromatic color when mixed. In other words, when lights obtained from substances which emit complementary colors are mixed, white emission can be obtained. This can be applied to a light-emitting element having three or more light-emitting units. For example, when the first light-emitting unit emits red light, the second light-emitting unit emits green light, and the third light-emitting unit emits blue light, white light can be emitted from the whole light-emitting element.

Note that this embodiment can be freely combined with any of the other embodiments.

(Embodiment 4)

Figure 3A:
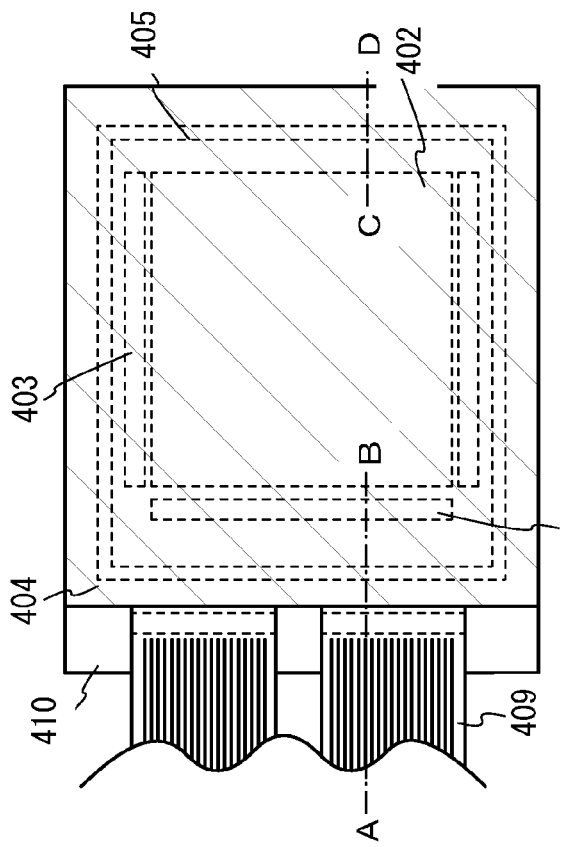
FIGS. 3A and 3B illustrate a light-emitting device of one embodiment of the present invention.
Figure 3B:
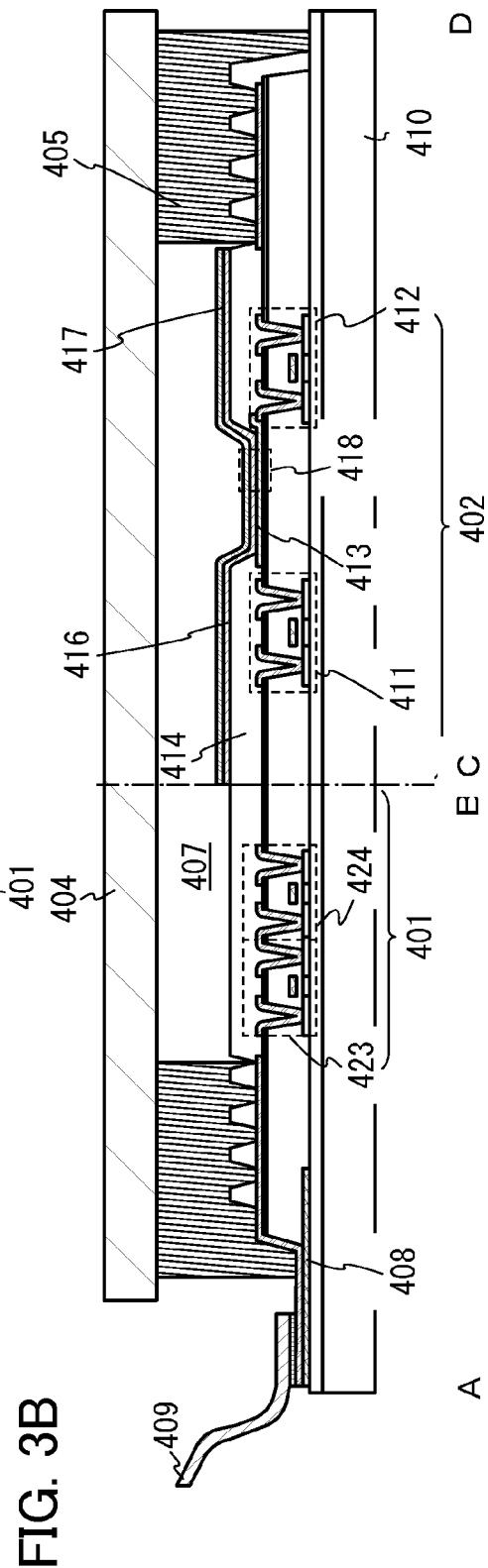

In this embodiment, a light-emitting device having a light-emitting element of one embodiment of the present invention will be described with reference to FIGS. 3A and 3B. FIG. 3A is a top view illustrating a light-emitting device. FIG. 3B is a cross-sectional view taken along lines A-B and C-D in FIG. 3A.

In FIG. 3A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Reference numeral 404 denotes a sealing substrate, reference numeral 405 denotes a sealant, and a portion enclosed by the sealant 405 is a space.

Note that a lead wiring 408 is a wiring for transmitting signals that are to be input to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, the cross-sectional structure will be described with reference to FIG. 3B. The driver circuit portion and the pixel portion are formed over an element substrate 410. Here, one pixel in the pixel portion 402 and the source side driver circuit 401 which is the driver circuit portion are illustrated.

Note that as the source side driver circuit 401, a CMOS circuit which is obtained by combining an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is formed using a positive photosensitive acrylic resin film.

In order to improve the coverage, the insulator 414 is provided such that either an upper end portion or a lower end portion of the insulator 414 has a curved surface with a curvature. For example, when positive type photosensitive acrylic is used as a material for the insulator 414, the insulator 414 preferably has a curved surface with a curvature radius (0.2 µm to 3 µm) only as the upper end. The insulator 414 can be formed using either a negative type which becomes insoluble in an etchant by light irradiation or a positive type which becomes soluble in an etchant by light irradiation.

An EL layer 416 and a second electrode 417 are formed over the first electrode 413. Here, a material having a high work function is preferably used as a material for forming the first electrode 413 functioning as the anode. For example, it is possible to use a single layer of an ITO film, an indium tin oxide film that includes silicon, an indium oxide film that contains 2 wt % to 20 wt % of zinc oxide, a titanium nitride film, a chromium film, a tungsten film, a Zn film, a Pt film, or the like, a stacked layer of a titanium nitride film and a film that mainly contains aluminum, a three-layer structure of a titanium nitride film, a film that mainly contains aluminum and a titanium nitride film, or the like. Note that, a stacked structure allows resistance of a wiring to be low and a good ohmic contact to be obtained.

The EL layer 416 is formed by any of a variety of methods such as an evaporation method using an evaporation mask, a droplet discharging method like an inkjet method, a printing method, and a spin coating method. The EL layer 416 contains the carbazole compound described in Embodiment 1. Further, another material included in the EL layer 416 may be a low molecular material, an oligomer, a dendrimer, a high molecular material, or the like.

It is preferable to use a material having a low work function (e.g., Al, Mg, Li, Ca, or an alloy or compound thereof such as Mg—Ag, Mg—In, or Al—Li) as a material used for the second electrode 417 which is formed over the EL layer 416 and functions as a cathode. In order that light generated in the EL layer 416 be transmitted through the second electrode 417, the second electrode 417 may be formed of a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide (ZnO)).

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 may be filled with filler such as an inert gas (e.g., nitrogen or argon) or with the sealant 405.

Note that an epoxy-based resin is preferably used as the sealant 405. It is preferable that the material do not transmit moisture or oxygen as much as possible. As a material used for the sealing substrate 404, a plastic substrate formed of FRP (fiberglass-reinforced plastics), PVF (polyvinyl fluoride), polyester, acrylic, or the like can be used other than a glass substrate or a quartz substrate.

As described above, the active matrix light-emitting device including the light-emitting element of one embodiment of the present invention can be obtained.

Figure 4A:
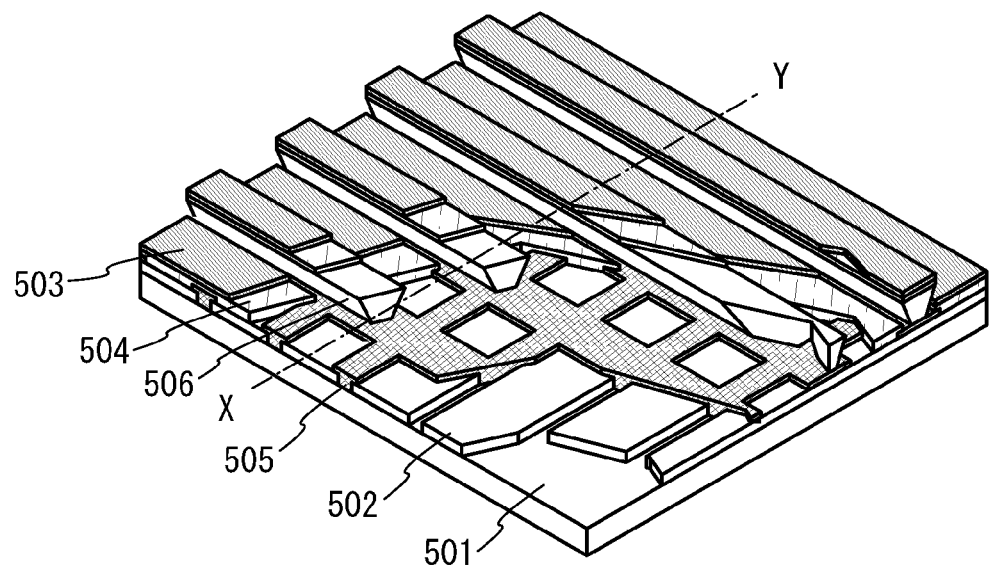
FIGS. 4A and 4B illustrate a light-emitting device of one embodiment of the present invention.
Figure 4B:
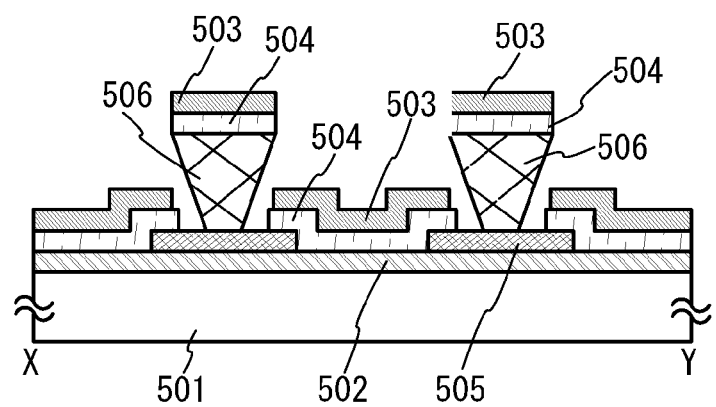

Further, a light-emitting element of one embodiment of the present invention can be used for a passive matrix light-emitting device as well as the above active matrix light-emitting device. FIGS. 4A and 4B illustrate a perspective view and a cross-sectional view of a passive matrix light-emitting device using a light-emitting element of one embodiment of the present invention. FIG. 4A is a perspective view of the light-emitting device. FIG. 4B is a cross-sectional view taken along a line X-Y in FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). With the partition layer 506 provided in such a way, a defect of a light-emitting element due to crosstalk or the like can be prevented.

Thus, the passive matrix light-emitting device including a light-emitting element of one embodiment of the present invention can be obtained.

The light-emitting devices described in this embodiment (the active matrix light-emitting device and the passive matrix light-emitting device) are both manufactured using the light-emitting element of one embodiment of the present invention, thereby having low power consumption.

Note that this embodiment can be freely combined with any of the other embodiments as appropriate.

(Embodiment 5)

In this embodiment, examples of a variety of electronic devices and lighting devices, which are completed using the light-emitting device of one embodiment of the present invention, will be described with reference FIGS. 5A to 5E and FIG. 6.

Examples of the electronic devices to which the light-emitting device is applied include television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 5A to 5E.

Figure 5A:
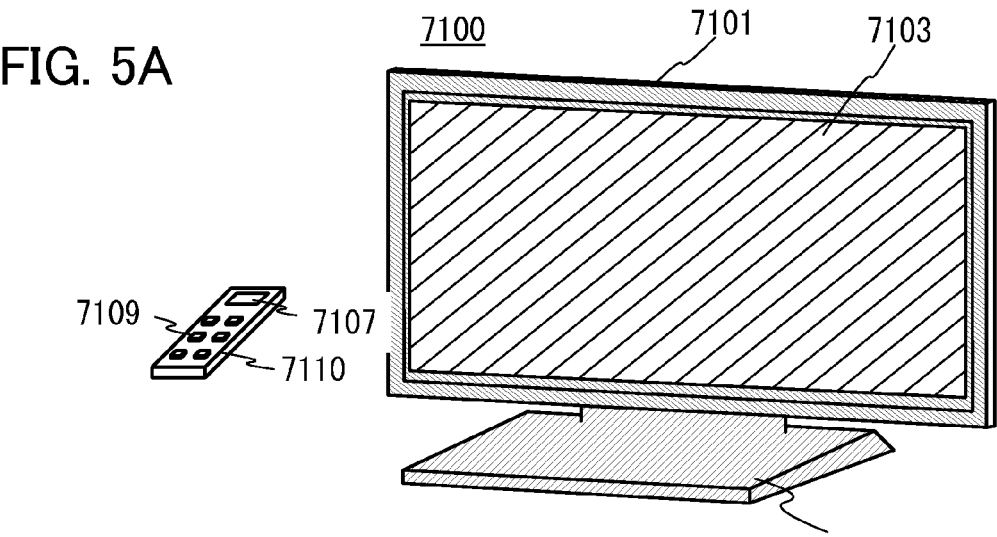
FIGS. 5A to 5E each illustrate an electronic device of one embodiment of the present invention.

FIG. 5A illustrates a television device 7100. In the television device 7100, a display portion 7103 is incorporated in a housing 7101. The display portion 7103 is capable of displaying images, and a light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. The remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
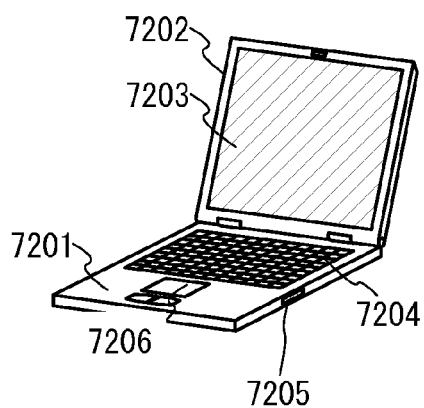

FIG. 5B illustrates a computer, which includes a main body 7201, a housing 7202, a display portion 7203, a keyboard 7204, an external connecting port 7205, a pointing device 7206, and the like. This computer is manufactured by using a light-emitting device for the display portion 7203.

Figure 5C:
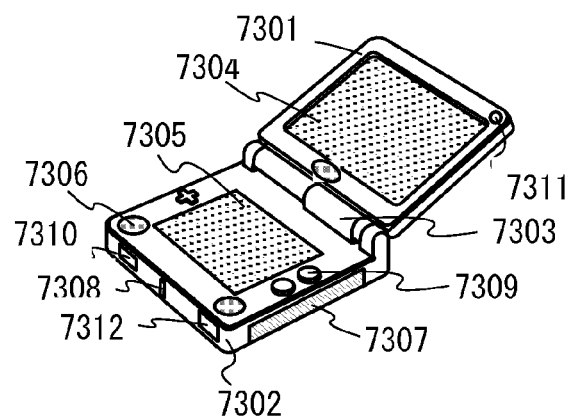

FIG. 5C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, smell, or infrared rays), or a microphone 7312), and the like. Needless to say, the structure of the portable game machine is not limited to the above as long as a light-emitting device can be used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
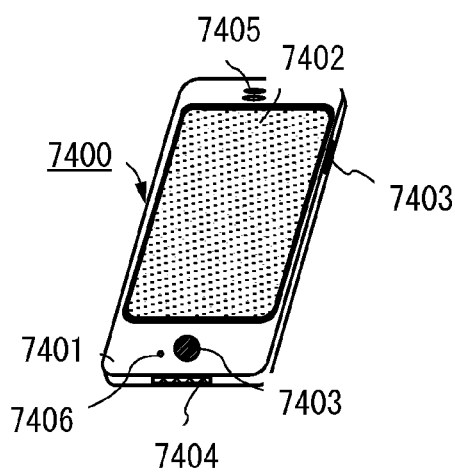

FIG. 5D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using a light-emitting device for the display portion 7402.

When the display portion 7402 of the mobile phone 7400 illustrated in FIG. 5D is touched with a finger or the like, data can be input into the cellular phone 7400. Users can make calls and compose e-mails by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on a screen can be input. In this case, a keyboard or number buttons are preferably displayed on almost the entire screen of the display portion 7402.

When a detection device including a sensor for detecting inclination, such as a gyroscope or an acceleration sensor, is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are switched by touch on the display portion 7402 or operation with the operation buttons 7403 of the housing 7401. Alternatively, the screen modes can be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Moreover, when a backlight or a sensing light source which emits near-infrared light is provided in the display portion, an image of finger veins, palm veins, or the like can be taken.

Figure 5E:
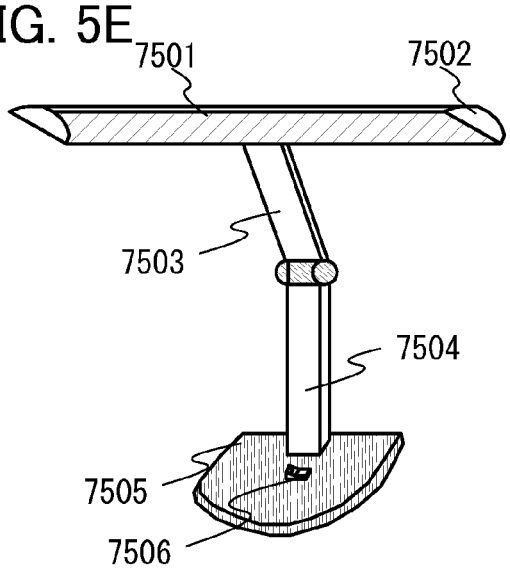

FIG. 5E illustrates a desk lamp, which includes a lighting portion 7501, a shade 7502, an adjustable arm 7503, a support 7504, a base 7505, and a power supply 7506. The desk lamp is manufactured using a light-emitting device for the lighting portion 7501. Note that a lamp includes a ceiling light, a wall light, and the like in its category.

Figure 6:
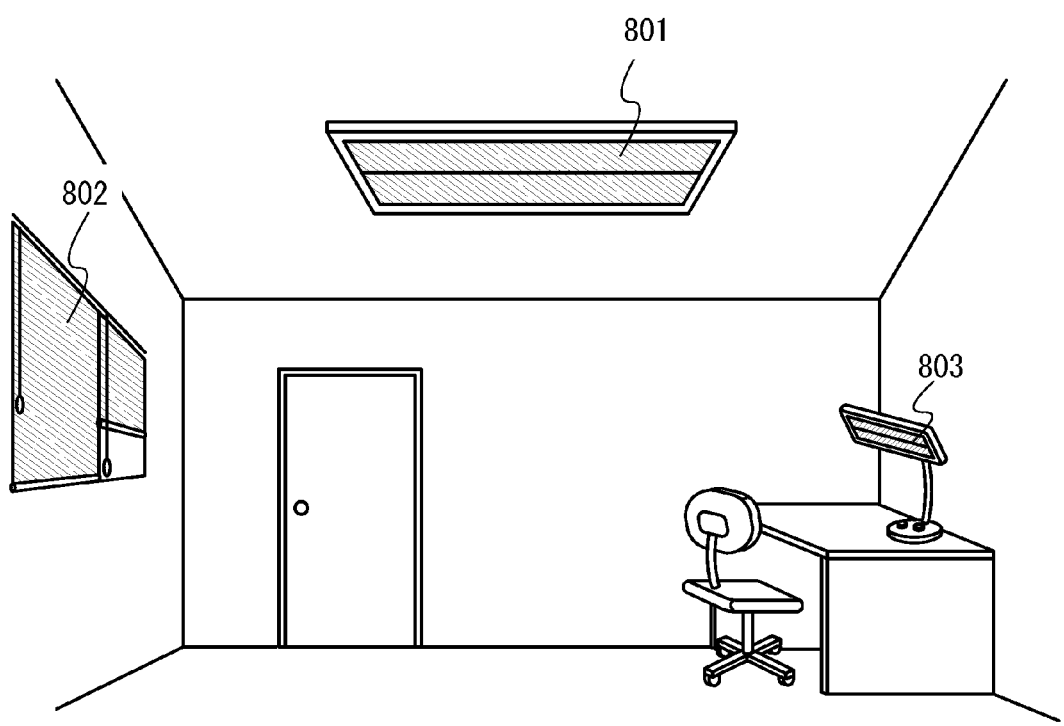
FIG. 6 illustrates a lighting device according to one embodiment of the present invention.

FIG. 6 illustrates an example in which a light-emitting device is used for an interior lighting device 801. Since the light-emitting device can have a larger area, it can be used as a lighting device having a large area. The light-emitting device can also be used as a roll-type lighting device 802. As illustrated in FIG. 6, a desk lamp 803 described with reference to FIG. 5E may also be used in a room provided with the interior lighting device 801.

In the above manner, electronic devices and lighting devices can be manufactured with the use of the light-emitting device. Application range of the light-emitting device is so wide that the light-emitting device can be used for electronic devices in a variety of fields.

Note that the structure described in this embodiment can be combined with any of the structures described in Embodiments 1 to 4 as appropriate.

EXAMPLE 1

In this example, Synthesis Example 1 and Synthesis Example 2 in each of which 3-[4-(1-naphthyl)-phenyl]-9-phenyl-9H-carbazole (abbreviation: PCPN) represented by Structural Formula (100) in Embodiment 1 is manufactured will be described.

[38]

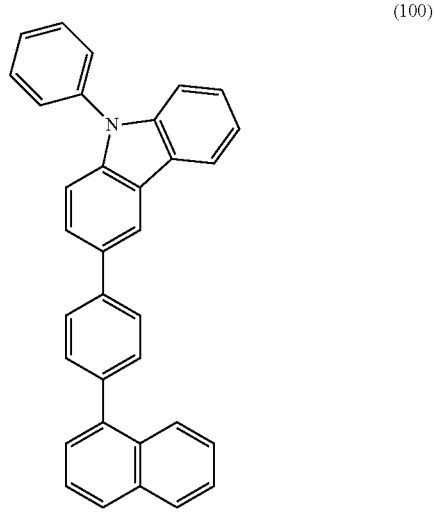

(100)

SYNTHESIS EXAMPLE 1

In a 200-mL three-neck flask, a mixture of 5.0 g (15.5 mmol) of 3-bromo-9-phenyl-9H-carbazole, 4.2 g (17.1 mmol) of 4-(1-naphthyl)-phenylboronic acid, 38.4 mg (0.2 mmol) of palladium(II) acetate, 104 mg (0.3 mmol) of tris(2-methylphenyl)phosphine, 50 mL of toluene, 5 mL of ethanol, and 30 mL of a potassium carbonate aqueous solution (2 mol/L) was deaerated while being stirred under reduced pressure, and then heated and stirred in a nitrogen atmosphere at 85° C. for 9 hours to be reacted.

After the reaction, 500 mL of toluene was added to the reaction mixture solution, and an organic layer of the mixture solution was filtrated through Florisil (Catalog No. 540-00135, produced by Wako Pure Chemical Industries, Ltd.), alumina (neutral, produced by Merck Ltd), and Celite (Catalog No. 531-16855, produced by Wako Pure Chemical Industries, Ltd.). The obtained filtrate was washed with water, and magnesium sulfate was added thereto so that moisture was adsorbed. This suspension was filtrated to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and methanol was added thereto. The mixture was irradiated with ultrasonic waves and then recrystallized to give 6.24 g of white powder that was an objective substance in a yield of 90%. The reaction scheme of Synthesis Example 1 above is shown in (F1-1).

[39]

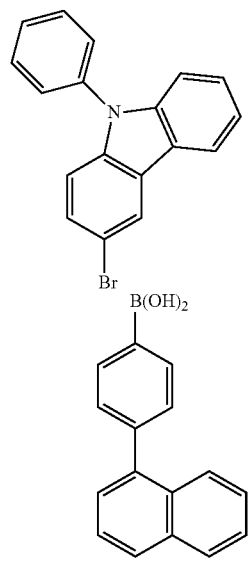

(F1-1)

The Rf values of the objective substance and 3-bromo-9-phenyl-9H-carbazole were respectively 0.42 and 0.58, which were obtained by silica gel thin layer chromatography (TLC) (with a developing solvent of ethyl acetate and hexane in a 1:10 ratio).

The compound obtained in Synthesis Example 1 was examined by a nuclear magnetic resonance (NMR) method. The measurement data are shown below.

$^1$H NMR (CDCl$_3$, 300 MHz): δ (ppm)=7.30-7.35 (m, 1H), 7.44-7.67 (m, 14H), 7.76 (dd, J=8.7 Hz, 1.8 Hz, 1H), 7.84-7.95 (m, 4H), 8.04 (d, J=7.8, 1H), 8.23 (d, J=7.8, 1H), 8.46 (d, J=1.5, 1H).

Figure 7A:
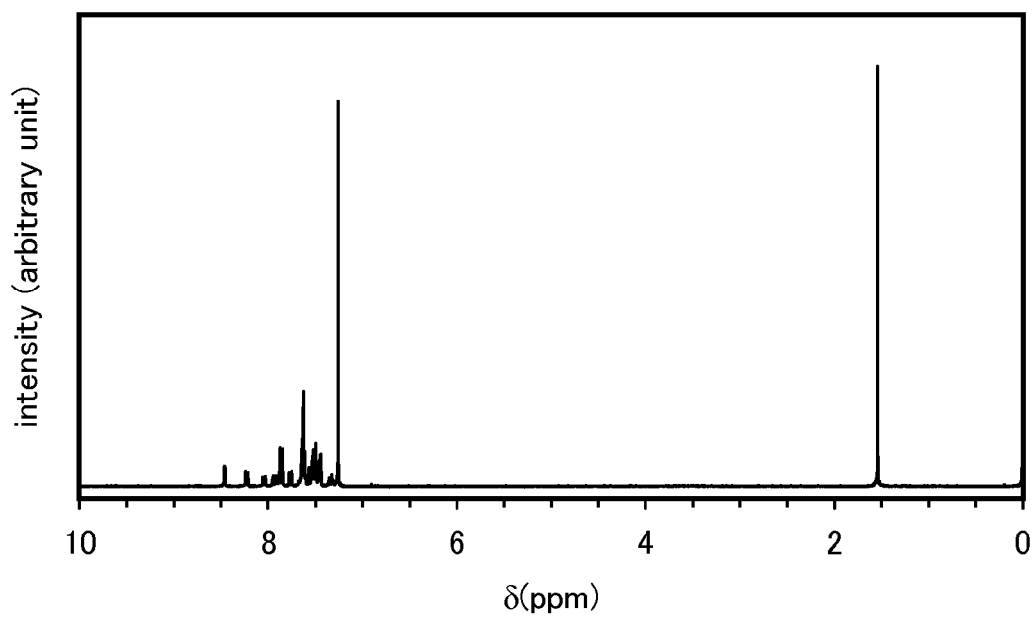
FIGS. 7A and 7B are NMR charts of PCPN.
Figure 7B:
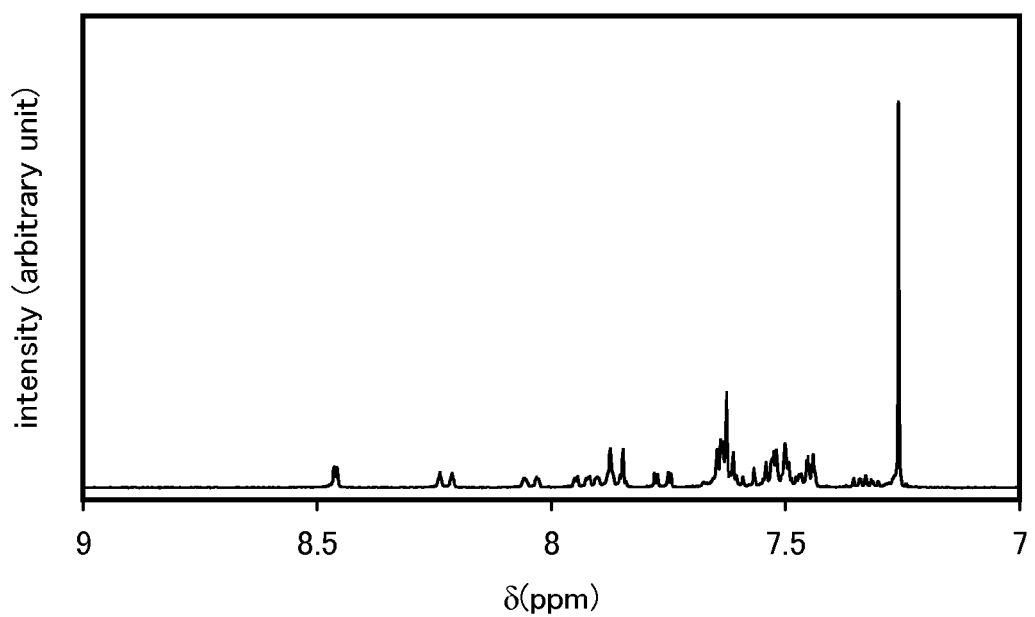

FIGS. 7A and 7B are $^1$H NMR charts. Note that FIG. 7B is a chart showing an enlarged part of FIG. 7A in the range of 7.0 ppm to 9.0 ppm. The measurement results confirmed that 3-[4-(1-naphthyl)-phenyl]-9-phenyl-9H-carbazole (abbreviation: PCPN) that was the objective substance was able to be obtained.

SYNTHESIS EXAMPLE 2

In this synthesis example, a synthesis example of PCPN, which is different from Synthesis Example 1, will be described.

Step 1: Synthesis Method of 3-(4-bromophenyl)-9-phenyl-9H-carbazole

In a 300-mL three-neck flask, a mixture of 14 g (50 mmol) of 4-bromoiodobenzene, 14 g (50 mmol) of 9-phenyl-9H-carbazol-3-boronic acid, 110 mg (0.5 mmol) of palladium(II) acetate, 300 mg (1.0 mmol) of tri(o-tolyl)phosphine, 50 mL of toluene, 10 mL of ethanol, and 25 mL of a potassium carbonate aqueous solution (2 mol/L) was deaerated while being stirred under reduced pressure, and then heated and stirred in a nitrogen atmosphere at 80° C. for 6 hours to be reacted.

After the reaction, 200 mL of toluene was added to the reaction mixture solution, and the resulting suspension was filtrated through Florisil and Celite. The obtained filtrate was washed with water, and magnesium sulfate was added thereto to adsorb moisture. This suspension was filtrated to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and hexane was added thereto. The mixture was irradiated with ultrasonic waves and then recrystallized to give 15 g of white powder that was an objective substance in a yield of 75%. The reaction scheme of Step 1 above is shown in (F1-2).

[40]

(F1-2)

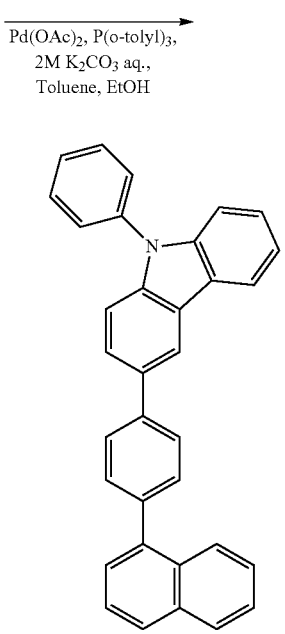

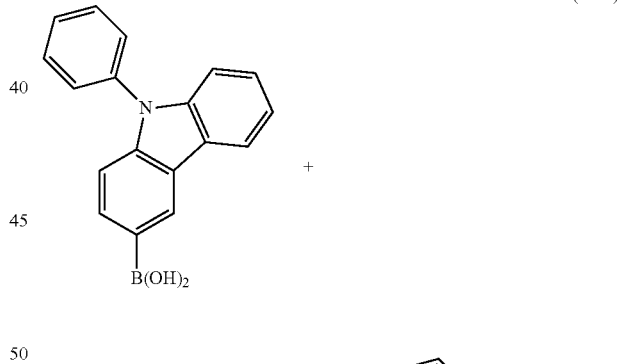

The Rf values of the objective substance and 4-bromoiodobenzene were respectively 0.32 and 0.74, which were obtained by silica gel thin layer chromatography (TLC) (with a developing solvent containing ethyl acetate and hexane in a 1:10 ratio).

The compound obtained in Step 1 was examined by a nuclear magnetic resonance (NMR) method. The measurement data are shown below.

$^1$H NMR (CDCl$_3$, 300 MHz): δ (ppm)=7.24-7.32 (m, 1H), 7.40-7.64 (m, 13H), 8.17 (d, J=7.2 Hz, 1H), 8.29 (s, 1H).

Figure 8A:
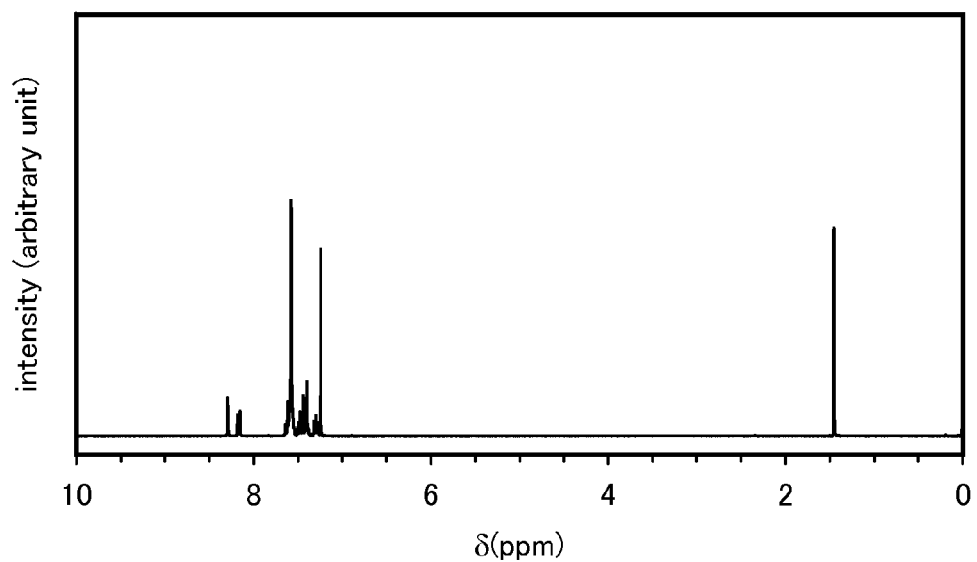
FIGS. 8A and 8B are NMR charts of 3-(4-bromophenyl)-9-phenyl-9H-carbazole.
Figure 8B:
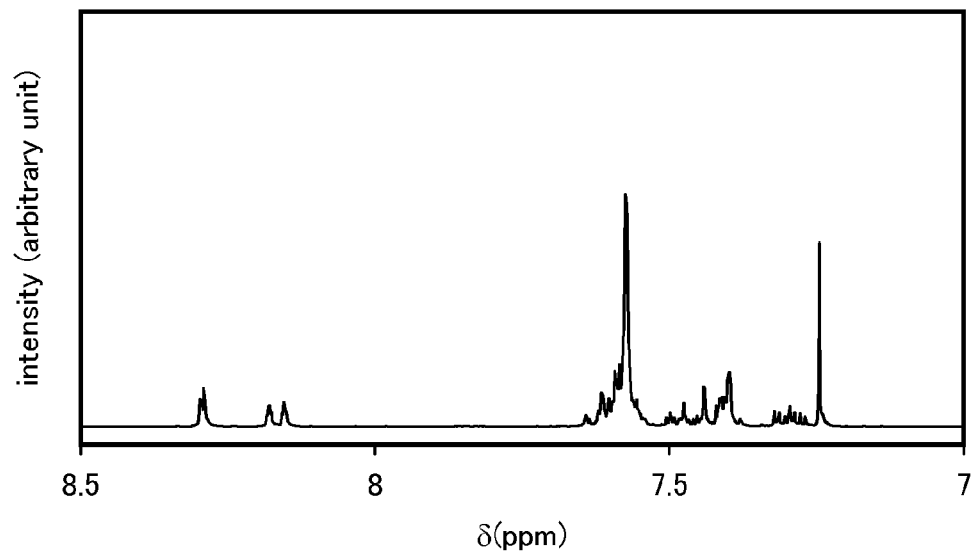

FIGS. 8A and 8B are $^1$H NMR charts. Note that FIG. 8B is a chart showing an enlarged part of FIG. 8A in the range of 7.0 ppm to 8.5 ppm. The measurement results confirmed that 3-(4-bromophenyl)-9-phenyl-9H-carbazole that was the objective substance was able to be obtained.

Figure 9:
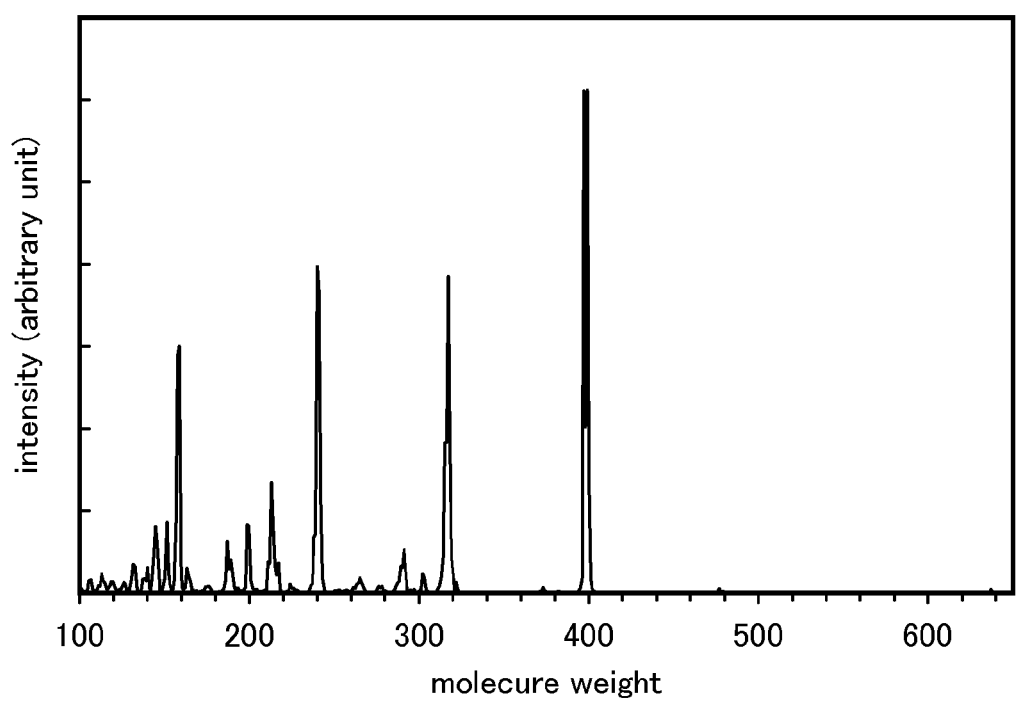
FIG. 9 is an MS chart of 3-(4-bromophenyl)-9-phenyl-9H-carbazole.

The molecular weight of the above compound was measured with a GC-MS detector (ITQ1100 ion trap GC/MS system, produced by Thermo Fisher Scientific K.K.). FIG. 9 is a chart thereof. The measurement detected a main peak at a molecular weight of 397.13 (the mode was EI+). The measurement results confirmed that 3-(4-bromophenyl)-9-phenyl-9H-carbazole that was the objective substance was able to be obtained.

Step 2: Synthesis Method of 3-[4-(1-naphthyl)-phenyl]-9-phenyl-9H-carbazole (abbreviation: PCPN)

In a 50-mL three-neck flask, a mixture of 2.4 g (5.0 mmol) of 3-(4-bromophenyl)-9-phenyl-9H-carbazole, 1.1 g (5.5 mmol) of naphthalene-1-boronic acid, 20 mg (0.1 mmol) of palladium(II) acetate, 36 mg (0.1 mmol) of tri(o-tolyl)phosphine, 10 mL of toluene, 1.5 mL of ethanol, and 5 mL of a potassium carbonate aqueous solution (2 mol/L) was deaerated while being stirred under reduced pressure and was heated and stirred in a nitrogen atmosphere at 90° C. for 14 hours to be reacted.

After the reaction, 200 mL of toluene was added to the reaction mixture solution, and an organic layer of the mixture solution was filtrated through Florisil, alumina, and Celite. The obtained filtrate was washed with water, and magnesium sulfate was added thereto so that moisture was adsorbed. This suspension was filtrated to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and acetone and methanol were added thereto. The mixture was irradiated with ultrasonic waves and then recrystallized to give 2.3 g of white powder that was an objective substance in a yield of 86%. The reaction scheme of Step 2 is shown in (F1-3).

[41]

(F1-3)

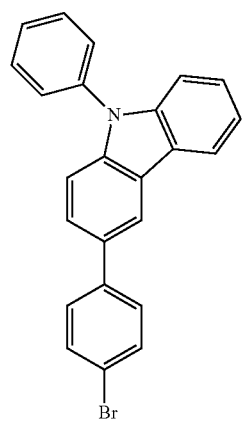

+

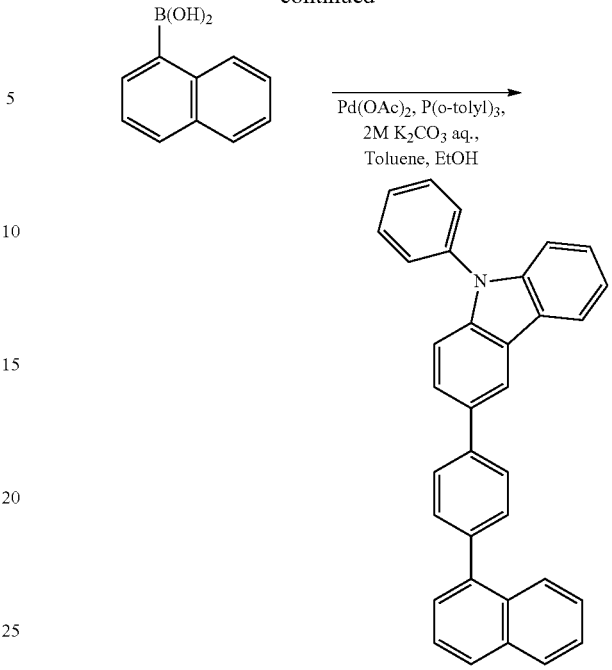

The Rf values of the objective substance and 3-(4-bromophenyl)-9-phenyl-9H-carbazole were respectively 0.57 and 0.65, which were obtained by silica gel thin layer chromatography (TLC) (with a developing solvent containing ethyl acetate and hexane in a 1:10 ratio).

Further, the nuclear magnetic resonance (NMR) confirmed that the compound obtained in Synthesis Example 2 was 3-[4-(1-naphthyl)-phenyl]-9-phenyl-9H-carbazole (abbreviation: PCPN) that was an objective substance.

Figure 10A:
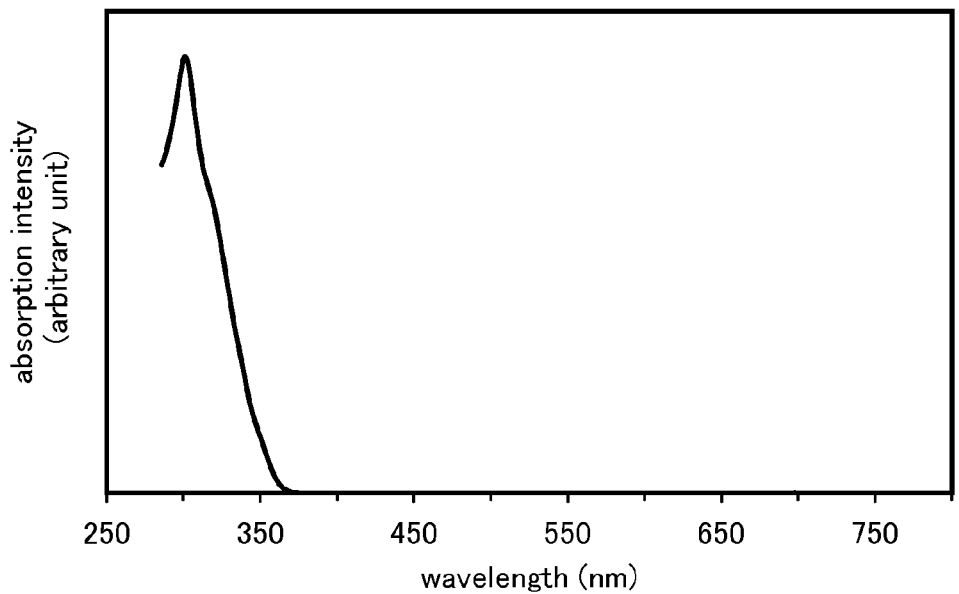
FIGS. 10A and 10B show an absorption spectrum and an emission spectrum of PCPN in a toluene solution of PCPN.
Figure 10B:
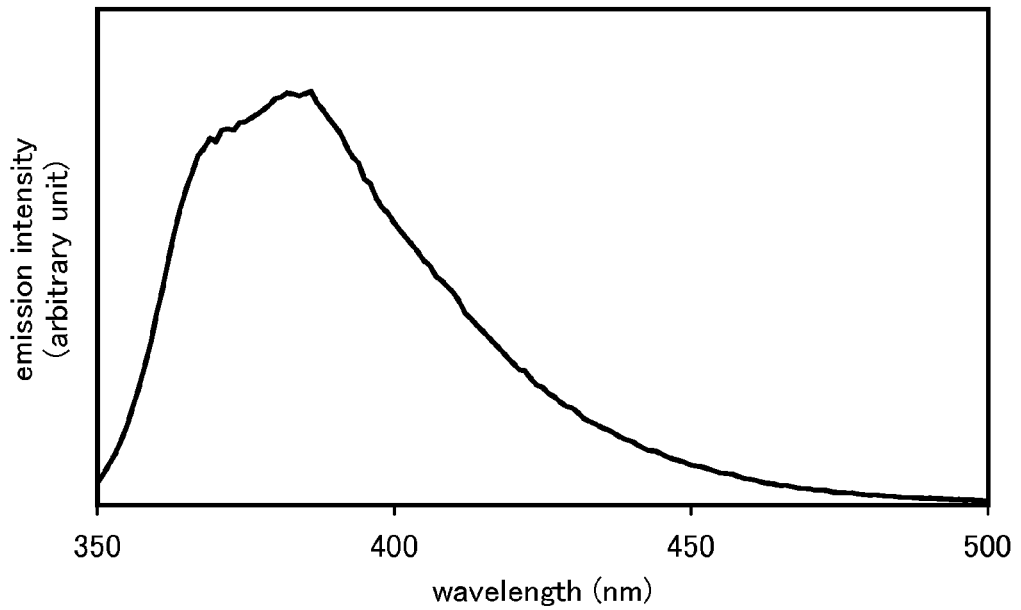
Figure 11A:
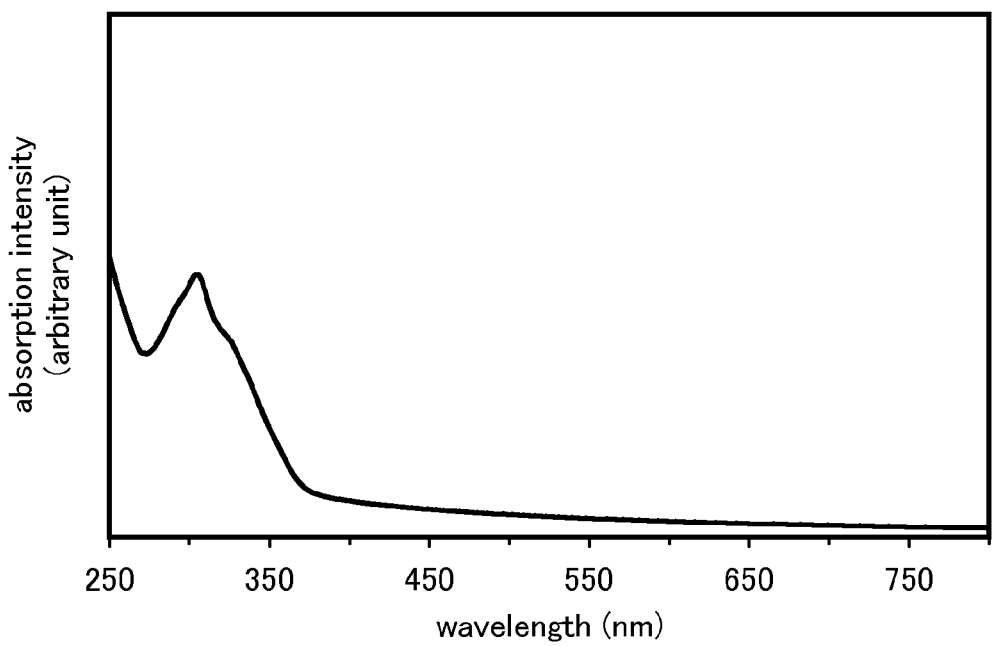
FIGS. 11A and 11B show an absorption spectrum and an emission spectrum of a thin film of PCPN.
Figure 11B:
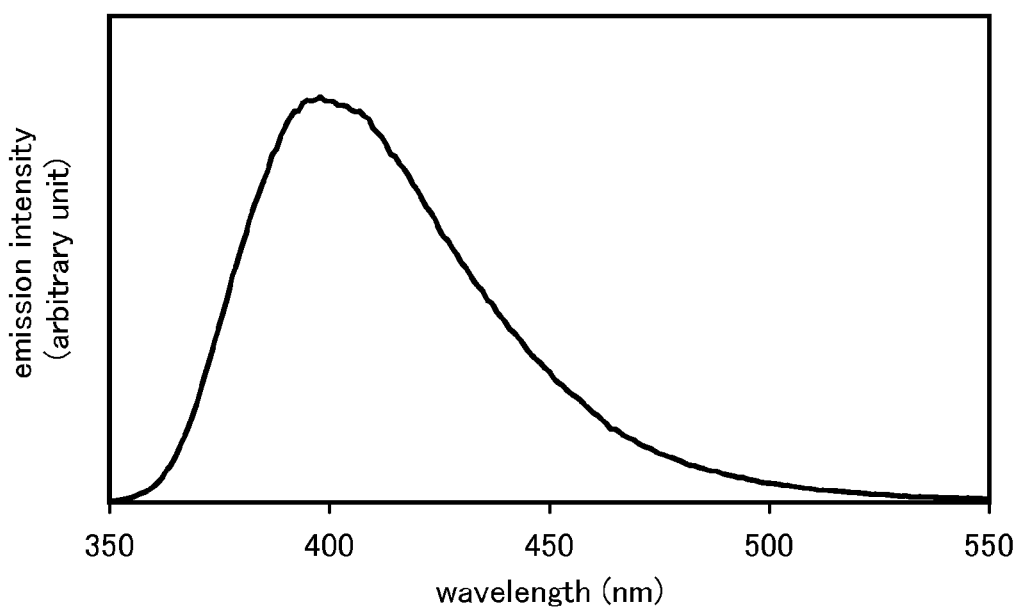

FIG. 10A shows an absorption spectrum of PCPN in a toluene solution of PCPN, and FIG. 10B shows an emission spectrum thereof. FIG. 11A shows an absorption spectrum of a thin film of PCPN, and FIG. 11B shows an emission spectrum thereof. The absorption spectrum was measured with an ultraviolet-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 10A show the absorption spectrum of PCPN in the solution of PCPN which was obtained by subtracting the absorption spectra of the quartz cell and toluene put therein. FIG. 11A shows the absorption spectrum of the thin film which was obtained by subtracting the absorption spectrum of the quartz substrate. In FIGS. 10A and 10B and FIGS. 11A and 11B, the horizontal axis represents wavelength (nm) and the vertical axis represents intensity (arbitrary unit). In the case of the toluene solution, the absorption peak was observed at around 300 nm, and the maximum emission wavelength was 384 nm (excitation wavelength: 320 nm). In the case of the thin film, the absorption peak was observed at around 322 nm, and the maximum emission wavelength was 398 nm (excitation wavelength: 324 nm).

The absorption spectrum shows that PCPN described in this example is a material having weak absorption of light in the visible region. In addition, the emission spectrum shows that PCPN exhibits blue-violet emission.

EXAMPLE 2

In this example, an example in which 3-[4-(9-phenanthryl)-phenyl]-9-phenyl-9H-carbazole (abbreviation: PCPPn) represented by Structural Formula (102) in Embodiment 1 is manufactured will be described.

[42]

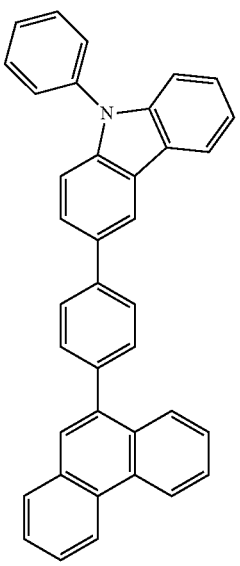

(102)

Step 1: Synthesis Method of 4-(9-phenyl-9H-carbazol-3-yl)phenylboronic acid

Into a 300-mL three-neck flask was put 8.0 g (20 mmol) of the 3-(4-bromophenyl)-9-phenyl-9H-carbazole obtained in Reaction Scheme (F1-2), the atmosphere in the flask was replaced with nitrogen, 100 mL of dehydrated tetrahydrofuran (abbreviation: THF) was then added to the flask, and the temperature was lowered to −78° C. To this mixture, 3.4 mL (30 mmol) of trimethyl borate was added, and the mixture with the trimethyl borate added was stirred at −78° C. for 2 hours and at room temperature for 18 hours. After the reaction, 1M diluted hydrochloric acid was added to this reaction solution until the solution became acid, and the solution with the diluted hydrochloric acid added was stirred for 7 hours. This solution was subjected to ethyl acetate extraction, and an organic layer obtained was washed with a saturated saline. After the washing, magnesium sulfate was added to the organic layer to remove moisture. This suspension was filtrated, and the obtained filtrate was concentrated, and hexane was added thereto. The mixture was irradiated with ultrasonic waves and then recrystallized to give 6.4 g of white powder that was an objective substance in a yield of 88%. The reaction scheme of Step 1 is shown (F2-1).

[43]

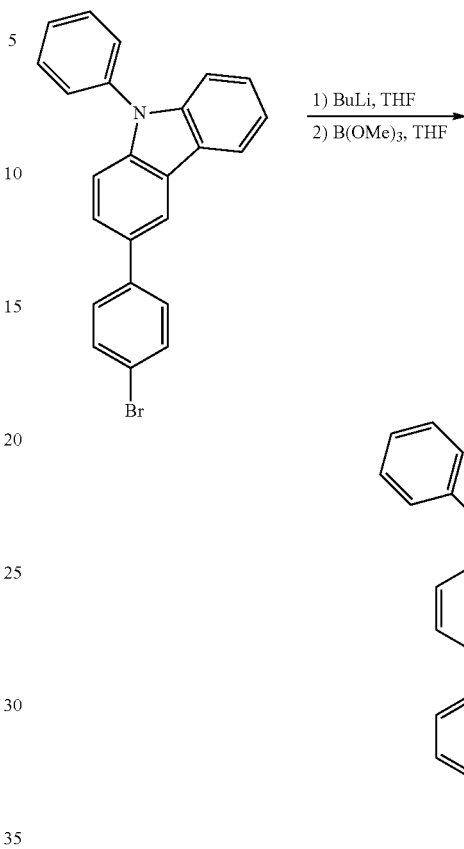

(F2-1)

The Rf values of the objective substance and 3-(4-bromophenyl)-9-phenyl-9H-carbazole were respectively 0 (origin) and 0.53, which were obtained by silica gel thin layer chromatography (TLC) (with a developing solvent containing ethyl acetate and hexane in a 1:10 ratio). In addition, the Rf values of the objective substance and 3-(4-bromophenyl)-9-phenyl-9H-carbazole were respectively 0.72 and 0.93, which were obtained by silica gel thin layer chromatography (TLC) using ethyl acetate as the developing solvent.

Step 2: Synthesis Method of 3-[4-(9-phenanthryl)-phenyl]-9-phenyl-9H-carbazole (abbreviation: PCPPn)

In a 200-mL three-neck flask, a mixture of 1.5 g (5.0 mmol) of 9-phenyl-9H-carbazole-3-yl-phenyl-4-boronic acid, 3.2 g (11 mmol) of 9-bromophenanthrene, 11 mg (0.1 mmol) of palladium(II) acetate, 30 mg (0.1 mmol) of tri(o-tolyl)phosphine, 30 mL of toluene, 3 mL of ethanol, and 5 mL of a potassium carbonate aqueous solution (2 mol/L) was deaerated while being stirred under reduced pressure, and then heated and stirred in a nitrogen atmosphere at 90° C. for 6 hours to be reacted.

After the reaction, 200 mL of toluene was added to the reaction mixture solution, and an organic layer of the mixture solution was filtrated through Florisil, alumina, and Celite. The obtained filtrate was washed with water, and magnesium sulfate was added thereto so that moisture was adsorbed. This suspension was filtrated to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and acetone and methanol were added thereto. The mixture was irradiated with ultrasonic waves and then recrystallized to give 2.2 g of white powder that was an objective substance in a yield of 75%. The reaction scheme of Step 2 is shown in (F2-2).

[44]

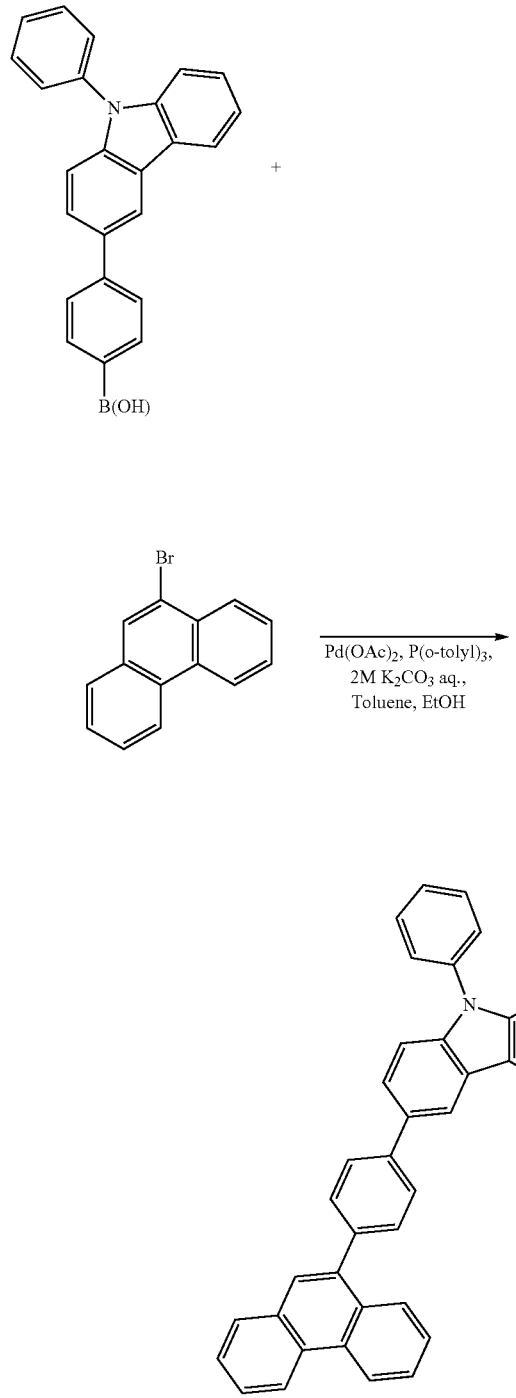

(F2-2)

The Rf values of the objective substance and 9-bromophenanthrene were respectively 0.33 and 0.70, which were obtained by silica gel thin layer chromatography (TLC) (with a developing solvent containing ethyl acetate and hexane in a 1:10 ratio).

The obtained compound was examined by a nuclear magnetic resonance (NMR) method. The measurement data are shown below.

$^1$H NMR (CDCl$_3$, 300 MHz): δ (ppm)=7.30-7.35 (m, 1H), 7.43-7.78 (m, 16H), 7.86-7.93 (m, 3H), 8.01 (dd, J=0.9 Hz, 7.8 Hz, 1H), 8.23 (d, J=7.8 Hz, 1H), 8.47 (d, J=1.5 Hz, 1H), 8.74 (d, J=8.1 Hz, 1H), 8.80 (d, J=7.8 Hz, 1H).

Figure 12A:
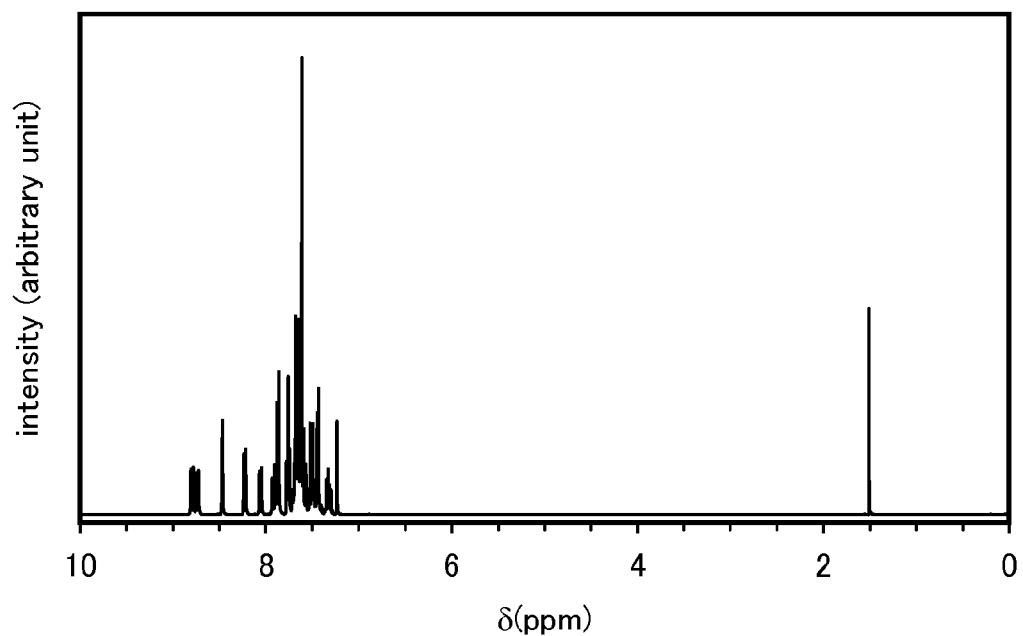
FIGS. 12A and 12B are NMR charts of PCPPn.
Figure 12B:
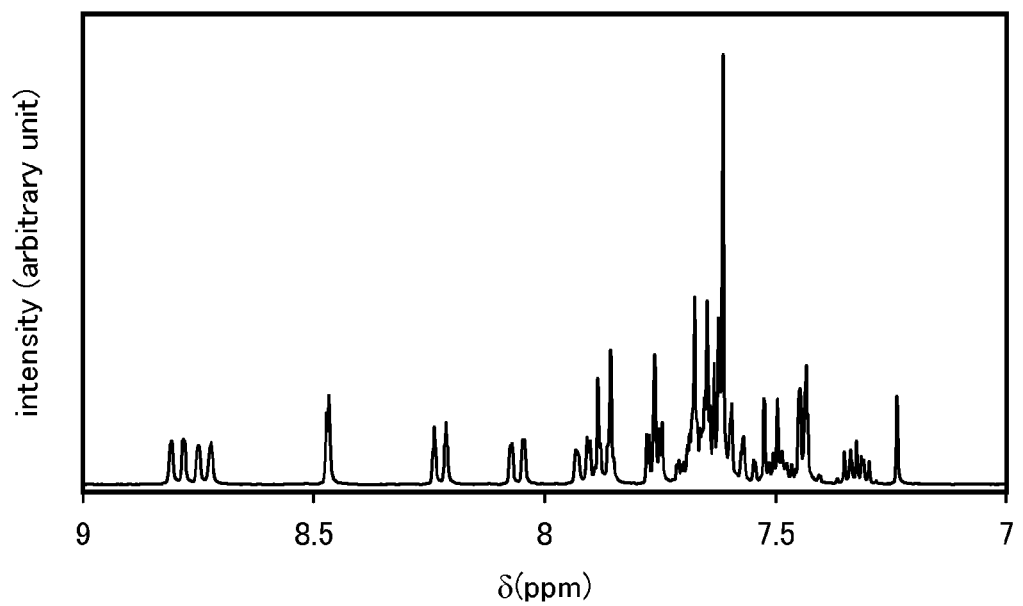

FIGS. 12A and 12B are $^1$H NMR charts. Note that FIG. 12B is a chart showing an enlarged part of FIG. 12A in the range of 7.0 ppm to 9.0 ppm. The measurement results confirmed that PCPPn (abbreviation) that was the objective substance was able to be obtained.

Figure 13A:
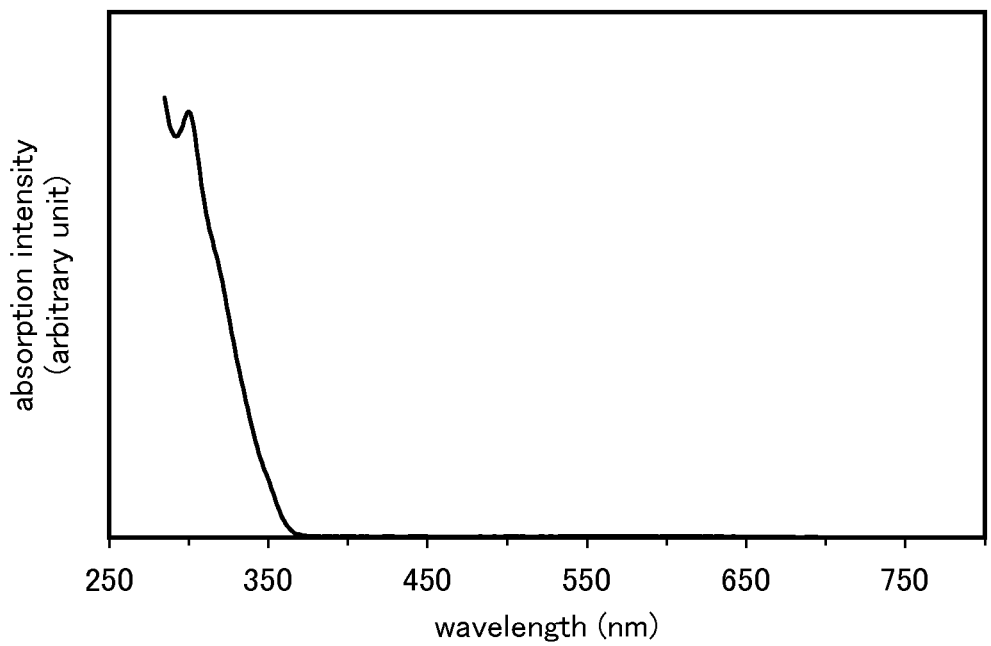
FIGS. 13A and 13B show an absorption spectrum and an emission spectrum of PCPPn in a toluene solution of PCPPn.
Figure 13B:
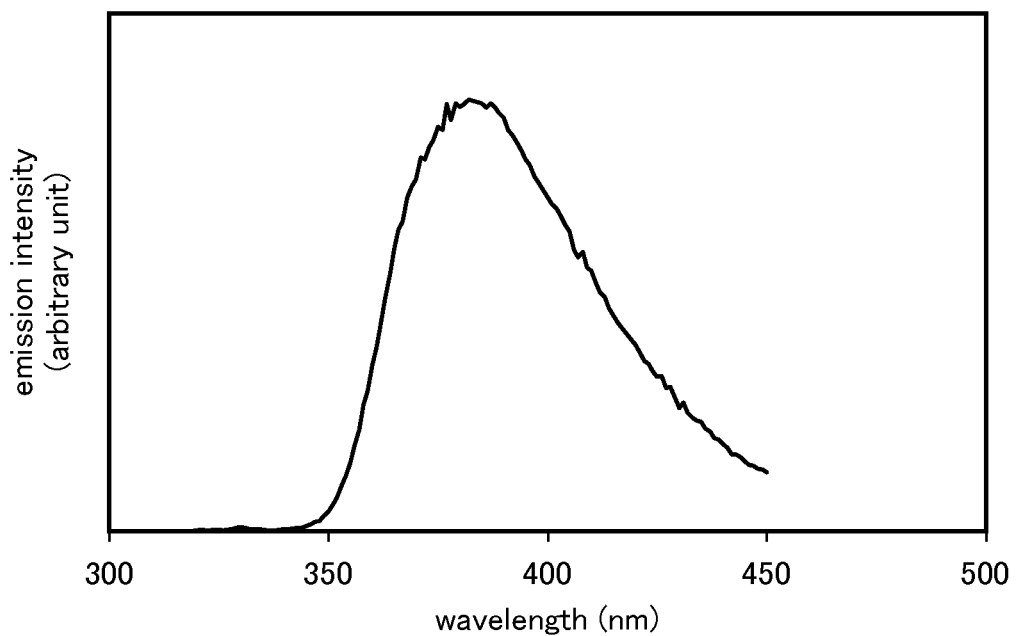
Figure 14A:
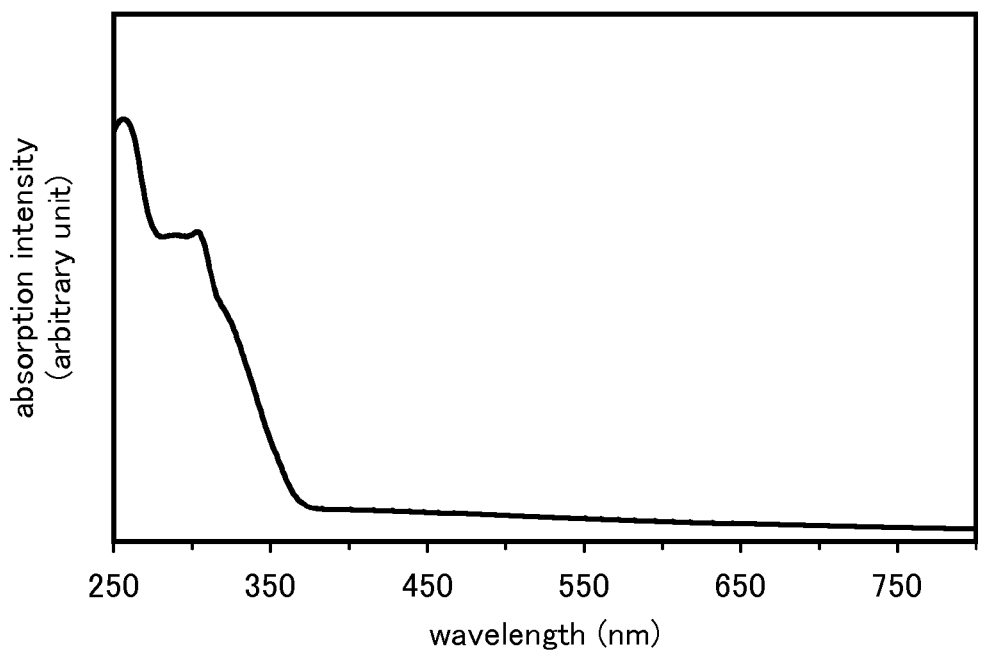
FIGS. 14A and 14B show an absorption spectrum and an emission spectrum of a thin film of PCPPn.
Figure 14B:
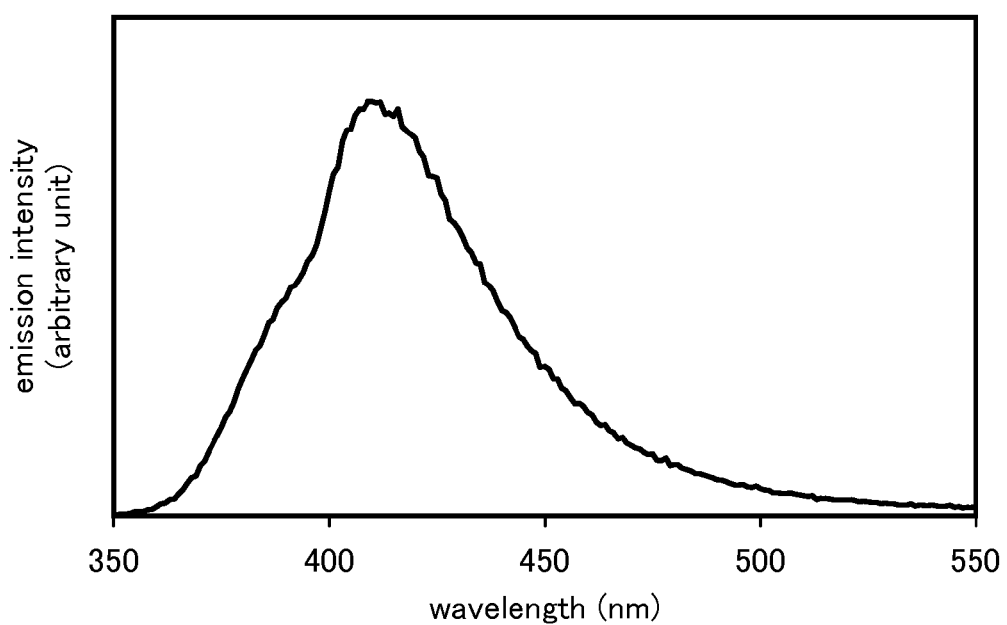

FIG. 13A shows an absorption spectrum of PCPPn in a toluene solution of PCPPn, and FIG. 13B shows an emission spectrum thereof. FIG. 14A shows an absorption spectrum of a thin film of PCPPn, and FIG. 14A shows an emission spectrum thereof. The absorption spectrum was measured with an ultraviolet-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 13A show the absorption spectrum of PCPPn in the solution of PCPPn which was obtained by subtracting the absorption spectra of the quartz cell and toluene put therein, and FIG. 14A shows the absorption spectrum of the thin film which was obtained by subtracting the absorption spectrum of the quartz substrate. In FIGS. 13A and 13B and FIGS. 14A and 14B, the horizontal axis represents wavelength (nm) and the vertical axis represents intensity (arbitrary unit). In the case of the toluene solution, the absorption peak was observed at around 300 nm, and the maximum emission wavelength was 383 nm (excitation wavelength: 300 nm). In the case of the thin film, the absorption peak was observed at around 321 nm, and the maximum emission wavelength was 410 nm (excitation wavelength: 331 nm).

The absorption spectrum showed that PCPPn described in this example is a material having weak absorption of light in the visible region. In addition, the emission spectrum shows that PCPPn exhibits blue-violet emission.

Further, the glass transition temperature (Tg) of PCPPn was examined with a differential scanning calorimeter (DSC). The measurement result showed that the glass transition temperature is 114° C. In this manner, PCPPn has a high glass transition temperature and favorable heat resistance. In addition, the crystallization peak was not observed, which shows that PCPPn is a substance which is difficult to be crystallized.

EXAMPLE 3

In this example, an example in which 9-phenyl-3-[4-(triphenylen-2-yl)-phenyl]-9H-carbazole (abbreviation: PCzPTp) represented by Structural Formula (105) in Embodiment 1 is manufactured will be described.

[45]

(105)

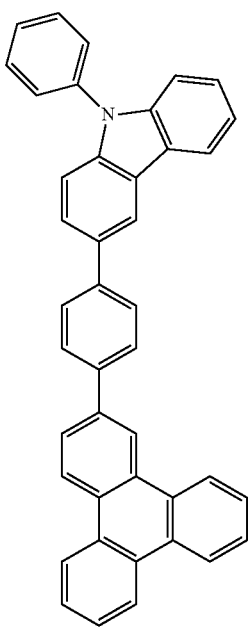

In a 100-mL three-neck flask, a mixture of 0.5 g (2.0 mmol) of 2-bromotriphenylene, 3.3 g (9.2 mmol) of 4-(9-phenyl-9H-carbazol-3-yl)phenylboronic acid, 20 mg (0.1 mmol) of palladium(II) acetate, 60 mg (0.2 mmol) of tri(o-tolyl)phosphine, 20 mL of toluene, 2 mL of ethanol, and 7.5 mL of a potassium carbonate aqueous solution (2 mol/L) was deaerated while being stirred under reduced pressure, and then heated and stirred in a nitrogen atmosphere at 85° C. for 16 hours to be reacted.

After the reaction, 500 mL of toluene was added to the reaction mixture solution, and an organic layer of the mixture solution was filtrated through Florisil, alumina, and Celite. The obtained filtrate was washed with water, and magnesium sulfate was added thereto so that moisture was adsorbed. This suspension was filtrated to obtain a filtrate. The obtained filtrate was concentrated and purified by silica gel column chromatography. At this time, toluene was used as a developing solvent for the chromatography. The obtained fraction was concentrated, and methanol was added thereto. The mixture was irradiated with ultrasonic waves and then recrystallized to give white powder that was an objective substance. The reaction scheme of the synthesis method is shown in (F3-1).

[46]

(F3-1)

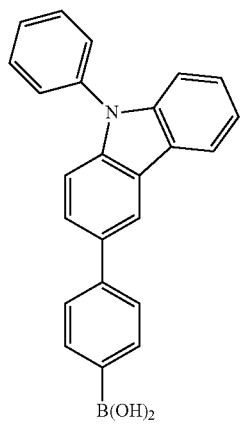

+

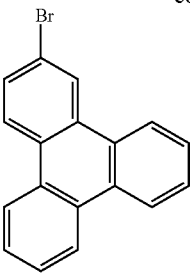

Pd(OAc)$_2$, P(o-tolyl)$_3$,
2M K$_2$CO$_3$ aq.,
Toluene, EtOH

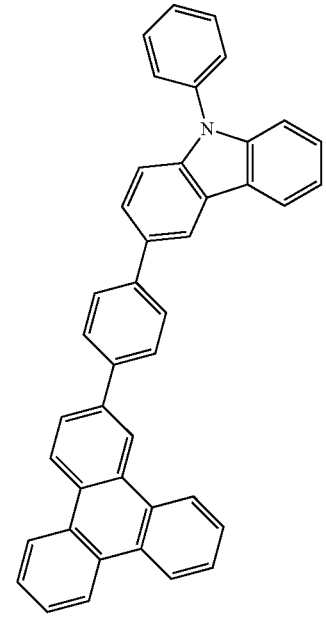

The Rf values of the objective substance and 2-bromotriphenylene were respectively 0.21 and 0.46, which were obtained by silica gel thin layer chromatography (TLC) (with a developing solvent containing ethyl acetate and hexane in a 1:10 ratio).

The obtained compound was examined by a nuclear magnetic resonance (NMR) method. The measurement data are shown below.

$^1$H NMR (CDCl$_3$, 300 MHz): δ (ppm)=7.31-7.36 (m, 1H), 7.45-7.53 (m, 4H), 7.61-7.78 (m, 9H), 7.89-8.01 (m, 5H), 8.24 (d, J=7.5 Hz, 1H), 8.46 (d, J=1.5 Hz, 1H), 8.67-8.82 (m, 5H), 8.95 (d, J=2.1 Hz, 1H).

Figure 15A:
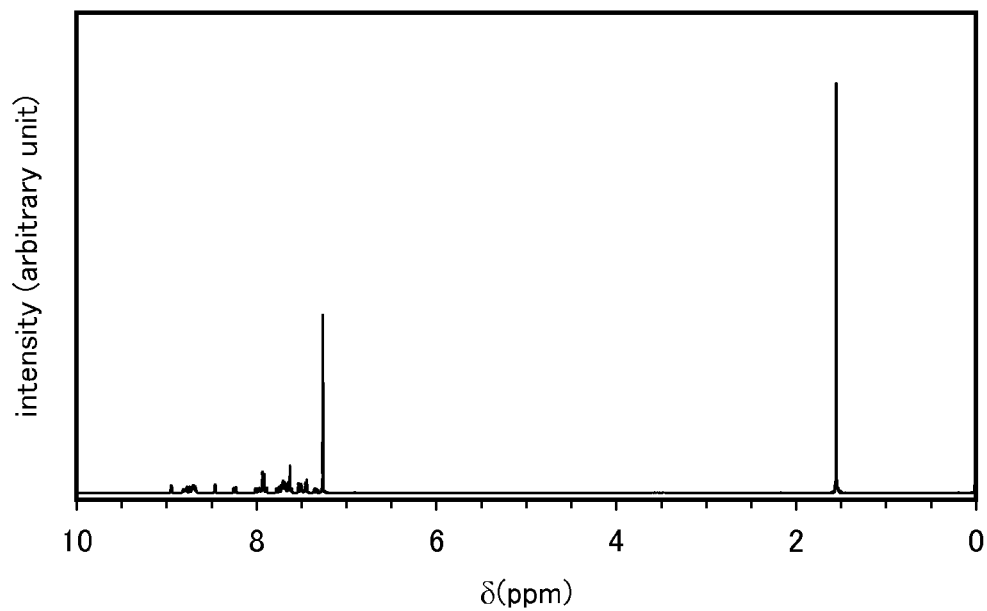
FIGS. 15A and 15B are NMR charts of PCzPTp.
Figure 15B:
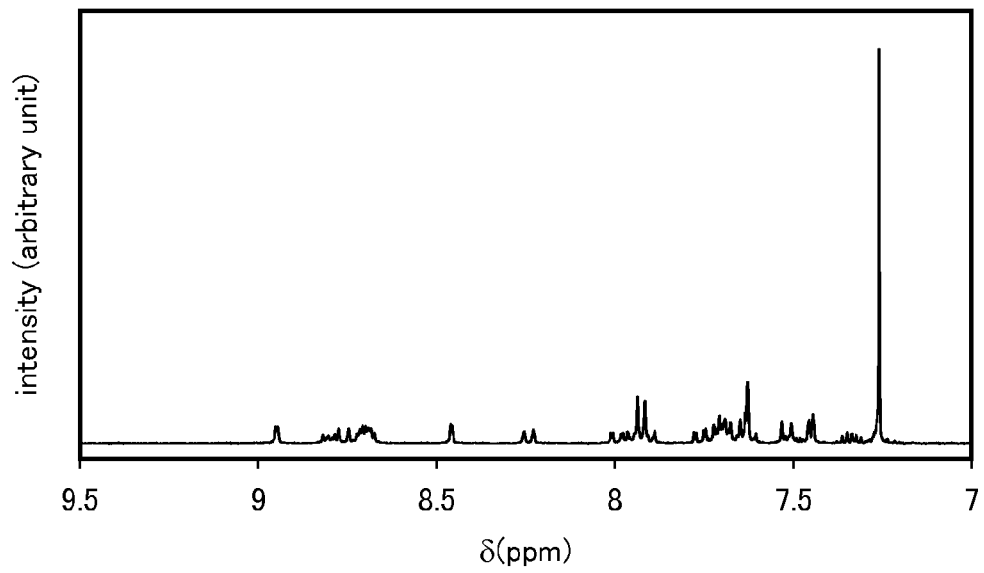

FIGS. 15A and 15B are $^1$H NMR charts. Note that FIG. 15B is a chart showing an enlarged part of FIG. 15A in the range of 7.0 ppm to 9.5 ppm. The measurement results confirmed that PCzPTp that was the objective substance was able to be obtained.

Figure 16A:
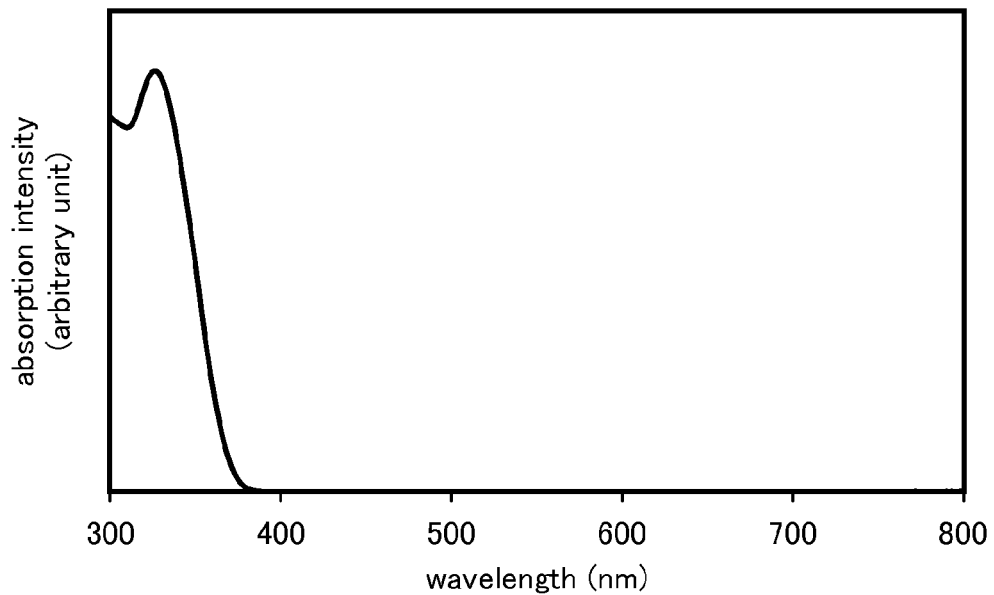
FIGS. 16A and 16B show an absorption spectrum and an emission spectrum of PCzPTp in a toluene solution of PCzPTp.
Figure 16B:
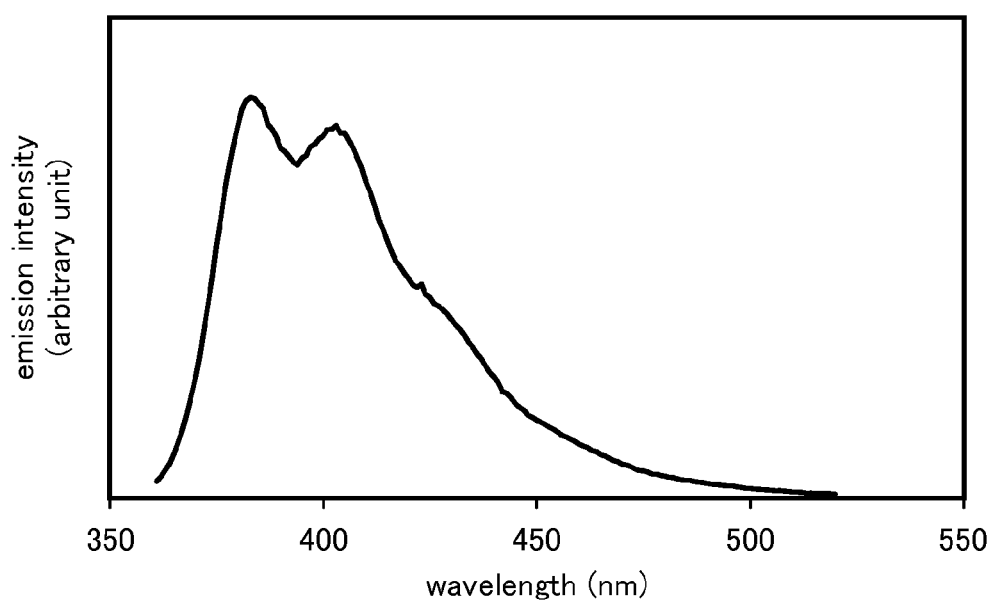

FIG. 16A shows an absorption spectrum of PCzPTp in a toluene solution of PCzPTp, and FIG. 16B shows an emission spectrum thereof. The absorption spectrum was measured with an ultraviolet-visible spectrophotometer (V550, produced by JASCO Corporation). The emission spectrum was measured with a fluorescence spectrophotometer (FS920, produced by Hamamatsu Photonics Corporation). The measurements were performed in such a manner that the solution was put in a quartz cell. FIG. 16A show the absorption spectrum of PCzPTp in the solution of PCzPTp which was obtained by subtracting the absorption spectra of the quartz cell and toluene put therein. In FIGS. 16A and 16B, the horizontal axis represents wavelength (nm) and the vertical axis represents intensity (arbitrary unit). In the case of the toluene solution, the absorption peak was observed at around 325 nm, and the maximum emission wavelength was 385 nm (excitation wavelength: 347 nm).

The absorption spectrum showed that PCzPTp described in this example is a material having weak absorption of light in the visible region. In addition, the emission spectrum shows that PCzPTp exhibits blue-violet emission.

EXAMPLE 4

In this example, an example in which 3-[3-(9-phenanthryl)-phenyl]-9-phenyl-9H-carbazole (abbreviation: mPCPPn) represented by Structural Formula (108) in Embodiment 1 is manufactured will be described.

[47]

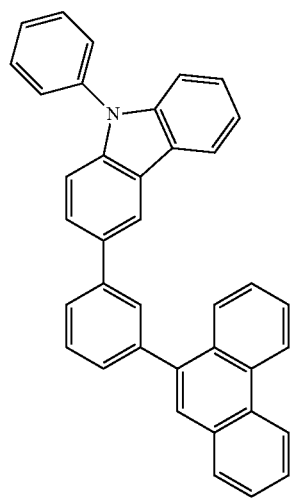

(108)

Step 1: Synthesis Method of 3-(3-bromophenyl)-9-phenyl-9H-carbazole

In a 500-mL three-neck flask, a mixture of 31 g (110 mmol) of 3-bromoiodobenzene, 29 g (100 mmol) of 9-phenyl-9H-carbazole-3-boronic acid, 22 mg (0.1 mmol) of palladium(II) acetate, 60 mg (1.2 mmol) of tri(o-tolyl)phosphine, 100 mL of toluene, 10 mL of ethanol, and 50 mL of a potassium carbonate aqueous solution (2 mol/L) was deaerated while being stirred under reduced pressure, and then heated and stirred in a nitrogen atmosphere at 80° C. for 2.5 hours to be reacted.

After the reaction, 200 mL of toluene was added to the reaction mixture solution, and the resulting suspension was filtrated through Florisil and Celite. The obtained filtrate was washed with water, and magnesium sulfate was added thereto to adsorb moisture. This suspension was filtrated to obtain a filtrate. The obtained filtrate was concentrated, and toluene and methanol were added thereto. The mixture was irradiated with ultrasonic waves and then recrystallized to give 22 g of white powder that was an objective substance in a yield of 54%. The reaction scheme of Step 1 is shown in (F4-1).

[48]

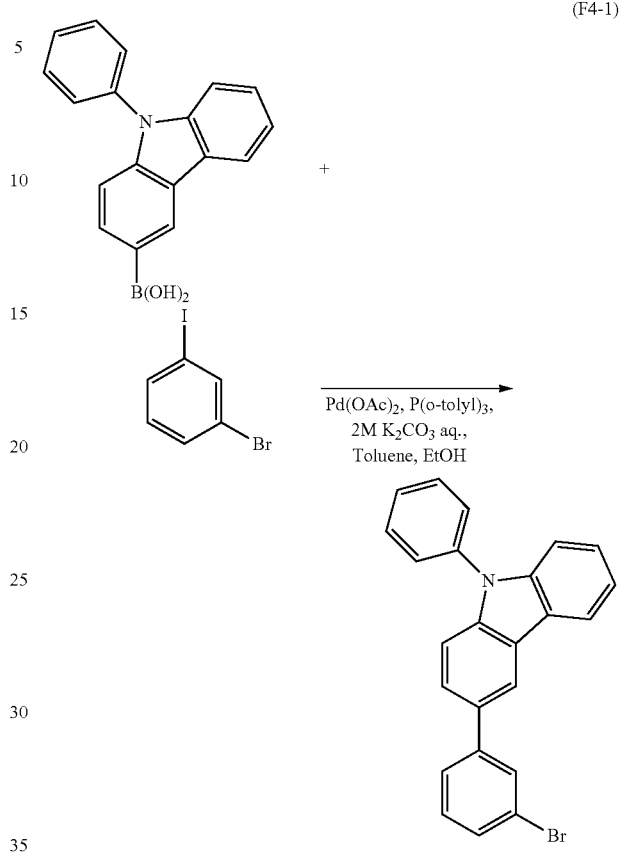

(F4-1)

The Rf values of the objective substance and 3-bromoiodobenzene were respectively 0.29 and 0.67, which were obtained by silica gel thin layer chromatography (TLC) (with a developing solvent containing ethyl acetate and hexane in a 1:10 ratio).

Step 2: Synthesis Method of 3-[3-(9-phenanthryl)-phenyl]-9-phenyl-9H-carbazole (abbreviation: mPCPPn)

In a 200-mL three-neck flask, a mixture of 3.0 g (7.5 mmol) of 3-(3-bromophenyl)-9-phenyl-9H-carbazole, 1.8 g (8.29 mmol) of phenanthrene-9-boronic acid, 19 mg (0.1 mmol) of palladium(II) acetate, 76 mg (0.2 mmol) of tris(2-methylphenyl)phosphine, 70 mL of toluene, 7 mL of ethanol, and 20 mL of a potassium carbonate aqueous solution (2 mol/L) was deaerated while being stirred under reduced pressure, and then heated and stirred in a nitrogen atmosphere at 100° C. for 5 hours to be reacted.

After the reaction, 500 mL of toluene was added to the reaction mixture solution, and an organic layer of the mixture solution was filtrated through Florisil, alumina, and Celite. The obtained filtrate was washed with water, and magnesium sulfate was added thereto to adsorb moisture. This suspension was filtrated to obtain a filtrate. The obtained filtrate was concentrated and purified by silica gel column chromatography. At this time, a mixed solvent of toluene and hexane (toluene:hexane=2:3) was used as a developing solvent for the chromatography. The obtained fraction was concentrated, and hexane was added thereto. The mixture was irradiated with ultrasonic waves and then recrystallized to give 2.76 g of white powder that was an objective substance in a yield of 74%. The reaction scheme of Step 2 is shown in (F4-2).

[49]

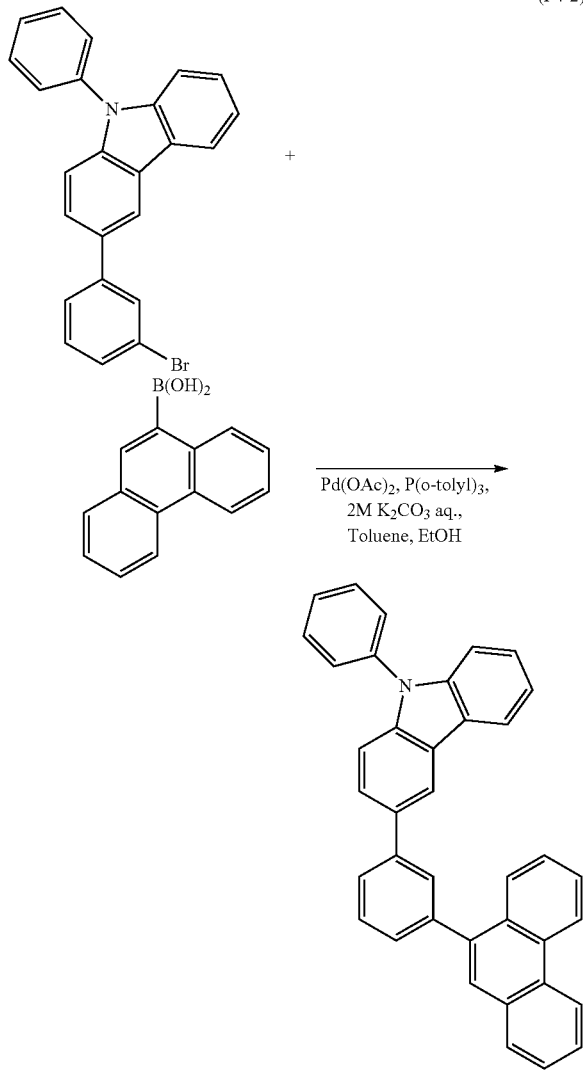

(F4-2)

The Rf values of the objective substance and 3-(3-bromophenyl)-9-phenyl-9H-carbazole were respectively 0.25 and 0.58, which were obtained by silica gel thin layer chromatography (TLC) (with a developing solvent containing ethyl acetate and hexane in a 1:10 ratio).

The obtained compound was examined by a nuclear magnetic resonance (NMR) method. The measurement data are shown below.

$^1$H NMR (CDCl$_3$, 300 MHz): δ (ppm)=7.28-7.32 (m, 1H), 7.42-7.76 (m, 15H), 7.81-7.84 (m, 2H), 7.92-7.95 (m, 2H), 8.06 (d, J=8.1 Hz, 1H), 8.18 (d, J=7.8 Hz, 1H), 8.44 (d, J=1.5 Hz, 1H), 8.76 (d, J=8.1 Hz, 1H), 8.81 (d, J=8.7 Hz, 1H).

Figure 17A:
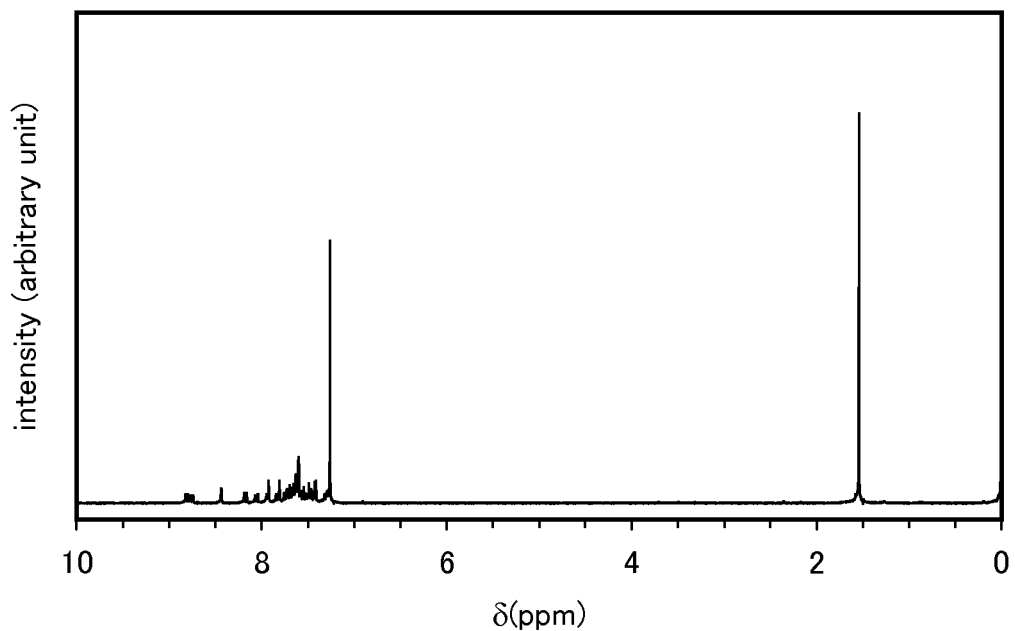
FIGS. 17A and 17B are NMR charts of mPCPPn.
Figure 17B:
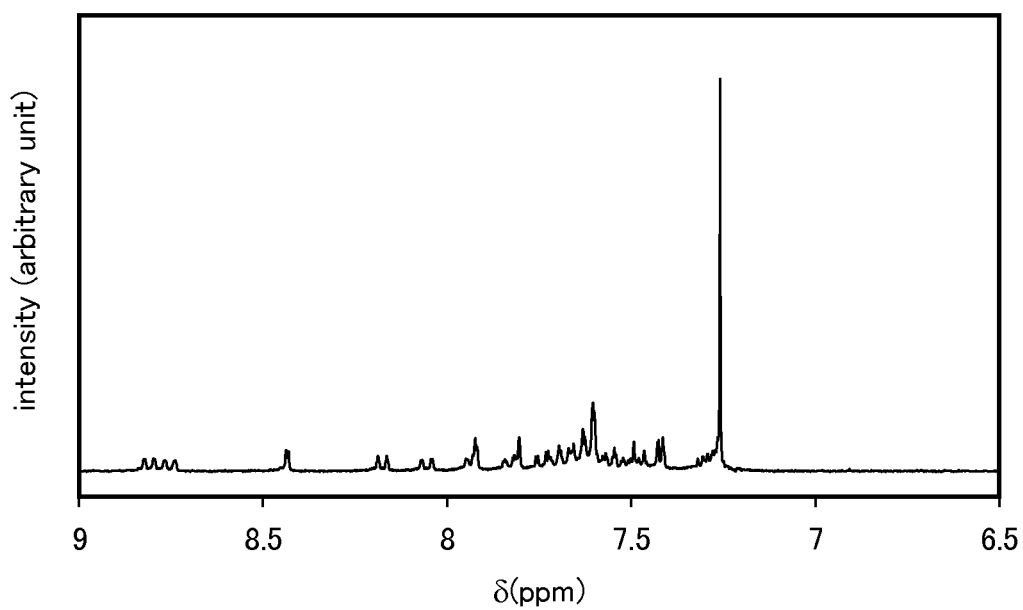

FIGS. 17A and 17B are $^1$H NMR charts. Note that FIG. 17B is a chart showing an enlarged part of FIG. 17A in the range of 6.5 ppm to 9.0 ppm. The measurement results confirmed that mPCPPn that was the objective substance was able to be obtained.

Figure 18A:
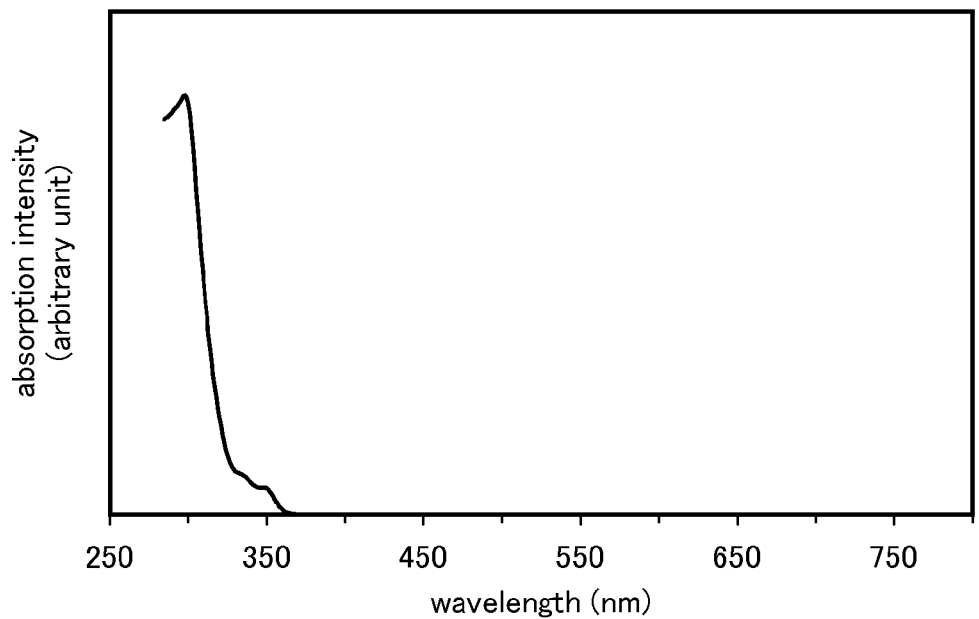
FIGS. 18A and 18B show an absorption spectrum and an emission spectrum of mPCPPn in a toluene solution of mPCPPn.
Figure 18B:
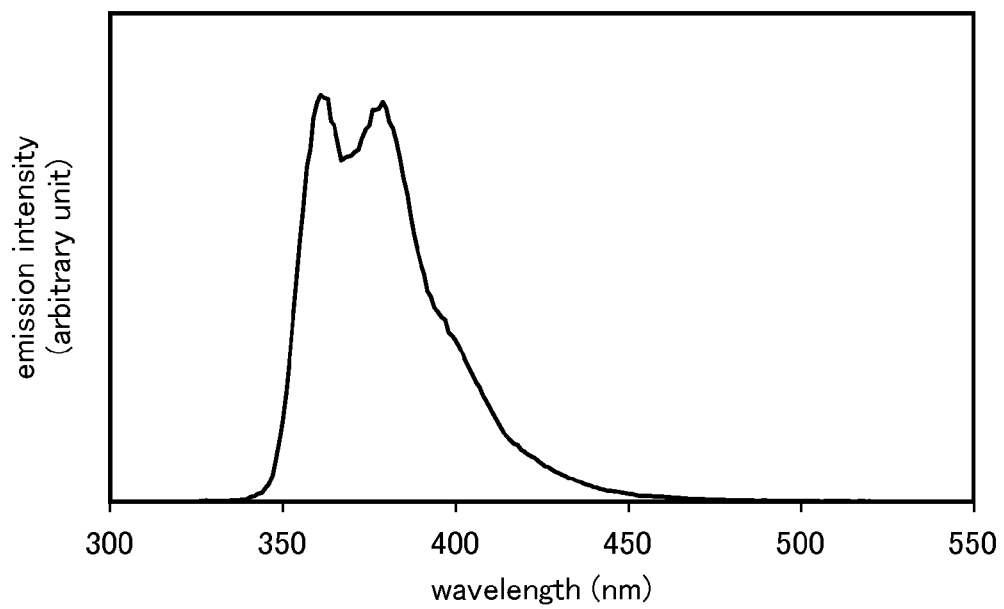
Figure 19A:
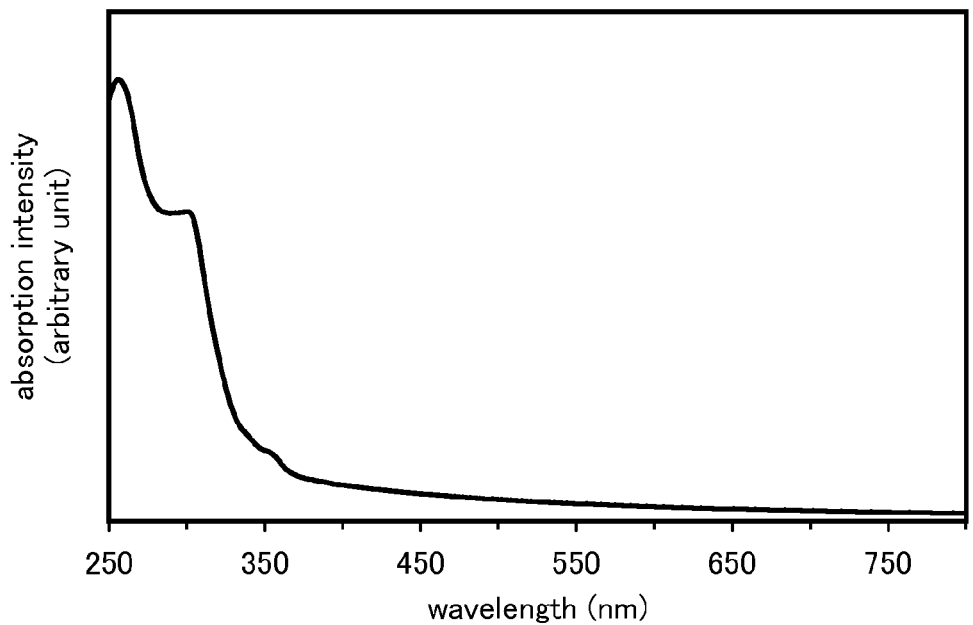
FIGS. 19A and 19B show an absorption spectrum and an emission spectrum of a thin film of mPCPPn.
Figure 19B:
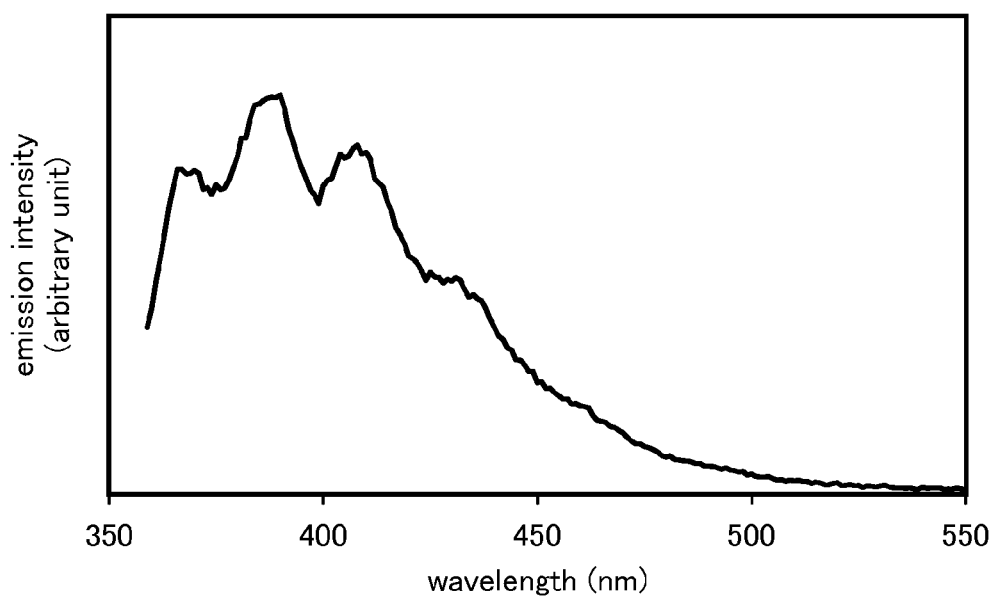

FIG. 18A shows an absorption spectrum of mPCPPn, in a toluene solution of mPCPPn, and FIG. 18B shows an emission spectrum thereof. FIG. 19A shows an absorption spectrum of a thin film of mPCPPn, and FIG. 19B shows an emission spectrum thereof. The absorption spectrum was measured with an ultraviolet-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 18A show the absorption spectrum of mPCPPn in the solution of mPCPPn which was obtained by subtracting the absorption spectra of the quartz cell and toluene put therein, and FIG. 19A shows the absorption spectrum of the thin film which was obtained by subtracting the absorption spectrum of the quartz substrate. In FIGS. 18A and 18B and FIGS. 19A and 19B, the horizontal axis represents wavelength (nm) and the vertical axis represents intensity (arbitrary unit). In the case of the toluene solution, the absorption peak was observed at around 298 nm, and the maximum emission wavelength was 363 nm (excitation wavelength: 311 nm). In the case of the thin film, the absorption peak was observed at around 350 nm, and the maximum emission wavelength was 389 nm (excitation wavelength: 353 nm).

The absorption spectrum showed that mPCPPn described in this example is a material having weak absorption of light in the visible region. In addition, the emission spectrum shows that mPCPPn exhibits blue-violet emission.

Further, the glass transition temperature (Tg) of mPCPPn was examined with a differential scanning calorimeter (DSC). The measurement result showed that the glass transition temperature is 109° C. In this manner, mPCPPn has a high glass transition temperature and favorable heat resistance. In addition, the crystallization peak was not observed, which shows that mPCPPn is a substance which is difficult to be crystallized.

EXAMPLE 5

In this example, an example in which 9-phenyl-3-[3-(triphenylen-2-yl)-phenyl]-9H-carbazole (abbreviation: mPCzPTp) represented by Structural Formula (111) in Embodiment 1 is manufactured will be described.

[50]

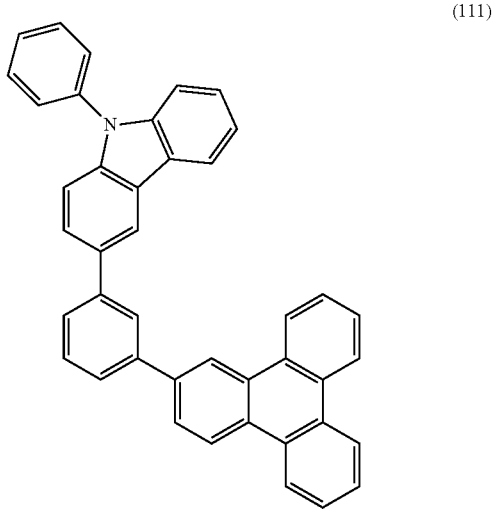

(111)

In a 50-mL three-neck flask, a mixture of 0.7 g (1.8 mmol) of 3-bromo-9-phenyl-9H-carbazole, 0.5 g (1.8 mmol) of triphenylene-2-boronic acid, 4.1 mg (18 μmol) of palladium (II) acetate, 28 mg (92 μmol) of tri(o-tolyl)phosphine, 6.9 mL of toluene, 2.3 mL of ethanol, and 1.9 mL of a potassium carbonate aqueous solution (2 mol/L) was deaerated while being stirred under reduced pressure, and then heated and stirred in a nitrogen atmosphere at 80° C. for 3 hours to be reacted.

After the reaction, an aqueous layer of the obtained suspension was extracted with toluene. The obtained extracted solution and the suspension were washed together with saturated saline, and then magnesium sulfate was added to the obtained solution so that moisture was adsorbed. The suspension was separated by gravity filtration, and the filtrate was concentrated to give an oily substance. This oily substance was purified by silica gel column chromatography. The column chromatography was performed first using a mixed solvent of toluene and hexane (toluene:hexane=1:9) as a developing solvent, and then using a mixed solvent of toluene and hexane (toluene:hexane=1:6) as a developing solvent. The obtained fractions were concentrated to give an oily substance. Toluene and hexane were added to the oily substance, and the mixture was crystallized to give 0.9 g of a white solid that was an objective substance in a yield of 90%. The reaction scheme of the synthesis method is shown in (F5-1).

[51]

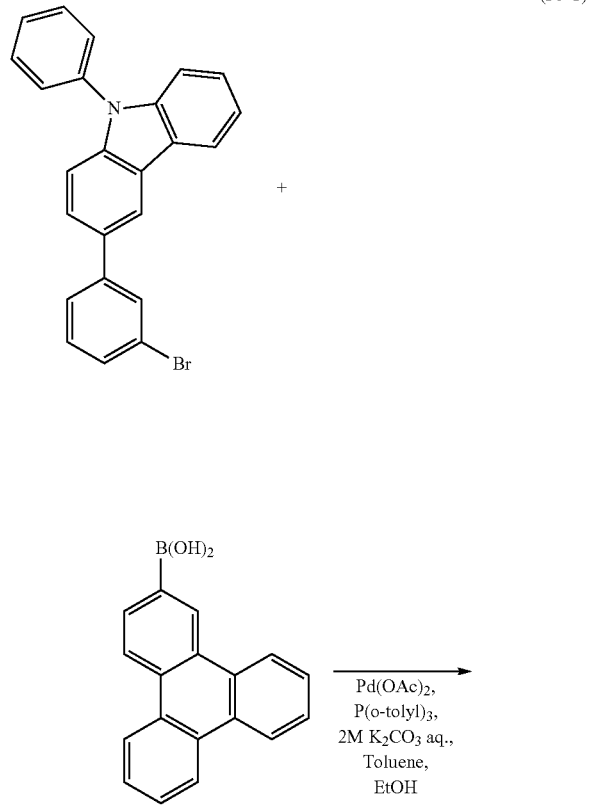

(F5-1)

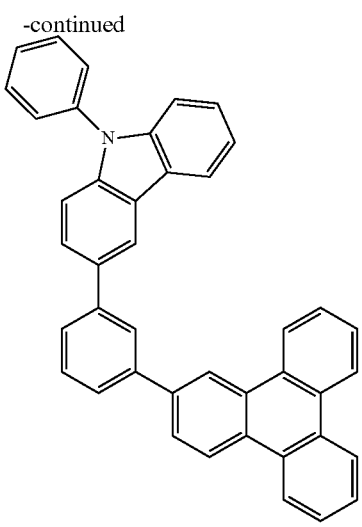

The obtained compound was examined by a nuclear magnetic resonance (NMR) method. The measurement data are shown below.

$^1$H NMR (CDCl$_3$, 300 MHz): δ (ppm)=7.30-7.54 (m, 5H), 7.60-7.80 (m, 12H), 8.01 (dd, J=8.4 Hz, 1.5 Hz, 1H), 8.14 (s, 1H), 8.23 (d, J=7.8 Hz, 1H), 8.47 (d, J=2.1 Hz, 1H), 8.67-8.80 (m, 5H), 8.95 (d, J=1.5 Hz, 1H).

Figure 20A:
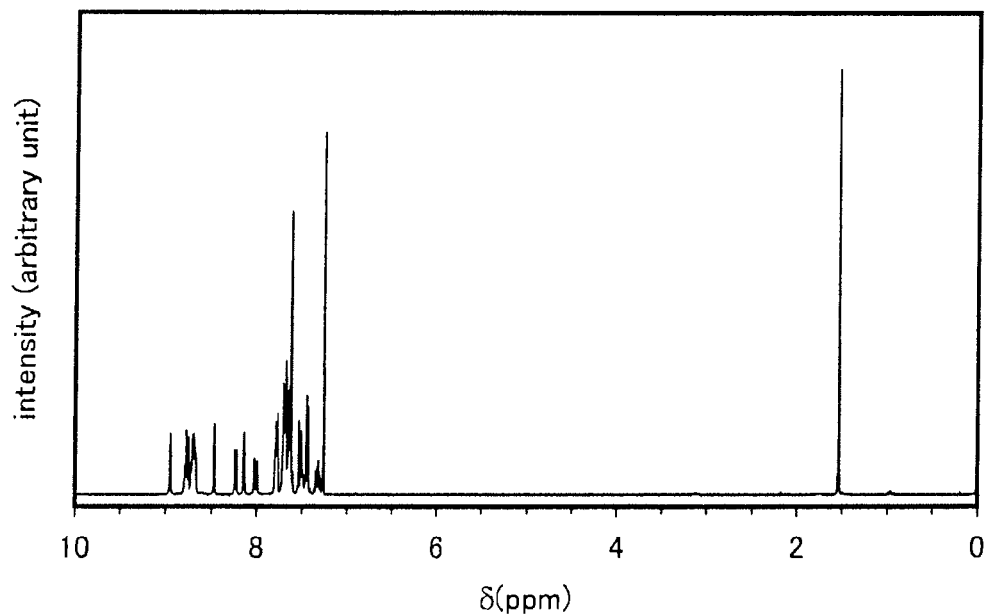
FIGS. 20A and 20B are NMR charts of mPCzPTp.
Figure 20B:
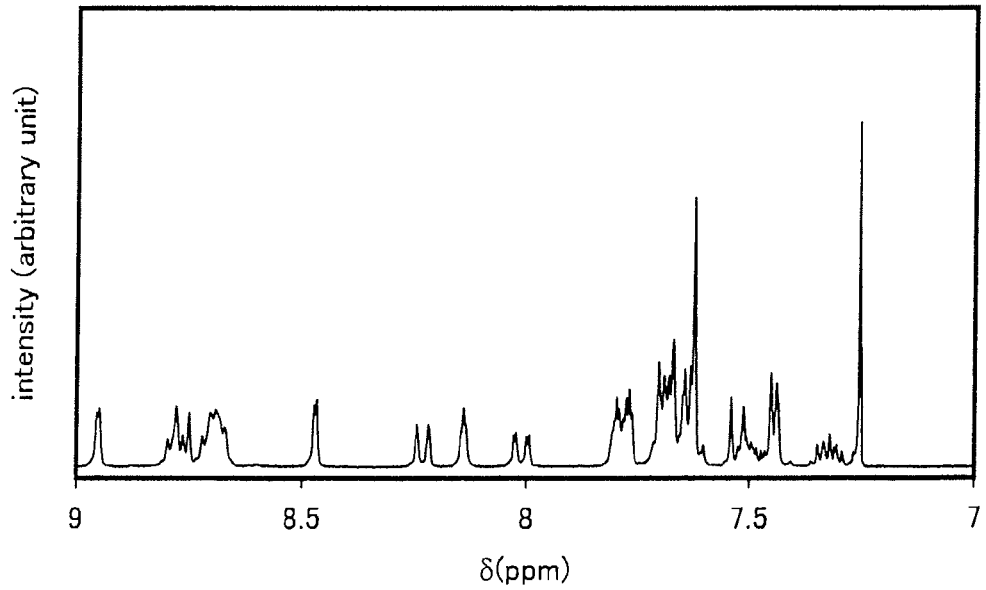

FIGS. 20A and 20B are $^1$H NMR charts. Note that FIG. 20B is a chart showing an enlarged part of FIG. 20A in the range of 7.0 ppm to 9.0 ppm. The measurement results confirmed that mPCzPTp that was the objective substance was able to be obtained.

Figure 21A:
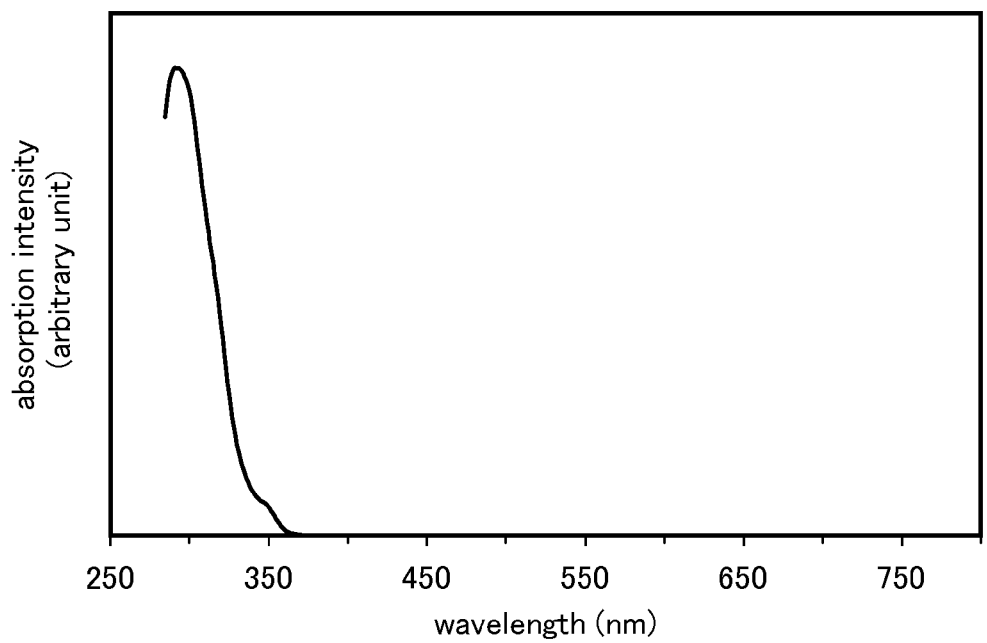
FIGS. 21A and 21B show an absorption spectrum and an emission spectrum of mPCzPTp in a toluene solution of mPCzPTp.
Figure 21B:
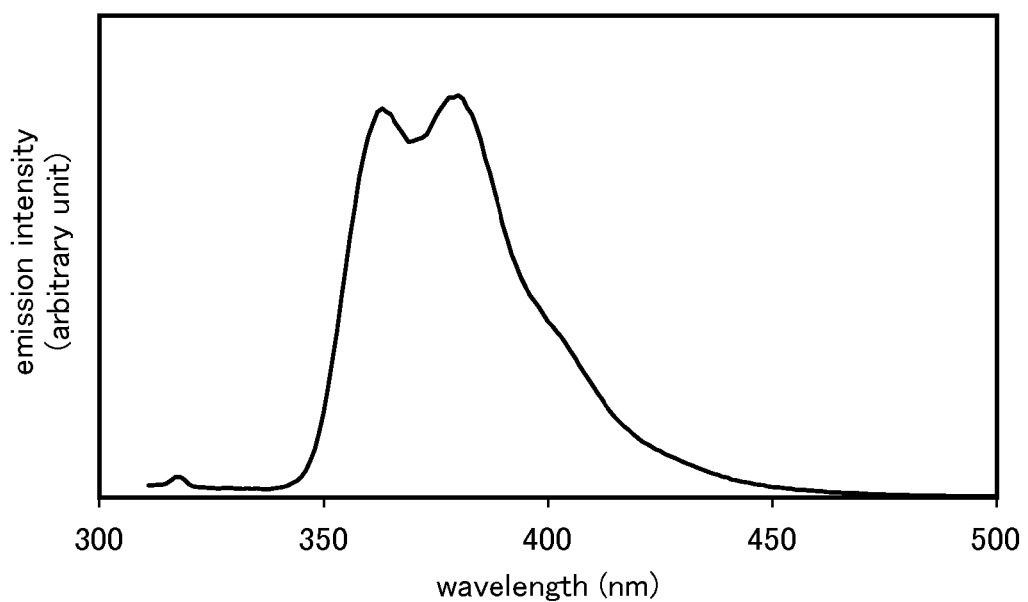
Figure 22A:
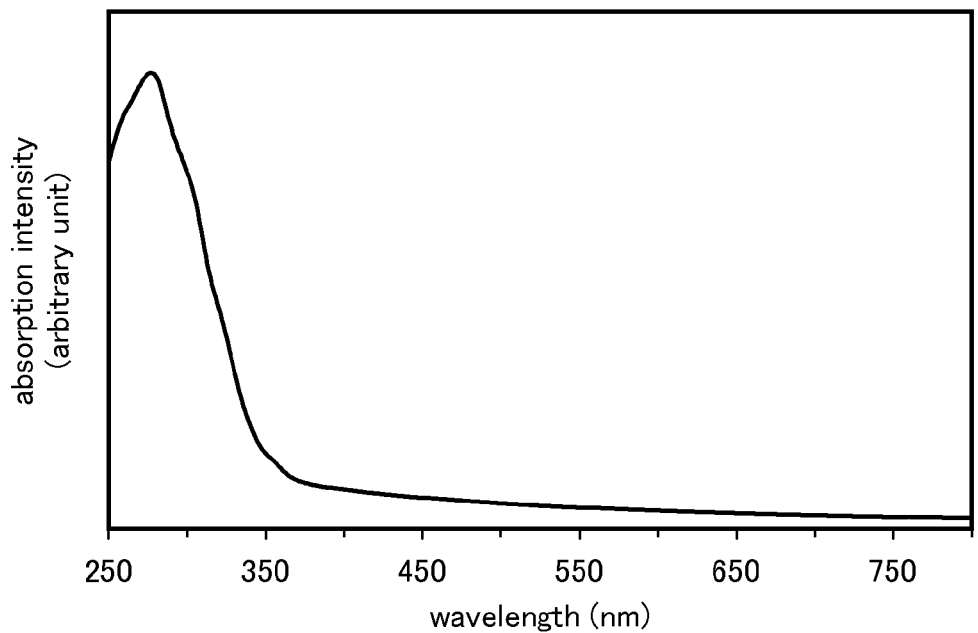
FIGS. 22A and 22B show an absorption spectrum and an emission spectrum of a thin film of mPCzPTp.
Figure 22B:
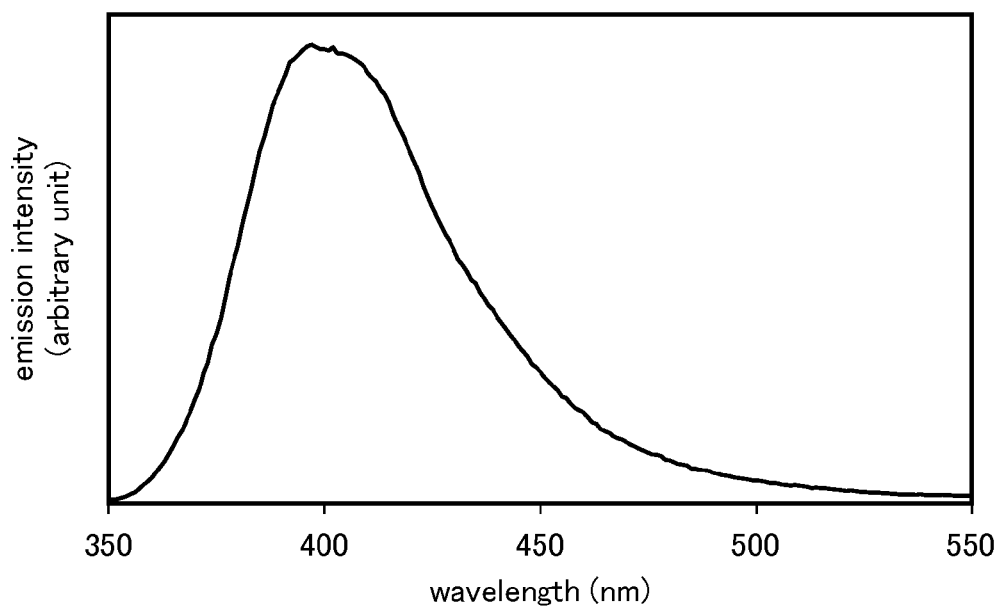

FIG. 21A shows an absorption spectrum of mPCzPTp in a toluene solution of mPCzPTp, and FIG. 21B shows an emission spectrum thereof. FIG. 22A shows an absorption spectrum of a thin film of mPCzPTp, and FIG. 22B shows an emission spectrum thereof. The absorption spectrum was measured with a UV-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 21A show the absorption spectrum of mPCzPTp in the solution of mPCzPTp which was obtained by subtracting the absorption spectra of the quartz cell and toluene put therein, and FIG. 22A shows the absorption spectrum of the thin film which was obtained by subtracting the absorption spectrum of the quartz substrate. In FIGS. 21A and 21B and FIGS. 22A and 22B, the horizontal axis represents wavelength (nm) and the vertical axis represents intensity (arbitrary unit). In the case of the toluene solution, the absorption peak was observed at around 290 nm, and the maximum emission wavelength was 381 nm (excitation wavelength: 290 nm). In the case of the thin film, the absorption peak was observed at around 277 nm, and the maximum emission wavelength was 397 nm (excitation wavelength: 306 nm).

The absorption spectrum showed that mPCzPTp described in this example is a material having weak absorption of light in the visible region. In addition, the emission spectrum shows that mPCzPTp exhibits blue-violet emission.

EXAMPLE 6

In this example, an example in which 9-(1-naphthyl)-3-[4-(1-naphthyl)-phenyl]-9H-carbazole (abbreviation: NCPN)

represented by Structural Formula (120) in Embodiment 1 is manufactured will be described.

[52]

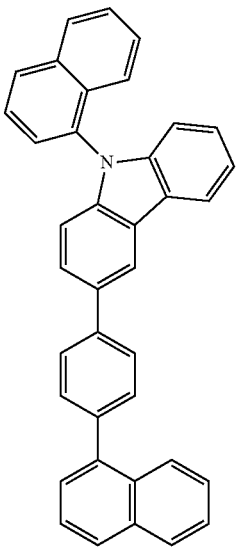

(120)

Step 1: Synthesis Method of 3-bromo-9-(1-naphthyl)-9H-carbazole

In a 200-mL conical flask, 5.9 g (20 mmol) of 9-(1-naphthyl)-9H-carbazole was dissolved in a mixture solvent of 50 mL of toluene and 70 mL of ethyl acetate, and then 3.6 g (20 mmol) of N-bromosuccinimide (abbreviation: NBS) was added to this solution. The mixture was stirred at room temperature for 36 hours. After completion of the reaction, this mixture solution was washed with water, and magnesium sulfate was added thereto so that moisture was adsorbed. This suspension was filtrated, and the obtained filtrate was concentrated and collected. As a result, 7.4 g of white powder that was an objective substance was obtained in a yield of 99%. The synthesis scheme of Step 1 is shown in (F6-1).

[53]

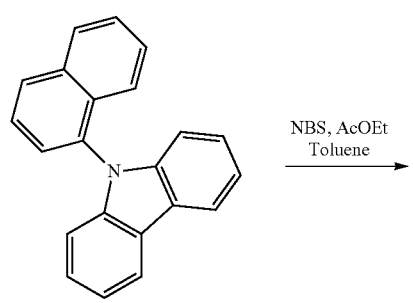

(F6-1)

Step 2: Synthesis Method of 9-(1-naphthyl)-3-[4-(1-naphthyl)-phenyl]-9H-carbazole (abbreviation: NCPN)

In a 200-mL three-neck flask, a mixture of 5.0 g (13 mmol) of 3-bromo-9-(1-naphthyl)-9H-carbazole, 3.7 g (15 mmol) of 4-(1-naphthyl)phenylboronic acid, 34 mg (0.2 mmol) of palladium(II) acetate, 91 mg (0.3 mmol) of tris(2-methylphenyl)phosphine, 50 mL of toluene, 5 mL of ethanol, and 30 mL of a potassium carbonate aqueous solution (2 mol/L) was deaerated while being stirred under reduced pressure, and then heated and stirred in a nitrogen atmosphere at 100° C. for 1 hour to be reacted. Furthermore, 334 mg (1.35 mmol) of 4-(1-naphthyl)phenylboronic acid, 15.0 mg (0.07 mmol) of palladium(II) acetate, and 45 mg (0.15 mmol) of tris(2-methylphenyl)phosphine were added, and the mixture was heated and stirred in a nitrogen atmosphere at 100° C. for 6 hours to be reacted.

After the reaction, 500 mL of toluene was added to the reaction mixture solution, and an organic layer of the mixture solution was filtrated through Florisil, alumina, and Celite. The obtained filtrate was washed with water, and magnesium sulfate was added thereto to adsorb moisture. This suspension was filtrated to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and hexane was added thereto. The mixture was irradiated with ultrasonic waves and then recrystallized to give 5.4 g of white powder that was an objective substance in a yield of 82%. The reaction scheme of Step 2 is shown in (F6-2).

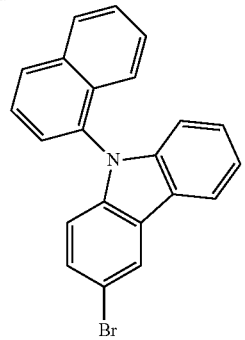

[54]

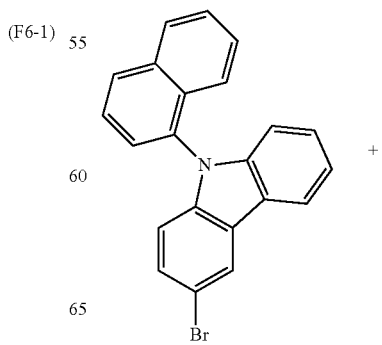

(F6-2)

-continued

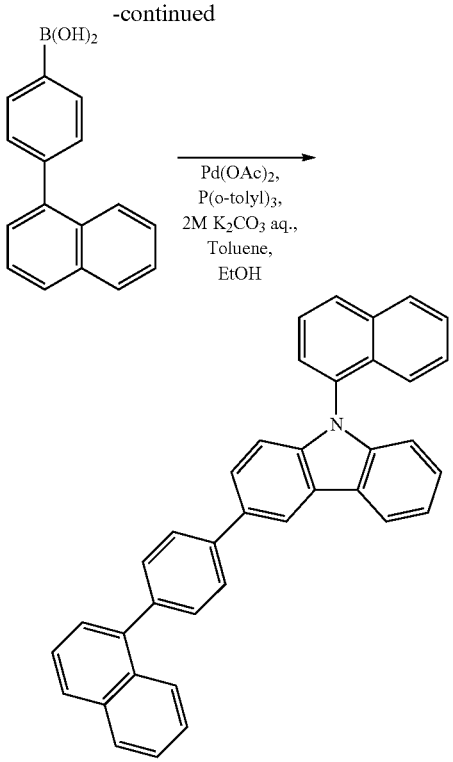

The Rf values of the objective substance and 3-bromo-9-(1-naphthyl)-9H-carbazole were respectively 0.25 and 0.53 which were obtained by silica gel thin layer chromatography (TLC) (with a developing solvent containing ethyl acetate and hexane in a 1:10 ratio).

The obtained compound was examined by a nuclear magnetic resonance (NMR) method. The measurement data are shown below.

$^1$H NMR (CDCl$_3$, 300 MHz): δ (ppm)=7.04 (dd, J=6.3 Hz, 1.5 Hz, 1H), 7.11 (d, J=8.4 Hz, 1H), 7.30-7.70 (m, 14H), 7.83-7.94 (m, 4H), 8.02-8.07 (m, 3H), 8.28 (dd, J=6.3 Hz, 2.4 Hz, 1H), 8.52 (d, J=1.5 Hz, 1H).

Figure 23A:
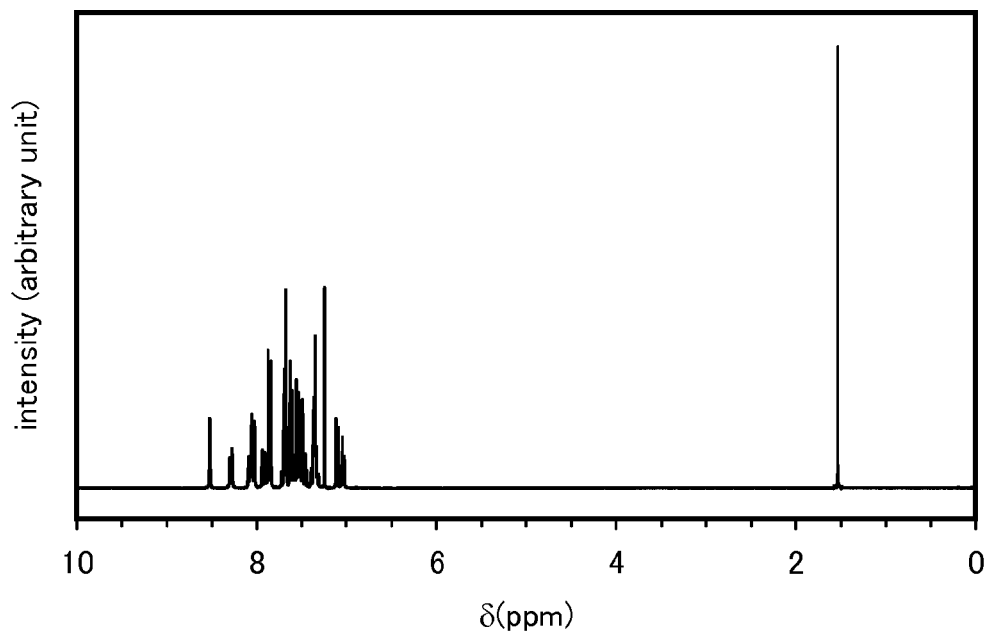
FIGS. 23A and 23B are NMR charts of NCPN.
Figure 23B:
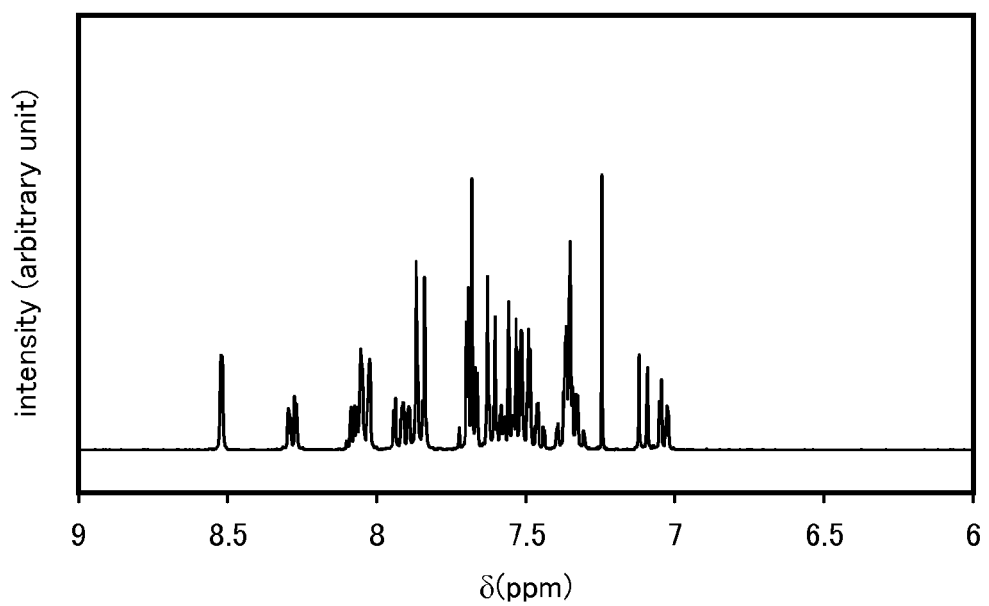

FIGS. 23A and 23B are $^1$H NMR charts. Note that FIG. 23B is a chart showing an enlarged part of FIG. 23A in the range of 6.0 ppm to 9.0 ppm. The measurement results confirmed that NCPN that was the objective substance was able to be obtained.

Figure 24A:
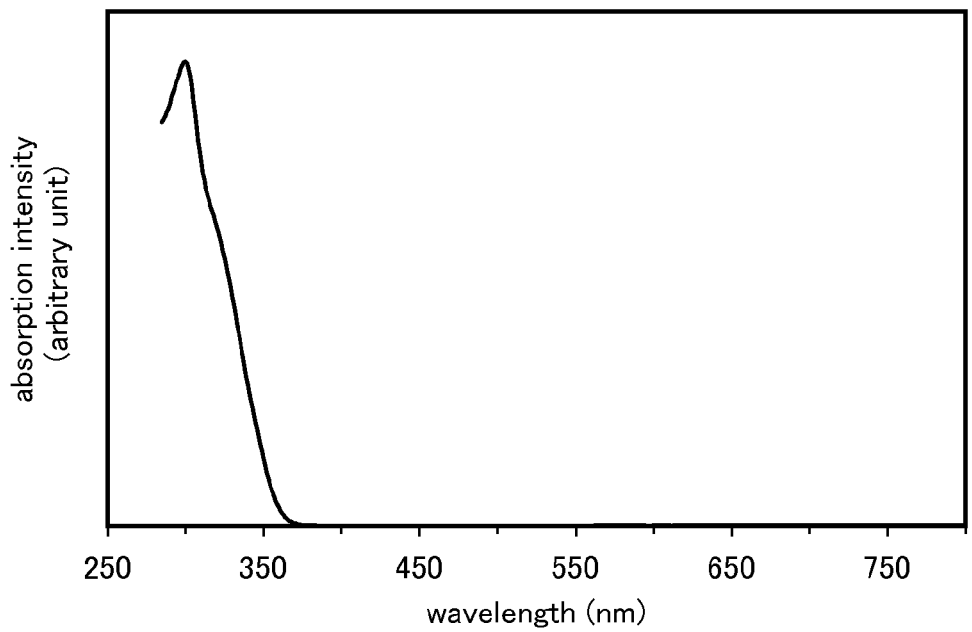
FIGS. 24A and 24B show an absorption spectrum and an emission spectrum of NCPN in a toluene solution of NCPN.
Figure 24B:
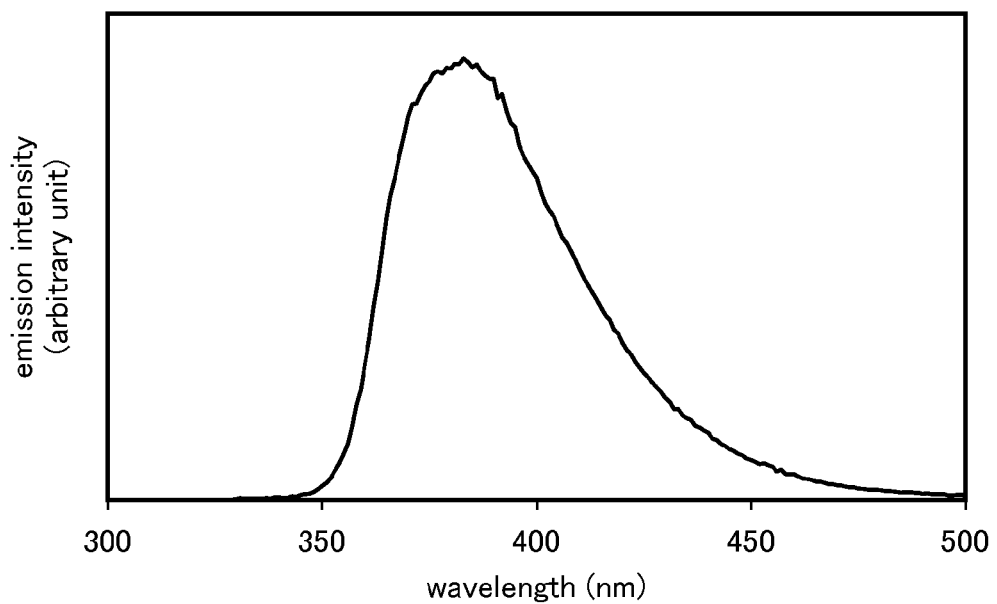
Figure 25A:
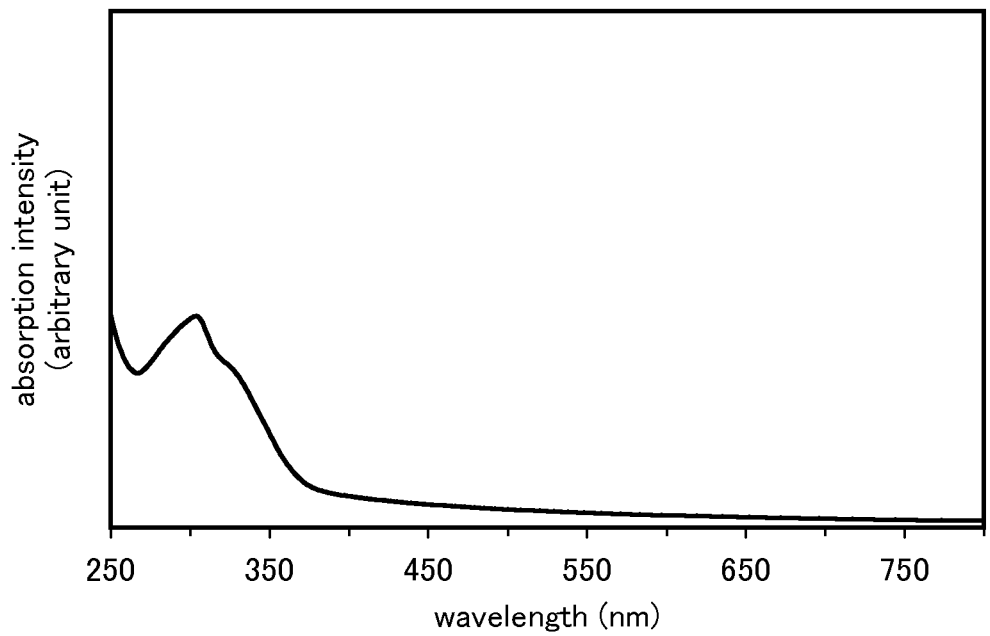
FIGS. 25A and 25B show an absorption spectrum and an emission spectrum of a thin film of NCPN.
Figure 25B:
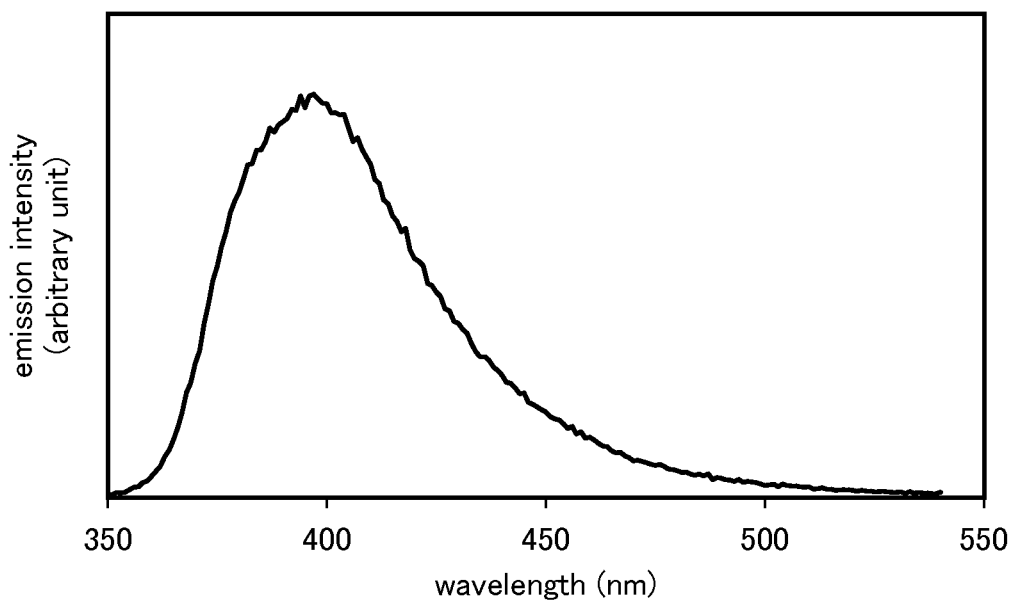

FIG. 24A shows an absorption spectrum of NCPN in a toluene solution of NCPN, and FIG. 24B shows an emission spectrum thereof. FIG. 25A shows an absorption spectrum of a thin film of NCPN, and FIG. 25B shows an emission spectrum thereof. The absorption spectrum was measured with a UV-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 24A show the absorption spectrum of NCPN in the solution of NCPN which was obtained by subtracting the absorption spectra of the quartz cell and toluene put therein, and FIG. 25A shows the absorption spectrum of the thin film which was obtained by subtracting the absorption spectrum of the quartz substrate. In FIGS. 24A and 24B and FIGS. 25A and 25B, the horizontal axis represents wavelength (nm) and the vertical axis represents intensity (arbitrary unit). In the case of the toluene solution, the absorption peak was observed at around 300 nm, and the maximum emission wavelength was 388 nm (excitation wavelength: 300 nm). In the case of the thin film, the absorption peak was observed at around 322 nm, and the maximum emission wavelength was 397 nm (excitation wavelength: 328 nm).

The absorption spectrum showed that NCPN described in this example is a material having weak absorption of light in the visible region. In addition, the emission spectrum shows that NCPN exhibits blue-violet emission.

EXAMPLE 7

In this example, an example in which 3,6-bis-[4-(1-naphthyl)-phenyl]-9-phenyl-9H-carbazole (abbreviation: NP2PC) represented by Structural Formula (112) in Embodiment 1 is manufactured will be described.

[55]

(112)

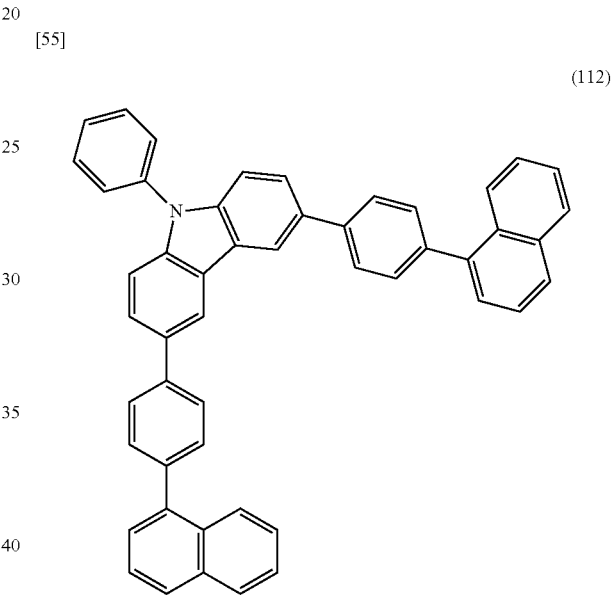

In a 200-mL three-neck flask, a mixture of 2.0 g (5.0 mmol) of 3,6-dibromo-9-phenyl-9H-carbazole, 2.7 g (11 mmol) of 4-(1-naphthyl)phenylboronic acid, 100 mg (0.5 mmol) of palladium(II) acetate, 41 mg (0.1 mmol) of tri(o-tolyl)phosphine, 20 mL of toluene, 2 mL of ethanol, and 30 mL of a potassium carbonate aqueous solution (2 mol/L) was deaerated while being stirred under reduced pressure, and then heated and stirred in a nitrogen atmosphere at 85° C. for 13 hours to be reacted.

After the reaction, 150 mL of toluene was added to the reaction mixture solution, and an organic layer of the mixture solution was filtrated through Florisil, alumina, and Celite. The obtained filtrate was washed with water, and magnesium sulfate was added thereto to adsorb moisture. This suspension was filtrated to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and acetone and methanol were added thereto. The mixture was irradiated with ultrasonic waves and then recrystallized to give 2.2 g of white powder that was an objective substance in a yield of 69%. The reaction scheme of the synthesis method is shown in (F7-1).

[56]

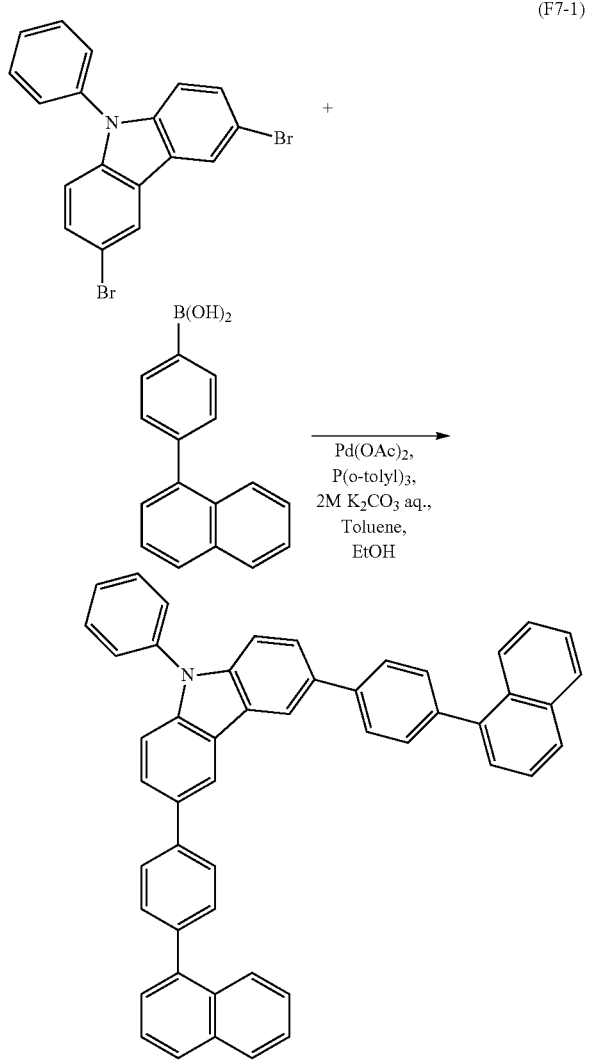

(F7-1)

The Rf values of the objective substance and 3,6-dibromo-9-phenyl-9H-carbazole were respectively 0.25 and 0.58 which were obtained by silica gel thin layer chromatography (TLC) (with a developing solvent containing ethyl acetate and hexane in a 1:10 ratio).

The obtained compound was examined by a nuclear magnetic resonance (NMR) method. The measurement data are shown below.

$^1$H NMR (CDCl$_3$, 300 MHz): δ (ppm)=7.45-7.68 (m, 19H), 8.02 (dd, J=2.1 Hz, 9.0 Hz, 2H), 7.87-7.95 (m, 8H), 8.05 (d, J=7.8 Hz, 2H), 8.55 (d, J=1.5 Hz, 2H).

Figure 26A:
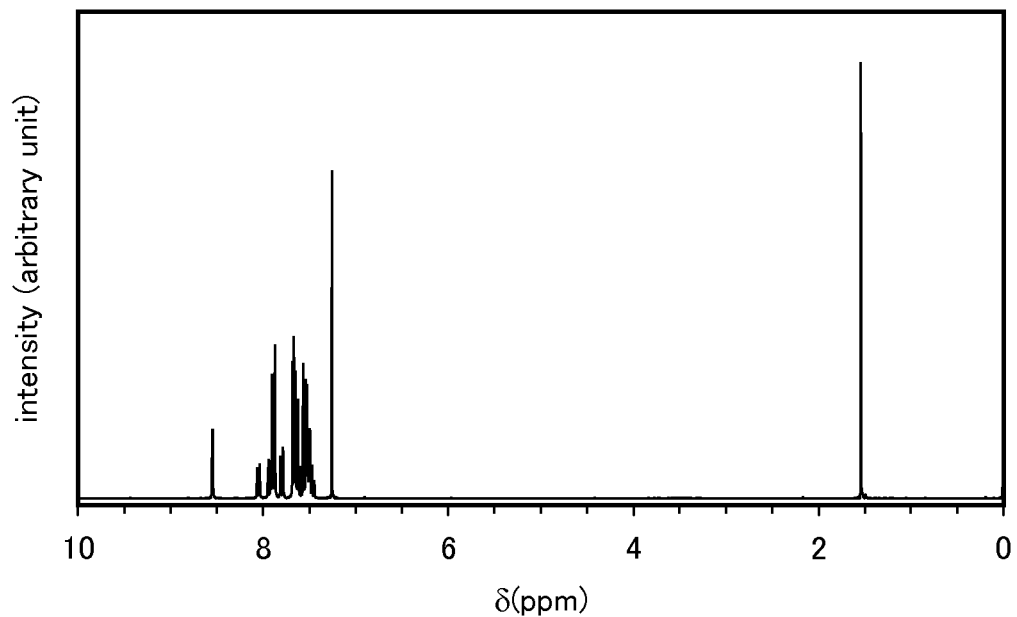
FIGS. 26A and 26B are NMR charts of NP2PC.
Figure 26B:
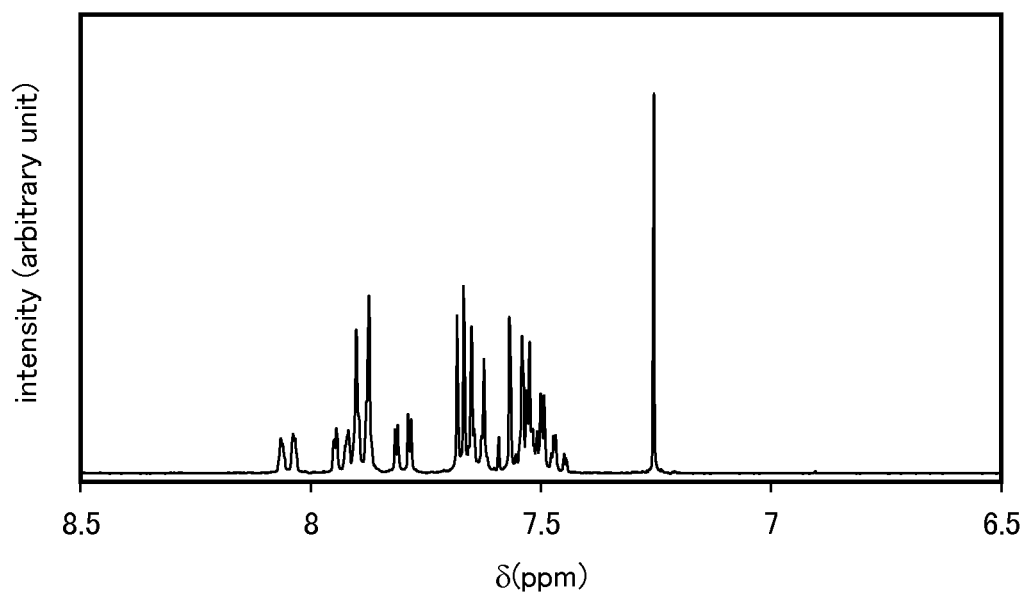

FIGS. 26A and 26B are $^1$H NMR charts. Note that FIG. 26B is a chart showing an enlarged part of FIG. 26A in the range of 7.0 ppm to 9.0 ppm. The measurement results confirmed that NP2PC that was the objective substance was able to be obtained.

Figure 27A:
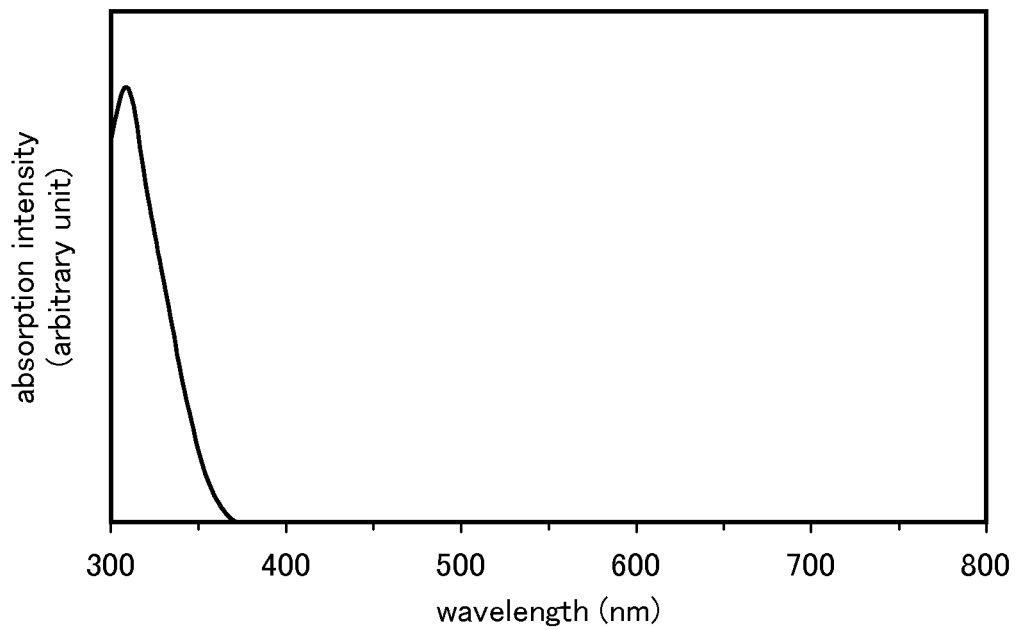
FIGS. 27A and 27B show an absorption spectrum and an emission spectrum of NP2PC in a toluene solution of NP2PC.
Figure 27B:
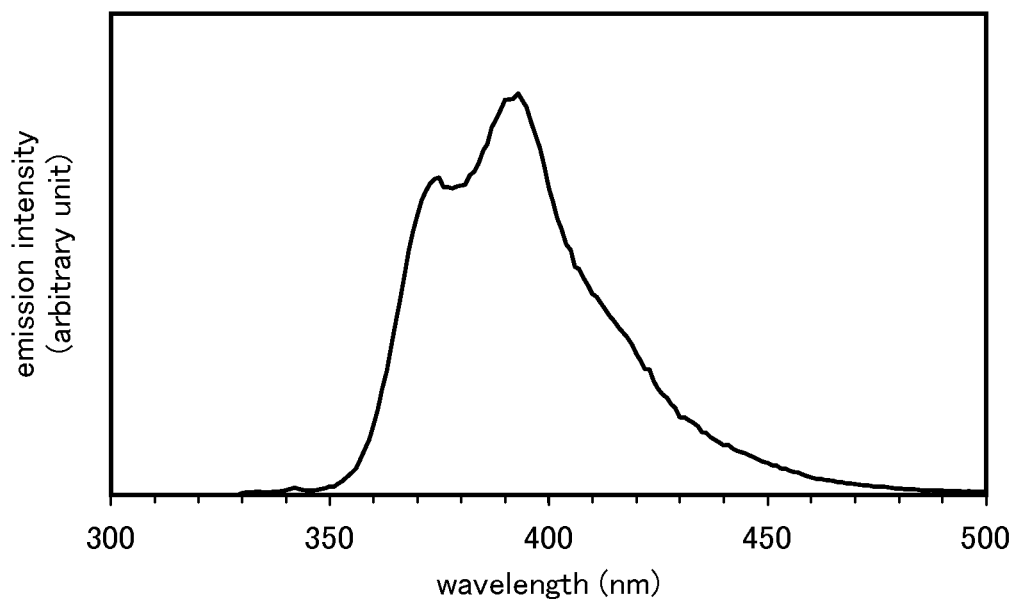
Figure 28A:
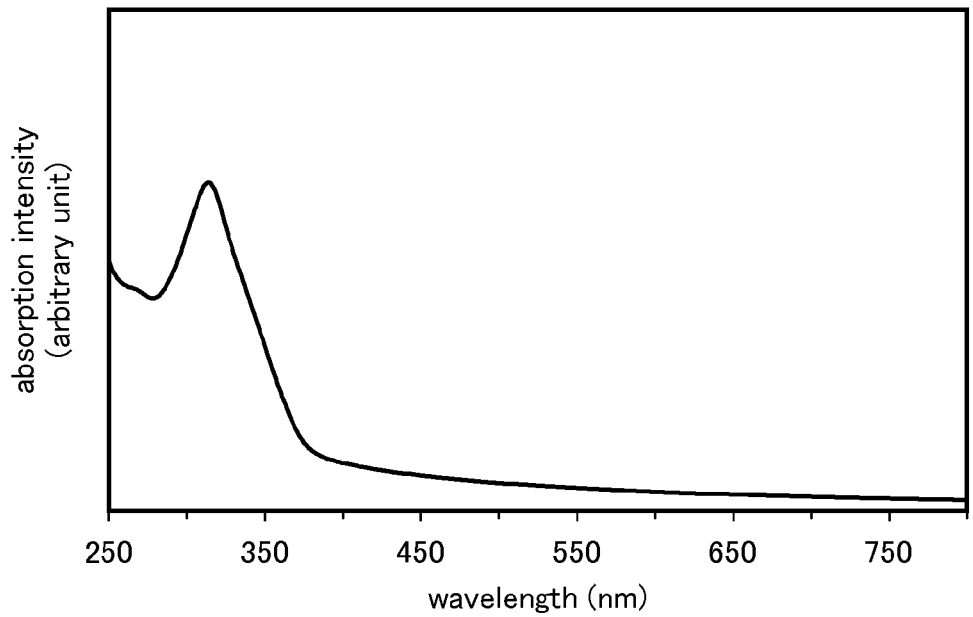
FIGS. 28A and 28B show an absorption spectrum and an emission spectrum of a thin film of NP2PC.
Figure 28B:
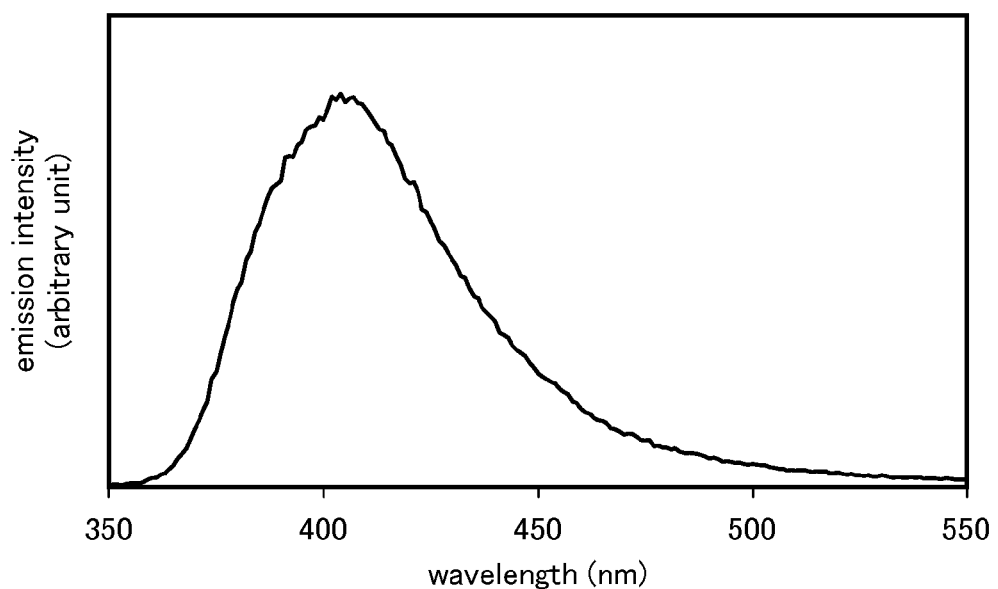

FIG. 27A shows an absorption spectrum of NP2PC in a toluene solution of NP2PC, and FIG. 27B shows an emission spectrum thereof. FIG. 28A shows an absorption spectrum of a thin film of NP2PC, and FIG. 28B shows an emission spectrum thereof. The absorption spectrum was measured with a UV-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 27A show the absorption spectrum of NP2PC in the solution of NP2PC which was obtained by subtracting the absorption spectra of the quartz cell and toluene put therein, and FIG. 28A shows the absorption spectrum of the thin film which was obtained by subtracting the absorption spectrum of the quartz substrate. In FIGS. 27A and 27B and FIGS. 28A and 28B, the horizontal axis represents wavelength (nm) and the vertical axis represents intensity (arbitrary unit). In the case of the toluene solution, the absorption peak was observed at around 314 nm, and the maximum emission wavelength was 392 nm (excitation wavelength: 310 nm). In the case of the thin film, the absorption peak was observed at around 314 nm, and the maximum emission wavelength was 404 nm (excitation wavelength: 315 nm).

The absorption spectrum showed that NP2PC described in this example is a material having weak absorption of light in the visible region. In addition, the emission spectrum shows that NP2PC exhibits blue-violet emission.

Further, the thermophysical property was examined with a differential scanning calorimeter (DSC). The measurement result showed that the melting point is 269° C. In addition, glass transition and a crystallization peak were not observed; thus, it was found that NP2PC is a substance which is difficult to be crystallized.

EXAMPLE 8

In this example, measurement results of the highest occupied molecular orbital (HOMO) level, the lowest unoccupied molecular orbital (LUMO) level, and the band gap (Bg) of each of the carbazole compounds according to one embodiment of the invention which were synthesized in Examples 1, 2, and 4 to 7, in a thin film state, will be described.

Note that the measurement in this example was performed as described below. The value of the HOMO level was obtained by conversion of a value of the ionization potential measured with a photoelectron spectrometer (AC-2, manufactured by Riken Keiki Co., Ltd.) in the air into a negative value. The value of the LUMO level was obtained in such a manner that the absorption edge, which is obtained from Tauc plot with an assumption of direct transition, using data on the absorption spectrum of the thin film described in each Example, is regarded as an optical energy gap and is added to the value of the HOMO level.

Table 1 shows the HOMO levels and the LUMO levels of PCPN, PCPPn, mPCPPn, mPCzPTp, NCPN, and NP2PC which were obtained by the measurement.

TABLE 1

| Abbreviation | HOMO level | LUMO level | Band gap |
|---|---|---|---|
| PCPN | −5.77 | −2.29 | 3.48 |
| PCPPn | −5.78 | −2.25 | 3.53 |
| mPCPPn | −5.69 | −2.37 | 3.32 |
| mPCzPTp | −5.70 | −2.41 | 3.29 |
| NCPN | −5.83 | −2.37 | 3.46 |
| NP2PC | −5.74 | −2.36 | 3.38 |

Table 1 confirms that PCPN, PCPPn, mPCPPn, mPCzPTp, NCPN, and NP2PC each of which is the carbazole compound according to one embodiment of the present invention have relatively deep HOMO levels, shallow LUMO levels, and wide band gaps.

EXAMPLE 9

In this example, manufacturing methods of light-emitting elements each of which is one embodiment of the present invention and measurement results of the element characteristics will be described together with measurement results of a comparative light-emitting element.

Figure 29:
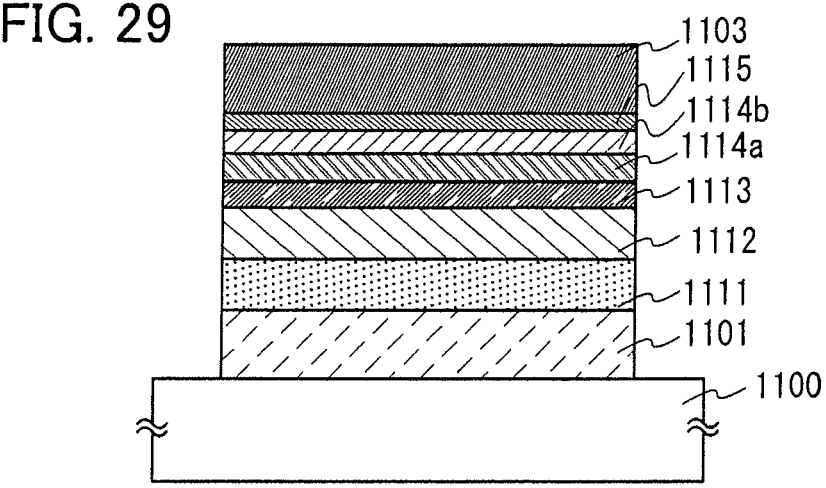
FIG. 29 illustrates a light-emitting element of Examples.

Manufacturing methods of a light-emitting element 1, a light-emitting element 2, and a comparative light-emitting element 1 will be described below with reference to FIG. 29. In addition, structural formulae of organic compounds used in this example are shown below.

[57]

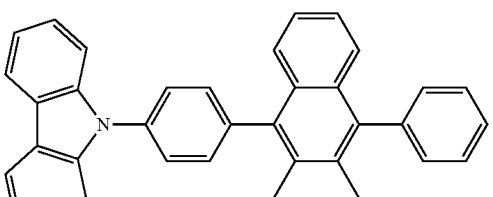

CzPA

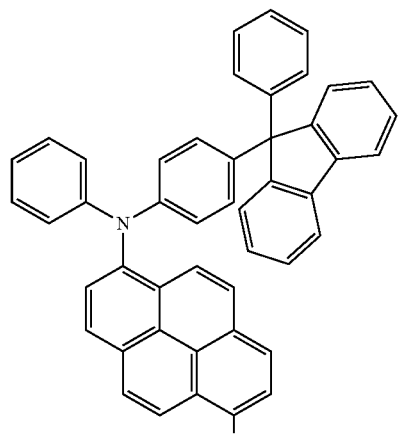

1,6FLPAPrn

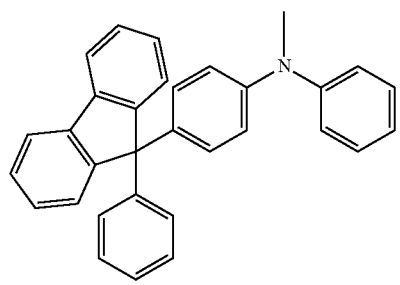

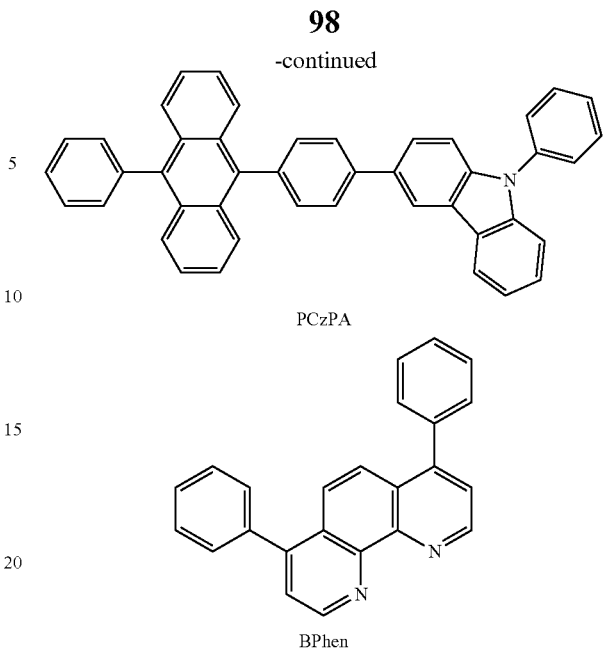

PCzPA

BPhen (Light-Emitting Element 1)

First, indium tin oxide containing silicon oxide (ITSO) was deposited by a sputtering method on a glass substrate 1100, so that a first electrode 1101 was formed. The thickness of the first electrode 1101 was 110 nm. The electrode area was 2 mm×2 mm. In this example, the first electrode 1101 was used as an anode.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. After that, 3-[4-(1-naphthyl)-phenyl]-9-phenyl-9H-carbazole (abbreviation: PCPN) synthesized in Example 1 and molybdenum(VI) oxide were co-evaporated to form a hole-injection layer 1111 on the first electrode 1101. The thickness of the hole-injection layer 1111 was 50 nm. The weight ratio of PCPN to molybdenum(VI) oxide was adjusted to be 4:2 (=PCPN:molybdenum oxide). Note that the co-evaporation method refers to an evaporation method in which evaporation is carried out from a plurality of evaporation sources at the same time in one treatment chamber.

Next, PCPN was deposited to a thickness of 10 nm on the hole-injection layer 1111 to form a hole-transport layer 1112.

Furthermore, 9-[4-(N-carbazolyl)phenyl]-10-phenylanthracene (abbreviation: CzPA) and N,N'-bis[4-(9-phenyl-9H-fluoren-9-yl)phenyl]-N,N'-diphenylpyrene-1,6-diamine (abbreviation: 1,6FLPAPrn) were co-evaporated to form a light-emitting layer 1113 on the hole-transport layer 1112. The weight ratio of CzPA to 1,6FLPAPrn was adjusted to 1:0.05 (=CzPA:1,6FLPAPrn). The thickness of the light-emitting layer 1113 was 30 nm.

Next, CzPA was deposited to a thickness of 10 nm on the light-emitting layer 1113 to form a first electron-transport layer 1114*a*.

After that, bathophenanthroline (abbreviation: BPhen) was deposited to a thickness of 15 nm on the first electron-transport layer 1114*a* to form a second electron-transport layer 1114*b*.

Furthermore, a lithium fluoride (LiF) film was formed to a thickness of 1 nm on the second electron-transport layer 1114*b* by evaporation to form an electron-injection layer 1115.

Lastly, a 200-nm-thick film of aluminum was formed by evaporation to form a second electrode 1103 functioning as a cathode. Thus, the light-emitting element 1 of this example was manufactured.

Note that, in the above evaporation process, evaporation was all performed by a resistance heating method.

(Light-Emitting Element 2)

The light-emitting element 2 was formed in a manner similar to that of the light-emitting element 1 except for the hole-injection layer 1111 and the hole-transport layer 1112.

In the light-emitting element 2, the hole-injection layer 1111 was formed in such a manner that 3-[4-(9-phenanthryl)-phenyl]-9-phenyl-9H-carbazole (abbreviation: PCPPn) synthesized in Example 2 and molybdenum(VI) oxide were co-evaporated on the first electrode 1101. The thickness of the hole-injection layer 1111 was 50 nm. The weight ratio of PCPPn to molybdenum(VI) oxide was adjusted to 4:2 (=PCPPn:molybdenum oxide).

Next, PCPPn was deposited to a thickness of 10 nm on the hole-injection layer 1111 to form the hole-transport layer 1112.

(Comparative Light-Emitting Element 1)

The comparative light-emitting element 1 was formed in a manner similar to that of the light-emitting element 1 except for the hole-injection layer 1111 and the hole-transport layer 1112.

In the comparative light-emitting element 1, the hole-injection layer 1111 was formed in such a manner that 9-[4-(9-phenylcarbazol-3-yl)phenyl]-10-phenylanthracene (abbreviation: PCzPA) and molybdenum(VI) oxide were co-evaporated on the first electrode 1101. The thickness of the hole-injection layer 1111 was 50 nm. The weight ratio of PCzPA to molybdenum(VI) oxide was adjusted to be 4:2 (=PCzPA:molybdenum oxide).

Next, PCzPA was deposited to a thickness of 10 nm on the hole-injection layer 1111 to form the hole-transport layer 1112.

Table 2 shows the element structures of the light-emitting element 1, the light-emitting element 2, and the comparative light-emitting element 1 that were manufactured as described above.

TABLE 2

|  | Light-Emitting Element 1 | Light-Emitting Element 2 | Comparative Light-Emitting Element 1 |
|---|---|---|---|
| First Electrode 1101 | ITSO 110 nm | ITSO 110 nm | ITSO 110 nm |
| Hole-injection Layer 1111 | PCPN:MoOx (=4:2) 50 nm | PCPPn:MoOx (=4:2) 50 nm | PCzPA:MoOx (=4:2) 50 nm |
| Hole-transport layer 1112 | PCPN 10 nm | PCPPn 10 nm | PCzPA 10 nm |
| Light-emitting layer 1113 | CzPA:1,6FLPAPrn (=1:0.05) 30 nm | CzPA:1,6FLPAPrn (=1:0.05) 30 nm | CzPA:1,6FLPAPrn (=1:0.05) 30 nm |
| Electron-transport layer 1114a | CzPA 10 nm | CzPA 10 nm | CzPA 10 nm |
| 1114b | BPhen 15 nm | BPhen 15 nm | BPhen 15 nm |
| Electron-injection layer 1115 | LiF 1 nm | LiF 1 nm | LiF 1 nm |
| Second Electrode 1103 | Al 200 nm | Al 200 nm | Al 200 nm |

*The mixture ratios are all represented in weight ratios.

In a glove box containing a nitrogen atmosphere, the light-emitting element 1, the light-emitting element 2, and the comparative light-emitting element 1 were sealed so as not to be exposed to the air. After that, the operating characteristics of these elements were measured. Note that the measurement was carried out at room temperature (in an atmosphere kept at 25° C.).

Note that the light-emitting element 1, the light-emitting element 2, and the comparative light-emitting element 1 were formed over the same substrate. In addition, in the above three light-emitting elements, the respective components other than the hole-injection layers and the hole-transport layers were formed at the same time, and the operating characteristics of the three light-emitting elements were measured at the same time.

Table 3 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 1, the light-emitting element 2, and the comparative light-emitting element 1 at a luminance of about 1000 cd/m$^2$.

TABLE 3

|  | Light-Emitting Element 1 | Light-Emitting Element 2 | Comparative Light-Emitting Element 1 |
|---|---|---|---|
| Voltage (V) | 3.0 | 3.0 | 3.0 |
| Current density (mA/cm$^2$) | 9.3 | 7.5 | 8.3 |
| Chromaticity coordinates (x, y) | (0.15, 0.21) | (0.15, 0.21) | (0.14, 0.20) |
| Luminance (cd/m$^2$) | 930 | 770 | 650 |
| Current efficiency (cd/A) | 10 | 10 | 8.0 |
| Power efficiency (lm/W) | 10 | 11 | 8.0 |
| External quantum efficiency (%) | 6.8 | 6.9 | 5.6 |

Figure 30:
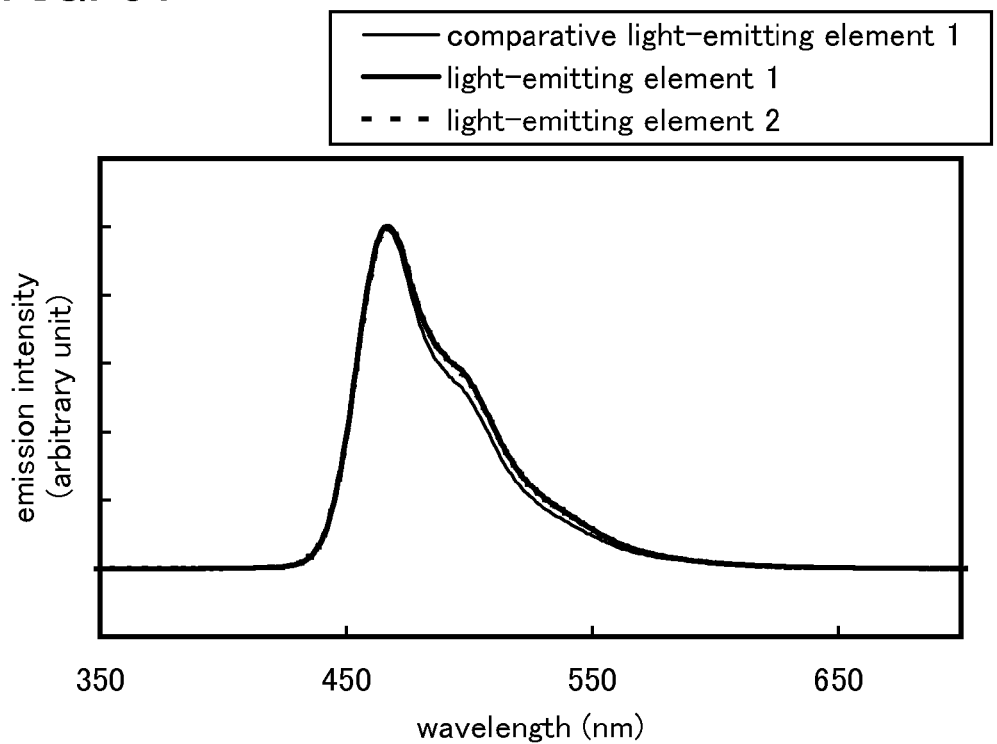
FIG. 30 shows emission spectra of light-emitting elements and a comparative light-emitting element of Example 9.
Figure 31:
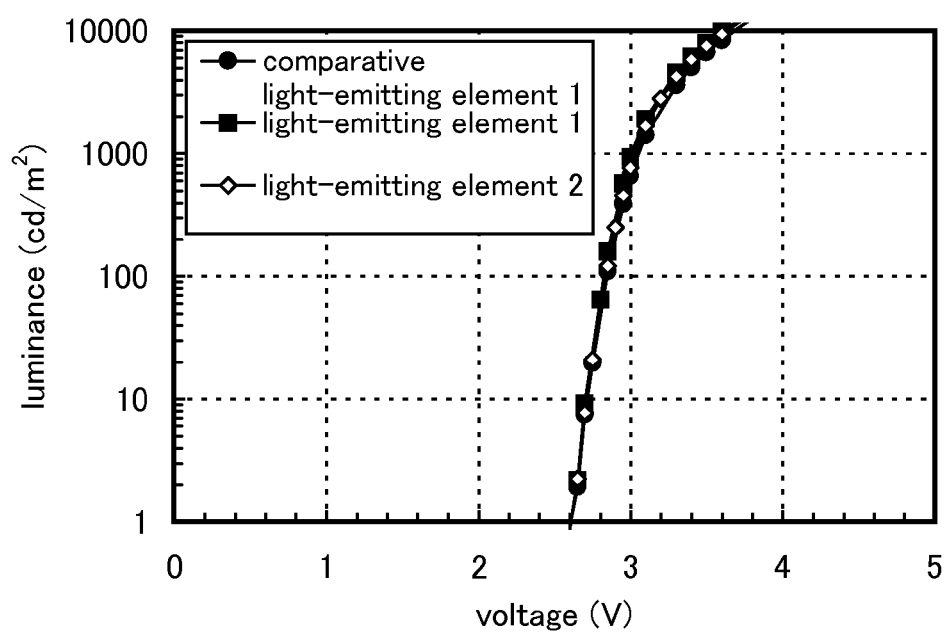
FIG. 31 shows voltage-luminance characteristics of the light-emitting elements and the comparative light-emitting element of Example 9.
Figure 32:
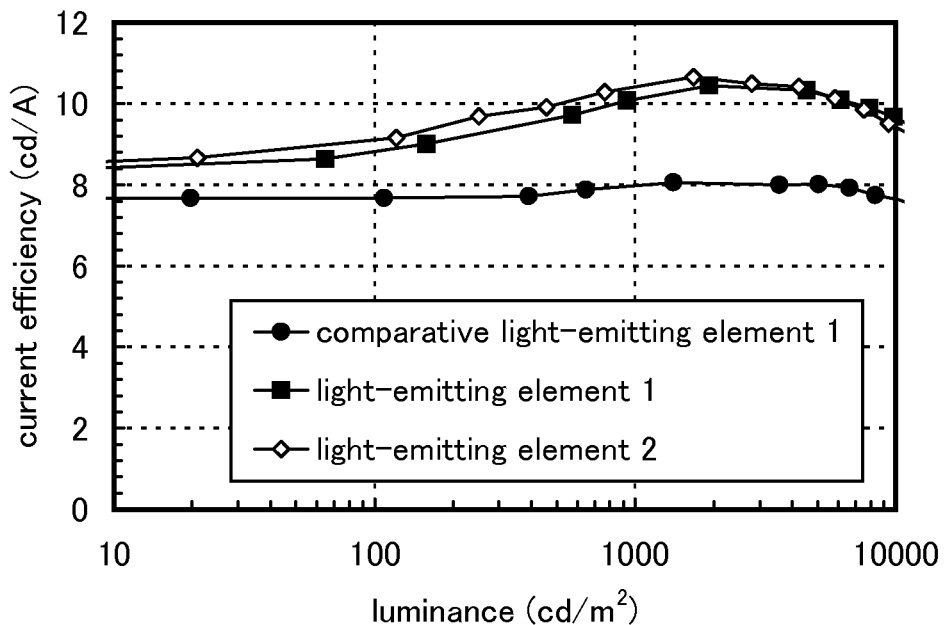
FIG. 32 shows luminance-current efficiency characteristics of the light-emitting elements and the comparative light-emitting element of Example 9.
Figure 33:
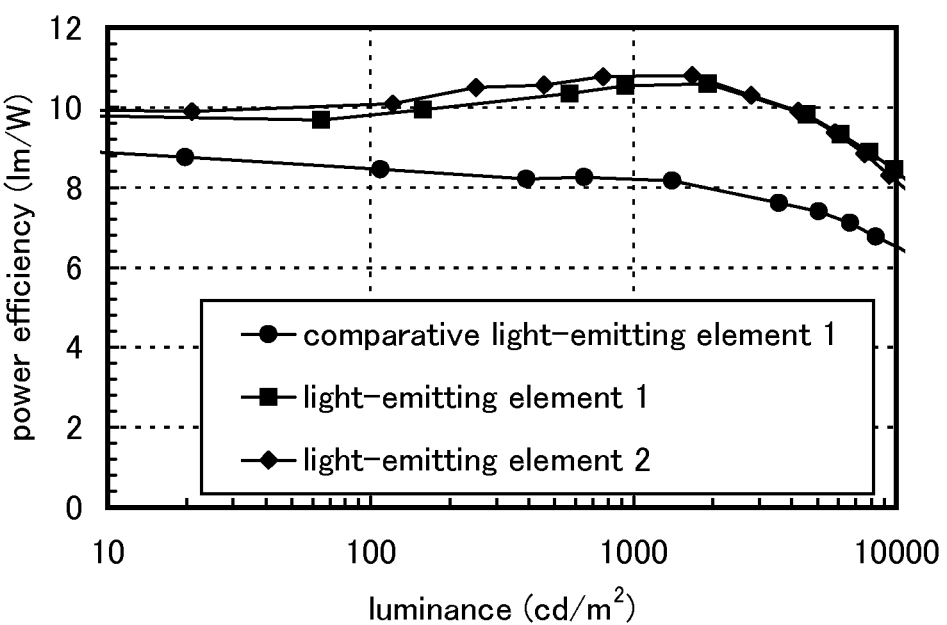
FIG. 33 shows luminance-power efficiency characteristics of the light-emitting elements and the comparative light-emitting element of Example 9.

FIG. 30 shows the emission spectra of the light-emitting element 1, the light-emitting element 2, and the comparative light-emitting element 1. In FIG. 30, the horizontal axis represents the wavelength (nm) and the vertical axis represents the emission intensity (arbitrary unit). FIG. 31, FIG. 32, and FIG. 33 respectively show the voltage-luminance characteristics, the luminance-current efficiency characteristics, and the luminance-power efficiency characteristics of the light-emitting element 1, the light-emitting element 2, and the comparative light-emitting element 1. In FIG. 31, the vertical axis represents the luminance (cd/m$^2$) and the horizontal axis represents the voltage (V). In FIG. 32, the vertical axis represents the current efficiency (cd/A) and the horizontal axis represents the luminance (cd/m$^2$). In FIG. 33, the vertical axis represents the power efficiency (lm/W) and the horizontal axis represents the luminance (cd/m$^2$).

According to FIG. 30, all of the emission spectra of the light-emitting element 1, the light-emitting element 2, and the comparative light-emitting element 1 have peaks around 470 nm. The CIE chromaticity coordinates in Table 3 also show that the light-emitting element 1, the light-emitting element 2, and the comparative light-emitting element 1 exhibit blue light emission originating from 1,6FLPAPrn and that all the elements have excellent carrier balance.

Further, FIGS. 31 to 33 and Table 3 show that the light-emitting element 1 and the light-emitting element 2 can be driven at a voltage as low as that of the comparative light-emitting element 1 and that the light-emitting element 1 and the light-emitting element 2 have higher efficiency than the comparative light-emitting element 1.

The reason for the above is probably as follows. The band gap of PCzPA used in the comparative light-emitting element 1 is 2.92 eV, and energy transfer from the light-emitting layer (transfer of excitons generated in the light-emitting layer) occurs when PCzPA is used for the hole-transport layer in contact with the light-emitting layer; in contrast, the band gaps of PCPN that was used for the hole-injection layer and the hole-transport layer of the light-emitting element 1 and of PCPPn that was used for the hole-injection layer and the hole-transport layer of the light-emitting element 2 in this example were respectively as large as 3.48 eV and 3.53 eV, which hinders the occurrence of energy transfer from the light-emitting layer.

The LUMO level of PCzPA is −2.77 eV and loss of carriers due to leakage of electrons from the light-emitting layer might occur. In contrast, the LUMO levels of PCPN and PCPPn are respectively as shallow as −2.29 eV and −2.25 eV, which hinders the occurrence of leakage of electrons from the respective light-emitting layers. Therefore, the light-emitting element 1 and the light-emitting element 2 were able to obtain high efficiency. In addition, the HOMO level of PCzPA is −5.69 eV, which is close to −5.70 eV that is the HOMO level of CzPA that is a host material of the adjacent light-emitting layer; thus, an excellent hole-injection property is obtained. The HOMO levels of PCPN and PCPPn are also as deep as −5.77 eV and −5.78 eV, respectively; thus, excellent hole-injection properties are obtained. In addition, the light-emitting elements 1 and 2 both can be driven at a voltage as low as that of the comparative light-emitting element 1, and thus have excellent carrier transfer.

Note that PCzPA is one of the materials that have excellent hole-transport properties and long lifetime.

Figure 34:
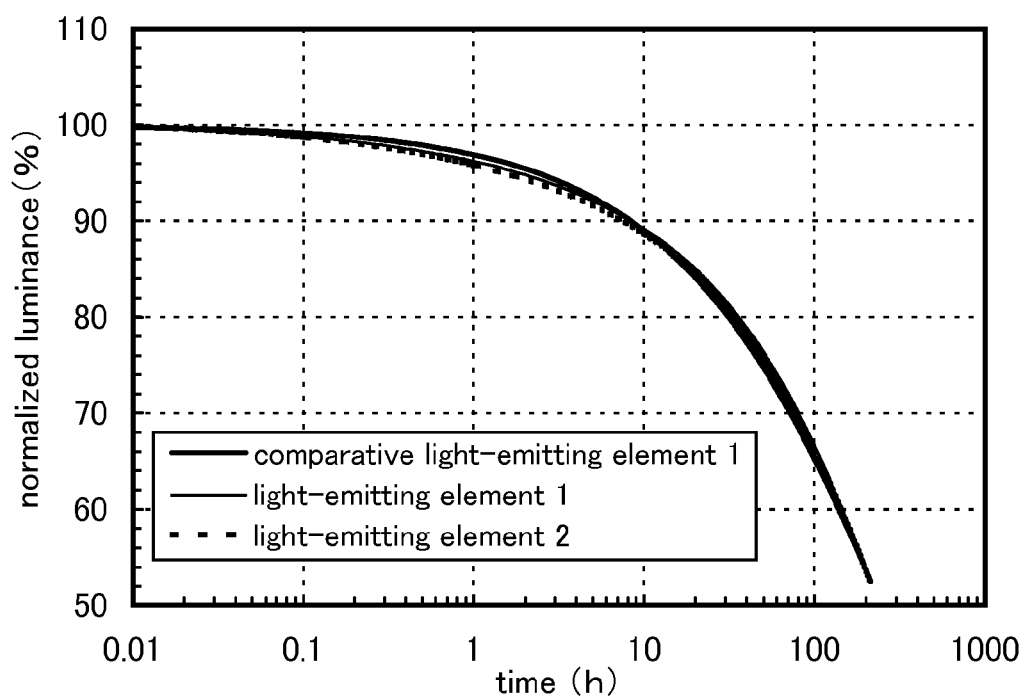
FIG. 34 shows results of a reliability test conducted on the light-emitting elements and the comparative light-emitting element of Example 9.

Further, a reliability test was conducted on the manufactured light-emitting element 1, light-emitting element 2, and comparative light-emitting element 1 were performed. In the reliability test, the initial luminance was set at 5000 cd/m$^2$, these elements were driven at a constant current density, and the luminance was measured at regular intervals. The results obtained by the reliability test are shown in FIG. 34. In FIG. 34, the horizontal axis represents the current flow time (hour) and the vertical axis represents the percentage of luminance to the initial luminance at each time, that is, normalized luminance (%).

According to FIG. 34, a reduction in the luminance of each of the light-emitting element 1, the light-emitting element 2, and the comparative light-emitting element 1 with time does not easily occur and the lifetime of each of the elements is long. The light-emitting element 1, the light-emitting element 2, and the comparative light-emitting element 1 maintained 52% of the initial luminance even after being driven for 210 hours.

As described above, the carbazole compound of one embodiment of the present invention is used for a hole-injection layer and a hole-transport layer, whereby an element with high emission efficiency can be obtained. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with low drive voltage can be manufactured.

Further, it was indicated that when the carbazole compound of one embodiment of the present invention is used for a hole-injection layer and a hole-transport layer, a light-emitting element with long lifetime can be manufactured.

EXAMPLE 10

In this example, manufacturing methods of light-emitting elements each of which is one embodiment of the present invention and measurement results of the element characteristics will be described together with the measurement results of a comparative light-emitting element.

Manufacturing methods of a light-emitting element 3, a light-emitting element 4, and a comparative light-emitting element 2 will be described below. Note that element structures of the light-emitting elements manufactured in this example are similar to that illustrated in FIG. 29. In addition, organic compounds used in this example were similar to those in Example 9; therefore, the description of the organic compounds is omitted.

(Light-Emitting Element 3)

The light-emitting element 3 was manufactured in a manner similar to that of the light-emitting element 1 in Example 9 except for the hole-injection layer 1111 and the hole-transport layer 1112.

In the light-emitting element 3, a film of molybdenum(VI) oxide was formed to a thickness of 10 nm by evaporation on the first electrode 1101 to form the hole-injection layer 1111.

Next, PCPN synthesized in Example 1 was deposited to a thickness of 30 nm on the hole-injection layer 1111 to form the hole-transport layer 1112.

(Light-Emitting Element 4)

The light-emitting element 4 was manufactured in a manner similar to that of the light-emitting element 3 except for the hole-transport layer 1112.

In the light-emitting element 4, PCPPn synthesized in Example 2 was deposited to a thickness of 30 nm to form the hole-transport layer 1112.

(Comparative Light-Emitting Element 2)

The comparative light-emitting element 2 was manufactured in a manner similar to that of the light-emitting element 3 except for the hole-transport layer 1112.

In the comparative light-emitting element 2, PCzPA was deposited to a thickness of 30 nm to form the hole-transport layer 1112.

Table 4 shows the element structures of the light-emitting element 3, the light-emitting element 4, and the comparative light-emitting element 2 that were manufactured as described above.

TABLE 4

|  | Light-Emitting Element 3 | Light-Emitting Element 4 | Comparative Light-Emitting Element 2 |
|---|---|---|---|
| First Electrode 1101 | ITSO 110 nm | ITSO 110 nm | ITSO 110 nm |
| Hole-injection Layer 1111 | MoOx 10 nm | MoOx 10 nm | MoOx 10 nm |
| Hole-transport layer 1112 | PCPN 30 nm | PCPPn 30 nm | PCzPA 30 nm |
| Light-emitting layer 1113 | CzPA:1,6FLPAPrn (=1:0.05) 30 nm | CzPA:1,6FLPAPrn (=1:0.05) 30 nm | CzPA:1,6FLPAPrn (=1:0.05) 30 nm |
| Electron-transport layer 1114a | CzPA 10 nm | CzPA 10 nm | CzPA 10 nm |
| 1114b | BPhen 15 nm | BPhen 15 nm | BPhen 15 nm |
| Electron-injection layer 1115 | LiF 1 nm | LiF 1 nm | LiF 1 nm |
| Second Electrode 1103 | Al 200 nm | Al 200 nm | Al 200 nm |

*The mixture ratios are all represented in weight ratios.

In a glove box containing a nitrogen atmosphere, the light-emitting element 3, the light-emitting element 4, and the comparative light-emitting element 2 were sealed so as not to be exposed to the air. After that, the operating characteristics of these elements were measured. Note that the measurement was carried out at room temperature (in an atmosphere kept at 25° C.).

Note that the light-emitting element 3, the light-emitting element 4, and the comparative light-emitting element 2 were formed over the same substrate. In addition, in the above three light-emitting elements, the respective components other than the hole-transport layers were formed at the same time, and the operating characteristics of three light-emitting elements were measured at the same time.

Table 5 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 3, the light-emitting element 4, and the comparative light-emitting element 2 at a luminance of about 1000 cd/m$^2$.

TABLE 5

|  | Light-Emitting Element 3 | Light-Emitting Element 4 | Comparative Light-Emitting Element 2 |
|---|---|---|---|
| Voltage (V) | 3.2 | 3.2 | 3.4 |
| Current density (mA/cm$^2$) | 6.9 | 6.2 | 8.9 |
| Chromaticity coordinates (x, y) | (0.15, 0.25) | (0.15, 0.26) | (0.15, 0.24) |
| Luminance (cd/m$^2$) | 930 | 820 | 920 |
| Current efficiency (cd/A) | 13 | 13 | 10 |
| Power efficiency (lm/W) | 13 | 13 | 9.5 |
| External quantum efficiency (%) | 8.1 | 8.0 | 6.5 |

Figure 35:
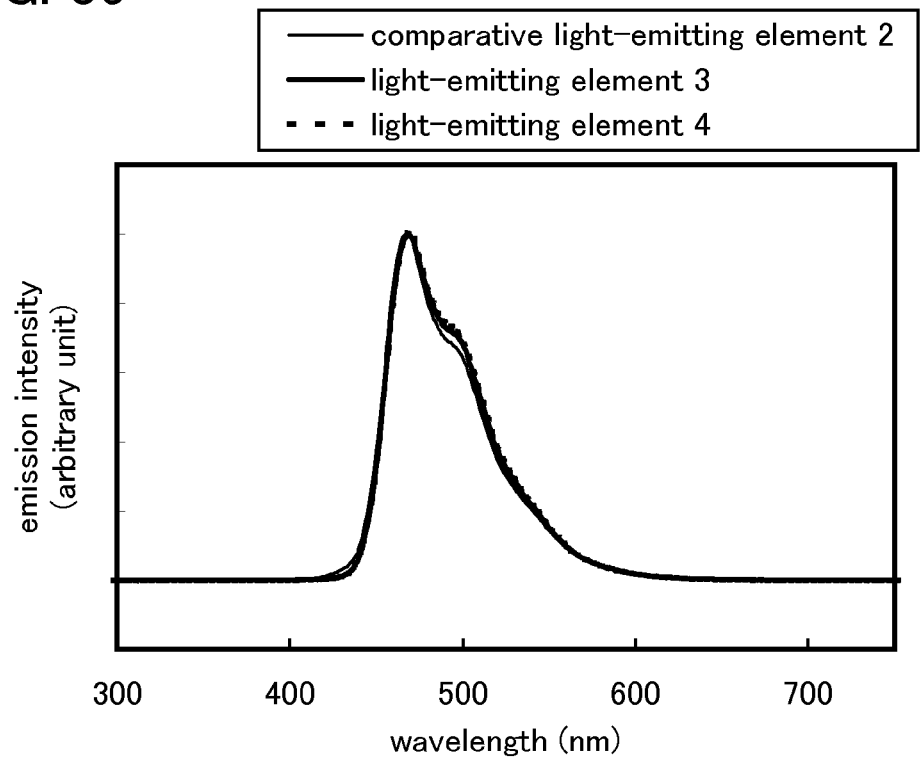
FIG. 35 shows emission spectra of light-emitting elements and a comparative light-emitting element of Example 10.
Figure 36:
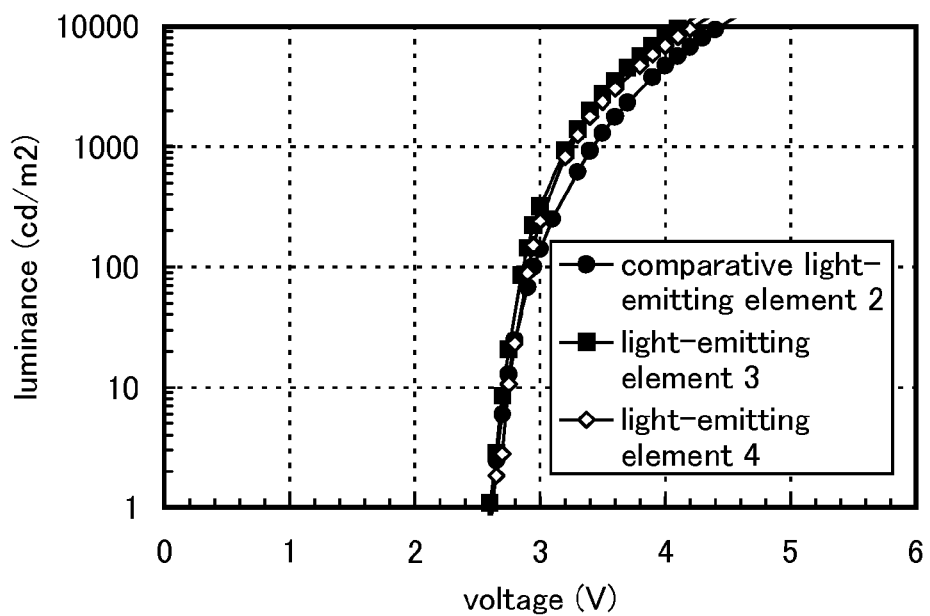
FIG. 36 shows voltage-luminance characteristics of the light-emitting elements and the comparative light-emitting element of Example 10.
Figure 37:
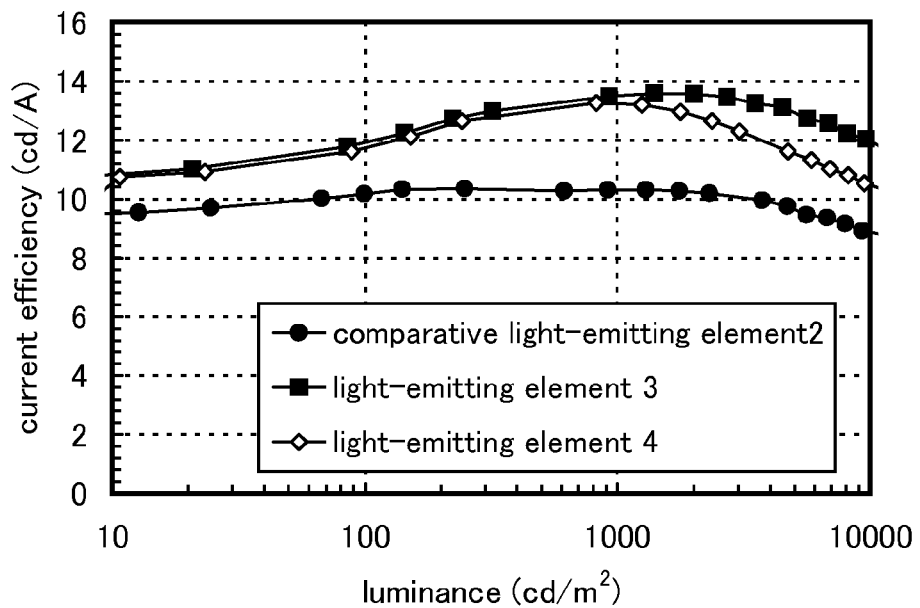
FIG. 37 shows luminance-current efficiency characteristics of the light-emitting elements and the comparative light-emitting element of Example 10.
Figure 38:
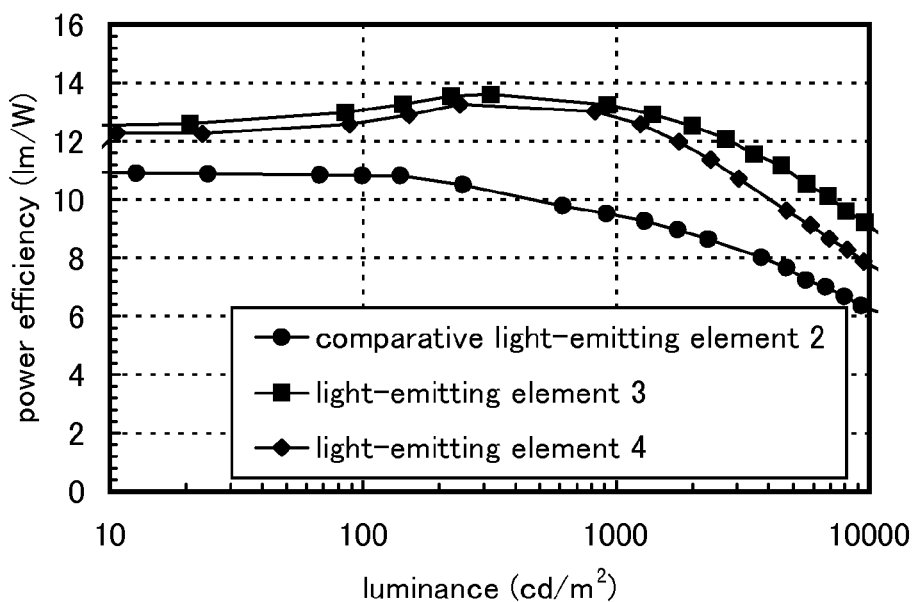
FIG. 38 shows luminance-power efficiency characteristics of the light-emitting elements and the comparative light-emitting element of Example 10.

FIG. 35 shows the emission spectra of the light-emitting element 3, the light-emitting element 4, and the comparative light-emitting element 2. In FIG. 35, the horizontal axis represents the wavelength (nm) and the vertical axis represents the emission intensity (arbitrary unit). FIG. 36, FIG. 37, and FIG. 38 respectively show the voltage-luminance characteristics, the luminance-current efficiency characteristics, and the luminance-power efficiency characteristics of the light-emitting element 3, the light-emitting element 4, and the comparative light-emitting element 2. In FIG. 36, the vertical axis represents the luminance (cd/m$^2$) and the horizontal axis represents the voltage (V). In FIG. 37, the vertical axis represents the current efficiency (cd/A) and the horizontal axis represents the luminance (cd/m$^2$). In FIG. 38, the vertical axis represents the power efficiency (lm/W) and the horizontal axis represents the luminance (cd/m$^2$).

According to FIG. 35, all of the emission spectra of the light-emitting element 3, the light-emitting element 4, and the comparative light-emitting element 2 have peaks around 470 nm. The CIE chromaticity coordinates in Table 5 also show that the light-emitting element 3, the light-emitting element 4, and the comparative light-emitting element 2 exhibit blue light emission originating from 1,6FLPAPrn and that all the elements have excellent carrier balance.

Further, FIG. 36, FIG. 37, FIG. 38, and Table 5 show that the light-emitting element 3 and the light-emitting element 4 have higher efficiency than the comparative light-emitting element 2. The reasons for the above are probably as follows: the band gaps of PCPN used for the hole-transport layer of the light-emitting element 3 and of PCPPn used for the hole-transport layer of the light-emitting element 4 in this example are wider than the band gap of PCzPA used for the comparative light-emitting element 2; energy transfer from the light-emitting layer does not easily occur; and the LUMO levels of PCPN and PCPPn are shallow enough to suppress leakage of electrons.

Figure 39:
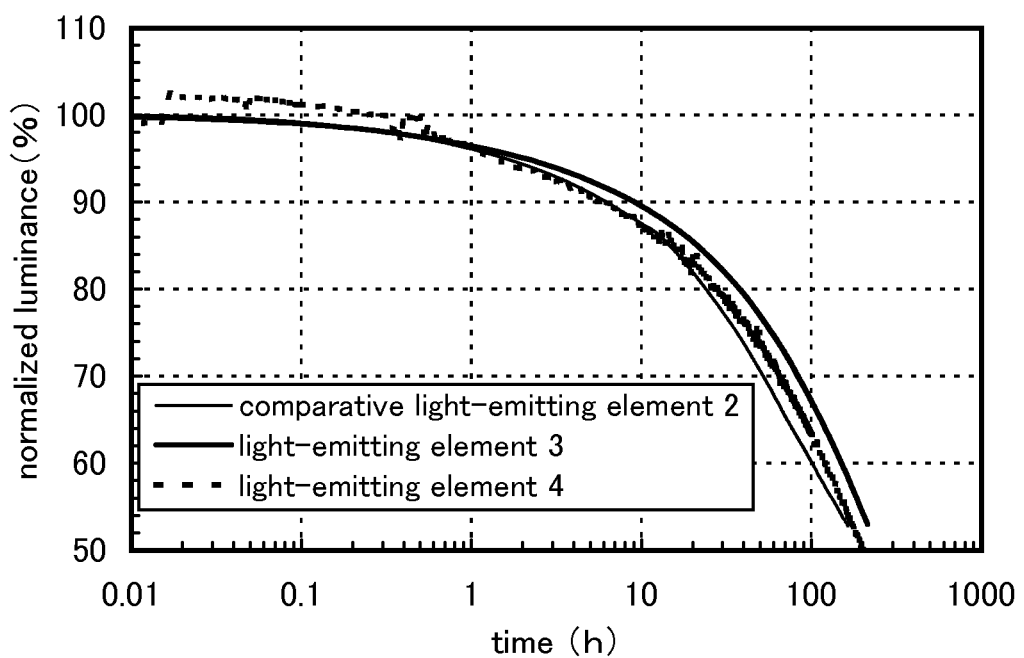
FIG. 39 shows results of a reliability test conducted on the light-emitting elements and the comparative light-emitting element of Example 10.

Further, a reliability test was conducted on the manufactured light-emitting element 3, light-emitting element 4, and comparative light-emitting element 2. In the reliability test, the initial luminance was set at 5000 cd/m$^2$, these elements were operated at a constant current density, and the luminance was measured at regular intervals. The results obtained by the reliability test are shown in FIG. 39. In FIG. 39, the horizontal axis represents the current flow time (hour) and the vertical axis represents the percentage of luminance to the initial luminance at each time, that is, normalized luminance (%).

According to FIG. 39, a reduction in the luminance of each of the light-emitting element 3, the light-emitting element 4, and the comparative light-emitting element 2 with time does not easily occur and the lifetime of each of the elements is long. The light-emitting element 3, the light-emitting element 4, and the comparative light-emitting element 2 respectively maintained 60%, 56%, and 54% of the initial luminance even after being driven for 150 hours.

In this example, a single film of molybdenum oxide was used for the hole-injection layer. The drive voltage of all the elements in this example was slightly higher than that in Example 9, in which the mixed material of the carbazole compound of one embodiment of the present invention and molybdenum oxide was used for the hole-injection layer. This indicates that when a mixed material of the carbazole compound of one embodiment of the present invention and molybdenum oxide is used for a hole-injection layer, an element with an excellent hole-injection property can be obtained.

As described above, the carbazole compound of one embodiment of the present invention is used for a hole-injection layer and a hole-transport layer, whereby an element with high emission efficiency can be manufactured. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with long lifetime can be obtained.

Further, it was indicated that even in a light-emitting element in which a hole-injection layer is formed of a single layer of molybdenum oxide, excellent characteristics can be obtained. Note that a hole-injection layer is preferably formed using a composite material, in which case a short circuit of a light-emitting element which is attributed to film quality of an anode can be prevented.

EXAMPLE 11

In this example, manufacturing methods of a light-emitting element which is one embodiment of the present invention and the measurement results of the element characteristics will be described together with the measurement results of a comparative light-emitting element.

Manufacturing methods of a light-emitting element 5 and a comparative light-emitting element 3 will be described below. Note that element structures of the light-emitting elements manufactured in this example are similar to that illustrated in FIG. 29. In addition, organic compounds used in this example were similar to those in Example 9; therefore, the description of the organic compounds is omitted.
(Light-Emitting Element 5)

The light-emitting element 5 was manufactured in a manner similar to that of the light-emitting element 1 in Example 9 except for the hole-injection layer 1111 and the hole-transport layer 1112.

In the light-emitting element 5, the hole-injection layer 1111 was formed in such a manner that 9-(1-naphthyl)-3-[4-(1-naphthyl)-phenyl]-9H-carbazole (abbreviation: NCPN) synthesized in Example 6 and molybdenum(VI) oxide were co-evaporated on the first electrode 1101. The thickness of the hole-injection layer 1111 was 50 nm. The weight ratio of NCPN to molybdenum(VI) oxide was adjusted to 4:2 (=NCPN:molybdenum oxide).

Next, NCPN was deposited to a thickness of 10 nm on the hole-injection layer 1111 to form the hole-transport layer 1112.
(Comparative Light-Emitting Element 3)

The comparative light-emitting element 3 was manufactured in a manner similar to that of the comparative light-emitting element 1 in Example 9.

Table 6 shows the element structures of the light-emitting element 5 and the comparative light-emitting element 3 obtained as described above.

TABLE 6

|  | Light-Emitting Element 5 | Comparative Light-Emitting Element 3 |
|---|---|---|
| First Electrode 1101 | ITSO 110 nm | ITSO 110 nm |
| Hole-injection Layer 1111 | NCPN:MoOx (=4:2) 50 nm | PCzPA:MoOx (=4:2) 50 nm |
| Hole-transport layer 1112 | NCPN 10 nm | PCzPA 10 nm |
| Light-emitting layer 1113 | CzPA:1,6FLPAPrn (=1:0.05) 30 nm | CzPA:1,6FLPAPrn (=1:0.05) 30 nm |
| Electron-transport layer 1114a | CzPA 10 nm | CzPA 10 nm |
| 1114b | BPhen 15 nm | BPhen 15 nm |
| Electron-injection layer 1115 | LiF 1 nm | LiF 1 nm |
| Second Electrode 1103 | Al 200 nm | Al 200 nm |

*The mixture ratios are all represented in weight ratios.

In a glove box containing a nitrogen atmosphere, the light-emitting element 5 and the comparative light-emitting element 3 were sealed so as not to be exposed to the air. After that, the operating characteristics of these elements were measured. Note that the measurement was carried out at room temperature (in an atmosphere kept at 25° C.).

Note that the light-emitting element 5 and the comparative light-emitting element 3 were formed over the same substrate. In addition, in the above two light-emitting elements, the respective components other than the hole-injection layers and the hole-transport layers were formed at the same time, and the operating characteristics of the two light-emitting elements were measured at the same time.

Table 7 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 5 and the comparative light-emitting element 3 at a luminance of about 1000 cd/m$^2$.

TABLE 7

|  | Light-Emitting Element 5 | Comparative Light-Emitting Element 3 |
|---|---|---|
| Voltage (V) | 3.1 | 3.0 |
| Current density (mA/cm$^2$) | 11 | 11 |
| Chromaticity coordinates (x, y) | (0.15, 0.22) | (0.15, 0.22) |
| Luminance (cd/m$^2$) | 1000 | 800 |
| Current efficiency (cd/A) | 9.2 | 7.5 |
| Power efficiency (lm/W) | 9.5 | 7.8 |
| External quantum efficiency (%) | 6.2 | 5.1 |

Figure 40:
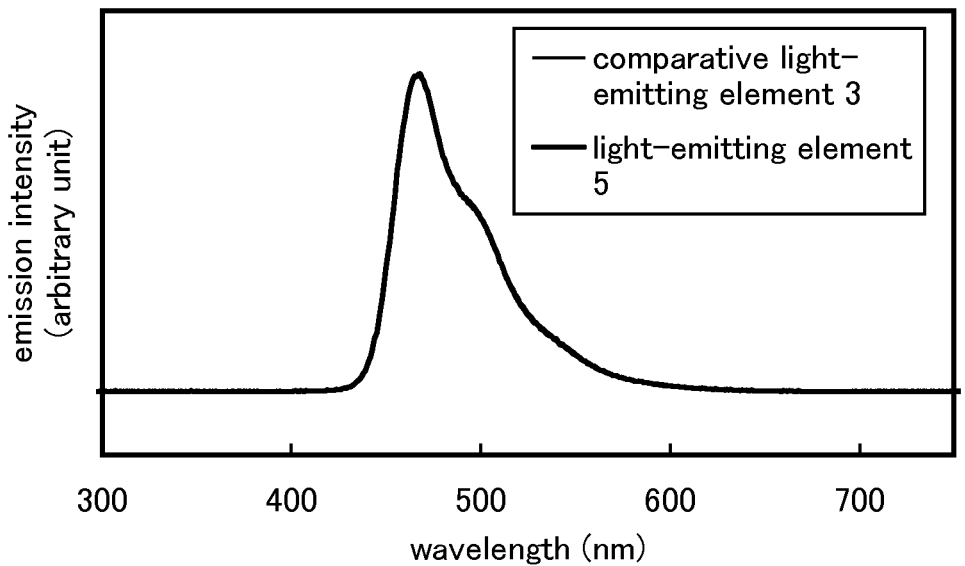
FIG. 40 shows emission spectra of a light-emitting element and a comparative light-emitting element of Example 11.
Figure 41:
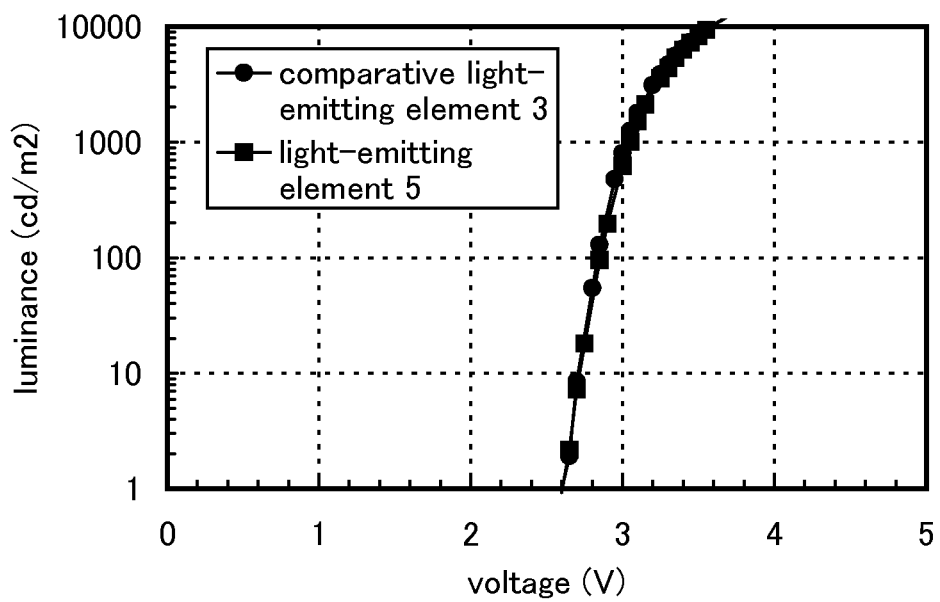
FIG. 41 shows voltage-luminance characteristics of the light-emitting element and the comparative light-emitting element of Example 11.
Figure 42:
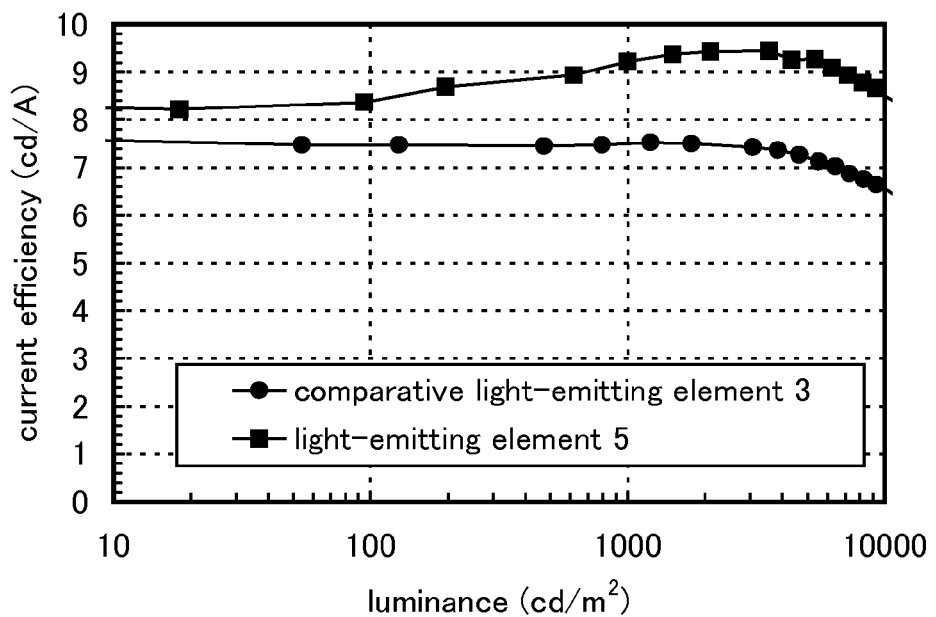
FIG. 42 shows luminance-current efficiency characteristics of the light-emitting element and the comparative light-emitting element of Example 11.
Figure 43:
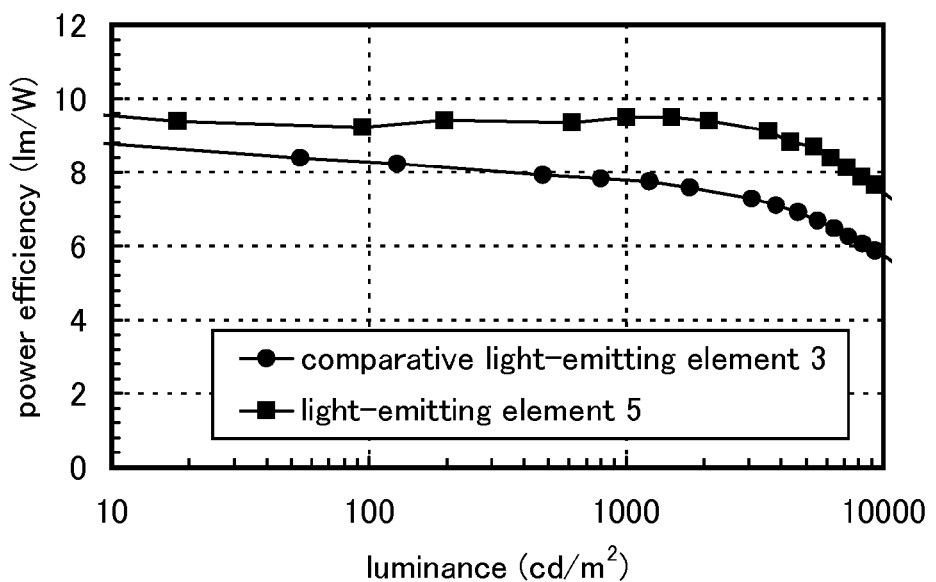
FIG. 43 shows luminance-power efficiency characteristics of the light-emitting element and the comparative light-emitting element of Example 11.

FIG. 40 shows the emission spectra of the light-emitting element 5 and the comparative light-emitting element 3. In FIG. 40, the horizontal axis represents the wavelength (nm) and the vertical axis represents the emission intensity (arbitrary unit). FIG. 41, FIG. 42, and FIG. 43 respectively show the voltage-luminance characteristics, the luminance-current efficiency characteristics, and the luminance-power efficiency characteristics of the light-emitting element 5 and the comparative light-emitting element 3. In FIG. 41, the vertical axis represents the luminance (cd/m²) and the horizontal axis represents the voltage (V). In FIG. 42, the vertical axis represents the current efficiency (cd/A) and the horizontal axis represents the luminance (cd/m²). In FIG. 43, the vertical axis represents the power efficiency (lm/W) and the horizontal axis represents the luminance (cd/m²).

According to FIG. 40, all of the emission spectra of the light-emitting element 5 and the comparative light-emitting element 3 have peaks around 470 nm. The CIE chromaticity coordinates in Table 7 also show that the light-emitting element 5 and the comparative light-emitting element 3 exhibit blue light emission originating from 1,6FLPAPrn and that all the elements have excellent carrier balance.

Further, FIG. 41, FIG. 42, FIG. 43, and Table 7 show that the light-emitting element 5 has higher efficiency than the comparative light-emitting element 3. The reasons for the above are probably as follows: the band gap of NCPN used for the hole-injection layer and the hole-transport layer of the light-emitting element 5 in this example is wider than the band gap of PCzPA used for the comparative light-emitting element 3; energy transfer from the light-emitting layer does not easily occur; and the LUMO level of NCPN is shallow enough to prevent electrons from passing through the light-emitting layer.

Further, FIGS. 41 to 43 and Table 7 show that the light-emitting element 5 and the comparative light-emitting element 3 can be driven at low voltage.

Figure 44:
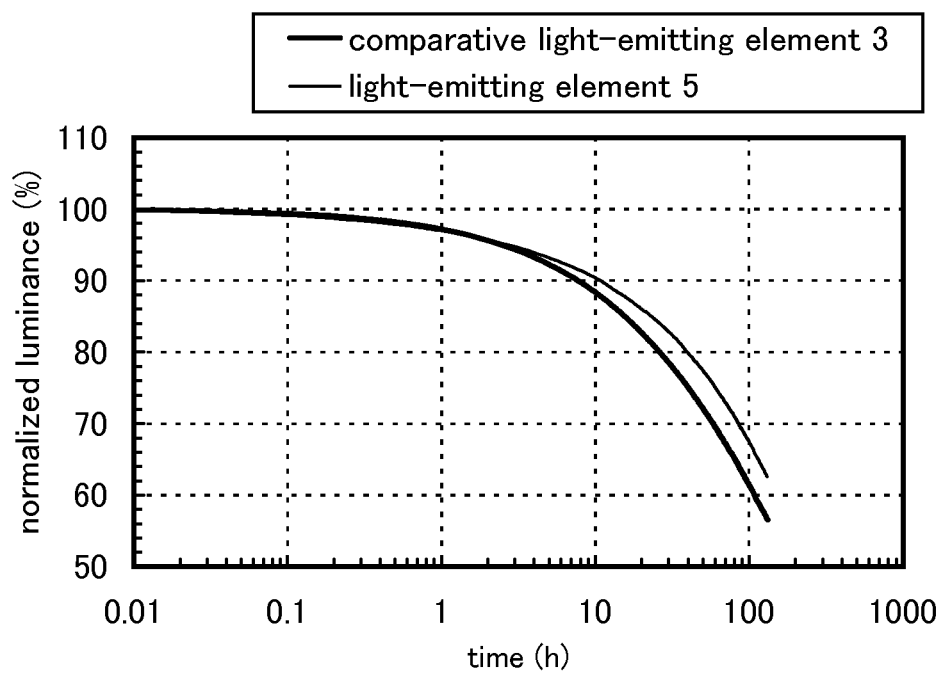
FIG. 44 shows results of a reliability test conducted on the light-emitting element and the comparative light-emitting element of Example 11.

Further, a reliability test was conducted on the manufactured light-emitting element 5 and comparative light-emitting element 3. In the reliability test, the initial luminance was set at 5000 cd/m², these elements were operated at a constant current density, and the luminance was measured at regular intervals. The results obtained by the reliability test are shown in FIG. 44. In FIG. 44, the horizontal axis represents the current flow time (hour) and the vertical axis represents the percentage of luminance to the initial luminance at each time, that is, normalized luminance (%).

As shown in FIG. 44, a reduction in the luminance of each of the light-emitting element 5 and the comparative light-emitting element 3 with time does not easily occur and the lifetime of each of the elements is long. The light-emitting element 5 and the comparative light-emitting element 3 respectively maintained 62% and 57% of the initial luminance even after being driven for 130 hours.

As described above, the carbazole compound of one embodiment of the present invention is used for a hole-injection layer and a hole-transport layer, whereby an element with high emission efficiency can be manufactured. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with low drive voltage can be manufactured.

Further, it was indicated that when the carbazole compound of one embodiment of the present invention is used for a hole-injection layer and a hole-transport layer, a light-emitting element with long lifetime can be manufactured.

EXAMPLE 12

In this example, manufacturing methods of a light-emitting element which is one embodiment of the present invention and the measurement results of the element characteristics will be described together with the measurement results of a comparative light-emitting element.

Manufacturing methods of a light-emitting element 6 and a comparative light-emitting element 4 will be described below. Note that element structures of the light-emitting elements manufactured in this example are similar to that illustrated in FIG. 29. In addition, organic compounds used in this example were similar to those in Example 9 were used in this example; therefore, the description of the organic compounds is omitted.

(Light-Emitting Element 6)

The light-emitting element 6 was manufactured in a manner similar to that of the light-emitting element 1 in Example 9 except for the hole-injection layer 1111 and the hole-transport layer 1112.

In the light-emitting element 6, the hole-injection layer 1111 was formed in such a manner that 3,6-bis-[4-(1-naphthyl)-phenyl]-9-phenyl-9H-carbazole (abbreviation: NP2PC) synthesized in Example 7 and molybdenum(VI) oxide were co-evaporated on the first electrode 1101. The thickness of the hole-injection layer 1111 was 50 nm. The weight ratio of NP2PC to molybdenum(VI) oxide was adjusted to 4:2 (=NP2PC:molybdenum oxide).

Next, NP2PC was deposited to a thickness of 10 nm on the hole-injection layer 1111 to form the hole-transport layer 1112.

(Comparative Light-Emitting Element 4)

The comparative light-emitting element 4 was manufactured in a manner similar to that of the comparative light-emitting element 1 in Example 9.

Table 8 shows the element structures of the light-emitting element 6 and the comparative light-emitting element 4 obtained as described above.

TABLE 8

|  | Light-Emitting Element 6 | Comparative Light-Emitting Element 4 |
| --- | --- | --- |
| First Electrode 1101 | ITSO 110 nm | ITSO 110 nm |
| Hole-injection Layer 1111 | NP2PC:MoOx (=4:2) 50 nm | PCzPA:MoOx (=4:2) 50 nm |
| Hole-transport layer 1112 | NP2PC 10 nm | PCzPA 10 nm |
| Light-emitting layer 1113 | CzPA:1,6FLPAPrn (=1:0.05) 30 nm | CzPA:1,6FLPAPrn (=1:0.05) 30 nm |
| Electron-transport layer 1114a | CzPA 10 nm | CzPA 10 nm |
| 1114b | BPhen 15 nm | BPhen 15 nm |
| Electron-injection layer 1115 | LiF 1 nm | LiF 1 nm |
| Second Electrode 1103 | Al 200 nm | Al 200 nm |

*The mixture ratios are all represented in weight ratios.

In a glove box containing a nitrogen atmosphere, the light-emitting element 6 and the comparative light-emitting element 4 were sealed so as not to be exposed to the air. After that, the operating characteristics of these elements were measured. Note that the measurement was carried out at room temperature (in an atmosphere kept at 25° C.).

Note that the light-emitting element 6 and the comparative light-emitting element 4 were formed over the same substrate. In addition, in the above two light-emitting elements, the respective components other than the hole-injection layers and the hole-transport layers were formed at the same time, and the operating characteristics of the two light-emitting elements were measured at the same time.

Table 9 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 6 and the comparative light-emitting element 4 at a luminance of about 1000 cd/m$^2$.

TABLE 9

|  | Light-Emitting Element 6 | Comparative Light-Emitting Element 4 |
| --- | --- | --- |
| Voltage (V) | 3.1 | 3.1 |
| Current density (mA/cm$^2$) | 13 | 15 |
| Chromaticity coordinates (x, y) | (0.15, 0.23) | (0.15, 0.22) |
| Luminance (cd/m$^2$) | 1120 | 1090 |
| Current efficiency (cd/A) | 8.9 | 7.4 |
| Power efficiency (lm/W) | 9.1 | 7.6 |
| External quantum efficiency (%) | 5.8 | 5.1 |

Figure 45:
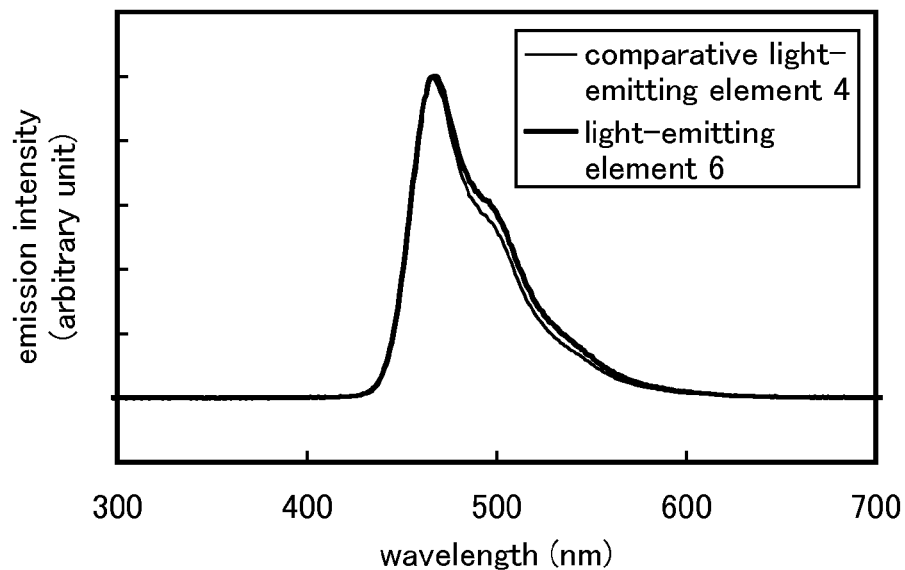
FIG. 45 shows emission spectra of a light-emitting element and a comparative light-emitting element of Example 12.
Figure 46:
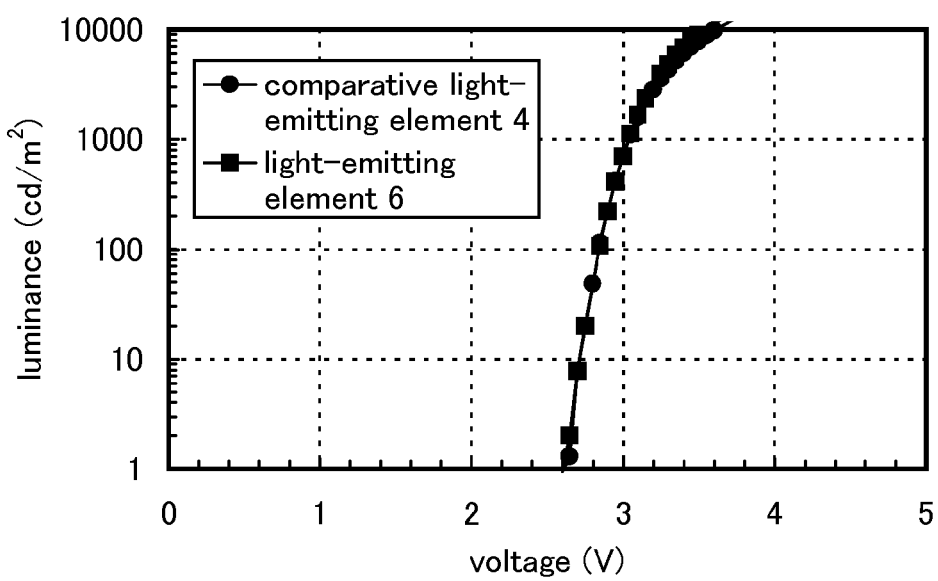
FIG. 46 shows voltage-luminance characteristics of the light-emitting element and the comparative light-emitting element of Example 12.
Figure 47:
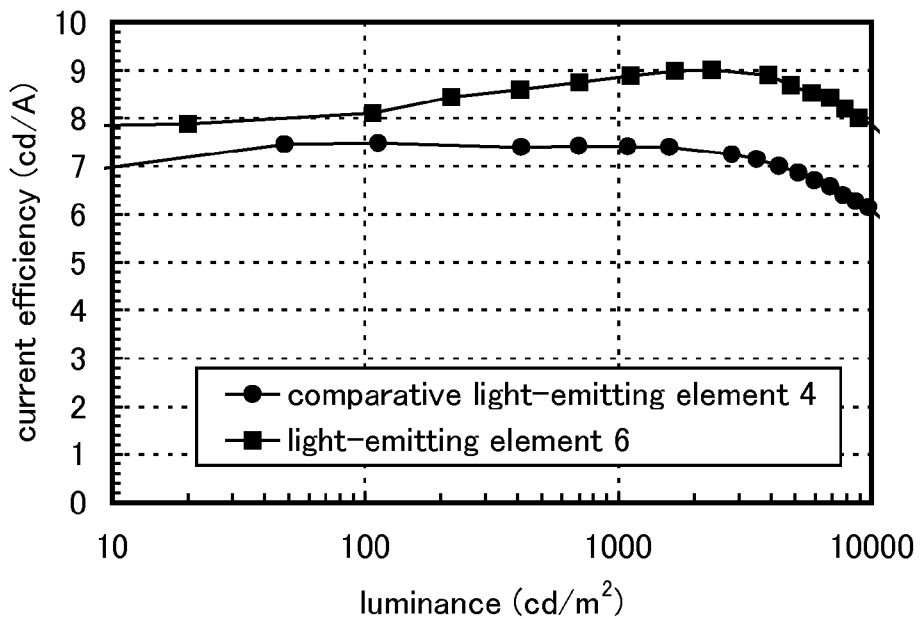
FIG. 47 shows luminance-current efficiency characteristics of the light-emitting element and the comparative light-emitting element of Example 12.
Figure 48:
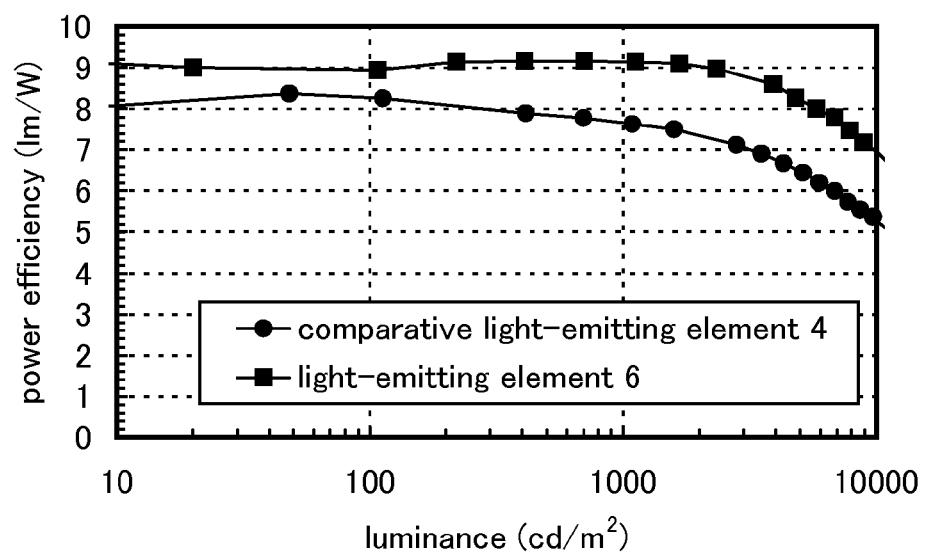
FIG. 48 shows luminance-power efficiency characteristics of the light-emitting element and the comparative light-emitting element of Example 12.

FIG. 45 shows the emission spectra of the light-emitting element 6 and the comparative light-emitting element 4. In FIG. 45, the horizontal axis represents the wavelength (nm) and the vertical axis represents the emission intensity (arbitrary unit). FIG. 46, FIG. 47, and FIG. 48 respectively show the voltage-luminance characteristics, the luminance-current efficiency characteristics, and the luminance-power efficiency characteristics of the light-emitting element 6 and the comparative light-emitting element 4. In FIG. 46, the vertical axis represents the luminance (cd/m$^2$) and the horizontal axis represents the voltage (V). In FIG. 47, the vertical axis represents the current efficiency (cd/A) and the horizontal axis represents the luminance (cd/m$^2$). In FIG. 48, the vertical axis represents the power efficiency (lm/W) and the horizontal axis represents the luminance (cd/m$^2$).

According to FIG. 45, all of the emission spectra of the light-emitting element 6 and the comparative light-emitting element 4 have peaks around 470 nm. The CIE chromaticity coordinates in Table 9 also show that the light-emitting element 6 and the comparative light-emitting element 4 exhibit blue light emission originating from 1,6FLPAPrn and that all the elements have excellent carrier balance.

Further, FIG. 46, FIG. 47, FIG. 48, and Table 9 show that the light-emitting element 6 has higher efficiency than the comparative light-emitting element 4. The reasons for the above are probably as follows: the band gap of NP2PC used for the hole-injection layer and the hole-transport layer of the light-emitting element 6 in this example is wider than the band gap of PCzPA used for the comparative light-emitting element 4; energy transfer from the light-emitting layer does not easily occur; and the LUMO level of NP2PC is shallow enough to prevent electrons from passing through the light-emitting layer.

Further, FIGS. 46 to 48 and Table 9 show that the light-emitting element 6 and the comparative light-emitting element 4 can be driven at low voltage.

Figure 49:
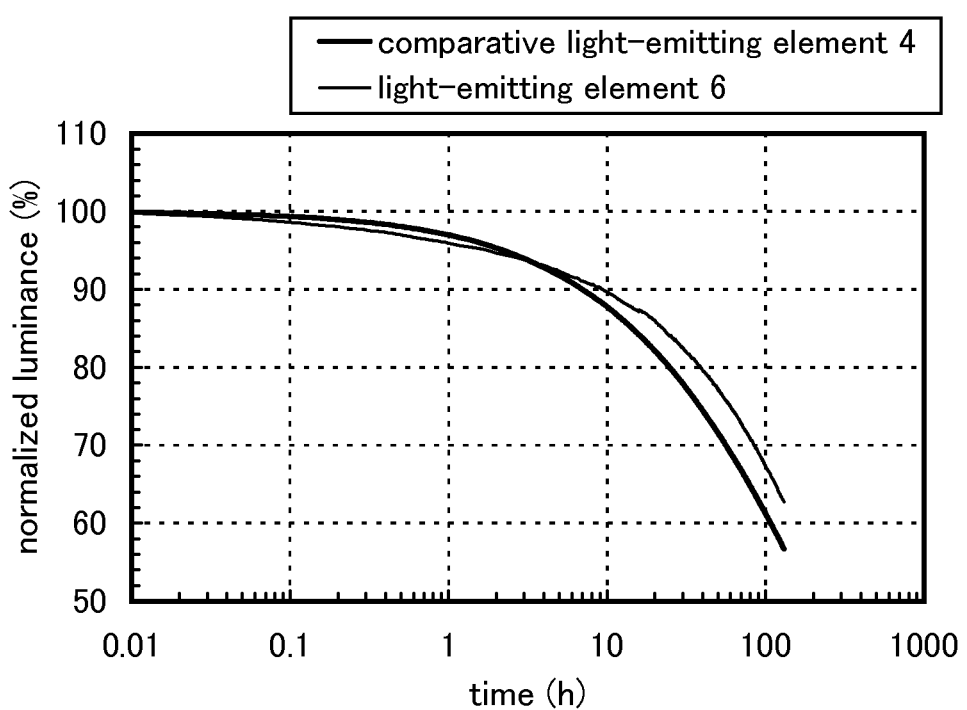
FIG. 49 shows results of a reliability test conducted on the light-emitting element and the comparative light-emitting element of Example 12.

Further, a reliability test was conducted on the manufactured light-emitting element 6 and comparative light-emitting element 4. In the reliability test, the initial luminance was set at 5000 cd/m$^2$, these elements were operated at a constant current density, and the luminance was measured at regular intervals. The results obtained by the reliability test are shown in FIG. 49. In FIG. 49, the horizontal axis represents the current flow time (hour) and the vertical axis represents the percentage of luminance to the initial luminance at each time, that is, normalized luminance (%).

As shown in FIG. 49, a reduction in the luminance of each of the light-emitting element 6 and the comparative light-emitting element 4 with time does not easily occur and the lifetime of each of the elements is long. The light-emitting element 6 and the comparative light-emitting element 4 respectively maintained 63% and 57% of the initial luminance even after being driven for 130 hours.

As described above, the carbazole compound of one embodiment of the present invention is used for a hole-injection layer and a hole-transport layer, whereby an element with high emission efficiency can be manufactured. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with low drive voltage can be manufactured.

Further, it was indicated that when the carbazole compound of one embodiment of the present invention is used for a hole-injection layer and a hole-transport layer, a light-emitting element with long lifetime can be manufactured.

EXAMPLE 13

In this example, a manufacturing method of a light-emitting element which is one embodiment of the present invention and measurement results of element characteristics will be described together with measurement results of a comparative light-emitting element.

Manufacturing methods of a light-emitting element 7 and a comparative light-emitting element 5 will be described below. Note that element structures of the light-emitting elements manufactured in this example are similar to that illustrated in FIG. 29. In addition, organic compound used in this example were similar to those in Example 9; therefore, the description of the organic compounds is omitted.

(Light-Emitting Element 7)

The light-emitting element 7 was manufactured in a manner similar to that of the light-emitting element 1 in Example 9 except for the hole-injection layer 1111 and the hole-transport layer 1112.

In the light-emitting element 7, the hole-injection layer 1111 was formed in such a manner that 3-[3-(9-phenanthryl)-phenyl]-9-phenyl-9H-carbazole (abbreviation: mPCPPn) synthesized in Example 4 and molybdenum(VI) oxide were co-evaporated on the first electrode 1101. The thickness of the hole-injection layer 1111 was 50 nm. The weight ratio of mPCPPn to molybdenum(VI) oxide was adjusted to 4:2 (=mPCPPn:molybdenum oxide).

Next, mPCPPn was deposited to a thickness of 10 nm on the hole-injection layer 1111 to form the hole-transport layer 1112.

(Comparative Light-Emitting Element 5)

The comparative light-emitting element 5 was manufactured in a manner similar to that of the comparative light-emitting element 1 in Example 9.

Table 10 shows the element structures of the light-emitting element 7 and the comparative light-emitting element 5 that were obtained as described above.

TABLE 10

|  | Light-Emitting Element 7 | Comparative Light-Emitting Element 5 |
|---|---|---|
| First Electrode 1101 | ITSO 110 nm | ITSO 110 nm |
| Hole-injection Layer 1111 | mPCPPn:MoOx (=4:2) 50 nm | PCzPA:MoOx (=4:2) 50 nm |
| Hole-transport layer 1112 | mPCPPn 10 nm | PCzPA 10 nm |
| Light-emitting layer 1113 | CzPA:1,6FLPAPrn (=1:0.05) 30 nm | CzPA:1,6FLPAPrn (=1:0.05) 30 nm |
| Electron-transport 1114a layer | CzPA 10 nm | CzPA 10 nm |
| 1114b | BPhen 15 nm | BPhen 15 nm |
| Electron-injection layer 1115 | LiF 1 nm | LiF 1 nm |
| Second Electrode 1103 | Al 200 nm | Al 200 nm |

*The mixture ratios are all represented in weight ratios.

In a glove box containing a nitrogen atmosphere, the light-emitting element 7 and the comparative light-emitting element 5 were sealed so as not to be exposed to the air. After that, the operating characteristics of these elements were measured. Note that the measurement was carried out at room temperature (in an atmosphere kept at 25° C.).

Note that the light-emitting element 7 and the comparative light-emitting element 5 were formed over the same substrate. In addition, in the above two light-emitting elements, the respective components other than the hole-injection layers and the hole-transport layers were formed at the same time, and the operating characteristics of the two light-emitting elements were measured at the same time.

Table 11 shows the voltage (V), current density (mA/cm$^2$), CIE chromaticity coordinates (x, y), luminance (cd/m$^2$), current efficiency (cd/A), power efficiency (lm/W), and external quantum efficiency (%) of each of the light-emitting element 7 and the comparative light-emitting element 5 at a luminance of about 1000 cd/m$^2$.

TABLE 11

|  | Light-Emitting Element 7 | Comparative Light-Emitting Element 5 |
|---|---|---|
| Voltage (V) | 3.1 | 3.0 |
| Current density (mA/cm$^2$) | 8.8 | 7.0 |
| Chromaticity coordinates (x, y) | (0.15, 0.20) | (0.15, 0.20) |
| Luminance (cd/m$^2$) | 880 | 500 |
| Current efficiency (cd/A) | 10 | 7.2 |
| Power efficiency (lm/W) | 10 | 7.5 |
| External quantum efficiency (%) | 7.1 | 5.2 |

Figure 50:
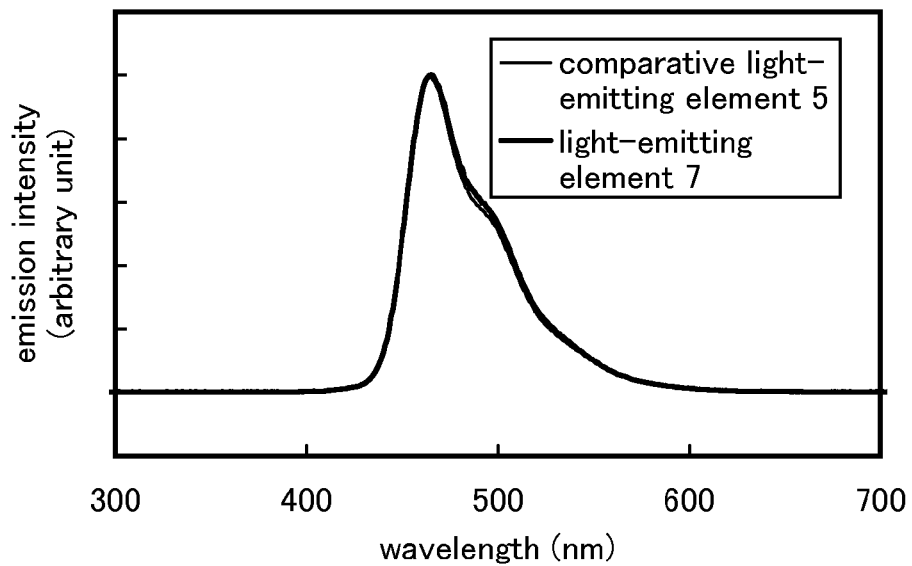
FIG. 50 shows emission spectra of a light-emitting element and a comparative light-emitting element of Example 13.
Figure 51:
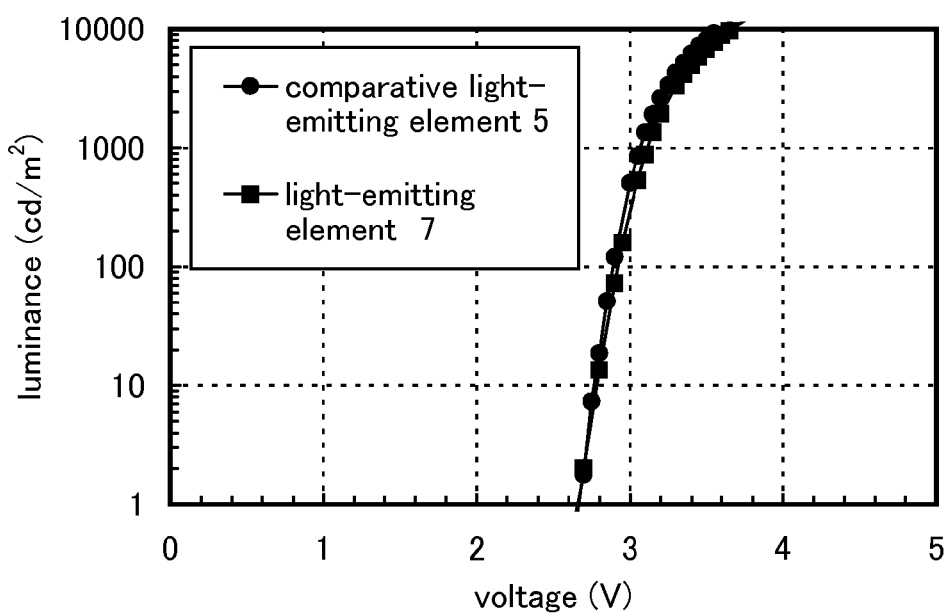
FIG. 51 shows voltage-luminance characteristics of the light-emitting element and the comparative light-emitting element of Example 13.
Figure 52:
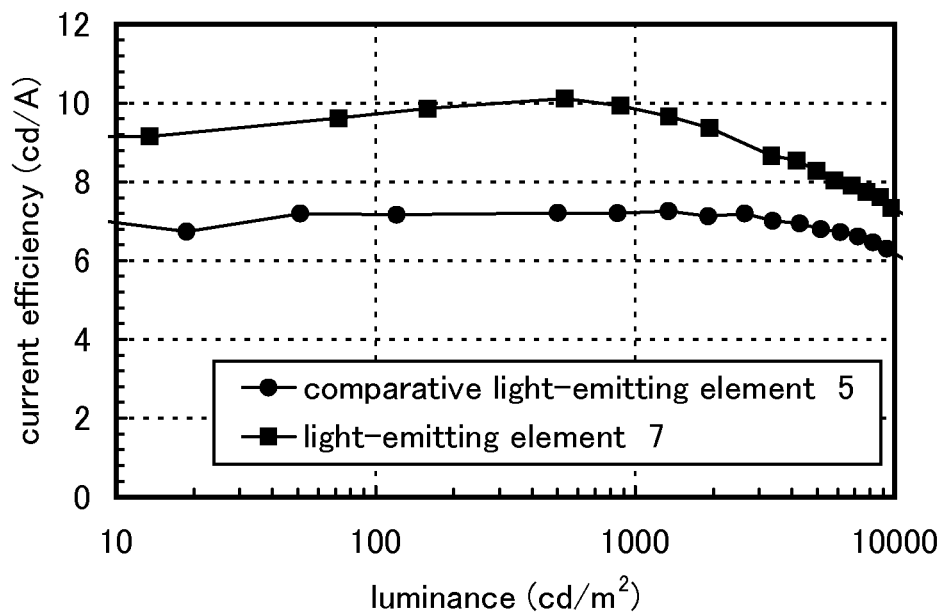
FIG. 52 shows luminance-current efficiency characteristics of the light-emitting element and the comparative light-emitting element of Example 13.
Figure 53:
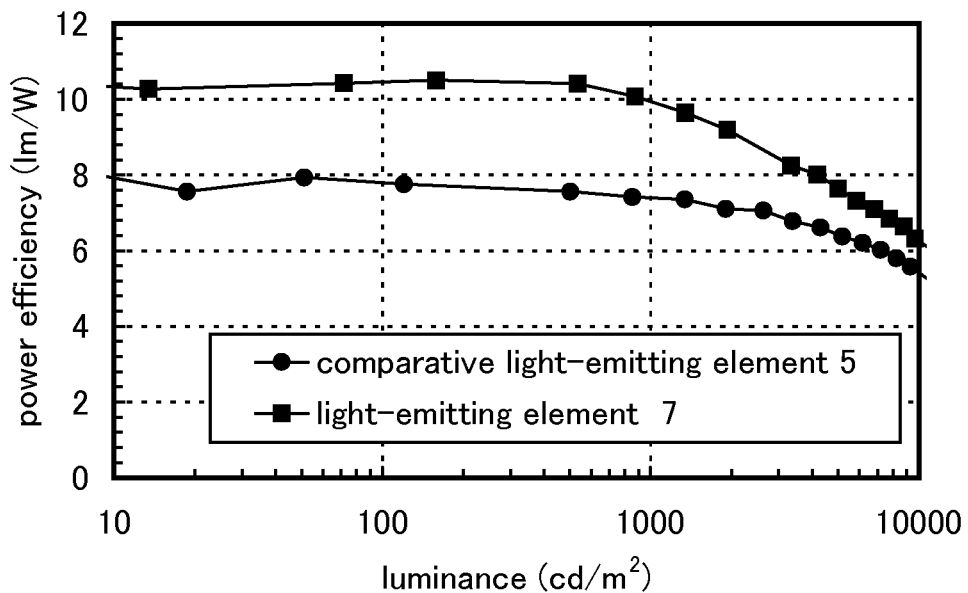
FIG. 53 shows luminance-power efficiency characteristics of the light-emitting element and the comparative light-emitting element of Example 13.

FIG. 50 shows the emission spectra of the light-emitting element 7 and the comparative light-emitting element 5. In FIG. 50, the horizontal axis represents the wavelength (nm) and the vertical axis represents the emission intensity (arbitrary unit). FIG. 51, FIG. 52, and FIG. 53 respectively show the voltage-luminance characteristics, the luminance-current efficiency characteristics, and the luminance-power efficiency characteristics of the light-emitting element 7 and the comparative light-emitting element 5. In FIG. 51, the vertical axis represents the luminance (cd/m$^2$) and the horizontal axis represents the voltage (V). In FIG. 52, the vertical axis represents the current efficiency (cd/A) and the horizontal axis represents the luminance (cd/m$^2$). In FIG. 53, the vertical axis represents the power efficiency (lm/W) and the horizontal axis represents the luminance (cd/m$^2$).

According to FIG. 50, all of the emission spectra of the light-emitting element 7 and the comparative light-emitting element 5 have peaks around 470 nm. The CIE chromaticity coordinates in Table 11 also show that the light-emitting element 7 and the comparative light-emitting element 5 exhibit blue light emission originating from 1,6FLPAPrn and that all the elements have excellent carrier balance.

Further, FIG. 51, FIG. 52, and Table 11 show that the light-emitting element 7 has higher efficiency than the comparative light-emitting element 5. The reasons for the above are probably as follows: the band gap of mPCPPn used for the hole-injection layer and the hole-transport layer of the light-emitting element 7 in this example is wider than the band gap of PCzPA used for the comparative light-emitting element 5; energy transfer from the light-emitting layer does not easily occur; and the LUMO level of mPCPPn is shallow enough to prevent electrons from passing through the light-emitting layer.

Further, FIG. 51, FIG. 52, FIG. 53, and Table 11 show that the light-emitting element 7 and the comparative light-emitting element 5 can be driven at low voltage.

As described above, the carbazole compound of one embodiment of the present invention is used for a hole-injection layer and a hole-transport layer, whereby an element with high emission efficiency can be manufactured. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with low drive voltage can be manufactured.

EXAMPLE 14

In this example, a manufacturing method of a light-emitting element which is one embodiment of the present invention and measurement results of element characteristics will be described together with measurement results of a comparative light-emitting element.

Manufacturing methods of a light-emitting element 8 and a comparative light-emitting element 6 will be described below. Note that element structures of the light-emitting elements manufactured in this example are similar to that illustrated in FIG. 29. The structural formula of an organic compound used in this example is shown below. Note that the organic compounds whose structural formulae have been already shown are omitted.

[58]

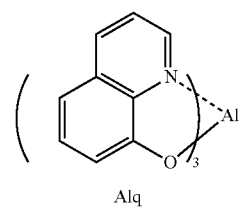

Alq (Light-Emitting Element 8)

The light-emitting element 8 was manufactured in a manner similar to that of the light-emitting element 7 in Example 13 except for the first electron-transport layer 1114a.

In the light-emitting element 8, tris(8-quinolinolato)aluminum(III) (abbreviation: Alq) was deposited to a thickness of 10 nm on the light-emitting layer 1113 to form the first electron-transport layer 1114a.

(Comparative Light-Emitting Element 6)

The comparative light-emitting element 6 was manufactured in a manner similar to that of the comparative light-emitting element 1 in Example 9 except for the first electron-transport layer 1114a.

In the light-emitting element 6, Alq was deposited to a thickness of 10 nm on the light-emitting layer 1113 to form the first electron-transport layer 1114a.

Table 12 shows the element structures of the light-emitting element 8 and the comparative light-emitting element 6 that were obtained as described above.

TABLE 12

|  | Light-Emitting Element 8 | Comparative Light-Emitting Element 6 |
|---|---|---|
| First Electrode 1101 | ITSO 110 nm | ITSO 110 nm |
| Hole-injection Layer 1111 | mPCPPn:MoOx (=4:2) 50 nm | PCzPA:MoOx (=4:2) 50 nm |
| Hole-transport layer 1112 | mPCPPn 10 nm | PCzPA 10 nm |
| Light-emitting layer 1113 | CzPA:1,6FLPAPrn (=1:0.05) 30 nm | CzPA:1,6FLPAPrn (=1:0.05) 30 nm |
| Electron-transport layer 1114a | Alq 10 nm | Alq 10 nm |
| 1114b | BPhen 15 nm | BPhen 15 nm |
| Electron-injection layer 1115 | LiF 1 nm | LiF 1 nm |
| Second Electrode 1103 | Al 200 nm | Al 200 nm |

*The mixture ratios are all represented in weight ratios.

In a glove box containing a nitrogen atmosphere, the light-emitting element 8 and the comparative light-emitting element 6 were sealed so as not to be exposed to the air. After that, the operating characteristics of these elements were measured. Note that the measurement was carried out at room temperature (in an atmosphere kept at 25° C.).

Note that the light-emitting element 8 and the comparative light-emitting element 6 were formed over the same substrate. In addition, in the above two light-emitting elements, the respective components other than the hole-injection layers and the hole-transport layers were formed at the same time, and the operating characteristics of the two light-emitting elements were measured at the same time.

Table 13 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 8 and the comparative light-emitting element 6 at a luminance of about 1000 cd/m$^2$.

TABLE 13

|  | Light-Emitting Element 8 | Comparative Light-Emitting Element 6 |
|---|---|---|
| Voltage (V) | 4.0 | 4.0 |
| Current density (mA/cm$^2$) | 9.6 | 12 |
| Chromaticity coordinates (x, y) | (0.15, 0.21) | (0.15, 0.20) |
| Luminance (cd/m$^2$) | 930 | 840 |
| Current efficiency (cd/A) | 9.7 | 7.1 |
| Power efficiency (lm/W) | 7.7 | 5.5 |
| External quantum efficiency (%) | 6.9 | 5.1 |

Figure 54:
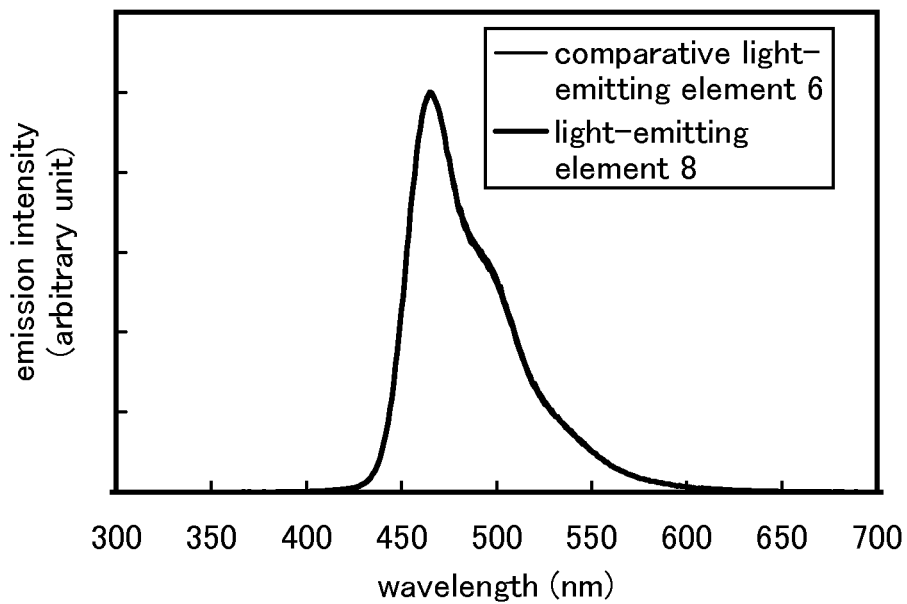
FIG. 54 shows emission spectra of a light-emitting element and a comparative light-emitting element of Example 14.
Figure 55:
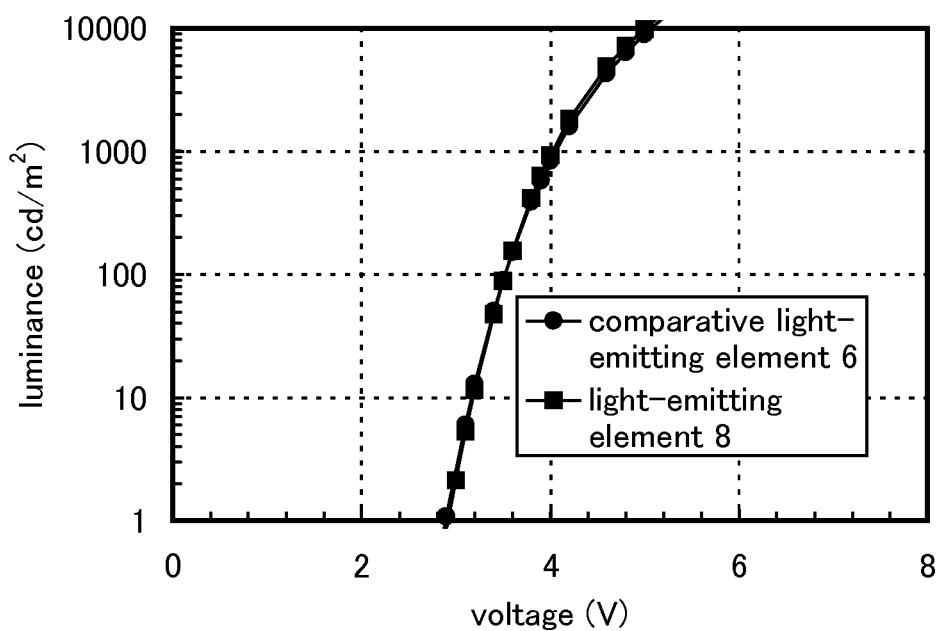
FIG. 55 shows voltage-luminance characteristics of the light-emitting element and the comparative light-emitting element of Example 14.
Figure 56:
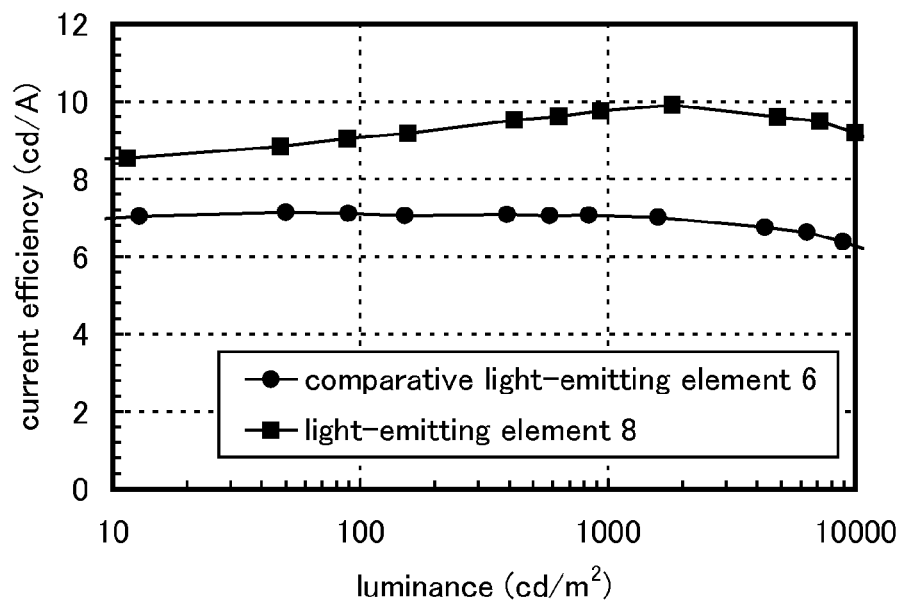
FIG. 56 shows luminance-current efficiency characteristics of the light-emitting element and the comparative light-emitting element of Example 14.
Figure 57:
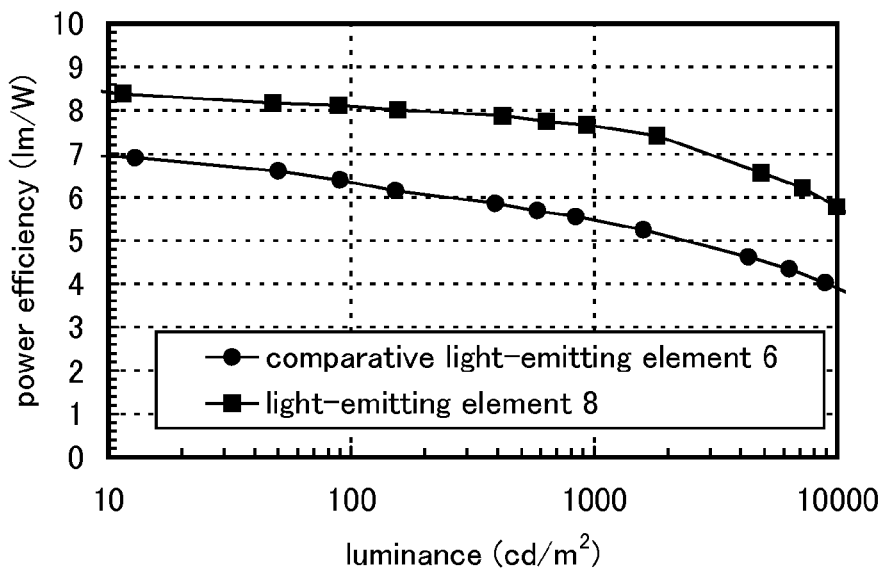
FIG. 57 shows luminance-power efficiency characteristics of the light-emitting element and the comparative light-emitting element of Example 14.

FIG. 54 shows the emission spectra of the light-emitting element 8 and the comparative light-emitting element 6. In FIG. 54, the horizontal axis represents the wavelength (nm) and the vertical axis represents the emission intensity (arbitrary unit). FIG. 55, FIG. 56, and FIG. 57 respectively show the voltage-luminance characteristics, the luminance-current efficiency characteristics, and the luminance-power efficiency characteristics of the light-emitting element 8 and the comparative light-emitting element 6. In FIG. 55, the vertical axis represents the luminance (cd/m$^2$) and the horizontal axis represents the voltage (V). In FIG. 56, the vertical axis represents the current efficiency (cd/A) and the horizontal axis represents the luminance (cd/m$^2$). In FIG. 57, the vertical axis represents the power efficiency (lm/W) and the horizontal axis represents the luminance (cd/m$^2$).

According to FIG. 54, the emission spectra of the light-emitting element 8 and the comparative light-emitting element 6 have peaks around 470 nm. The CIE chromaticity coordinates in Table 13 also show that the light-emitting element 8 and the comparative light-emitting element 6 exhibit blue light emission originating from 1,6FLPAPrn and that all the elements have excellent carrier balance.

Further, FIG. 55, FIG. 56, FIG. 57, and Table 13 show that the light-emitting element 8 has higher efficiency than the comparative light-emitting element 6. The reasons for the above are probably as follows: the band gap of mPCPPn used for the hole-injection layer and the hole-transport layer of the light-emitting element 8 in this example is wider than the band gap of PCzPA used for the comparative light-emitting element 6; energy transfer from the light-emitting layer does not easily occur; and the LUMO level of mPCPPn is shallow enough to prevent electrons from passing through the light-emitting layer.

Further, FIG. 55, FIG. 56, and Table 13 show that the light-emitting element 8 and the comparative light-emitting element 6 can be driven at low voltage.

Figure 58:
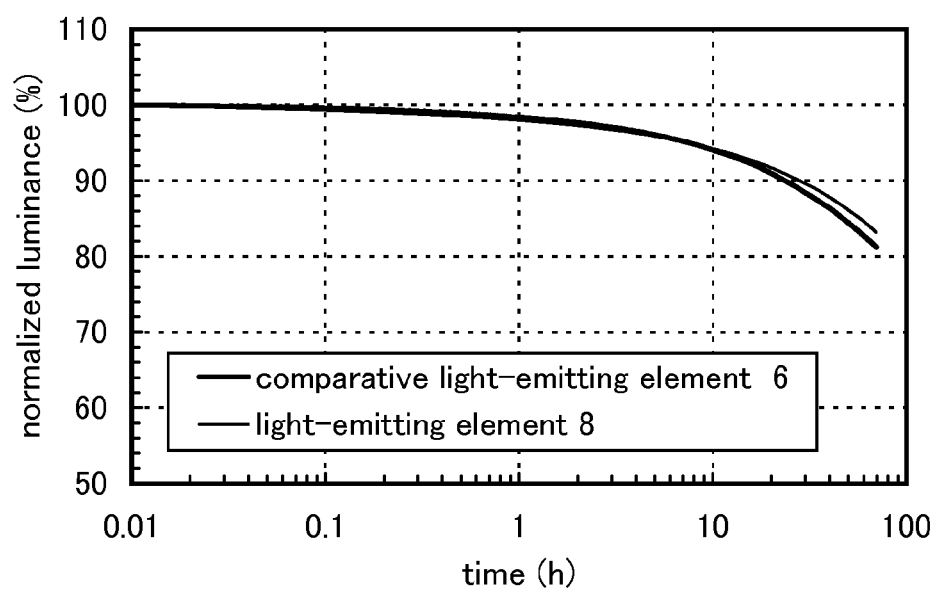
FIG. 58 shows results of a reliability test conducted on the light-emitting element and the comparative light-emitting element of Example 14.

Further, a reliability test was conducted on the manufactured light-emitting element 8 and comparative light-emitting element 6. In the reliability test, the initial luminance was set at 5000 cd/m$^2$, these elements were operated at a constant current density, and the luminance was measured at regular intervals. The results obtained by the reliability test are shown in FIG. 58. In FIG. 58, the horizontal axis represents the current flow time (hour) and the vertical axis represents the percentage of luminance to the initial luminance at each time, that is, normalized luminance (%).

As shown in FIG. 58, a reduction in the luminance of each of the light-emitting element 8 and the comparative light-emitting element 6 with time does not easily occur and the lifetime of each of the elements is long. The light-emitting element 8 and the comparative light-emitting element 6 respectively maintained 83% and 81% of the initial luminance even after being driven for 70 hours.

As described above, the carbazole compound of one embodiment of the present invention is used for a hole-injection layer and a hole-transport layer, whereby an element with high emission efficiency can be manufactured. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with low drive voltage can be manufactured.

Further, it was indicated that when the carbazole compound of one embodiment of the present invention is used for a hole-injection layer and a hole-transport layer, a light-emitting element with long lifetime can be manufactured.

EXAMPLE 15

In this example, a manufacturing method of a light-emitting element which is one embodiment of the present invention and measurement results of element characteristics will be described together with measurement results of a comparative light-emitting element.

Manufacturing methods of a light-emitting element 9 and a comparative light-emitting element 7 will be described below. Note that element structures of the light-emitting elements manufactured in this example are similar to that illustrated in FIG. 29. The structural formula of an organic compound used in this example is shown below. Note that the organic compounds whose structural formulae have been already shown are omitted.

[59]

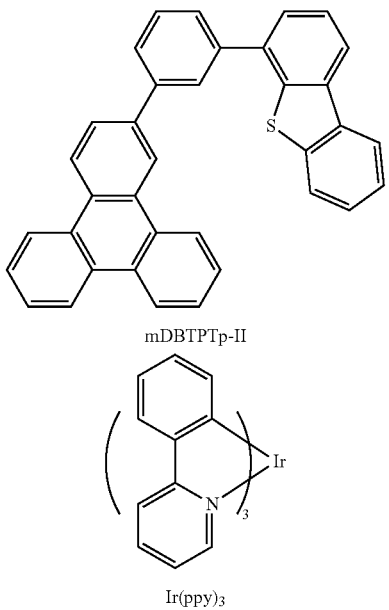

mDBTPTp-II

Ir(ppy)₃

(Light-Emitting Element 9)

The light-emitting element 9 was manufactured in a manner similar to that of the light-emitting element 1 in Example 9 except for the hole-injection layer 1111, the hole-transport layer 1112, the light-emitting layer 1113, and the first electron-transport layer 1114a.

In the light-emitting element 9, the hole-injection layer 1111 was formed in such a manner that 9-phenyl-3-[3-(triphenylen-2-yl)-phenyl]-9H-carbazole (abbreviation: mPCzPTp) synthesized in Example 5 and molybdenum(VI) oxide were co-evaporated on the first electrode 1101. The thickness of the hole-injection layer 1111 was 50 nm. The weight ratio of mPCzPTp to molybdenum(VI) oxide was adjusted to 4:2 (=mPCzPTp:molybdenum oxide).

Next, mPCzPTp was deposited to a thickness of 10 nm on the hole-injection layer 1111 to form the hole-transport layer 1112.

Furthermore, 4-[3-(triphenylen-2-yl)phenyl]dibenzothiophene (abbreviation: mDBTPTp-II) and tris(2-phenylpyridinato-N,C$^{2'}$)iridium(III) (abbreviation: Ir(ppy)$_3$) were co-evaporated to form the light-emitting layer 1113 on the hole-transport layer 1112. Here, the weight ratio of mDBTPTp-II to Ir(ppy)$_3$ was adjusted to be 1:0.06 (=mDBTPTp-II:Ir(ppy)$_3$). The thickness of the light-emitting layer 1113 was 40 nm.

Next, Alq was deposited to a thickness of 15 nm on the light-emitting layer 1113 to form the first electron-transport layer 1114a.

(Comparative Light-Emitting Element 7)

The comparative light-emitting element 7 was manufactured in a manner similar to that of the comparative light-emitting element 1 in Example 9 except for the light-emitting layer 1113 and the first electron-transport layer 1114a.

In the comparative light-emitting element 7, structures of the light-emitting layer 1113 and the first electron-transport layer 1114a are similar to those in the above light-emitting element 9.

Table 14 shows the element structures of the light-emitting element 9 and the comparative light-emitting element 7 that were obtained as described above.

TABLE 14

| | Light-Emitting Element 9 | Comparative Light-Emitting Element 7 |
|---|---|---|
| First Electrode 1101 | ITSO 110 nm | ITSO 110 nm |
| Hole-injection Layer 1111 | mPCzPTp:MoOx (=4:2) 50 nm | PCzPA:MoOx (=4:2) 50 nm |
| Hole-transport layer 1112 | mPCzPTp 10 nm | PCzPA 10 nm |
| Light-emitting layer 1113 | mDBTPTpII:Ir(ppy)3 (=1:0.06) 40 nm | mDBTPTpII:Ir(ppy)3 (=1:0.06) 40 nm |
| Electron- 1114a transport layer 1114b | Alq 15 nm BPhen 15 nm | Alq 15 nm BPhen 15 nm |
| Electron-injection layer 1115 | LiF 1 nm | LiF 1 nm |
| Second Electrode 1103 | Al 200 nm | Al 200 nm |

*The mixture ratios are all represented in weight ratios.

In a glove box containing a nitrogen atmosphere, the light-emitting element 9 and the comparative light-emitting element 7 were sealed so as not to be exposed to the air. After that, the operating characteristics of these elements were measured. Note that the measurement was carried out at room temperature (in an atmosphere kept at 25° C.).

Note that the light-emitting element 9 and the comparative light-emitting element 7 were formed over the same substrate. In addition, in the above two light-emitting elements, the respective components other than the hole-injection layers and the hole-transport layers were formed at the same time, and the operating characteristics of the two light-emitting elements were measured at the same time.

Table 15 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 9 and the comparative light-emitting element 7 at a luminance of about 1000 cd/m$^2$.

TABLE 15

|  | Light-Emitting Element 9 | Comparative Light-Emitting Element 7 |
|---|---|---|
| Voltage (V) | 7.0 | 7.0 |
| Current density (mA/cm$^2$) | 2.1 | 3.5 |
| Chromaticity coordinates (x, y) | (0.34, 0.61) | (0.34, 0.61) |
| Luminance (cd/m$^2$) | 990 | 910 |
| Current efficiency (cd/A) | 47 | 26 |
| Power efficiency (lm/W) | 21 | 12 |
| External quantum efficiency (%) | 14 | 8.0 |

Figure 59:
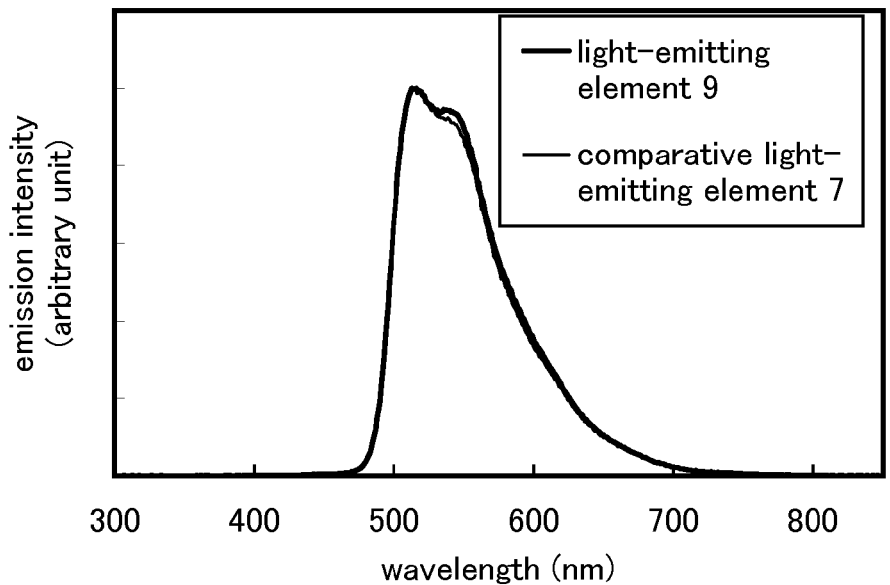
FIG. 59 shows emission spectra of a light-emitting element and a comparative light-emitting element of Example 15.
Figure 60:
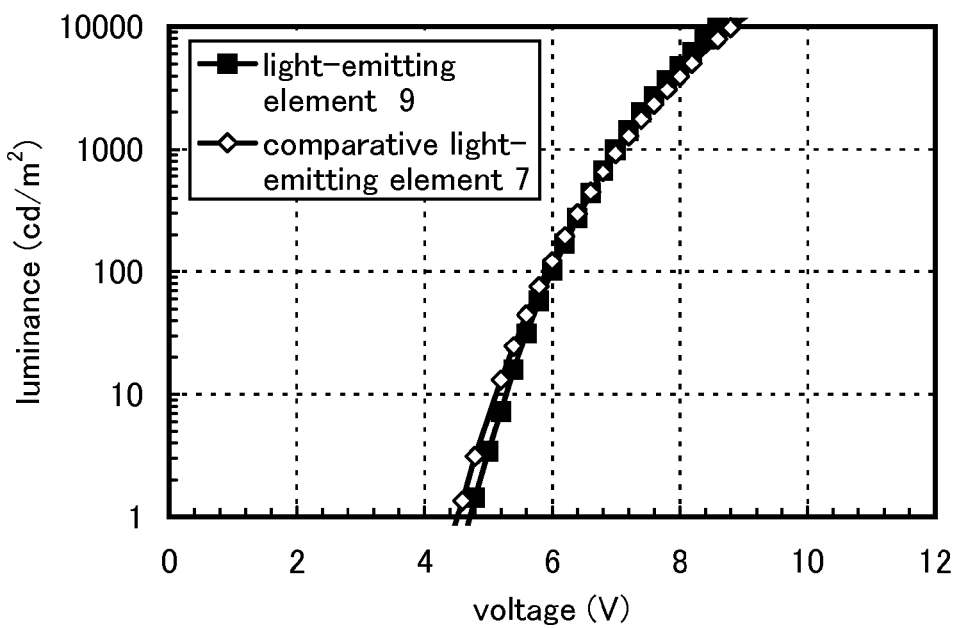
FIG. 60 shows voltage-luminance characteristics of the light-emitting element and the comparative light-emitting element of Example 15.
Figure 61:
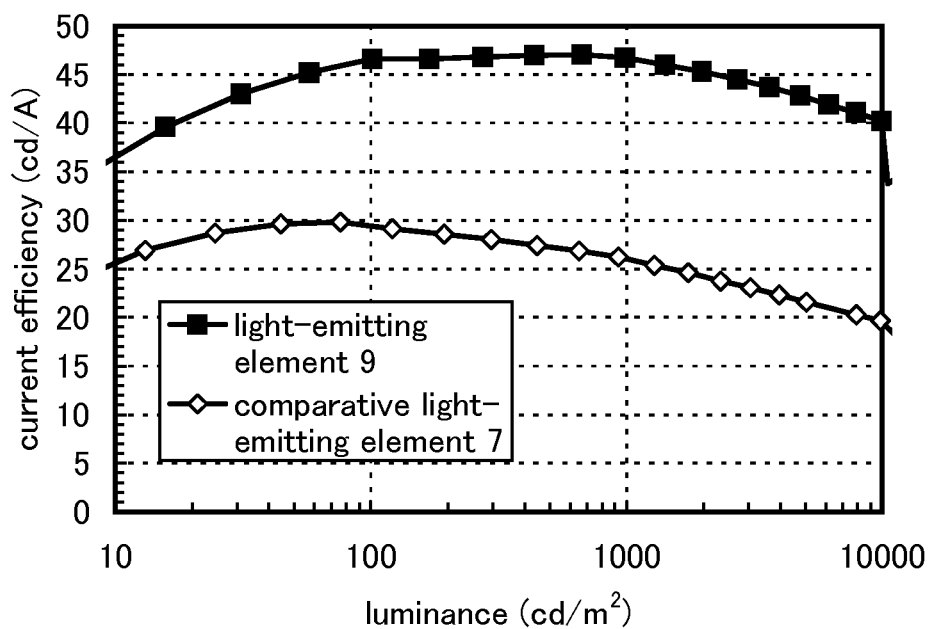
FIG. 61 shows luminance-current efficiency characteristics of the light-emitting element and the comparative light-emitting element of Example 15.

FIG. 59 shows the emission spectra of the light-emitting element 9 and the comparative light-emitting element 7. In FIG. 59, the horizontal axis represents the wavelength (nm) and the vertical axis represents the emission intensity (arbitrary unit). FIG. 60 and FIG. 61 respectively show the voltage-luminance characteristics and the luminance-power efficiency characteristics of the light-emitting element 9 and the comparative light-emitting element 7. In FIG. 60, the vertical axis represents the luminance (cd/m$^2$) and the horizontal axis represents the voltage (V). In FIG. 61, the vertical axis represents the current efficiency (cd/A) and the horizontal axis represents the luminance (cd/m$^2$).

According to FIG. 59, the emission spectra of the light-emitting element 9 and the comparative light-emitting element 7 have peaks around 520 nm. The CIE chromaticity coordinates in Table 15 also show that the light-emitting element 9 and the comparative light-emitting element 7 exhibit green phosphorescence emission originating from Ir(ppy)$_3$ and that all the elements have excellent carrier balance.

Further, FIG. 60, FIG. 61, and Table 15 show that the light-emitting element 9 has higher efficiency than the comparative light-emitting element 7. The reasons for the above are probably as follows: the band gap of mPCzPTp used for the hole-injection layer and the hole-transport layer of the light-emitting element 9 in this example is wider than the band gap of PCzPA used for the comparative light-emitting element 7; energy transfer from the light-emitting layer does not easily occur; and the LUMO level of mPCzPTp is shallow enough to prevent electrons from passing through the light-emitting layer.

Further, FIG. 60, FIG. 61, and Table 15 show that the light-emitting element 9 and the comparative light-emitting element 7 can be driven at low voltage.

As described above, the carbazole compound of one embodiment of the present invention is used for a hole-injection layer and a hole-transport layer, whereby an element with high emission efficiency can be manufactured. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with low drive voltage can be manufactured.

EXAMPLE 16

In this example, a manufacturing method of a light-emitting element which is one embodiment of the present invention and measurement results of element characteristics will be described together with measurement results of a comparative light-emitting element.

Figure 62:
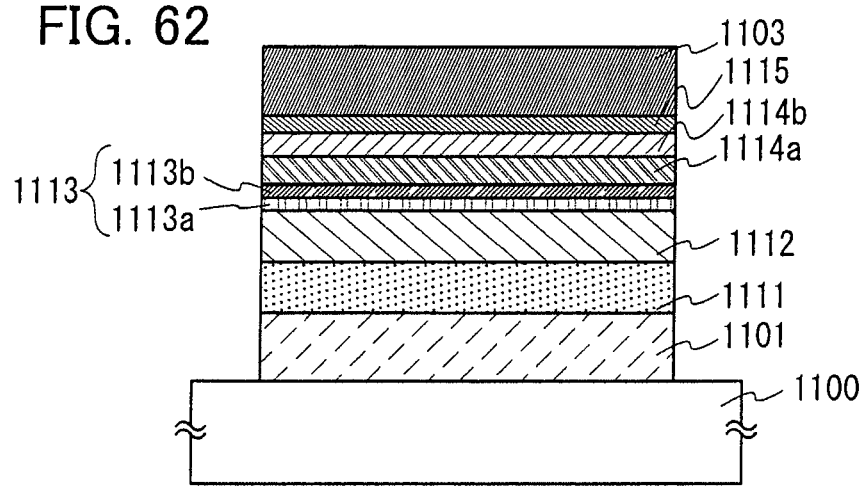
FIG. 62 shows a structure of a light-emitting element of Examples.

Manufacturing methods of a light-emitting element 10 and a comparative light-emitting element 8 will be described below. The element structure of the light-emitting elements manufactured in this example is illustrated in FIG. 62. Note that organic compounds used in this example are similar to those in the above examples; therefore, the description of the organic compounds is omitted.

(Light-Emitting Element 10)

The light-emitting element 10 was manufactured in a manner similar to that of the light-emitting element 9 in Example 15 except for the light-emitting layer 1113.

In the light-emitting element 10, a first light-emitting layer 1113a and a second light-emitting layer 1113b were stacked in this order on the first electrode 1101 to form the light-emitting layer 1113.

The first light-emitting layer 1113a was formed by co-evaporation of mPCzPTp synthesized in Example 5 and tris(2-phenylpyridinato-N,C$^{2'}$)iridium(III) (abbreviation: Ir(ppy)$_3$). Here, the weight ratio of mPCzPTp to Ir(ppy)$_3$ was adjusted to be 1:0.06 (=mPCzPTp:Ir(ppy)$_3$). The thickness of the first light-emitting layer 1113a was 20 nm.

Next, 4-[3-(triphenylen-2-yl)phenyl]dibenzothiophene (abbreviation: mDBTPTp-II) and Ir(ppy)$_3$ were co-evaporated to form the second light-emitting layer 1113b on the first light-emitting layer 1113a. The weight ratio of mDBTPTp-II to Ir(ppy)$_3$ was adjusted to be 1:0.06 (=mDBTPTp-II:Ir(ppy)$_3$). The thickness of the second light-emitting layer 1113b was 20 nm.

(Comparative Light-Emitting Element 8)

The comparative light-emitting element 8 was manufactured in a manner similar to that of the comparative light-emitting element 7 in Example 15 except for the light-emitting layer 1113.

In the comparative light-emitting element 8, a structure of the light-emitting layer 1113 was similar to that in the above light-emitting element 10.

Table 16 shows the element structures of the light-emitting element 10 and the comparative light-emitting element 8 that were obtained as described above.

TABLE 16

|  |  | Light-Emitting Element 10 | Comparative Light-Emitting Element 8 |
|---|---|---|---|
| First Electrode 1101 | | ITSO 110 nm | ITSO 110 nm |
| Hole-injection Layer 1111 | | mPCzPTp:MoOx (=4:2) 50 nm | PCzPA:MoOx (=4:2) 50 nm |
| Hole-transport layer 1112 | | mPCzPTp 10 nm | PCzPA 10 nm |
| Light-Emitting Layer 1113 | 1113a | mPCzPTp:Ir(ppy)3 (=1:0.06) 20 nm | mPCzPTp:Ir(ppy)3 (=1:0.06) 20 nm |
| | 1113b | mDBTPTp-II:Ir(ppy)3 (=1:0.06) 20 nm | mDBTPTp-II:Ir(ppy)3 (=1:0.06) 20 nm |

TABLE 16-continued

|  |  | Light-Emitting Element 10 | Comparative Light-Emitting Element 8 |
| --- | --- | --- | --- |
| Electron-transport layer | 1114a | Alq 15 nm | Alq 15 nm |
|  | 1114b | BPhen 15 nm | BPhen 15 nm |
| Electron-injection layer 1115 |  | LiF 1 nm | LiF 1 nm |
| Second Electrode 1103 |  | Al 200 nm | Al 200 nm |

*The mixture ratios are all represented in weight ratios.

In a glove box containing a nitrogen atmosphere, the light-emitting element 10 and the comparative light-emitting element 8 were sealed so as not to be exposed to the air. After that, the operating characteristics of these elements were measured. Note that the measurement was carried out at room temperature (in an atmosphere kept at 25° C.).

Note that the light-emitting element 10 and the comparative light-emitting element 8 were formed over the same substrate. In addition, in the above two light-emitting elements, the respective components other than the hole-injection layers and the hole-transport layers were formed at the same time, and the operating characteristics of the two light-emitting elements were measured at the same time.

Table 17 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 10 and the comparative light-emitting element 8 at a luminance of about 1000 cd/m$^2$.

TABLE 17

|  | Light-Emitting Element 10 | Comparative Light-Emitting Element 8 |
| --- | --- | --- |
| Voltage (V) | 6.8 | 6.8 |
| Current density (mA/cm$^2$) | 2.4 | 3.9 |
| Chromaticity coordinates (x, y) | (0.34, 0.61) | (0.33, 0.61) |
| Luminance (cd/m$^2$) | 1100 | 1100 |
| Current efficiency (cd/A) | 47 | 28 |
| Power efficiency (lm/W) | 22 | 13 |
| External quantum efficiency (%) | 14 | 8.3 |

Figure 63:
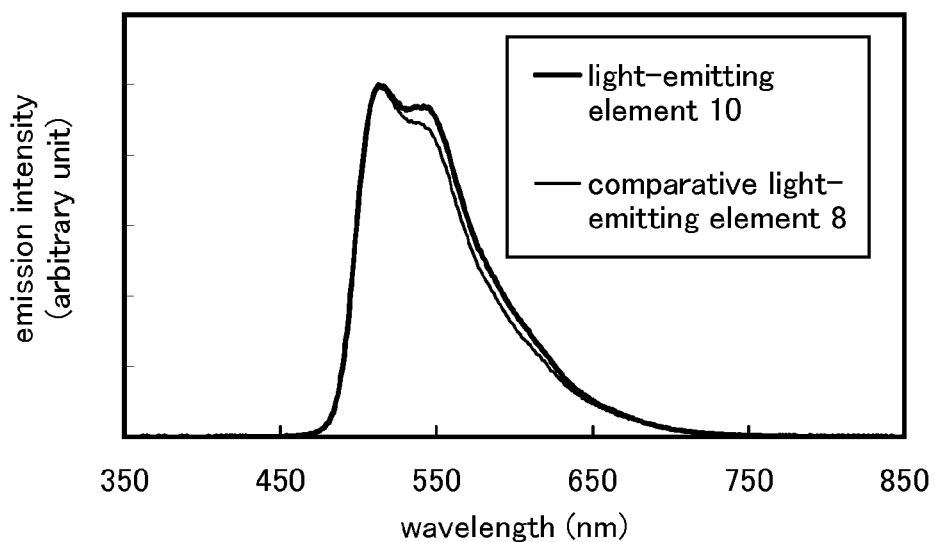
FIG. 63 shows emission spectra of a light-emitting element and a comparative light-emitting element of Example 16.
Figure 64:
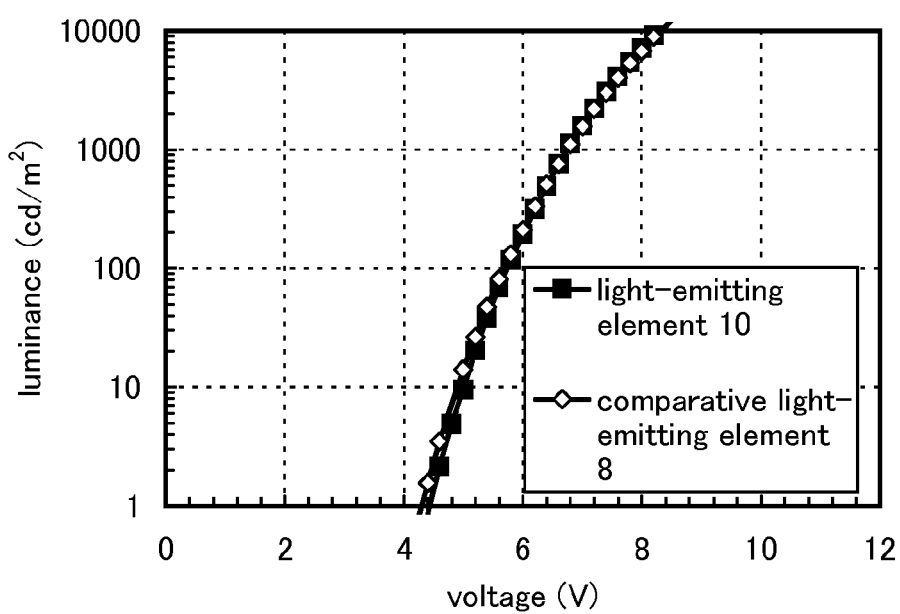
FIG. 64 shows voltage-luminance characteristics of the light-emitting element and the comparative light-emitting element of Example 16.
Figure 65:
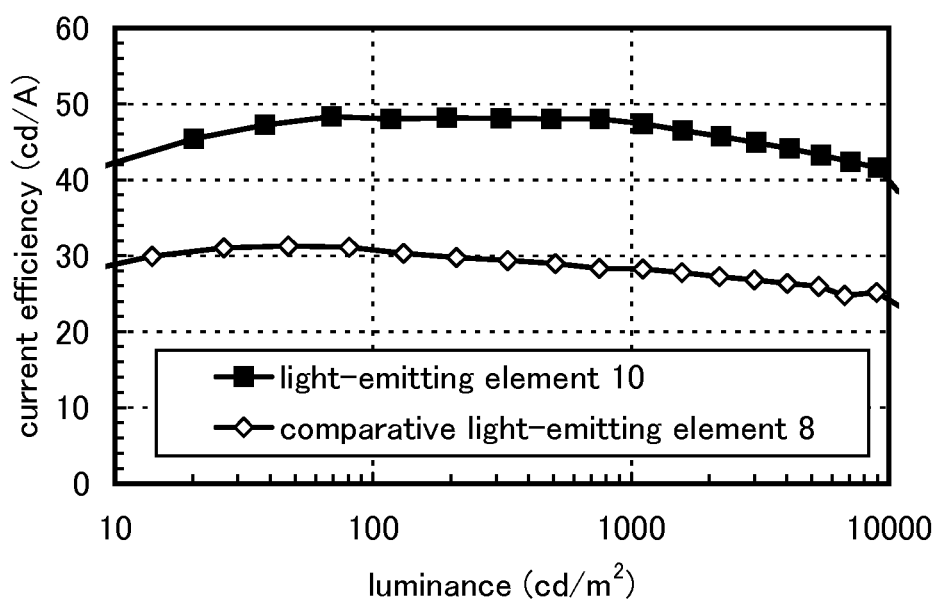
FIG. 65 shows luminance-current efficiency characteristics of the light-emitting element and the comparative light-emitting element of Example 16.

FIG. 63 shows the emission spectra of the light-emitting element 10 and the comparative light-emitting element 8. In FIG. 63, the horizontal axis represents the wavelength (nm) and the vertical axis represents the emission intensity (arbitrary unit). FIG. 64 and FIG. 65 respectively show the voltage-luminance characteristics and the luminance-power efficiency characteristics of the light-emitting element 10 and the comparative light-emitting element 8. In FIG. 64, the vertical axis represents the luminance (cd/m$^2$) and the horizontal axis represents the voltage (V). In FIG. 65, the vertical axis represents the current efficiency (cd/A) and the horizontal axis represents the luminance (cd/m$^2$).

According to FIG. 63, the emission spectra of the light-emitting element 10 and the comparative light-emitting element 8 have peaks around 515 nm. The CIE chromaticity coordinates in Table 17 also show that the light-emitting element 10 and the comparative light-emitting element 8 exhibit green phosphorescence emission originating from Ir(ppy)$_3$ and that the elements both have excellent carrier balance. Further, in the light-emitting element 10 and the comparative light-emitting element 8, the carbazole compound according to one embodiment of the present invention is used as a host material of a phosphorescent compound which emits green light, and the T1 level of the carbazole compound according to one embodiment of the present invention was confirmed to be sufficiently high (higher than the T1 level of at least a phosphorescent compound which emits green light).

Further, FIG. 64, FIG. 65, and Table 17 show that the light-emitting element 10 has higher efficiency than the comparative light-emitting element 8. The reasons for the above are probably as follows: the band gap of mPCzPTp used for the hole-injection layer and the hole-transport layer of the light-emitting element 10 in this example is wider than the band gap of PCzPA used for the comparative light-emitting element 8; energy transfer from the light-emitting layer does not easily occur; and the LUMO level of mPCzPTp is shallow enough to prevent electrons from passing through the light-emitting layer.

Further, FIG. 64, FIG. 65, and Table 17 show that the light-emitting element 10 and the comparative light-emitting element 8 can be driven at low voltage.

As described above, the carbazole compound of one embodiment of the present invention is used for a hole-injection layer and a hole-transport layer, whereby an element with high emission efficiency can be manufactured. The reasons for the above are probably as follows: the LUMO level of the carbazole compound of one embodiment of the present invention is shallow enough to suppress leakage of electrons from a light-emitting layer; the HOMO level is deep enough to make a property of injecting holes into a light-emitting layer excellent; and the band gap is wide enough to suppress a reduction in efficiency due to energy transfer of excitons.

Further, it was indicated that when the carbazole compound of one embodiment of the present invention is used for a hole-injection layer and a hole-transport layer, a light-emitting element with low drive voltage can be manufactured.

The carbazole compound of one embodiment of the present invention has a wide band gap, and thus can be favorably used as a host material of a phosphorescent material.

EXAMPLE 17

In this example, a manufacturing method of a light-emitting element of one embodiment of the present invention and measurement results of element characteristics thereof will be described.

A manufacturing method of a light-emitting element 11 of this example will be described below. FIG. 29 illustrates the element structure of the light-emitting element manufactured in this example. A structural formula of an organic compound used in this example is shown below. Note that the description of the structural formulae shown in the above examples is omitted.

[60]

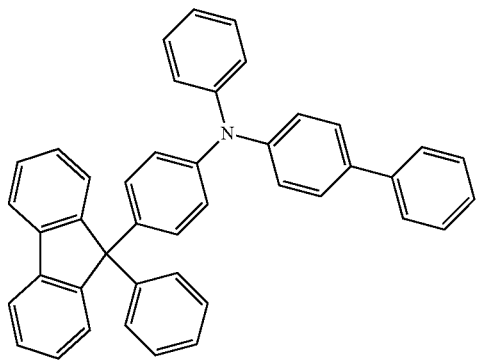

BPAFLP (Light-Emitting Element 11)

In the light-emitting element 11, the first electrode 1101, the electron-injection layer 1115, and the second electrode 1103 were formed in manners similar to that of the light-emitting element 1 in Example 9.

In the light-emitting element 11, 4-phenyl-4'-(9-phenylfluoren-9-yl)triphenylamine (abbreviation: BPAFLP) and molybdenum(VI) oxide were co-evaporated on the first electrode 1101 to form the hole-injection layer 1111. The thickness of the hole-injection layer 1111 was 50 nm. The weight ratio of BPAFLP to molybdenum(VI) oxide was adjusted to be 4:2 (=BPAFLP:molybdenum oxide). Note that the co-evaporation method refers to an evaporation method in which evaporation is carried out from a plurality of evaporation sources at the same time in one treatment chamber.

Next, BPAFLP was deposited to a thickness of 10 nm on the hole-injection layer 1111 to form the hole-transport layer 1112.

The light-emitting layer 1113 was formed by co-evaporation of mPCzPTp synthesized in Example 5 and tris(2-phenylpyridinato-N,$C^{2'}$)iridium(III) (abbreviation: Ir(ppy)$_3$). The weight ratio of mPCzPTp to Ir(ppy)$_3$ was adjusted to be 1:0.08 (=mPCzPTp: Ir(ppy)$_3$). The thickness of the light-emitting layer 1113 was 40 nm.

Next, the first electron-transport layer 1114a was formed on the light-emitting layer 1113 by evaporation of mPCzPTp. The thickness of the first electron-transport layer 1114a was 10 nm.

Then, bathophenanthroline (abbreviation: BPhen) was deposited to a thickness of 20 nm on the first electron-transport layer 1114a to form a second electron-transport layer 1114b.

Table 18 shows the element structure of the light-emitting element 11 obtained as described above.

TABLE 18

|  |  | Light-Emitting Element 11 |
| --- | --- | --- |
| First Electrode 1101 |  | ITSO 110 nm |
| Hole-injection Layer 1111 |  | BPAFLP:MoOx (=4:2) 50 nm |
| Hole-transport layer 1112 |  | BPAFLP 10 nm |
| Light-emitting layer 1113 |  | mPCzPTp:Ir(ppy)3 (=1:0.08) 40 nm |
| Electron-transport layer | 1114a | mPCzPTp 10 nm |
|  | 1114b | BPhen 20 nm |
| Electron-injection layer 1115 |  | LiF 1 nm |
| Second Electrode 1103 |  | Al 200 nm |

*The mixture ratios are all represented in weight ratios.

In a glove box containing a nitrogen atmosphere, the light-emitting element 11 was sealed so as not to be exposed to the air. After that, the operating characteristics of the light-emitting element were measured. Note that the measurement was carried out at room temperature (in an atmosphere kept at 25° C.).

Table 19 shows the voltage (V), current density (mA/cm$^2$), CIE chromaticity coordinates (x,y), luminance (cd/m$^2$), current efficiency (cd/A), power efficiency (lm/W), and external quantum efficiency (%) of the light-emitting element 11 at a luminance of about 1000 cd/m$^2$.

TABLE 19

|  | Light-Emitting Element 11 |
| --- | --- |
| Voltage (V) | 5.2 |
| Current density (mA/cm$^2$) | 1.7 |
| Chromaticity coordinates (x, y) | (0.33, 0.61) |
| Luminance (cd/m$^2$) | 870 |
| Current efficiency (cd/A) | 52 |
| Power efficiency (lm/W) | 32 |
| External quantum efficiency (%) | 15 |

Figure 66:
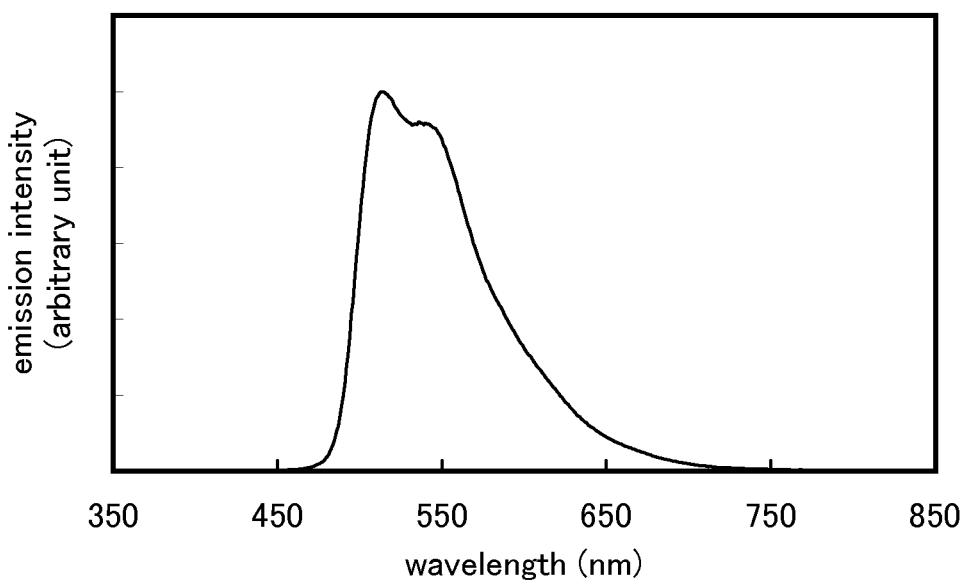
FIG. 66 shows emission spectrum of a light-emitting element of Example 17.
Figure 67:
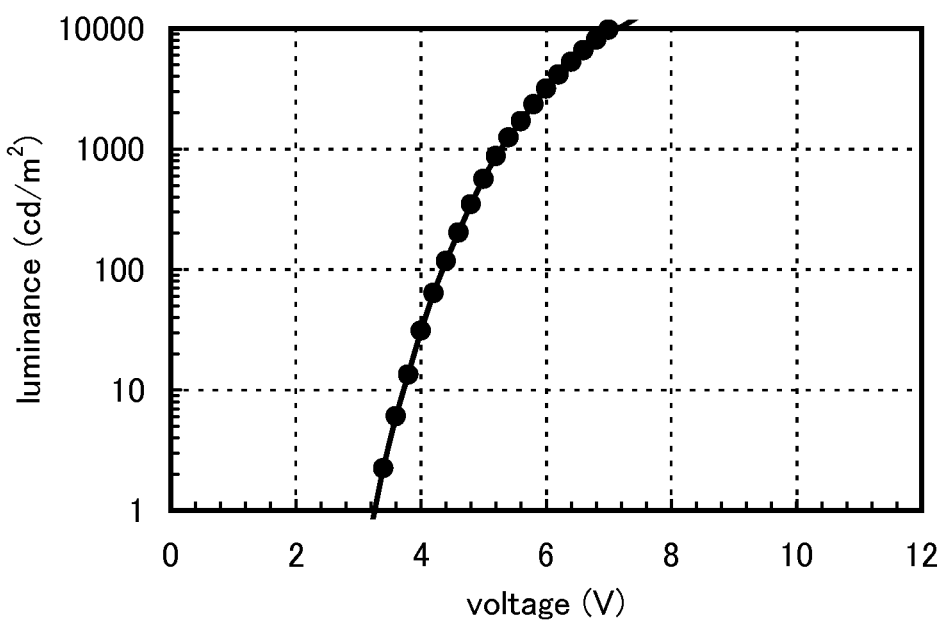
FIG. 67 shows voltage-luminance characteristic of the light-emitting element of Example 17.
Figure 68:
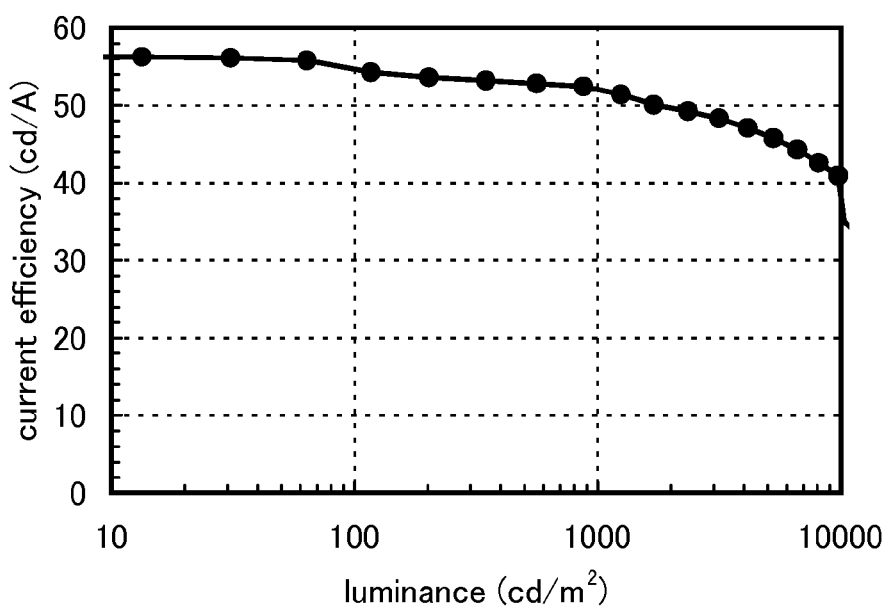
FIG. 68 shows luminance-current efficiency characteristic of the light-emitting element of Example 17.

FIG. 66 shows the emission spectrum of the light-emitting element 11. In FIG. 66, the horizontal axis represents the wavelength (nm) and the vertical axis represents the emission intensity (arbitrary unit). FIG. 67 and FIG. 68 respectively show the voltage-luminance characteristics and the luminance-power efficiency characteristics of the light-emitting element 11. In FIG. 67, the vertical axis represents the luminance (cd/m$^2$) and the horizontal axis represents the voltage (V). In FIG. 68, the vertical axis represents the current efficiency (cd/A) and the horizontal axis represents the luminance (cd/m$^2$).

According to FIG. 66, the emission spectrum of the light-emitting element 11 has a peak around 515 nm. The CIE chromaticity coordinate in Table 19 also shows that the light-emitting element 11 exhibits green phosphorescence emission originating from Ir(ppy)$_3$ and that all the elements have excellent carrier balance. Further, in the light-emitting element 11, the carbazole compound according to one embodiment of the present invention is used as a host material of a phosphorescent compound which emits green light, and the T1 level of the carbazole compound according to one embodiment of the present invention was confirmed to be sufficiently high (higher than the T1 level of at least a phosphorescent compound which emits green light).

Further, in the light-emitting element 11 of this example, the carbazole compound according to one embodiment of the present invention is used as an electron-transport material, and the carbazole compound according to one embodiment of the present invention was confirmed to be a material with an excellent electron-transport property.

Further, FIG. 67, FIG. 68, and Table 19 show that the light-emitting element 11 has high efficiency.

As described above, the carbazole compound of one embodiment of the present invention is used as a material of a light-emitting element, whereby the light-emitting element can have high efficiency. The carbazole compound of one embodiment of the present invention has a wide band gap, and thus can be used favorably as a host material of a phosphorescent material.

EXAMPLE 18

In this example, manufacturing methods of light-emitting elements of one embodiment of the present invention and measurement results of element characteristics thereof will be described.

Manufacturing methods of a light-emitting element 12 and a light-emitting element 13 will be described below. Note that element structures of the light-emitting elements manufactured in this example are similar to that in FIG. 29. A structural formula of an organic compound used in this example is shown below. Note that the description of the organic compounds whose structural formulae have already been shown is omitted.

[61]

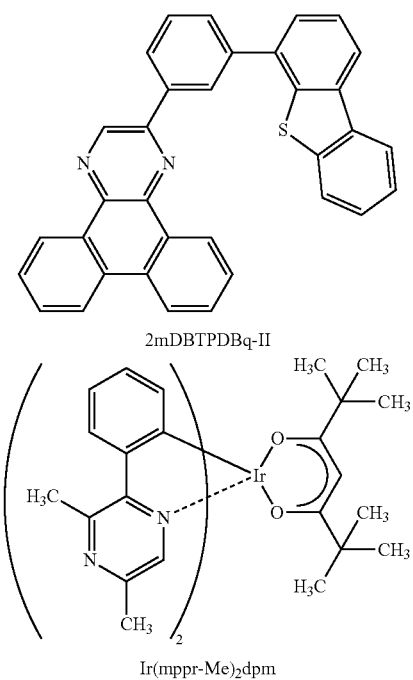

2mDBTPDBq-II

Ir(mppr-Me)₂dpm (Light-Emitting Element 12)

In the light-emitting element 12, the first electrode 1101, the electron-injection layer 1115, and the second electrode 1103 were formed in a manner similar to that of the light-emitting element 1 in Example 9.

In the light-emitting element 12, 3-[4-(1-naphthyl)-phenyl]-9-phenyl-9H-carbazole (abbreviation: PCPN) synthesized in Example 1 and molybdenum(VI) oxide were co-evaporated on the first electrode 1101 to form the hole-injection layer 1111. The thickness of the hole-injection layer 1111 was 40 nm. The weight ratio of PCPN to molybdenum (VI) oxide was adjusted to be 4:2 (=PCPN:molybdenum oxide). Note that the co-evaporation method refers to an evaporation method in which evaporation is carried out from a plurality of evaporation sources at the same time in one treatment chamber.

Next, PCPN was deposited to a thickness of 20 nm on the hole-injection layer 1111 to form the hole-transport layer 1112.

The light-emitting layer 1113 was formed by co-evaporation of 2-[3-(dibenzothiophen-4-yl)phenyl]dibenzo[f,h]quinoxaline (abbreviation: 2mDBTPDBq-II) and (dipivaloylmethanato)bis(3,5-dimethyl-2-phenylpyrazinato)iridium (III) (abbreviation: Ir(mppr-Me)₂dpm). The weight ratio of 2mDBTPDBq-II to Ir(mppr-Me)₂dpm was adjusted to be 1:0.05 (=2mDBTPDBq-II: Ir(mppr-Me)₂dpm). The thickness of the light-emitting layer 1113 was 30 nm.

Next, the first electron-transport layer 1114a was formed on the light-emitting layer 1113 by evaporation of 2mDBTPDBq-II. The thickness of the first electron-transport layer 1114a was 10 nm.

Then, bathophenanthroline (abbreviation: BPhen) was deposited to a thickness of 20 nm on the first electron-transport layer 1114a to form a second electron-transport layer 1114b.

(Light-Emitting Element 13)

The light-emitting element 13 was manufactured in a manner similar to that of the above light-emitting element 12 except for the light-emitting layer 1113.

In the light-emitting element 13, the light-emitting layer 1113 was formed by co-evaporation of 2mDBTPDBq-II, PCPN, and Ir(mppr-Me)₂dpm. The weight ratio of 2mDBTPDBq-II to PCPN and Ir(mppr-Me)₂dpm was adjusted to 0.7:0.3:0.05 (=2mDBTPDBq-III: PCPN: Ir(mppr-Me)₂ dpm). The thickness of the light-emitting layer 1113 was 30 nm.

Table 20 shows the element structures of the light-emitting element 12 and the light-emitting element 13 that were obtained as described above.

TABLE 20

| | Light-Emitting Element 12 | Light-Emitting Element 13 |
|---|---|---|
| First Electrode 1101 | ITSO 110 nm | ITSO 110 nm |
| Hole-injection Layer 1111 | PCPN:MoOx (=4:2) 40 nm | PCPN:MoOx (=4:2) 40 nm |
| Hole-transport layer 1112 | PCPN 20 nm | PCPN 20 nm |
| Light-emitting layer 1113 | 2mDBTPDBq-II:Ir(mppr-Me)2dpm (=1:0.05) 30 nm | 2mDBTPDBq-II:PCPN:Ir(mppr-Me)2dpm (=0.7:0.3:0.05) 30 nm |
| Electron-transport layer 1114a | 2mDBTPDBq-II 10 nm | 2mDBTPDBq-II 10 nm |
| 1114b | BPhen 20 nm | BPhen 20 nm |
| Electron-injection layer 1115 | LiF 1 nm | LiF 1 nm |
| Second Electrode 1103 | Al 200 nm | Al 200 nm |

*The mixture ratios are all represented in weight ratios.

In a glove box containing a nitrogen atmosphere, the light-emitting element 12 and the light-emitting element 13 were sealed so as not to be exposed to the air. After that, the operating characteristics of these elements were measured. Note that the measurement was carried out at room temperature (in an atmosphere kept at 25° C.).-

Note that the light-emitting element 12 and the light-emitting element 13 were formed over the same substrate. In addition, in the above two light-emitting elements, the respective components other than the light-emitting layer 1113 were formed at the same time, and the operating characteristics of the two light-emitting elements were measured at the same time.

Table 21 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting element 12 and the light-emitting element 13 at a luminance of about 1000 cd/m$^2$.

TABLE 21

|  | Light-Emitting Element 12 | Light-Emitting Element 13 |
| --- | --- | --- |
| Voltage (V) | 2.9 | 3.0 |
| Current density (mA/cm$^2$) | 2.1 | 1.8 |
| Chromaticity coordinates (x, y) | (0.53, 0.47) | (0.52, 0.47) |
| Luminance (cd/m$^2$) | 1200 | 1200 |
| Current efficiency (cd/A) | 59 | 66 |
| Power efficiency (lm/W) | 64 | 69 |
| External quantum efficiency (%) | 21 | 23 |

Figure 69:
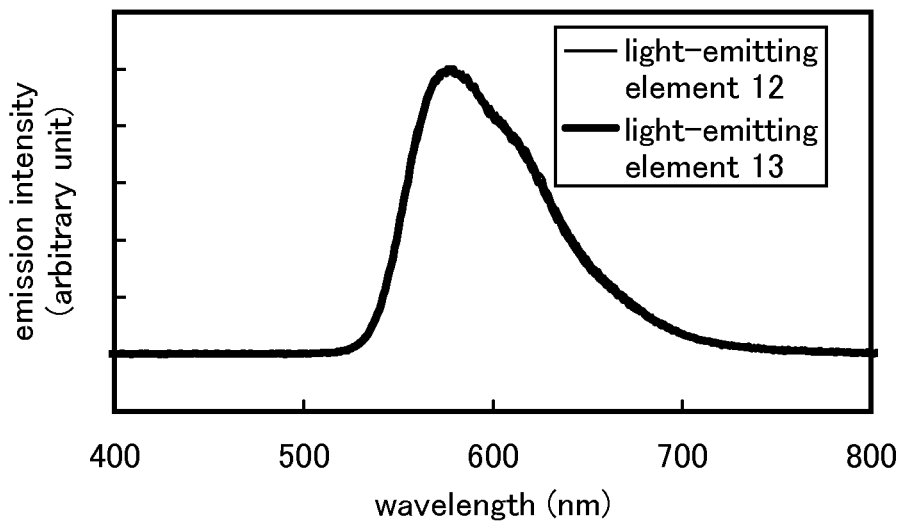
FIG. 69 shows emission spectra of light-emitting elements of Example 18.
Figure 70:
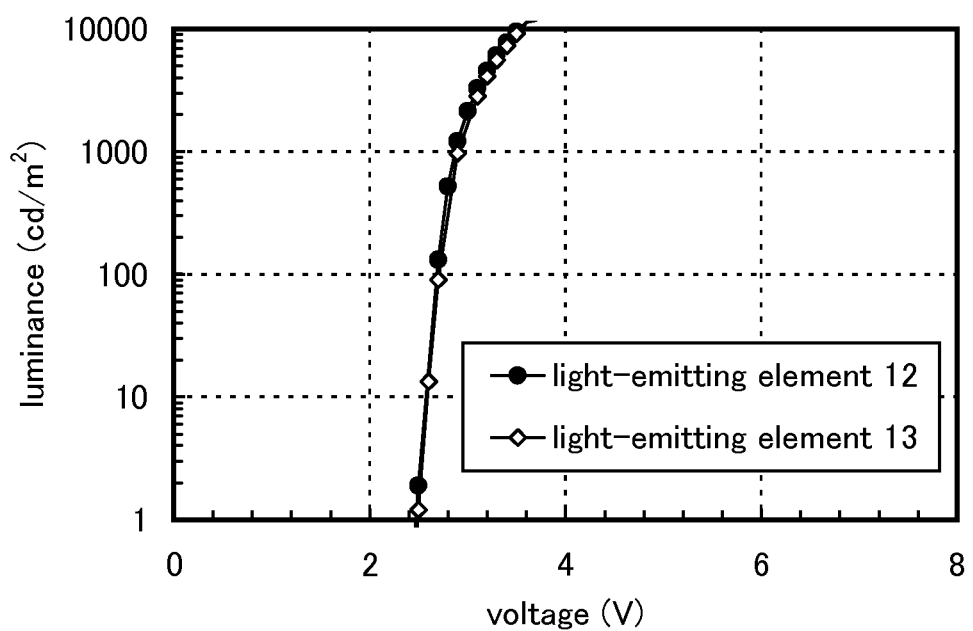
FIG. 70 shows voltage-luminance characteristics of the light-emitting elements of Example 18.
Figure 71:
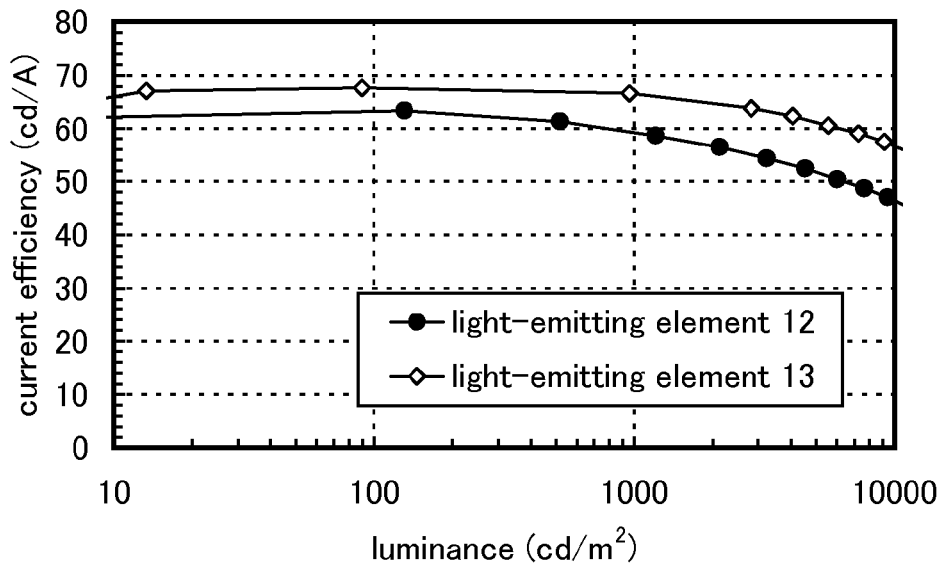
FIG. 71 shows luminance-current efficiency characteristics of the light-emitting elements of Example 18.
Figure 72:
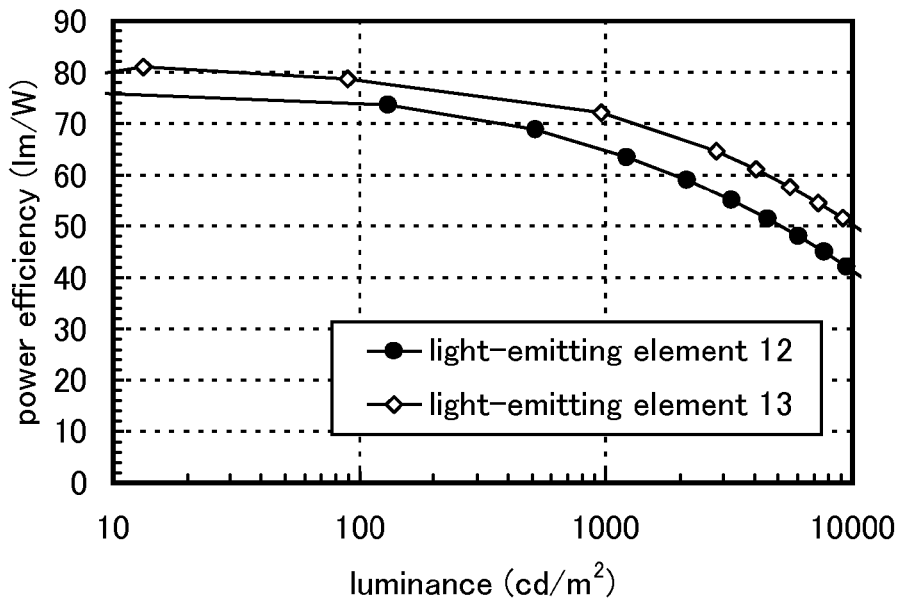
FIG. 72 shows luminance-power efficiency characteristics of the light-emitting elements of Example 18.

FIG. 69 shows the emission spectra of the light-emitting element 12 and the light-emitting element 13. In FIG. 69, the horizontal axis represents the wavelength (nm) and the vertical axis represents the emission intensity (arbitrary unit). FIG. 70, FIG. 71, and FIG. 72 respectively show the voltage-luminance characteristics, the luminance-current efficiency, and the luminance-power efficiency characteristics of the light-emitting element 12 and the light-emitting element 13. In FIG. 70, the vertical axis represents the luminance (cd/m$^2$) and the horizontal axis represents the voltage (V). In FIG. 71, the vertical axis represents the current efficiency (cd/A) and the horizontal axis represents the luminance (cd/m$^2$). In FIG. 72, the vertical axis represents power efficiency (lm/W) and the horizontal axis represents the luminance (cd/m$^2$).

According to FIG. 69, the emission spectra of the light-emitting element 12 and the light-emitting element 13 have a peak around 580 nm. The CIE chromaticity coordinate in Table 21 also shows that the light-emitting element 12 and the light-emitting element 13 exhibit orange phosphorescence emission originating from Ir(mppr-Me)$_2$dpm and that the light-emitting elements have excellent carrier balance.

Further, in the light-emitting element 13 of this example, the carbazole compound according to one embodiment of the present invention is used as a host material of a phosphorescent compound which emits orange light, and the T1 level of the carbazole compound according to one embodiment of the present invention was confirmed to be sufficiently high (higher than the T1 level of at least a phosphorescent compound which emits orange light). In addition, it was found that the elements are both driven at low voltage.

Further, FIG. 70, FIG. 71, FIG. 72, and Table 21 show that the light-emitting element 12 and the light-emitting element 13 have high efficiency.

As described above, the carbazole compound of one embodiment of the present invention is used as a material of a light-emitting element, whereby the light-emitting element can have high efficiency. The carbazole compound of one embodiment of the present invention has a wide band gap, and thus can be used favorably as a host material of a phosphorescent material.

Further, it was indicated that when the carbazole compound of one embodiment of the present invention is used for a hole-injection layer and a hole-transport layer, a light-emitting element with low drive voltage can be manufactured.

REFERENCE EXAMPLE

Examples of synthesis methods of the materials for the light-emitting elements, which were used in this example, will be described below.

SYNTHESIS EXAMPLE OF 2mDBTPDBq-II

A synthesis method of 2-[3-(dibenzothiophen-4-yl)phenyl]dibenzo[f,h]quinoxaline (abbreviation: 2mDBTPDBq-II) will be described. The synthesis scheme thereof is shown in (R-1).

[62]

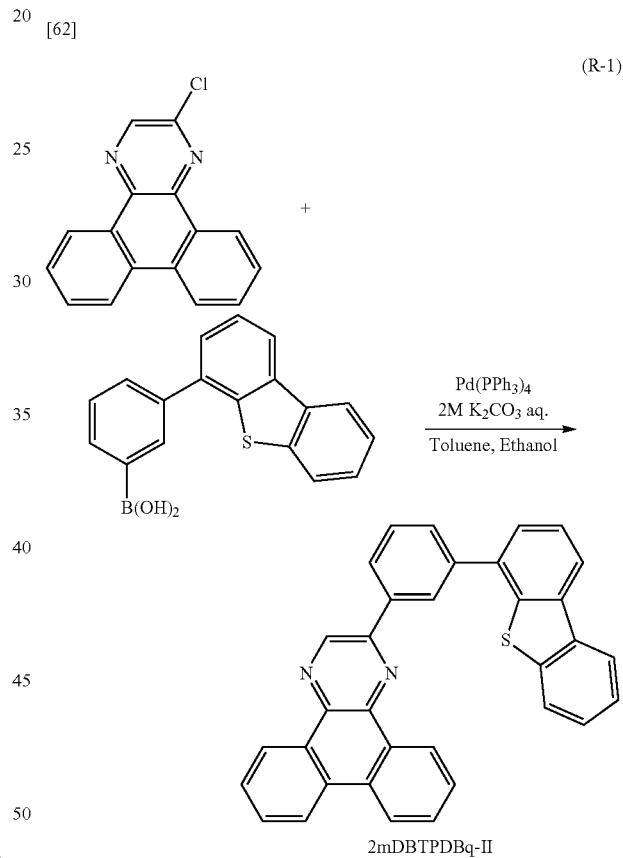

(R-1)

2mDBTPDBq-II

In a 2-L three-neck flask were put 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M aqueous potassium carbonate solution. The mixture was deaerated by being stirred under reduced pressure, and the atmosphere in the flask was replaced with nitrogen. This mixture was stirred under a nitrogen stream at 100° C. for 7.5 hours. After being cooled to room temperature, the obtained mixture was filtered to give a white substance. The substance obtained by the filtration was washed well with water and ethanol in this order, and then dried. The obtained solid was dissolved in about 600 mL of hot toluene, followed by suction filtration through Celite and Florisil, whereby a clear colorless filtrate was obtained. The obtained filtrate was concentrated and purified by silica gel column chromatography. The chromatography was carried out using toluene at a temperature of about 40° C. as a developing solvent. Acetone and ethanol were added to the solid obtained here, followed by irradiation with ultrasonic waves. Then, the generated suspended solid was filtrated and the obtained solid was dried to give 7.85 g of white powder that was the objective substance in a yield of 80%.

The above objective substance was relatively soluble in hot toluene, but is easily precipitated when cooled. Further, the substance was poorly soluble in other organic solvents such as acetone and ethanol. Thus, the utilization of these different degrees of solubility resulted in a high-yield synthesis by a simple method as above. Specifically, after the reaction finished, the mixture was returned to room temperature and the precipitated solid was collected by filtration, whereby most impurities were able to be easily removed. Further, by the column chromatography using hot toluene as a developing solvent, the generated substance, which was easily precipitated, was able to be readily purified.

By a train sublimation method, 4.0 g of the obtained white powder was sublimated and purified. In the sublimation purification, the white powder was heated at 300° C. under a pressure of 5.0 Pa with a flow rate of argon gas of 5 mL/min. After the sublimation purification, 3.5 g of white powder that was the objective substance was obtained in a yield of 88%.

A nuclear magnetic resonance (NMR) method identified this compound as 2-[3-(dibenzothiophen-4-yl)phenyl]dibenzo[f,h]quinoxaline (abbreviation: 2mDBTPDBq-II) that was the objective substance.

$^1$H NMR data of the obtained substance is shown below.

$^1$H NMR (CDCl$_3$, 300 MHz): δ (ppm)=7.45-7.52 (m, 2H), 7.59-7.65 (m, 2H), 7.71-7.91 (m, 7H), 8.20-8.25 (m, 2H), 8.41 (d, J=7.8 Hz, 1H), 8.65 (d, J=7.5 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

SYNTHESIS EXAMPLE OF Ir(mppr-Me)$_2$dpm

A synthesis method of (dipivaloylmethanato)bis(3,5-dimethyl-2-phenylpyrazinato)iridium(III) (abbreviation: Ir(mppr-Me)$_2$dpm) will be described. The synthesis scheme thereof is shown in (R-2).

[63]

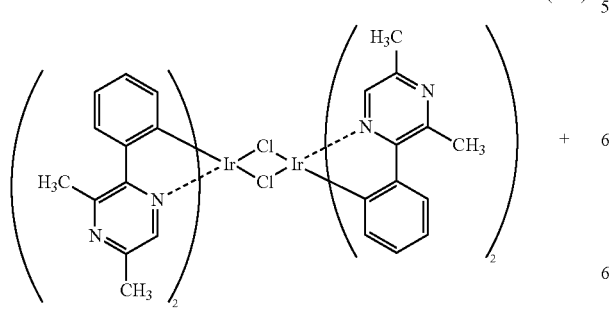

(R-2)

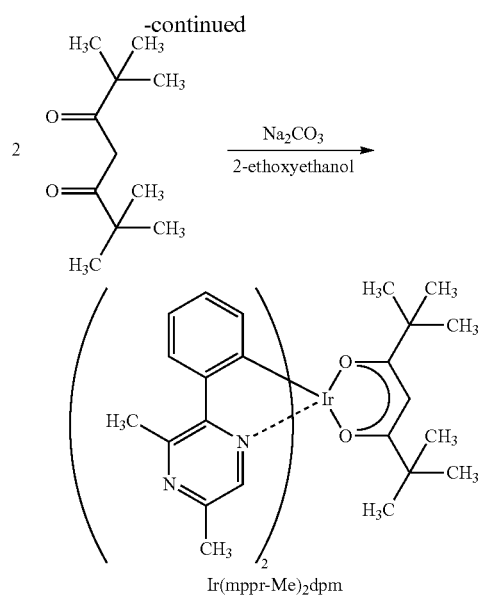

Ir(mppr-Me)$_2$dpm

First, 20 mL of 2-ethoxyethanol, 1.55 g of a binuclear complex di-μ-chloro-bis[bis(3,5-dimethyl-2-phenylpyrazinato)iridium(III)] (abbreviation: [Ir(mppr-Me)$_2$Cl]$_2$), 0.8 ml of dipivaloylmethane, and 1.38 g of sodium carbonate were mixed. The mixture was irradiated with microwaves under argon bubbling for 30 minutes to be reacted. After the reaction, the reaction solution was cooled down to room temperature, and water was added thereto. This mixture solution was separated into an organic layer and an aqueous layer, and the aqueous layer was subjected to extraction with dichloromethane. The organic layer was combined with the solution of the extract, the mixture was washed with water, followed by drying with anhydrous magnesium sulfate. After that, the mixture was gravity-filtered, and the filtrate was concentrated to be dried and hardened. This solid was recrystallized from a mixed solvent of dichloromethane and ethanol to give red powder in a yield of 67%. Note that the irradiation with microwaves was performed using a microwave synthesis system (Discover, manufactured by CEM Corporation).

Note that a nuclear magnetic resonance (NMR) method identified this compound as an organometallic complex [Ir(mppr-Me)$_2$dpm] that was the objective substance.

$^1$H NMR data of the obtained compound is shown below.

$^1$H NMR. δ (CDCl$_3$): 0.90 (s, 1H), 2.59 (s, 6H), 3.04 (s, 6H), 5.49 (s, 1H), 6.32 (dd, 2H), 6.70 (dt, 2H), 6.88 (dt, 2H), 7.86 (d, 2H), 8.19 (s, 2H).

EXAMPLE 19

In this example, manufacturing methods of light-emitting elements of one embodiment of the present invention and measurement results of element characteristics thereof will be described.

Hereinafter, manufacturing methods of light-emitting elements 14 to 17 will be described. Note that element structures of the light-emitting elements manufactured in this example are the same as that in FIG. 29. A structural formula of an organic compound used in this example is shown below. Note that the description of the organic compounds whose structural formulae have already been shown is omitted.

[64]

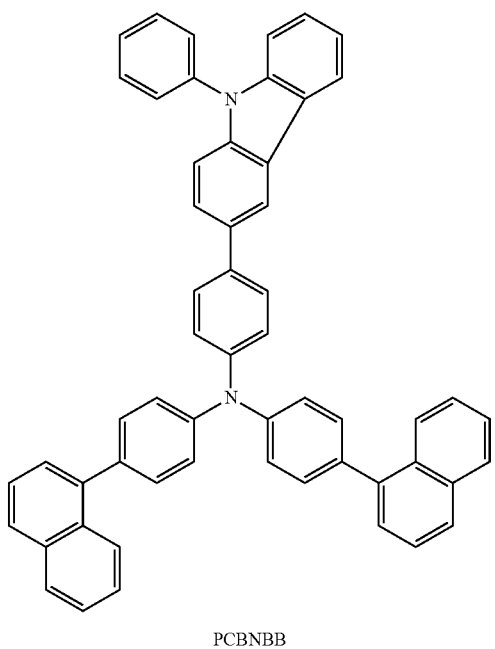

PCBNBB (Light-Emitting Element 14)

The light-emitting element 14 was manufactured in a manner similar to that of the light-emitting element 12 in Example 18 except for the light-emitting layer 1113.

In the light-emitting element 14, the light-emitting layer 1113 was formed by co-evaporation of 2-[3-(dibenzothiophen-4-yl)phenyl]dibenzo[f,h]quinoxaline (abbreviation: 2mDBTPDBq-II), 4,4'-di(1-naphthyl)-4"-(9-phenyl-9H-carbazol-3-yl)triphenylamine (abbreviation: PCBNBB), and (dipivaloylmethanato)bis(3,5-dimethyl-2-phenylpyrazinato)iridium(III) (abbreviation: Ir(mppr-Me)$_2$dpm). The weight ratio of 2mDBTPDBq-II to PCBNBB and Ir(mppr-Me)$_2$dpm was adjusted to 0.8:0.2:0.05 (=2mDBTPDBq-II: PCBNBB:Ir(mppr-Me)$_2$dpm). The thickness of the light-emitting layer 1113 was 40 nm.

(Light-Emitting Element 15)

The light-emitting element 15 was manufactured in a manner similar to that of the above light-emitting element 14 except for the hole-injection layer 1111 and the hole-transport layer 1112.

In the light-emitting element 15, the hole-injection layer 1111 was formed in such a manner that 3-[4-(9-phenanthryl)-phenyl]-9-phenyl-9H-carbazole (abbreviation: PCPPn) synthesized in Example 2 and molybdenum(VI) oxide were co-evaporated on the first electrode 1101. The thickness of the hole-injection layer 1111 was 40 nm, The weight ratio of PCPPn to molybdenum(VI) oxide was adjusted to 4:2 (=PCPPn:molybdenum oxide).

Next, PCPPn was deposited to a thickness of 20 nm on the hole-injection layer 1111 to form the hole-transport layer 1112.

(Light-Emitting Element 16)

The light-emitting element 16 was manufactured in a manner similar to that of the above light-emitting element 14 except for the hole-injection layer 1111.

In the light-emitting element 16, the hole-injection layer 1111 was formed in such a manner that 9-[4-(9-phenylcarbazol-3-yl)phenyl]-10-phenylanthracene (abbreviation: PCzPA) and molybdenum(VI) oxide were co-evaporated on the first electrode 1101. The thickness of the hole-injection layer 1111 was 40 nm. The weight ratio of PCzPA to molybdenum(VI) oxide was adjusted to be 4:2 (=PCzPA:molybdenum oxide).

(Light-Emitting Element 17)

The light-emitting element 17 was manufactured in a manner similar to that of the above light-emitting element 15 except for the hole-injection layer 1111. The hole-injection layer 1111 of the light-emitting element 17 was manufactured in a manner similar to that of the above light-emitting element 16.

Table 22 shows the element structures of the light-emitting elements 14 to 17 manufactured as described above.

TABLE 22

|  | Light-Emitting Element 14 | Light-Emitting Element 15 | Light-Emitting Elementt 16 | Light-Emitting Element 17 |
|---|---|---|---|---|
| First Electrode 1101 | ITSO 110 nm | ITSO 110 nm | ITSO 110 nm | ITSO 110 nm |
| Hole-injection Layer 1111 | PCPN:MoOx (=4:2) 40 nm | PCPPn:MoOx (=4:2) 40 nm | PCzPA:MoOx (=4:2) 40 nm | PCzPA:MoOx (=4:2) 40 nm |
| Hole-transport layer 1112 | PCPN 20 nm | PCPPn 20 nm | PCPN 20 nm | PCPPn 20 nm |
| Light-emitting layer 1113 | 2mDBTPDBq-II:CBNBB:Ir(mppr-Me)2dpm (=0.8:0.2:0.05) 40 nm | 2mDBTPDBq-II:CBNBB:Ir(mppr-Me)2dpm (=0.8:0.2:0.05) 40 nm | 2mDBTPDBq-II:CBNBB:Ir(mppr-Me)2dpm (=0.8:0.2:0.05) 40 nm | 2mDBTPDBq-II:CBNBB:Ir(mppr-Me)2dpm (=0.8:0.2:0.05) 40 nm |
| Electron-transport layer 1114a | 2mDBTPDBq-II 10 nm | 2mDBTPDBq-II 10 nm | 2mDBTPDBq-II 10 nm | 2mDBTPDBq-II 10 nm |
| 1114b | BPhen 20 nm | BPhen 20 nm | BPhen 20 nm | BPhen 20 nm |
| Electron-injection layer 1115 | LiF 1 nm | LiF 1 nm | LiF 1 nm | LiF 1 nm |
| Second Electrode 1103 | Al 200 nm | Al 200 nm | Al 200 nm | Al 200 nm |

*The mixture ratios are all represented in weight ratios.

In a glove box containing a nitrogen atmosphere, the light-emitting elements 14 to 17 were sealed so as not to be exposed to the air. After that, the operating characteristics of these elements were measured. Note that the measurement was carried out at room temperature (in an atmosphere kept at 25° C.).

Note that the light-emitting elements 14 to 17 were formed over the same substrate. In addition, in the above four light-emitting elements, the components other than the hole-injection layers 1111 and the hole-transport layers 1112 were formed at the same time, and measurement of the operating characteristics of the four light-emitting elements were performed at the same time.

Table 23 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting elements 14 to 17 at a luminance of about 1000 cd/m$^2$.

TABLE 23

|  | Light-Emitting Element 14 | Light-Emitting Element 15 | Light-Emitting Element 16 | Light-Emitting Element 17 |
| --- | --- | --- | --- | --- |
| Voltage (V) | 2.8 | 2.9 | 2.8 | 2.9 |
| Current density (mA/cm$^2$) | 1.5 | 1.8 | 1.5 | 1.9 |
| Chromaticity coordinates (x, y) | (0.52, 0.47) | (0.52, 0.47) | (0.52, 0.47) | (0.52, 0.47) |
| Luminance (cd/m$^2$) | 1050 | 1200 | 980 | 1200 |
| Current efficiency (cd/A) | 68 | 68 | 65 | 66 |
| Power efficiency (lm/W) | 77 | 74 | 73 | 71 |
| External quantum efficiency (%) | 24 | 24 | 23 | 23 |

Figure 73:
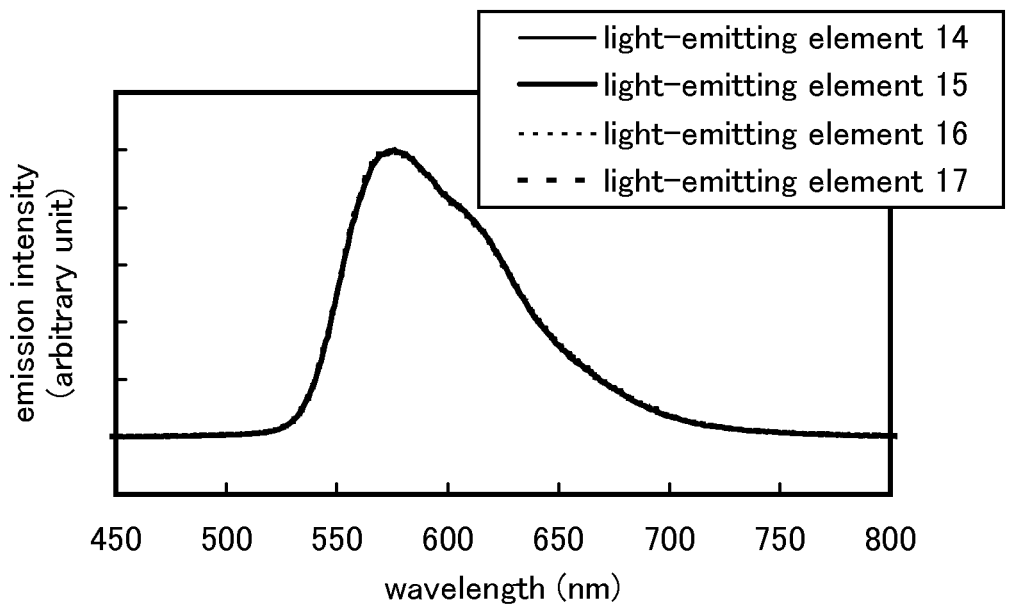
FIG. 73 shows emission spectra of light-emitting elements of Example 19.
Figure 74:
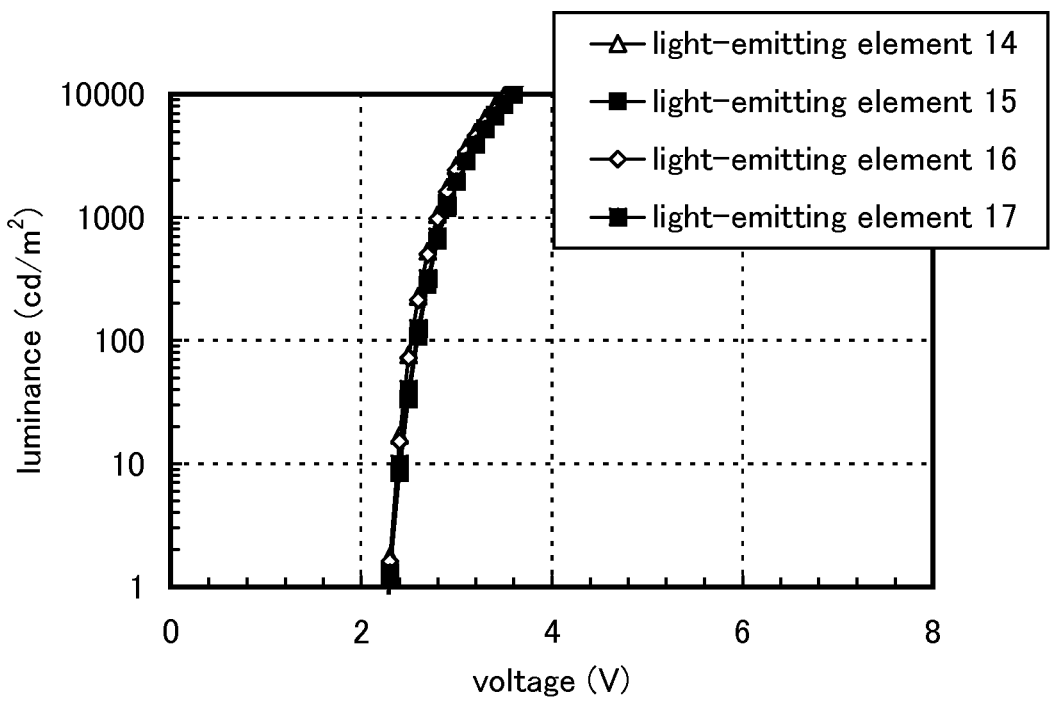
FIG. 74 shows voltage-luminance characteristics of the light-emitting elements of Example 19.
Figure 75:
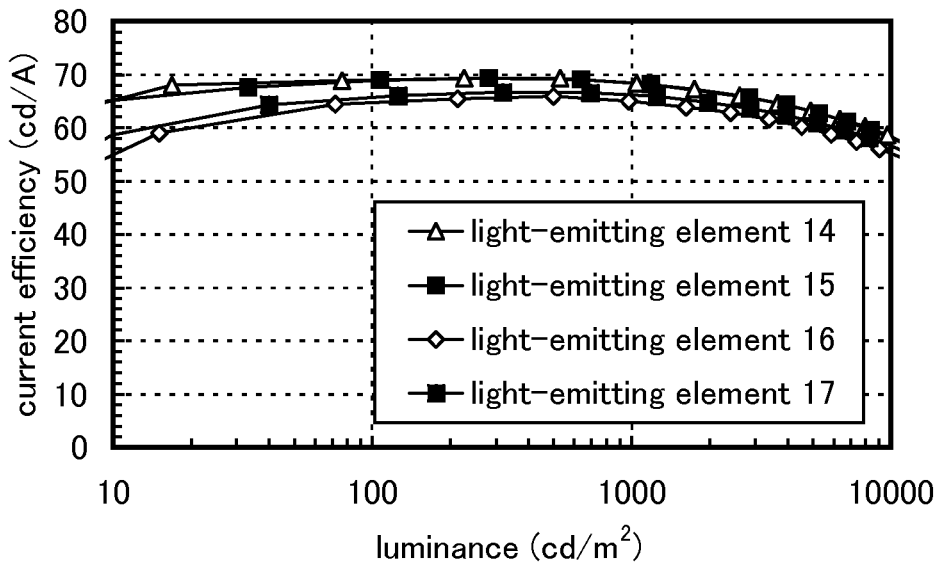
FIG. 75 shows luminance-current efficiency characteristics of the light-emitting elements of Example 19.
Figure 76:
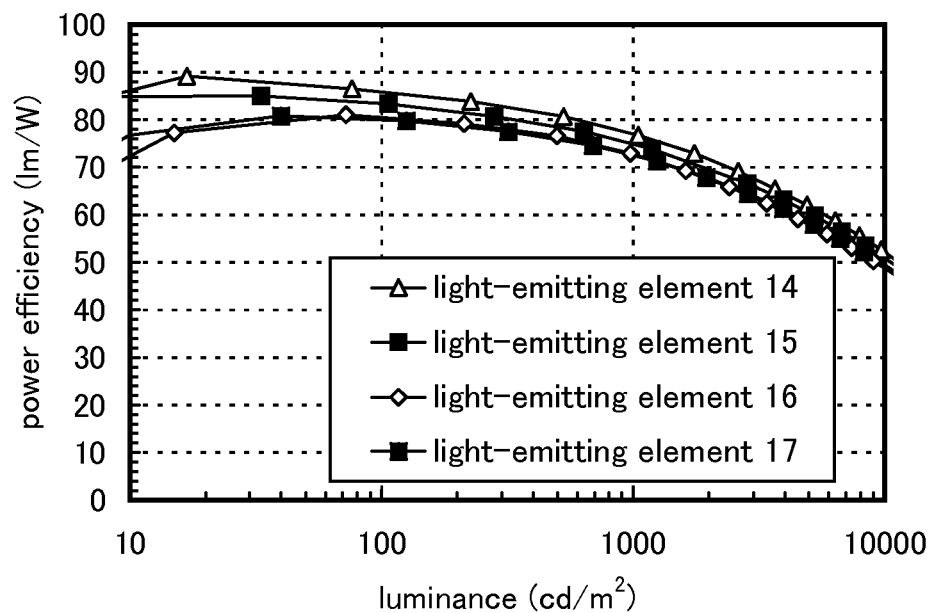
FIG. 76 shows luminance-power efficiency characteristics of the light-emitting elements of Example 19.

FIG. 73 shows the emission spectra of the light-emitting elements 14 to 17. In FIG. 73, the horizontal axis represents the wavelength (nm) and the vertical axis represents the emission intensity (arbitrary unit). FIG. 74, FIG. 75, and FIG. 76 respectively show the voltage-luminance characteristics, the luminance-current efficiency characteristics, and the luminance-power efficiency characteristics of the light-emitting elements 14 to 17. FIG. 74, the vertical axis represents the luminance (cd/m$^2$) and the horizontal axis represents the voltage (V). In FIG. 75, the vertical axis represents the current efficiency (cd/A) and the horizontal axis represents the luminance (cd/m$^2$). In FIG. 76, the vertical axis represents the power efficiency (lm/W) and the horizontal axis represents the luminance (cd/m$^2$).

According to FIG. 73, the light-emitting elements 14 to 17 have peaks around 580 nm. The CIE chromaticity coordinates in Table 23 also show that the light-emitting elements 14 to 17 exhibit orange phosphorescence emission originating from Ir(mppr-Me)$_2$dpm and that all the elements have excellent carrier balance.

Further, FIG. 74, FIG. 75, FIG. 76, and Table 23 show that the light-emitting elements 14 to 17 have high efficiency.

Further, it was also found that the light-emitting elements 14 and 15 in each of which the layer containing the carbazole compound of one embodiment of the present invention is used for the hole-injection layer 1111 have higher efficiency than the light-emitting elements 16 and 17. In addition, it was found that the light-emitting elements 14 and 15 can be driven at a voltage as low as that of the comparative light-emitting elements 16 and 17.

Figure 77:
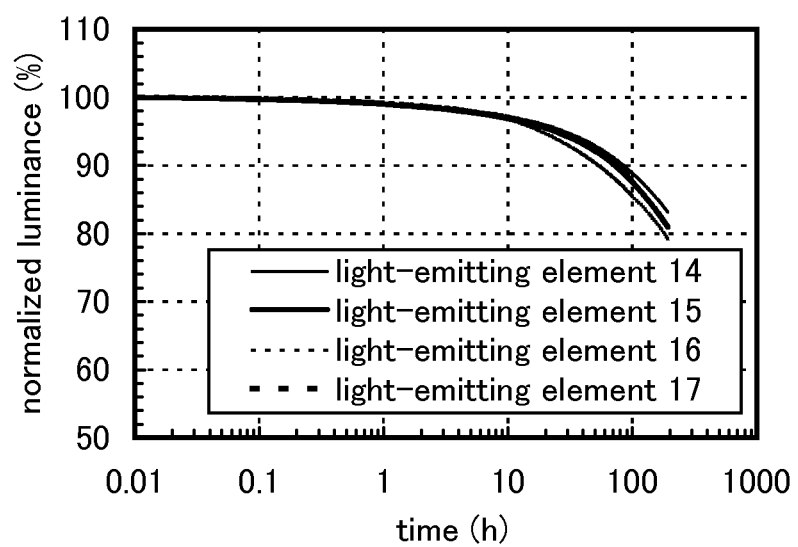
FIG. 77 shows results of a reliability test conducted on the light-emitting elements of Example 19.

Further, a reliability test was conducted on the manufactured light-emitting elements 14 to 17. In the reliability test, the initial luminance was set at 5000 cd/m$^2$, these elements were operated at a constant current density, and the luminance was measured at regular intervals. The results obtained by the reliability test are shown in FIG. 77. In FIG. 77, the horizontal axis represents the current flow time (hour) and the vertical axis represents the percentage of luminance to the initial luminance at each time, that is, normalized luminance (%).

As shown in FIG. 77, a reduction in the luminance of each of the light-emitting elements 14 to 17 with time does not easily occur and the lifetime of each of the elements is long. The light-emitting elements 14, 15, 16, and 17 respectively maintained 87%, 83%, 81%, and 79% of the initial luminance even after being driven for 190 hours.

As described above, the carbazole compound of one embodiment of the present invention is used as a material for a light-emitting element, whereby the light-emitting element can have high efficiency.

Further, it was indicated that when the carbazole compound of one embodiment of the present invention is used for a hole-injection layer and a hole-transport layer, a light-emitting element with low drive voltage can be manufactured.

Further, it was indicated that when the carbazole compound of one embodiment of the present invention is used for a hole-injection layer and a hole-transport layer, a light-emitting element with long lifetime can be manufactured.

EXAMPLE 20

In this example, manufacturing methods of light-emitting elements each of which is one embodiment of the present invention and measurement results of element characteristics thereof will be described together with measurement results of a comparative light-emitting element.

Manufacturing methods of a light-emitting element 18, a light-emitting element 19, and a comparative light-emitting element 9 of this example will be described below. Note that element structures of the light-emitting elements manufactured in this example are similar to that in FIG. 62. In addition, organic compounds used in this example are the ones whose structural formulae have already been shown; therefore, the description thereof is omitted.

(Light-Emitting Element 18)

The light-emitting element 18 was manufactured in a manner similar to that of the above light-emitting element 8 in Example 14 except for the hole-injection layer 1111, the hole-transport layer 1112, and the light-emitting layer 1113.

In the light-emitting element 18, the hole-injection layer 1111 was formed in such a manner that PCPN synthesized in Example 1 and molybdenum(VI) oxide were co-evaporated on the first electrode 1101. The thickness of the hole-injection layer 1111 was 50 nm. The weight ratio of PCPN to molybdenum(VI) oxide was adjusted to be 4:2 (=PCPN:molybdenum oxide).

Next, PCPN was deposited to a thickness of 10 nm on the hole-injection layer 1111 to form the hole-transport layer 1112.

In the light-emitting element 18, the first light-emitting layer 1113a and the second light-emitting layer 1113b were stacked in this order on the first electrode 1101 to form the light-emitting layer 1113.

The first light-emitting layer 1113a was formed by co-evaporation of PCPN and 1,6FLPAPrn. The weight ratio of PCPN to 1,6FLPAPrn was adjusted to be 1:0.05 (=PCPN:1,6FLPAPrn). The thickness of the first light-emitting layer 1113a was 10 nm.

The second light-emitting layer 1113b was formed by co-evaporation of CzPA and 1,6FLPAPrn. The weight ratio of CzPA to 1,6FLPAPrn was adjusted to be 1:0.05 (=CzPA: 1,6FLPAPrn). The thickness of the second light-emitting layer 1113b was 25 nm.

(Light-Emitting Element 19)

The light-emitting element 19 was manufactured in a manner similar to that of the above light-emitting element 18 except for the hole-injection layer 1111, the hole-transport layer 1112, and the first light-emitting layer 1113a.

In the light-emitting element 19, the hole-injection layer 1111 was formed in such a manner that PCPPn synthesized in Example 2 and molybdenum(VI) oxide were co-evaporated on the first electrode 1101. The thickness of the hole-injection layer 111 was 50 nm. The weight ratio of PCPPn to molybdenum(VI) oxide was adjusted to be 4:2 (=PCPPn:molybdenum oxide).

Next, PCPPn was deposited to a thickness of 10 nm on the hole-injection layer 1111 to form the hole-transport layer 1112.

In the light-emitting element 19, the first light-emitting layer 1113a was formed by co-evaporation of PCPPn and 1,6FLPAPrn. The weight ratio of PCPN to 1,6FLPAPrn was adjusted to be 1:0.05 (=PCPPn: 1,6FLPAPrn). The thickness of the first light-emitting layer 1113a was 10 nm.

(Comparative Light-Emitting Element 9)

The comparative light-emitting element 9 was manufactured in a manner similar to that of the light-emitting element 18 except for the hole-injection layer 1111, the hole-transport layer 1112, and the first light-emitting layer 1113a.

In the comparative light-emitting element 9, the hole-injection layer 1111 was formed in such a manner that PCzPA and molybdenum(VI) oxide were co-evaporated on the first electrode 1101. The thickness of the hole-injection layer 1111 was 50 nm. The weight ratio of PCzPA to molybdenum(VI) oxide was adjusted to be 4:2 (=PCzPA:molybdenum oxide).

Next, PCzPA was deposited to a thickness of 10 nm on the hole-injection layer 1111 to form the hole-transport layer 1112.

In the comparative light-emitting element 9, the first light-emitting layer 1113a was formed by co-evaporation of PCzPA and 1,6FLPAPrn. The weight ratio of PCzPA to 1,6FLPAPrn was adjusted to be 1:0.05 (=PCzPA: 1,6FLPAPrn). The thickness of the first light-emitting layer 1113a was 10 nm.

Table 24 shows the element structures of the light-emitting elements 18 and 19 and the comparative light-emitting element 9 that were manufactured as described above.

TABLE 24

|  |  | Light-Emitting Element 18 | Light-Emitting Element 19 | Comparative Light-Emitting Element 9 |
|---|---|---|---|---|
| First Electrode 1101 | | ITSO 110 nm | ITSO 110 nm | ITSO 110 nm |
| Hole-injection Layer 1111 | | PCPN:MoOx (=4:2) 50 nm | PCPPn:MoOx (=4:2) 50 nm | PCzPA:MoOx (=4:2) 50 nm |
| Hole-transport layer 1112 | | PCPN 10 nm | PCPPn 10 nm | PCzPA 10 nm |
| Light-Emitting Layer 1113 | 1113a | PCPN:1,6FLPAPrn (=1:0.05) 10 nm | PCPPn:1,6FLPAPrn (=1:0.05) 10 nm | PCzPA:1,6FLPAPrn (=1:0.05) 10 nm |
| | 1113b | CzPA:1,6FLPAPrn (=1:0.05) 25 nm | CzPA:1,6FLPAPrn (=1:0.05) 25 nm | CzPA:1,6FLPAPrn (=1:0.05) 25 nm |
| Electron-transport layer | 1114a | Alq 10 nm | Alq 10 nm | Alq 10 nm |
| | 1114b | BPhen 15 nm | BPhen 15 nm | BPhen 15 nm |
| Electron-injection layer 1115 | | LiF 1 nm | LiF 1 nm | LiF 1 nm |
| Second Electrode 1103 | | Al 200 nm | Al 200 nm | Al 200 nm |

*The mixture ratios are all represented in weight ratios.

In a glove box containing a nitrogen atmosphere, the light-emitting elements 18 and 19 and the comparative light-emitting element 9 were sealed so as not to be exposed to the air. After that, the operating characteristics of these elements were measured. Note that the measurement was carried out at room temperature (in an atmosphere kept at 25° C.).

Note that the light-emitting elements 18 and 19 and the comparative light-emitting element 9 were formed over the same substrate. In addition, in the above three light-emitting elements, the components other than the hole-injection layers 1111, the hole-transport layers 1112, and the first light-emitting layer 1113a were formed at the same time, and the three light-emitting elements were operated at the same time.

Table 25 shows the voltage (V), current density (mA/cm$^2$), CIE chromaticity coordinates (x,y), luminance (cd/m$^2$), current efficiency (cd/A), power efficiency (lm/W), and external quantum efficiency (%) of each of the light-emitting elements 18 and 19 and the comparative light-emitting element 9 at a luminance of about 1000 cd/m$^2$.

TABLE 25

| | Light-Emitting Element 18 | Light-Emitting Element 19 | Comparative Light-Emitting Element 9 |
|---|---|---|---|
| Voltage (V) | 4.6 | 4.4 | 4.4 |
| Current density (mA/cm$^2$) | 8.5 | 7.6 | 12 |
| Chromaticity coordinates (x, y) | (0.15, 0.20) | (0.15, 0.21) | (0.15, 0.19) |
| Luminance (cd/m$^2$) | 920 | 810 | 1000 |
| Current efficiency (cd/A) | 11 | 11 | 9 |
| Power efficiency (lm/W) | 7.4 | 7.6 | 6.1 |
| External quantum efficiency (%) | 8.0 | 7.4 | 6.5 |

Figure 78:
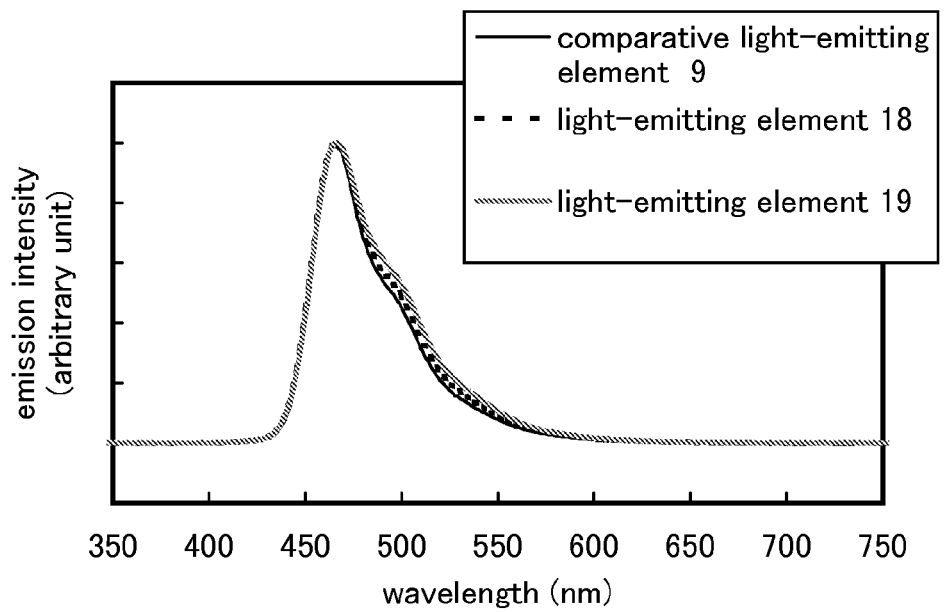
FIG. 78 shows emission spectra of light-emitting elements and a comparative light-emitting element of Example 20.
Figure 79:
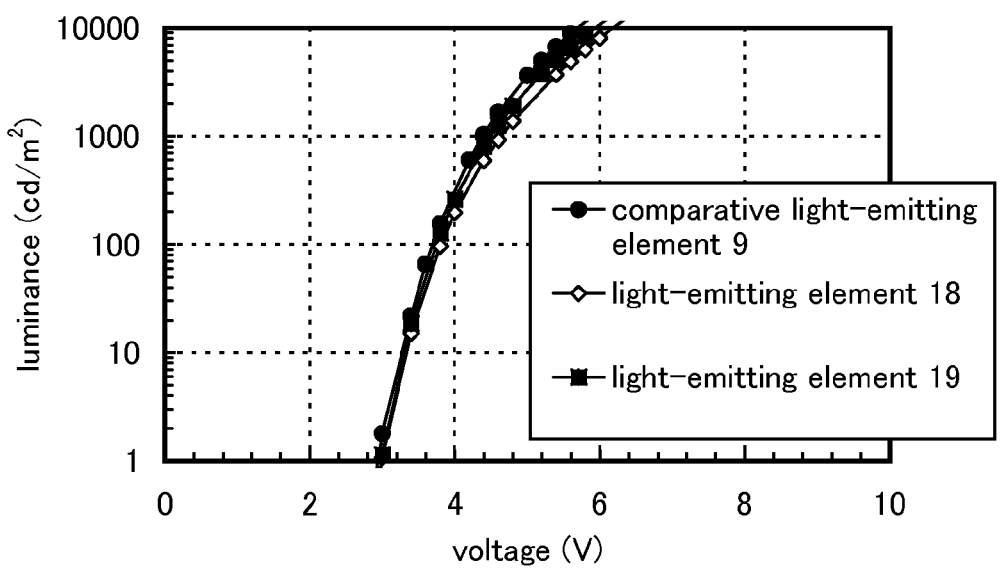
FIG. 79 shows voltage-luminance characteristics of the light-emitting elements and the comparative light-emitting element of Example 20.
Figure 80:
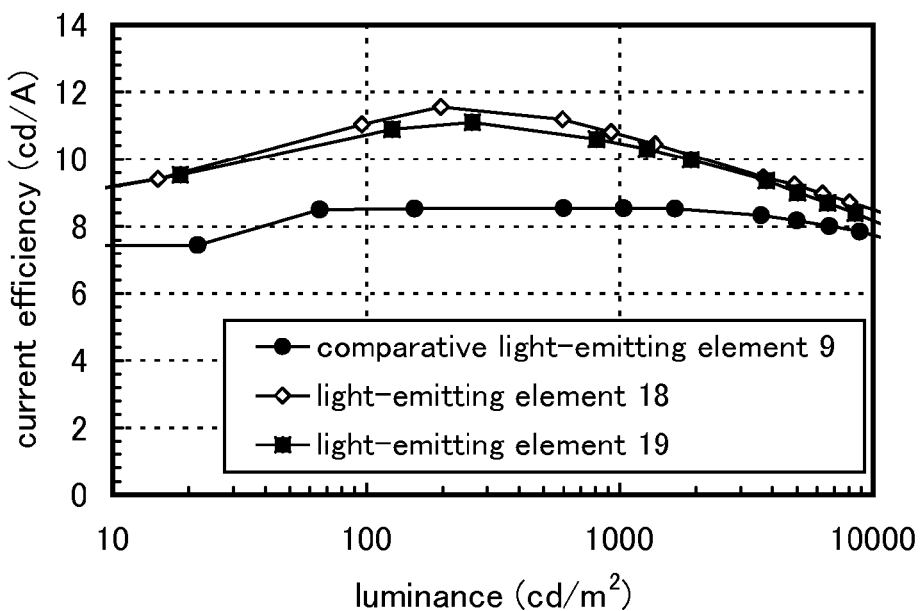
FIG. 80 shows luminance-current efficiency characteristics of the light-emitting elements and the comparative light-emitting element of Example 20.
Figure 81:
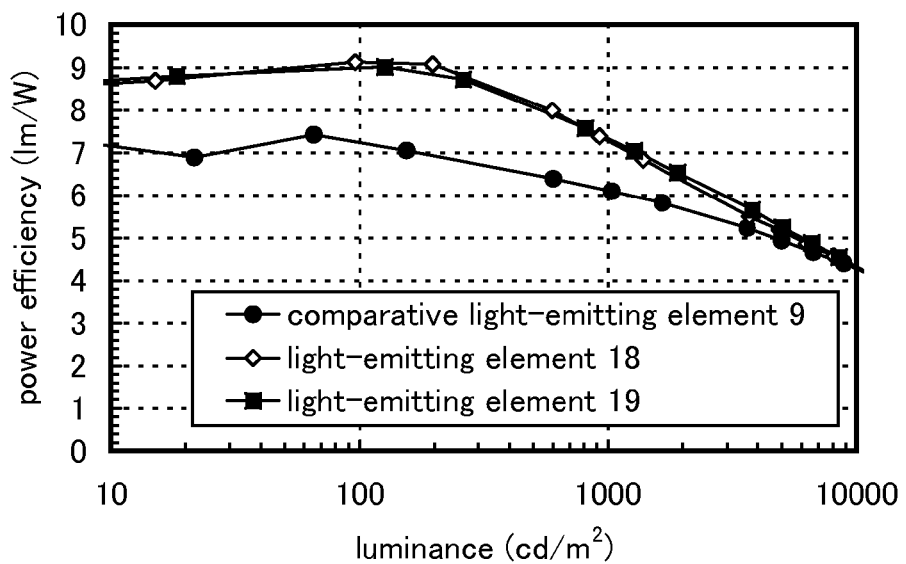
FIG. 81 shows luminance-power efficiency characteristics of the light-emitting elements and the comparative light-emitting element of Example 20.

FIG. 78 shows the emission spectra of the light-emitting elements 18 and 19 and the comparative light-emitting element 9. In FIG. 78, the horizontal axis represents the wavelength (nm) and the vertical axis represents the emission intensity (arbitrary unit). FIG. 79, FIG. 80, and FIG. 81 respectively show the voltage-luminance characteristics, the luminance-current efficiency characteristics, and the luminance-power efficiency characteristics of the light-emitting elements 18 and 19 and the comparative light-emitting element 9. FIG. 79, the vertical axis represents the luminance (cd/m$^2$) and the horizontal axis represents the voltage (V). In FIG. 80, the vertical axis represents the current efficiency (cd/A) and the horizontal axis represents the luminance (cd/m$^2$). In FIG. 81, the vertical axis represents the power efficiency (lm/W) and the horizontal axis represents the luminance (cd/m$^2$).

According to FIG. 78, all of the light-emitting elements 18 and 19 and the comparative light-emitting element 9 have peaks around 470 nm. The CIE chromaticity coordinates in Table 25 also show that the light-emitting elements 18 and 19 and the comparative light-emitting element 9 exhibit blue light emission originating from 1,6FLPAPrn and that the elements have excellent carrier balance. Further, in the light-emitting elements 18 and 19, the carbazole compound according to one embodiment of the present invention is used as a host material of a fluorescent compound which emits blue fluorescence, and the S1 level of the carbazole compound according to one embodiment of the present invention was confirmed to be sufficiently high (higher than the S1 level of at least a fluorescent compound which emits blue light).

In particular, the light-emitting elements 18 and 19 in each of which the carbazole compound according to one embodiment of the present invention is used in the first light-emitting layer 1113a have higher efficiency than the comparative light-emitting element 9. This shows that the S1 level of the carbazole compound according to one embodiment of the present invention is sufficiently high.

Further, FIG. 79, FIG. 80, FIG. 81, and Table 25 show that the light-emitting elements 18 and 19 can be driven at a voltage as low as that of the comparative light-emitting element 9 and that the light-emitting elements 18 and 19 have higher efficiency than the comparative light-emitting element 9. The reason for the above is probably as follows. The band gap of the carbazole compound of one embodiment of the present invention, which is used in the light-emitting elements 18 and 19 in this example, is wider than the band gap of PCzPA used in the comparative light-emitting element 9; thus, energy transfer from the light-emitting layer can be efficiently suppressed in the case where the carbazole compound is used as a material of the hole-transport layer in contact with the light-emitting layer. The LUMO level (absolute value) of the carbazole compound of one embodiment of the present invention, which is used in the light-emitting elements 18 and 19 in this example, is shallower (smaller) than the LUMO level of PCzPA used in the comparative light-emitting element 9; thus, loss of carriers due to leakage of electrons from the light-emitting layer can be suppressed. Moreover, the HOMO level (absolute value) of the carbazole compound of one embodiment of the present invention, which is used in the light-emitting elements 18 and 19 in this example, is deeper (larger) than the HOMO level of PCzPA used in the comparative light-emitting element 9; thus, injection of holes into the light-emitting layer can be performed efficiently.

Further, it was found that the light-emitting elements both can be driven at a voltage as low as that of the comparative light-emitting element and that the light-emitting elements both have good transfer of carriers. This shows that the carrier-transport property of the carbazole compound according to one embodiment of the present invention is excellent.

As described above, the carbazole compound of one embodiment of the present invention is used as a material of a light-emitting element, whereby the light-emitting element can have high efficiency. In addition, the carbazole compound of one embodiment of the present invention can be used as a host material of a blue fluorescent material.

EXAMPLE 21

In this example, an example of producing 9-phenyl-9H-3-{4-[3,5-di(phenanthren-9-yl)phenyl]phenyl}carbazole (abbreviation: Pn2BPPC) that is a carbazole compound of one embodiment of the present invention, in which R$^1$ is a phenyl group, R$^2$ is hydrogen, $\alpha^3$ is a biphenyldiyl group having a phenanthrenyl group as a substituent, and Ar$^3$ is a phenanthrenyl group in General Formula (G1) will be described.

[65]

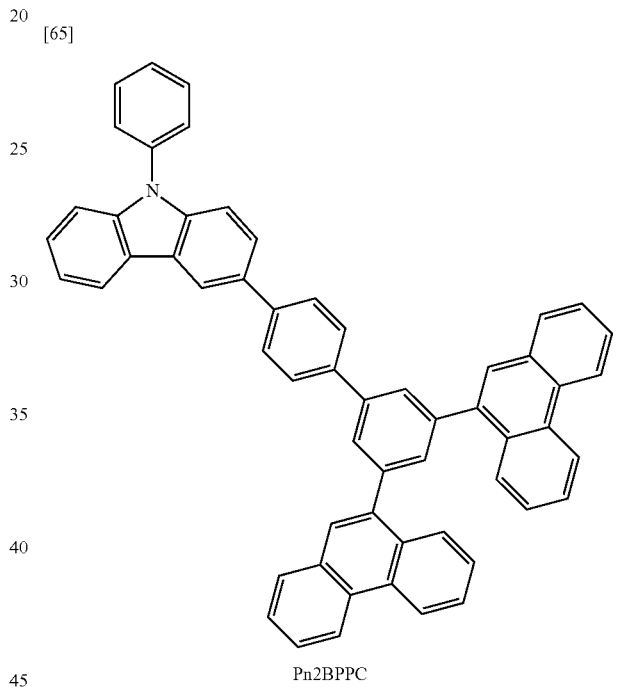

Pn2BPPC

Step 1: Synthesis Method of 9-[3-chloro-5-(phenanthren-9-yl)phenyl]phenanthrene (abbreviation: Cl-PPn2)

In a 200-mL three-neck flask, a mixture of 2.90 g (10.7 mmol) of 1,3-dibromo-5-chlorobenzene, 5.0 g (22.5 mmol) of 9-phenanthrene boronic acid, 50.6 mg (0.23 mmol) of palladium(II) acetate, 207 mg (0.68 mmol) of tri(o-tolyl)phosphine, 70 mL of toluene, 7 mL of ethanol, and 20 mL of a potassium carbonate aqueous solution (2 mol/L) was deaerated while being stirred under reduced pressure and was heated and stirred in a nitrogen atmosphere at 85° C. for 6 hours to be reacted. In addition, 50.6 mg (0.23 mmol) of palladium(II) acetate and 207 mg (0.68 mmol) of tri(o-tolyl)phosphine were added to the mixture, and the mixture was heated and stirred in a nitrogen atmosphere at 85° C. for 7.5 hours, and then heated and stirred at 110° C. for 7.5 hours to be reacted.

After reaction, 300 mL of toluene was added to the reaction mixture solution, and an organic layer of the mixture solution was filtrated through Florisil (produced by Wako Pure Chemical Industries, Ltd., Catalog No. 540-00135), alumina (neutral, produced by Merck Ltd), and Celite (produced by Wako Pure Chemical Industries, Ltd., Catalog No. 531-16855). The obtained filtrate was washed with water, and magnesium sulfate was added thereto so that moisture was adsorbed. This suspension was filtrated to obtain a filtrate. The obtained filtrate was concentrated and purified by silica gel column chromatography. At this time, a mixed solvent of toluene and hexane (toluene:hexane=1:5) was used as a developing solvent for the chromatography. The obtained fraction was concentrated, and toluene and hexane were added thereto. The mixture was irradiated with ultrasonic waves and then recrystallized to give 3.11 g of white powder that was an objective substance in a yield of 63%. The reaction scheme of the synthesis method is shown in (F8-1).

[66]

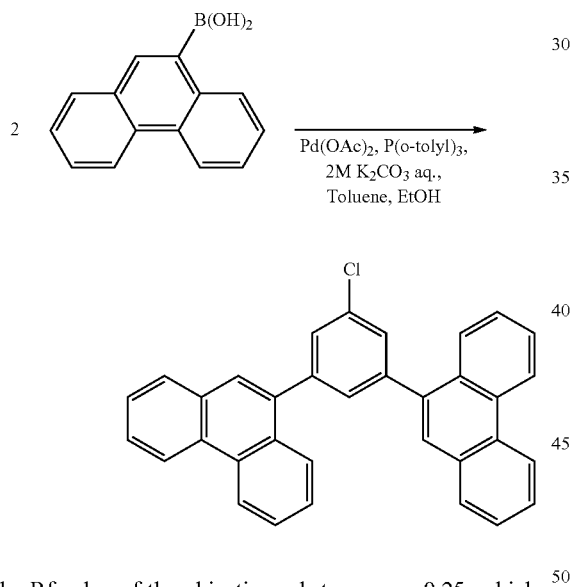

(F8-1)

The Rf value of the objective substance was 0.25, which was obtained by silica gel thin layer chromatography (TLC) (with a developing solvent containing ethyl acetate and hexane in a 1:10 ratio).

The compound obtained in Step 1 was examined by a nuclear magnetic resonance (NMR) method. The measurement data are shown below.

$^1$H NMR (CDCl$_3$, 300 MHz): δ (ppm)=7.59-7.73 (m, 11H), 7.79 (s, 2H), 7.92 (d, J=7.81 Hz, 2H), 8.06 (d, J=8.30 Hz, 2H), 8.73 (d, J=8.30 Hz, 2H), 8.79 (d, J=8.30 Hz, 2H).

Figure 82A:
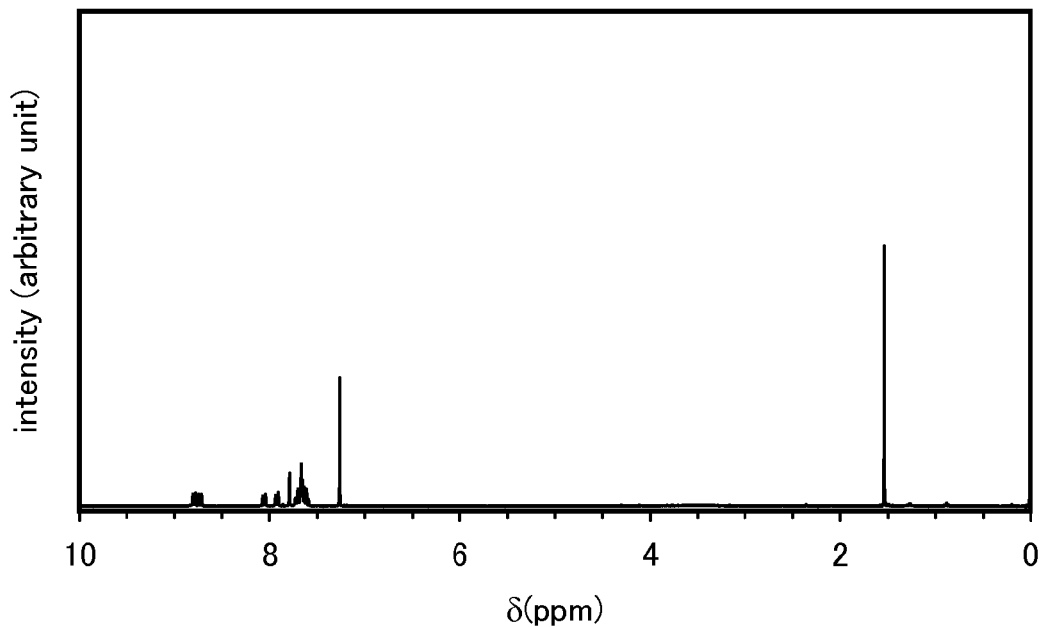
FIGS. 82A and 82B are NMR charts of Cl-PPn2.
Figure 82B:
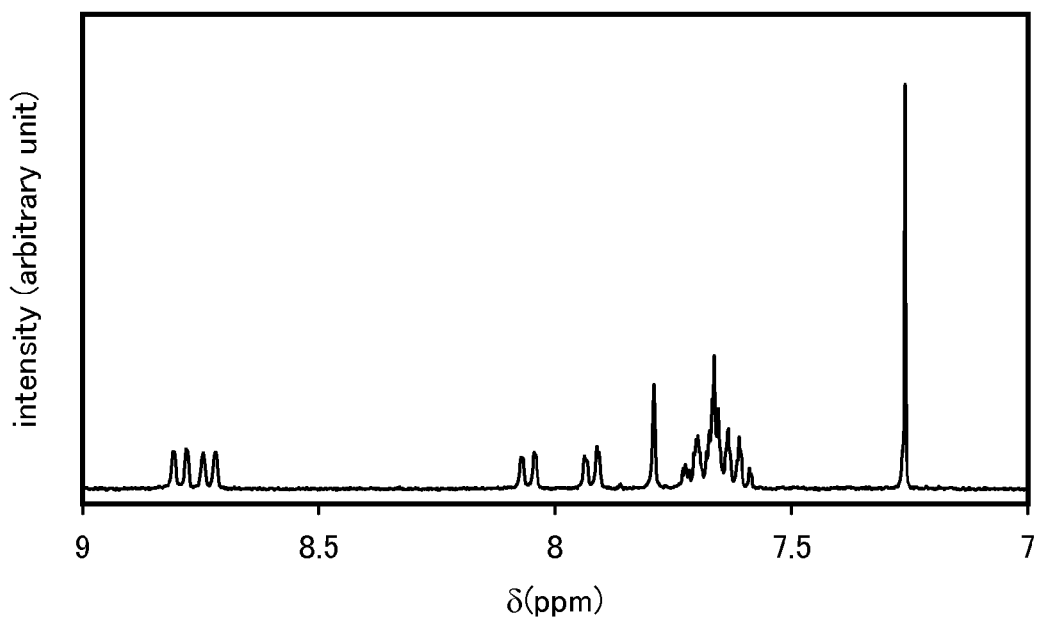

FIGS. 82A and 82B are $^1$H NMR charts. Note that FIG. 82B is a chart showing an enlarged part of FIG. 82A in the range of 7.00 ppm to 9.00 ppm. The measurement results confirmed that 9-[3-chloro-5-(phenanthren-9-yl)phenyl] phenanthrene (abbreviation: Cl-PPn2) that was the objective substance was able to be obtained.

Step 2: Synthesis Method of 9-phenyl-9H-3-{4-[3,5-di(phenanthren-9-yl)phenyl]phenyl}carbazole (abbreviation: Pn2BPPC)

In a 200-mL three-neck flask, a mixture of 1.04 g (2.87 mmol) of 9-[3-chloro-5-(phenanthren-9-yl)phenyl]phenanthrene, 2.00 g (4.31 mmol) of 3-(9-phenyl-9H-carbazole) phenyl-4-boronic acid, 49.5 mg (0.09 mmol) of bis(dibenzylideneacetone)palladium(0), 91.8 mg (0.24 mmol) of 2'-(dicyclohexylphosphino)acetophenone ethylene ketal, 1.31 g (8.61 mmol) of cesium(I) fluoride, and 30 ml of xylene was heated and stirred in a nitrogen atmosphere at 150° C. for 12 hours to be reacted.

After reaction, 500 mL of toluene was added to the reaction mixture solution, and the mixture solution was filtered through alumina (neutral, produced by Merck Ltd) and Celite (produced by Wako Pure Chemical Industries, Ltd., Catalog No. 531-16855). The obtained filtrate was concentrated and purified by silica gel column chromatography. At this time, a mixed solvent of toluene and hexane (toluene:hexane=1:5) was used as a developing solvent for the chromatography. The obtained fraction was concentrated, and hexane was added thereto. The mixture was irradiated with ultrasonic waves and then recrystallized to obtain 1.9 g of white powder that was an objective substance in a yield of 89%. The reaction scheme of the synthesis method is shown in (F8-2).

[67]

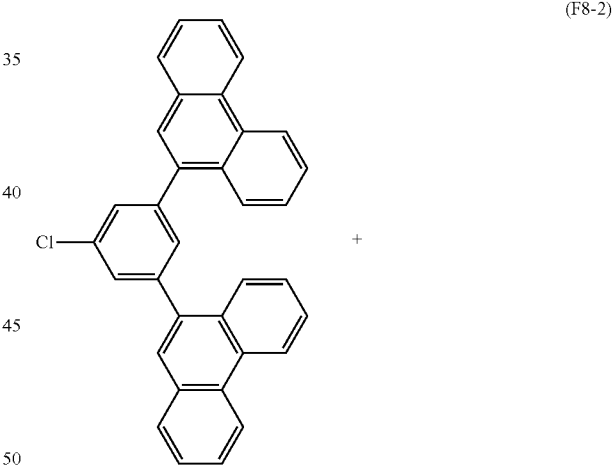

(F8-2)

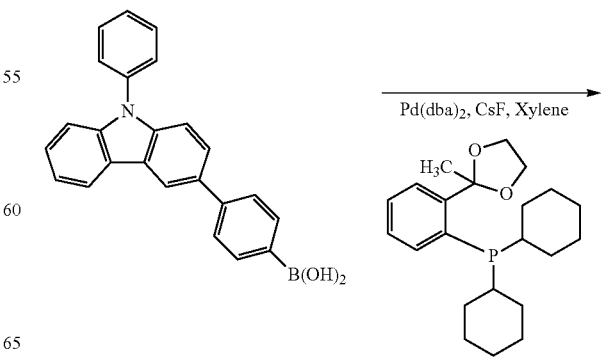

-continued

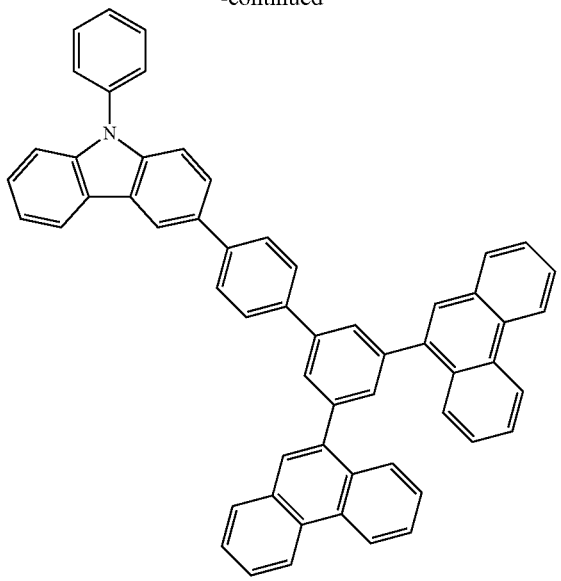

The Rf value of the objective substance was 0.29, which was obtained by silica gel thin layer chromatography (TLC) (with a developing solvent containing ethyl acetate and hexane in a 1:10 ratio).

The compound obtained in Step 2 above was examined by a nuclear magnetic resonance (NMR) method. The measurement data are shown.

$^1$H NMR (CDCl$_3$, 300 MHz): δ (ppm)=7.43 (d, J=3.4 Hz, 2H), 7.46-7.50 (m, 2H), 7.60-7.99 (m, 25H), 8.19-8.23 (m, 3H), 8.41 (d, J=0.98 Hz, 1H), 8.76 (d, J=8.30 Hz, 2H), 8.82 (d, J=7.32 Hz, 2H).

Figure 83A:
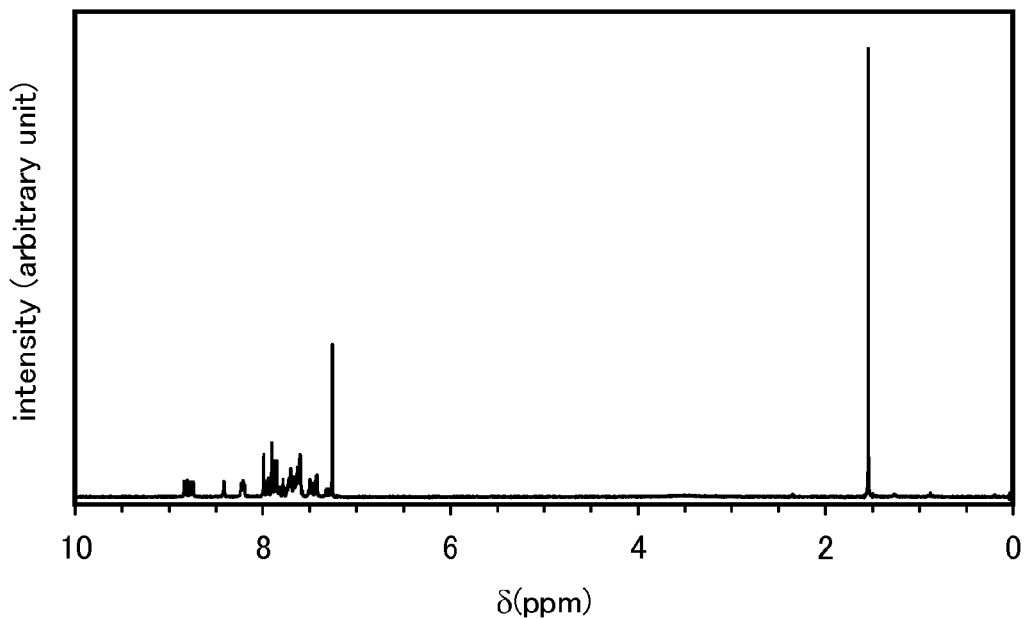
FIGS. 83A and 83B are NMR charts of Pn2BPPC.
Figure 83B:
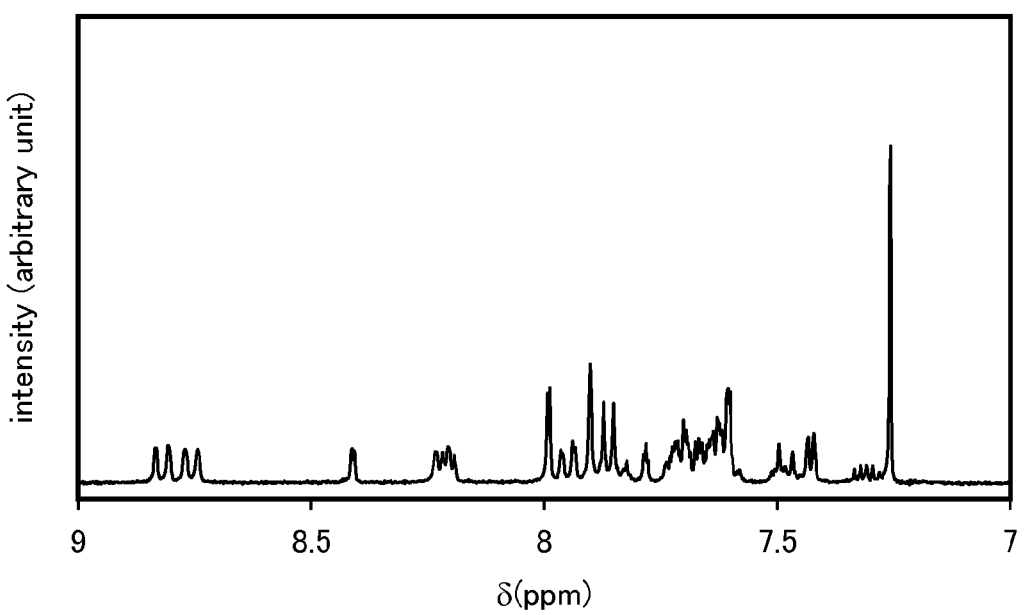

FIGS. 83A and 83B are $^1$H NMR charts. Note that FIG. 83B is a chart showing an enlarged part of FIG. 83A in the range of 7.00 ppm to 9.00 ppm. The measurement results confirmed that 9-phenyl-9H-3-{4-[3,5-di(phenanthren-9-yl)phenyl]phenyl}carbazole (abbreviation: Pn2BPPC) that was the objective substance was able to be obtained.

Note that although the example in which the phenanthrene compound having chlorine as a reaction group is coupled with the carbazole compound is described in this example, a phenanthrene compound having iodine or bromine as a reaction group may be used without limitation thereto. A phenanthrene compound that can be used in Step 2 above can be represented by General Formula (I1), for example. Note that in the case where the phenanthrene compound represented by General (I1) has bromine or iodine as a reaction group, Pn2BPPC (abbreviation) can be synthesized in a manner similar to that in Step 2 above. In Step 1, in the case of specifically reacting phenanthrene-9-boronic acid with trihalogenated benzene at 2:1, it is preferable that a halogen which reacts with boronic acid have a higher reaction property than a halogen represented by X. Thus, in the case where X bonded to benzene is chlorine, halogens at the 3-position and the 5-position are preferably bromine or iodine. In the case where X bonded to benzene is bromine, the halogens at the 3-position and the 5-position are preferably iodine.

[68]

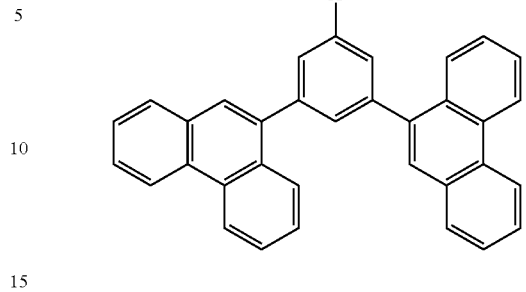

(I1)

Note that in General Formula (I1), X represents chlorine, bromine, or iodine.

Figure 84A:
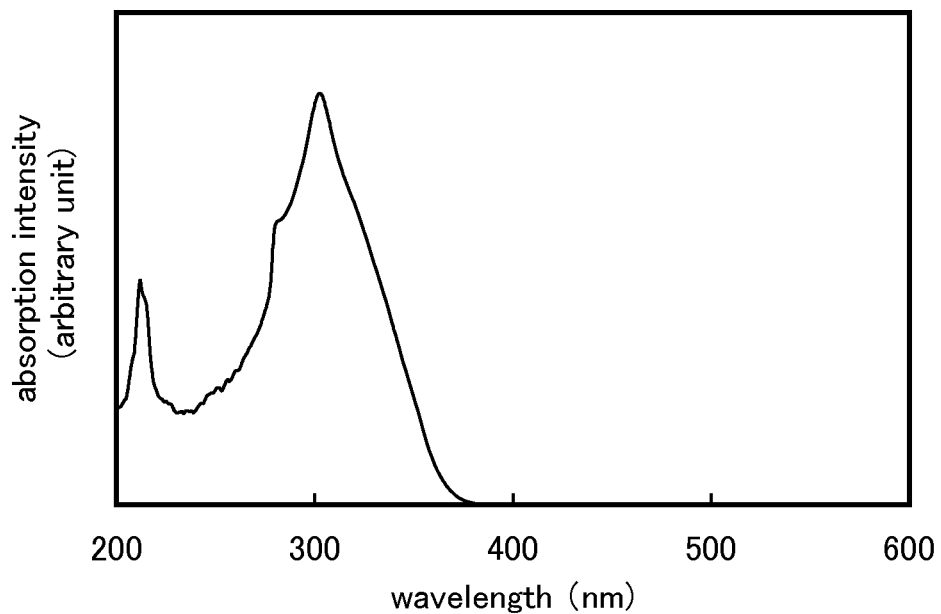
FIGS. 84A and 84B show an absorption spectrum and an emission spectrum of Pn2BPPC in a toluene solution of Pn2BPPC.
Figure 84B:
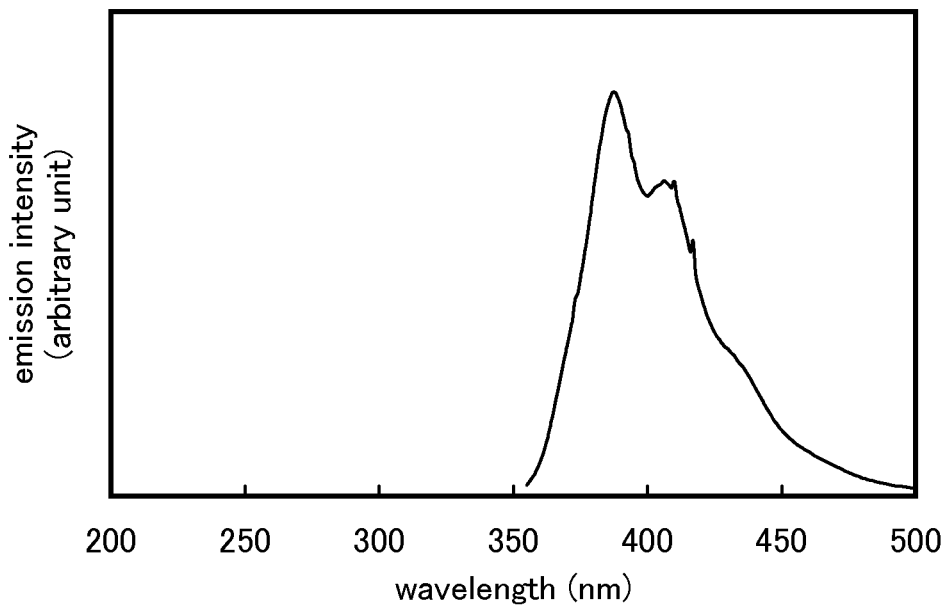
Figure 85A:
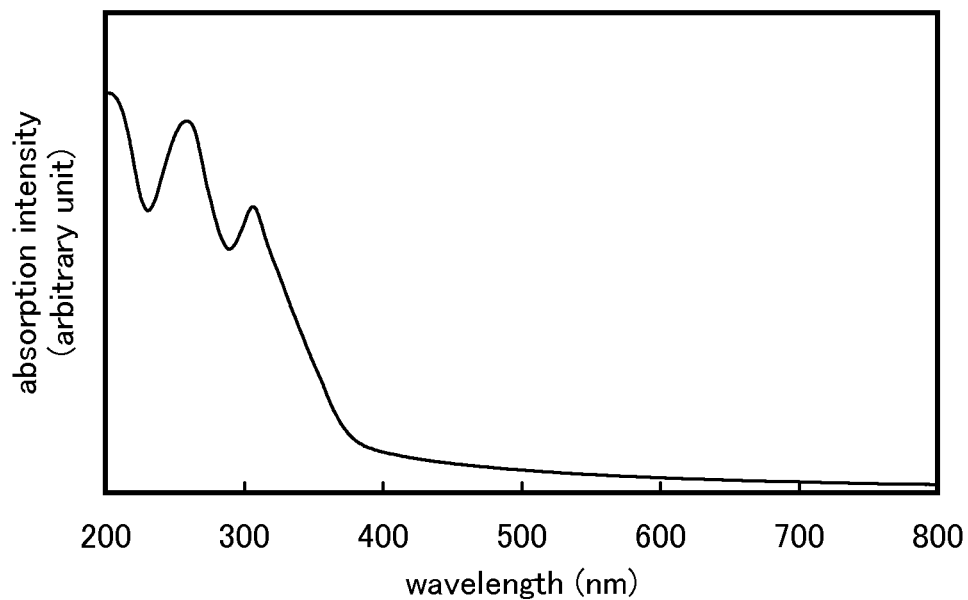
FIGS. 85A and 85B show an absorption spectrum and an emission spectrum of a thin film of Pn2BPPC.
Figure 85B:
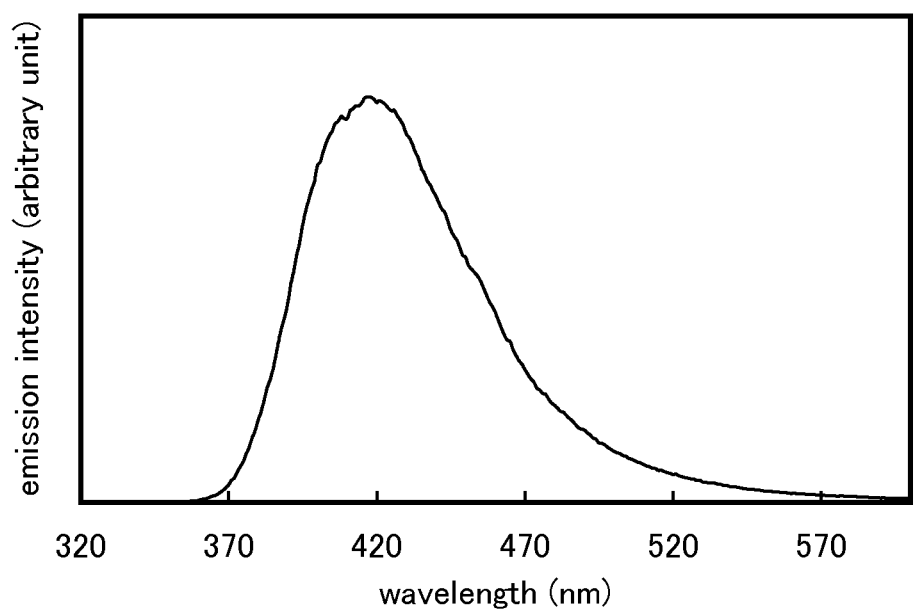

FIG. 84A shows an absorption spectrum of synthesized Pn2BPPC in a toluene solution of Pn2BPPC, and FIG. 84B shows an emission spectrum thereof. FIG. 85A shows an absorption spectrum of a thin film of Pn2BPPC, and FIG. 85B shows an emission spectrum thereof. The absorption spectrum was measured with an ultraviolet-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 84A show the absorption spectrum of Pn2BPPC in the solution of Pn2BPPC which was obtained by subtracting the absorption spectra of the quartz cell and toluene put therein. FIG. 85A shows the absorption spectrum of the thin film which was obtained by subtracting the absorption spectrum of the quartz substrate. In FIGS. 84A and 84B and FIGS. 85A and 85B, the horizontal axis represents wavelength (nm) and the vertical axis represents intensity (arbitrary unit). In the case of the toluene solution, the absorption peak was observed at around 303 nm, and the maximum emission wavelength was 388 nm (excitation wavelength: 340 nm). In the case of the thin film, the absorption peak was observed at around 306 nm, and the maximum emission wavelength was 417 nm (excitation wavelength: 306 nm).

The absorption spectrum showed that Pn2BPPC described in this example is a material having weak absorption of light in the visible region. In addition, the emission spectrum shows that Pn2BPPC exhibits blue-violet emission.

In this example, Pn2BPPC (abbreviation) of General Formula (G1) is preferable for the following reason: a biphenyl group of α$^3$ is bonded to the 3-position of carbazole at the para position, which allows high reliability.

EXAMPLE 22

In this example, a synthesis example of producing 9-phenyl-9H-3-[3,5-di(phenanthrene-9-yl)phenyl]carbazole (abbreviation: Pn2PPC) represented by Structural Formula (197) in Embodiment 1 will be described.

[69]

(197)

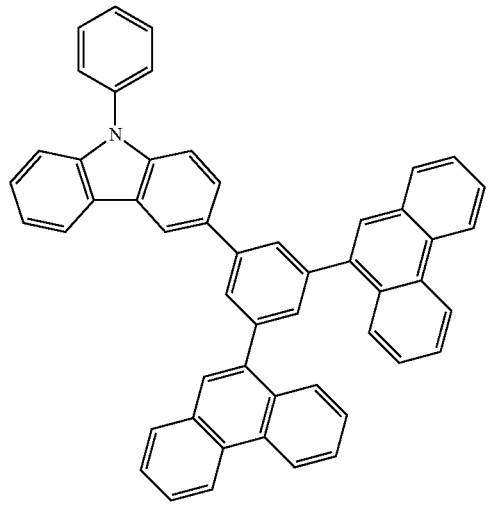

Step 1: Synthesis Method of 3-(3,5-dichlorophenyl)-9-phenyl-9H-carbazole (abbreviation: PCPCl₂)

In a 200-mL three-neck flask, a mixture of 5.0 g (22.1 mmol) of 3-(9-phenyl-9H-carbazole)boronic acid, 7.63 g (26.6 mmol) of 1-bromo-3,5-dichlorobenzene, 58.4 mg (0.26 mmol) of palladium(II) acetate, 237 mg (0.78 mmol) of tri(o-tolyl)phosphine, 98 mL of toluene, 10 mL of ethanol, and 32 mL of an aqueous solution of potassium carbonate (2 mol/L) was deaerated while being stirred under reduced pressure and was heated and stirred in a nitrogen atmosphere at 80° C. for 7 hours to be reacted.

After reaction, 500 mL of toluene was added to the reaction solution, and an organic layer of the reaction solution was filtered through Florisil, alumina, and Celite. The obtained filtrate was washed with water, and magnesium sulfate was added thereto so that moisture was adsorbed. This suspension was filtrated to obtain a filtrate. The obtained filtrate was concentrated and purified by silica gel column chromatography. At this time, a mixed solvent of toluene and hexane (toluene:hexane=1:10) was used as a developing solvent for the chromatography. The obtained fraction was concentrated, and toluene and hexane were added thereto. The mixture was irradiated with ultrasonic waves and then recrystallized to obtain 9.09 g of white powder that was an objective substance in a yield of 100%. The reaction scheme of the synthesis method is shown in (F9-1).

[70]

(F9-1)

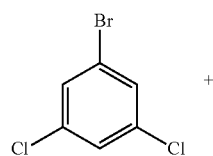 +

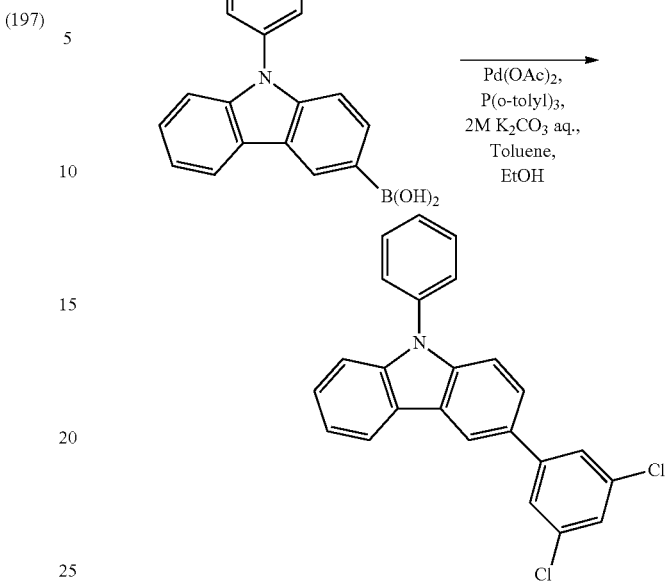

The Rf value of the objective substance was 0.43, which was obtained by silica gel thin layer chromatography (TLC) (with a developing solvent containing ethyl acetate and hexane in a 1:10 ratio).

The compound obtained in Step 1 was examined by a nuclear magnetic resonance (NMR) method. The measurement data are shown below.

¹H NMR (CDCl₃, 300 MHz): δ (ppm)=7.26-7.34 (m, 2H), 7.40-7.53 (m, 4H), 7.57-7.67 (m, 7H), 8.20 (d, J=7.81 Hz, 1H), 8.31 (d, J=0.98 Hz, 1H).

Figure 86A:
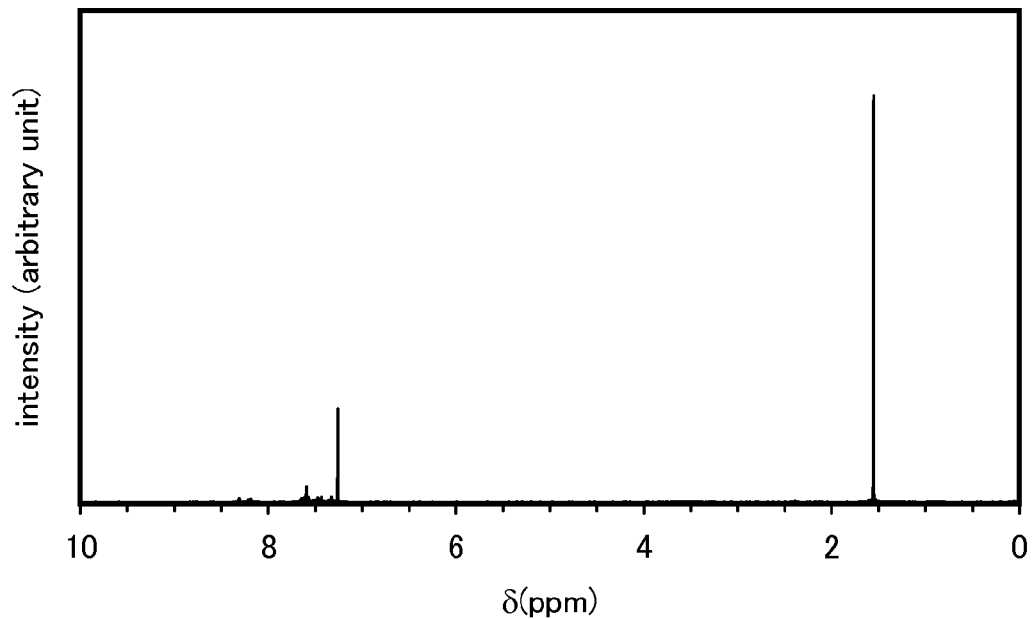
FIGS. 86A and 86B are NMR charts of PCPCl2.
Figure 86B:
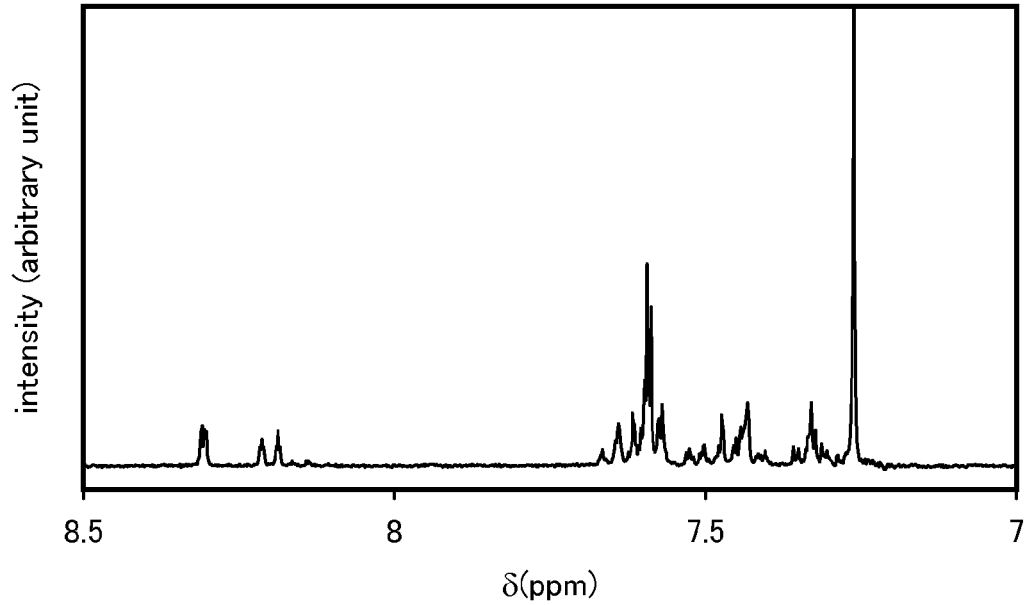

FIGS. 86A and 86B are ¹H NMR charts. Note that FIG. 86B is a chart showing an enlarged part of FIG. 86A in the range of 7.00 ppm to 8.50 ppm. The measurement results confirmed that 3-(3,5-dichlorophenyl)-9-phenyl-9H-carbazole (abbreviation: PCPCl₂) that was the objective substance was able to be obtained.

Step 2: Synthesis Method of 9-phenyl-9H-3-[3,5-di(phenanthrene-9-yl)phenyl]carbazole (abbreviation: Pn2PPC)

In a 200-mL three-neck flask, a mixture of 4.29 g (19.3 mmol) of 9-phenanthrene boronic acid, 3.0 g (7.73 mmol) of 3-(3,5-dichlorophenyl)-9-phenyl-9H-carbazole, 86.3 mg (0.15 mmol) of bis(dibenzylideneacetone)palladium(0), 166 mg (0.46 mmol) of 2'-(dicyclohexylphosphino)acetophenone ethylene ketal, 6.98 g (46 mmol) of cesium(I) fluoride, and 30 mL of xylene was heated and stirred in a nitrogen atmosphere at 120° C. for 10 hours to be reacted. Moreover, 858 mg (3.87 mmol) of 9-phenanthrene boronic acid, 86.3 mg (0.15 mmol) of bis(dibenzylideneacetone)palladium(0), and 166 mg (0.46 mmol) of 2'-(dicyclohexylphosphino)acetophenone ethylene ketal were added to the mixture, and the mixture was heated and stirred in a nitrogen atmosphere at 120° C. for 8 hours to be reacted.

After reaction, 500 mL of toluene was added to the reaction mixture solution, and an organic layer of the mixture solution was filtered through alumina and Celite. The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane (toluene:hexane=1:5) was used as a developing solvent for the chromatography. The obtained fraction was concentrated to give 0.93 g of white powder that was an objective substance in a yield of 18%. The reaction scheme of the synthesis method is shown in (F9-2).

[71]

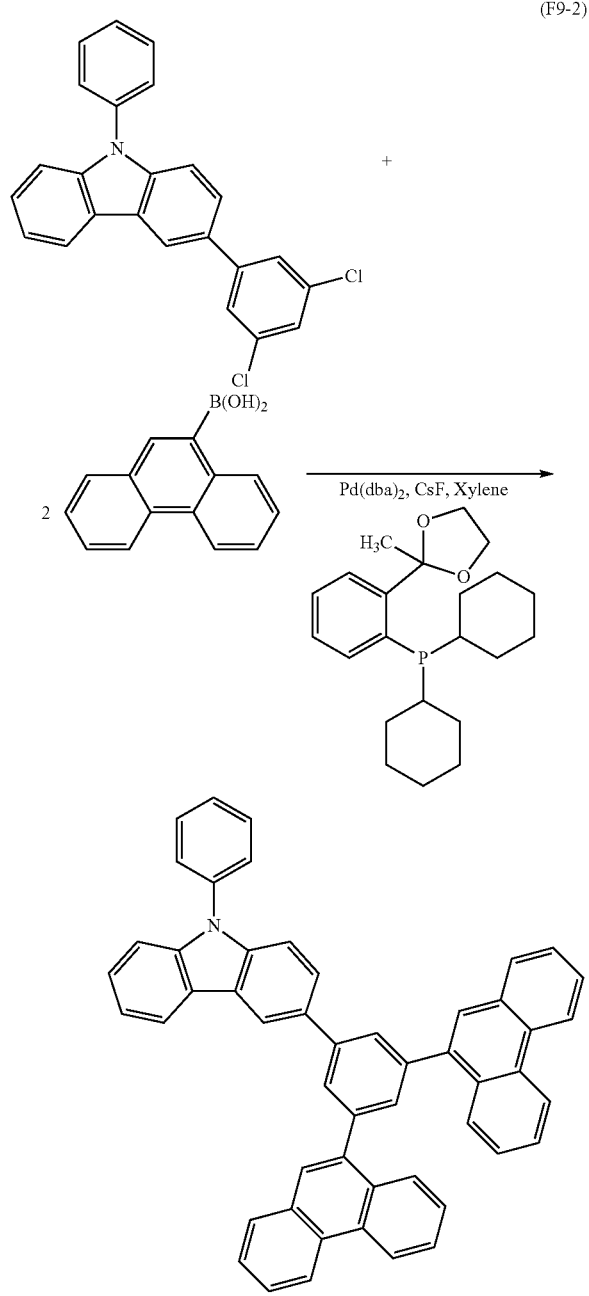

(F9-2)

The Rf value of the objective substance was 0.18, which was obtained by silica gel thin layer chromatography (TLC) (with a developing solvent containing ethyl acetate and hexane in a 1:10 ratio).

The compound obtained in Step 2 was examined by a nuclear magnetic resonance (NMR) method. The measurement data are shown below.

$^1$H NMR (CDCl$_3$, 300 MHz): δ (ppm)=7.41-7.643 (d, J=3.4 Hz, 2H), 7.48-7.51 (d, J=8.30 Hz, 2H), 7.60-8.05 (m, 20H), 8.15-8.18 (d, J=9.3 Hz, 2H), 8.41 (d, J=0.98 Hz, 1H), 8.79 (dd, J=8.3 Hz, 18.6 Hz, 4H).

Figure 87A:
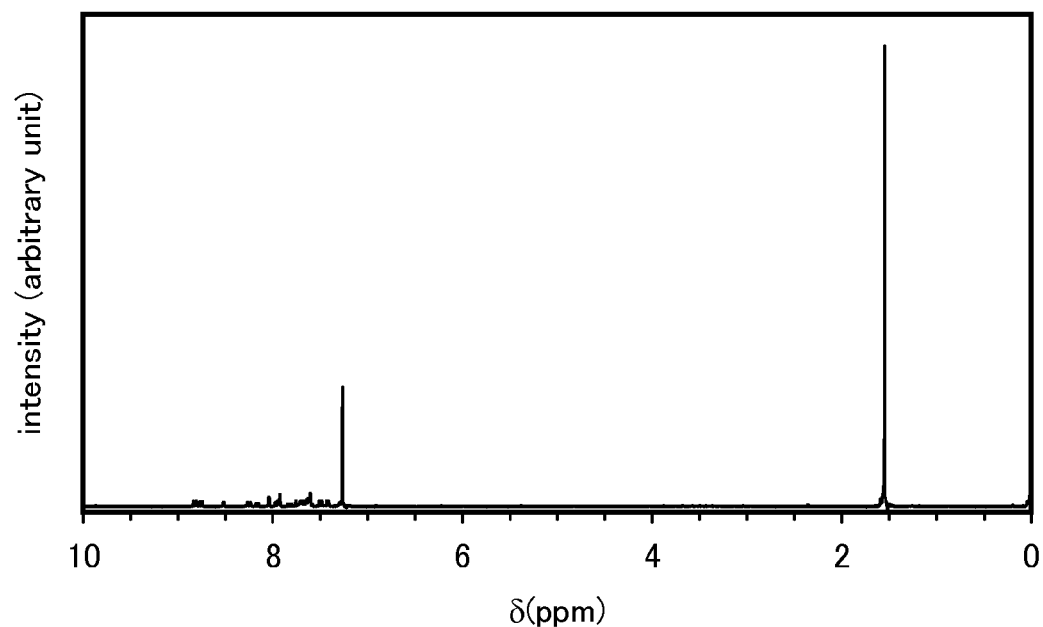
FIGS. 87A and 87B are NMR charts of Pn2PPC.
Figure 87B:
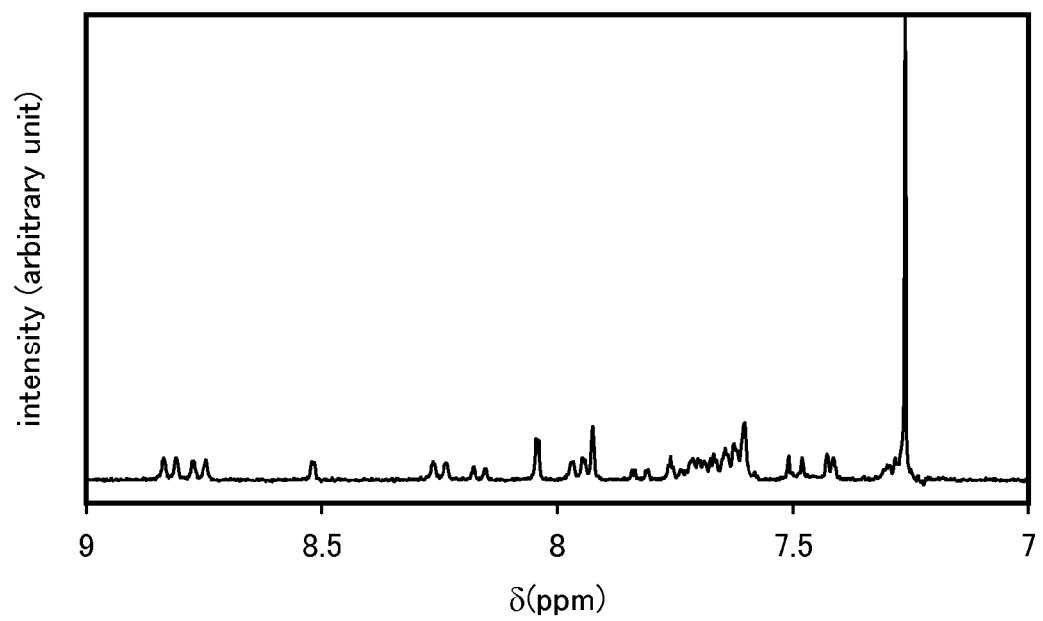

FIGS. 87A and 87B are $^1$H NMR charts. Note that FIG. 87B is a chart showing an enlarged part of FIG. 87A in the range of 7.00 ppm to 9.00 ppm. The measurement results confirmed that 9-phenyl-9H-3-[3,5-di(phenanthrene-9-yl)phenyl]carbazole (abbreviation: Pn2PPC) that was the objective substance was able to be obtained.

Note that although the example in which the carbazole compound having chlorine as a reaction group is coupled with the phenanthrene compound is described in this example, a carbazole compound having iodine or bromine as a reaction group may be used without limitation thereto. A carbazole compound that can be used in Step 2 above can be represented by General Formula (I2), for example. Note that in the case where the carbazole compound represented by General Formula (I2) has bromine or iodine as a reaction group, Pn2PPC can be synthesized in a manner similar to that in Step 2 above. In Step 1, in the case of specifically reacting 9-phenyl-9H-carbazol-3-boronic acid with trihalogenated benzene at 1:1, it is preferable that a halogen which reacts with boronic acid have a higher reaction property than a halogen represented by X. Thus, in the case where X bonded to benzene at each of the 1-position and the 3-position is chlorine, a halogen at the 5-position is preferably bromine or iodine. In the case where X bonded to benzene is bromine, the halogen at the 5-position is preferably iodine.

[72]

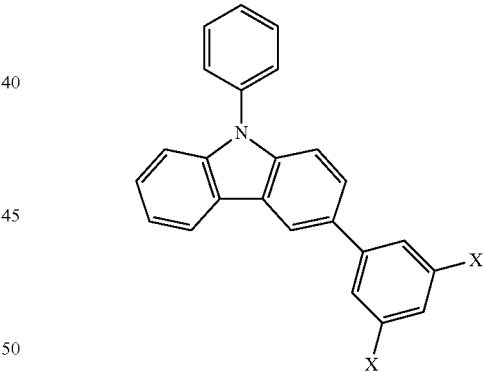

(I2)

Note that in General Formula (I2), X represents chlorine, bromine, or iodine.

Figure 88A:
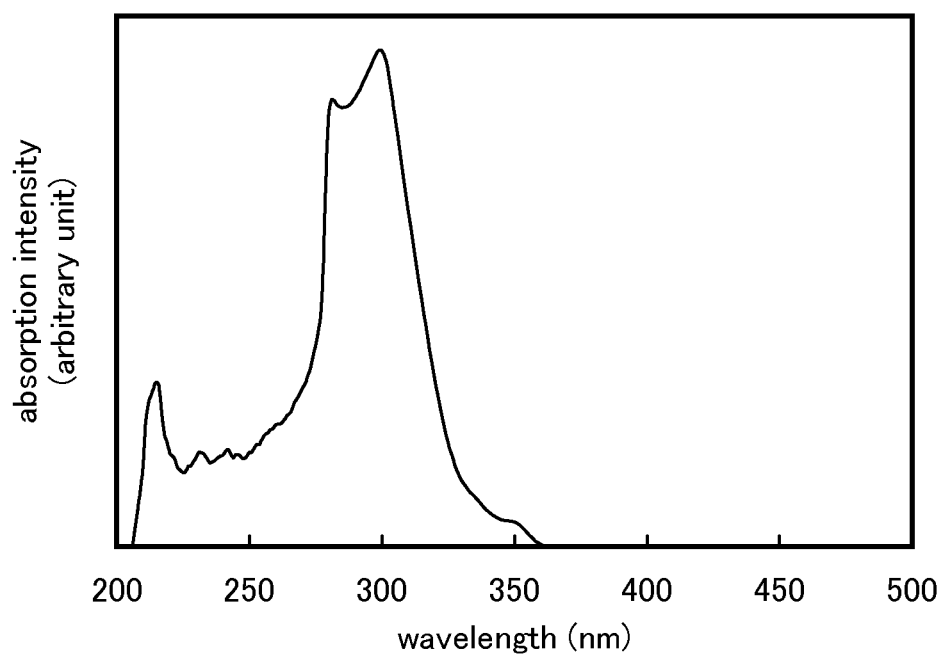
FIGS. 88A and 88B show an absorption spectrum and an emission spectrum of Pn2PPC in a toluene solution of Pn2PPC.
Figure 88B:
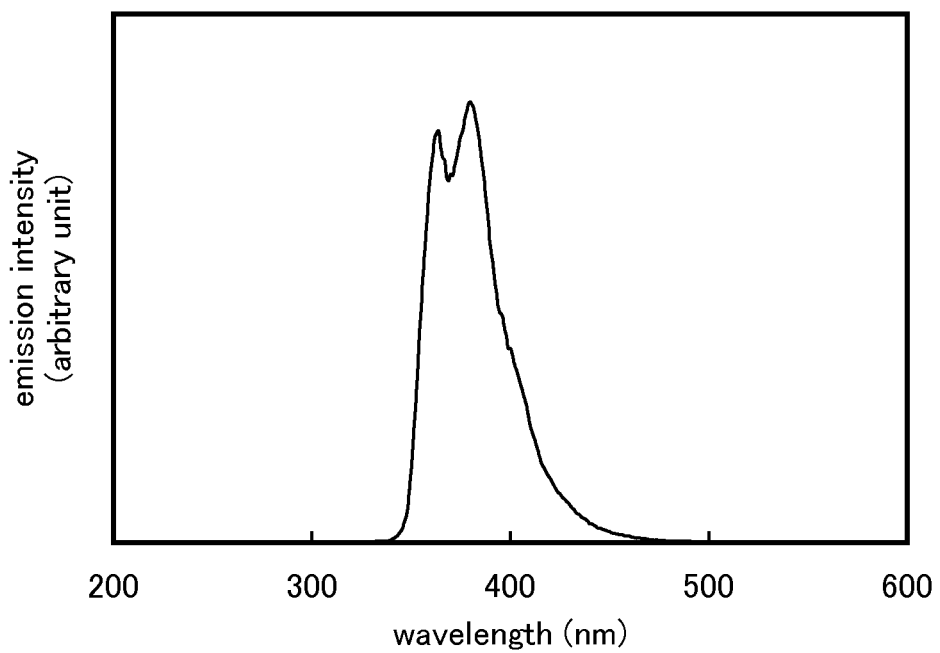
Figure 89A:
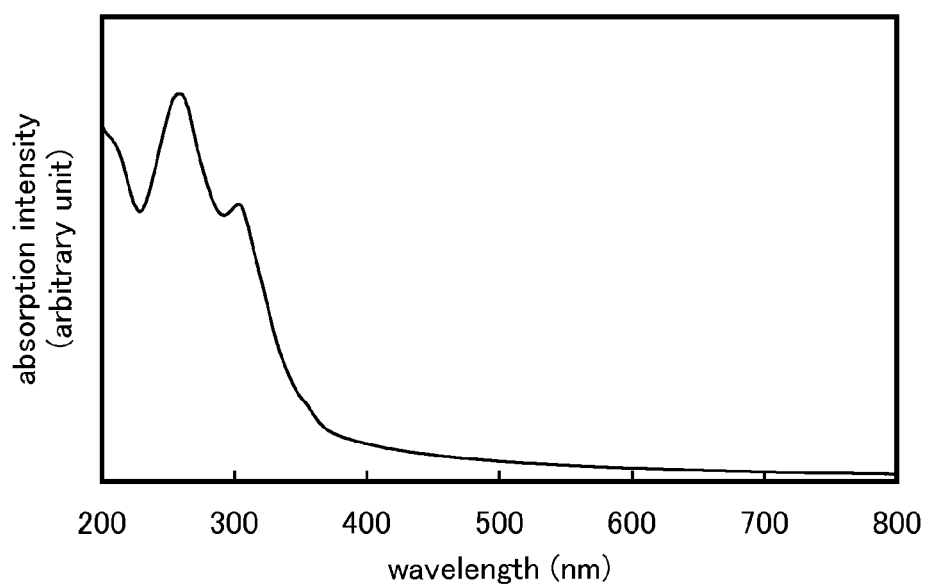
FIGS. 89A and 89B show an absorption spectrum and an emission spectrum of a thin film of Pn2PPC.
Figure 89B:
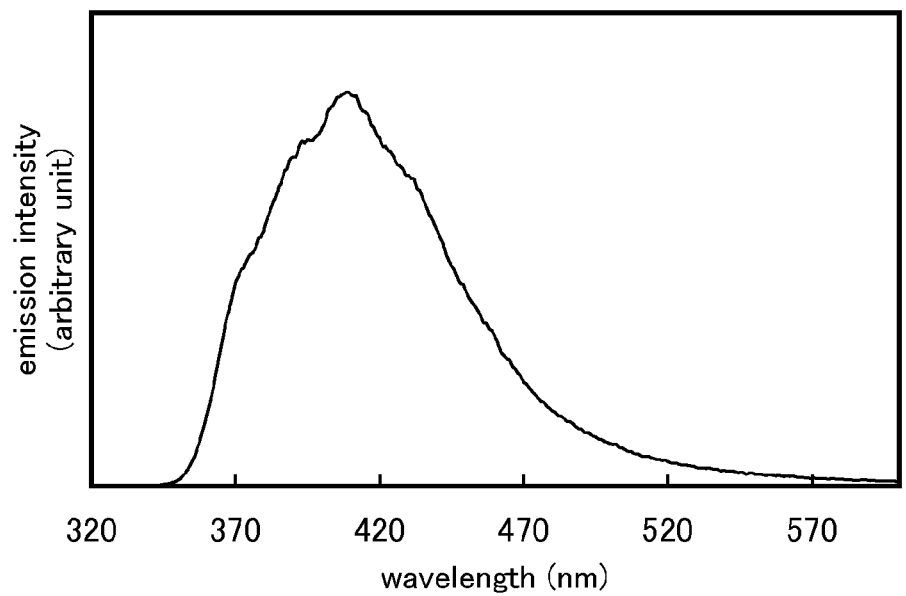

FIG. 88A shows an absorption spectrum of synthesized Pn2PPC in a toluene solution of Pn2PPC, and FIG. 88B shows an emission spectrum thereof. FIG. 89A shows an absorption spectrum of a thin film of Pn2PPC, and FIG. 89B shows an emission spectrum thereof. The absorption spectrum was measured with an ultraviolet-visible spectrophotometer (V550, produced by JASCO Corporation). The emission spectrum was measured with a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 88A show the absorption spectrum of Pn2PPC in the solution of Pn2PPC which was obtained by subtracting the absorption spectra of the quartz cell and toluene put therein, and FIG. 89A shows the absorption spectrum of the thin film which was obtained by subtracting the absorption spectrum of the quartz substrate. In FIGS. 88A and 88B and FIGS. 89A and 89B, the horizontal axis represents wavelength (nm) and the vertical axis represents intensity (arbitrary unit). In the case of the toluene solution, the absorption peak was observed at around 298 nm, and the maximum emission wavelength was 381 nm (excitation wavelength: 311 nm). In the case of the thin film, the absorption peak was observed at around 303 nm, and the maximum emission wavelength was 409 nm (excitation wavelength: 304 nm).

The absorption spectrum showed that Pn2PPC described in this example is a material having weak absorption of light in the visible region. In addition, the emission spectrum shows that Pn2PPC exhibits blue-violet emission.

This application is based on Japanese Patent Application serial no. 2010-215856 filed with Japan Patent Office on Sep. 27, 2010, the entire contents of which are hereby incorporated by reference.

What is claimed is:

1. A carbazole compound represented by General Formula (G1):

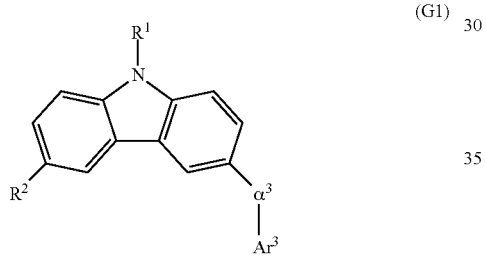

(G1)

wherein $R^1$ represents an alkyl group having 1 to 12 carbon atoms, a substituted or unsubstituted phenyl group, a substituted or unsubstituted biphenyl group, a substituted or unsubstituted naphthyl group, a substituted or unsubstituted phenanthrylgroup, a substituted or unsubstituted triphenylenyl group, or a substituent represented by General Formula (G1-1);

(G1-1)

wherein $R^2$ represents hydrogen, an alkyl group having 1 to 12 carbon atoms, a substituted or unsubstituted phenyl group, a substituted or unsubstituted biphenyl group, or a substituent represented by General Formula (G1-2);

(G1-2)

wherein $\alpha^3$ represents either a substituted or unsubstituted phenylene group or a substituted or unsubstituted biphenyldiyl group, wherein $Ar^3$ represents a substituted or unsubstituted naphthyl group, a substituted or unsubstituted phenanthryl group, or a substituted or unsubstituted triphenylenyl group, wherein $Ar^1$ represents an alkyl group having 1 to 12 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group, wherein $\alpha^1$ represents either a substituted or unsubstituted phenylene group or a substituted or unsubstituted biphenyldiyl group, wherein n represents 0 or 1, wherein $Ar^2$ represents an alkyl group having 1 to 12 carbon atoms, a substituted or unsubstituted phenyl group, a substituted or unsubstituted biphenylgroup, a substituted or unsubstituted naphthyl group, a substituted or unsubstituted phenanthryl group, or a substituted or unsubstituted triphenylenyl group, wherein $\alpha^2$ represents either a substituted or unsubstituted phenylene group or a substituted or unsubstituted biphenyldiyl group, wherein in the case where $R^1$, $R^2$, and $Ar^3$ have substituents, the subtituents are separately an alkyl group having 1 to 12 carbon atoms, an unsubstituted phenyl group, an unsubstituted biphenyl group, an unsubstituted naphthyl group, an unsubstituted phenanthryl group, or an unsubstituted triphenyl group, and wherein in the case where $\alpha^3$ has a substituent, the substituent of $\alpha^3$ is an alkyl group having 1 to 12 carbon atoms.

2. The carbazole compound according to claim 1, wherein $R^1$ in General Formula (G1) represents structures represented by Structural Formula (S-1), Structural Formula (S-2), Structural Formula (S-3), Structural Formula (S-4) or Structural Formula (S-5):

(S-1)

(S-2)

(S-3)

(S-4)

(S-5)

3. The carbazole compound according to claim 1, wherein $R^2$ in General Formula (G1) represents structures represented by Structural Formula (S-11), Structural Formula (S-12), Structural Formula (S-13), Structural Formula (S-14), Structural Formula (S-15) or Structural Formula (S-16):

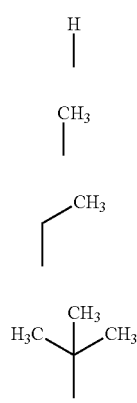

(S-11)
(S-12)
(S-13)
(S-14)
(S-15)
(S-16)

4. The carbazole compound according to claim 1, wherein $\alpha^3$ in General Formula (G1), $\alpha^1$ in General Formula (G1-1), and $\alpha^2$ in General Formula (G1-2) are separately structures represented by Structural Formula ($\alpha$-1), Structural Formula ($\alpha$-2), Structural Formula ($\alpha$-3), Structural Formula ($\alpha$-4), Structural Formula ($\alpha$-5), Structural Formula ($\alpha$-6) or Structural Formula ($\alpha$-7):

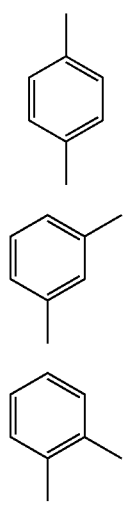

($\alpha$-1)
($\alpha$-2)
($\alpha$-3)

-continued

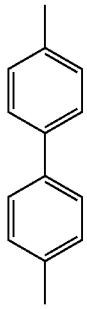

($\alpha$-4)

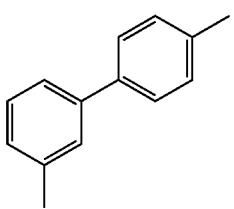

($\alpha$-5)

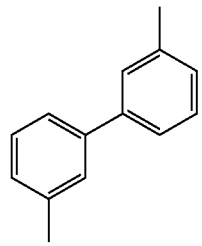

($\alpha$-6)

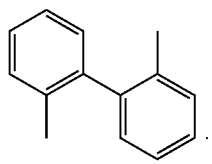

($\alpha$-7)

5. The carbazole compound according to claim 1, wherein $Ar^1$ in General Formula (G1-1) and $Ar^2$ in General Formula (G1-2) are separately structures represented by Structural Formula (Ar-1), Structural Formula (Ar-2), Structural Formula (Ar-3), Structural Formula (Ar-4), Structural Formula (Ar-5) Structural Formula (Ar-6 Structural Formula (Ar-7), Structural Formula (Ar-8), Structural Formula (Ar-9) or Structural Formula (Ar-10):

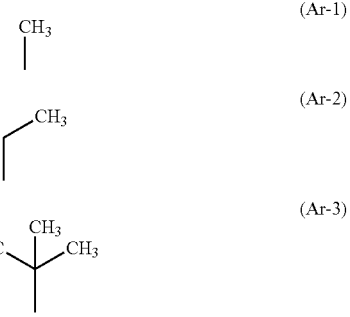

(Ar-1)
(Ar-2)
(Ar-3)

-continued

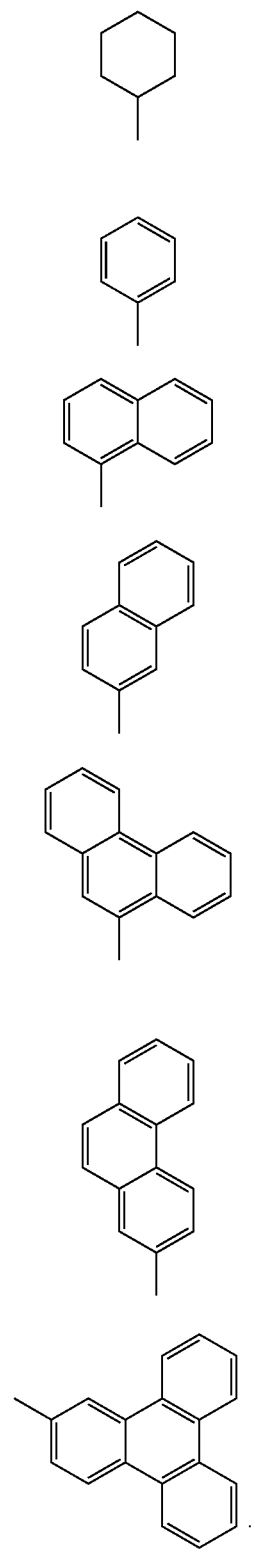

(Ar-4)

(Ar-5)

(Ar-6)

(Ar-7)

(Ar-8)

(Ar-9)

(Ar-10)

6. The carbazole compound according to claim 1, wherein Ar³ in General Formula (G1) represents structures represented by Structural Formula (Ar-11), Structural Formula (Ar-12), Structural Formula (Ar-13), Structural Formula (Ar-14), Structural Formula (Ar-15):

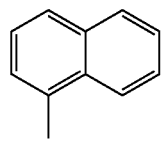
(Ar-11)

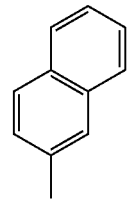
(Ar-12)

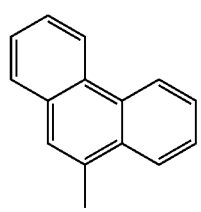
(Ar-13)

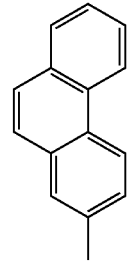
(Ar-14)

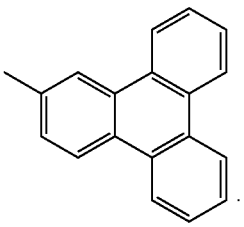
(Ar-15)

7. A light-emitting element comprising the carbazole compound according to claim 1.

8. A light-emitting device comprising the light-emitting element according to claim 7.

9. A lighting device comprising the light-emitting element according to claim 7.

10. An electronic device comprising the light-emitting element according to claim 7.

11. A carbazole compound represented by General Formula (G1):

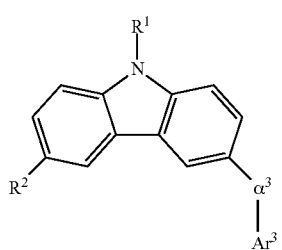
(G1)

wherein R¹ represents a substituted or unsubstituted phenyl group or a substituted or unsubstituted naphthyl group;

wherein R² represents hydrogen or a substituent represented by General Formula (G1-2);

(G1-2)

wherein α³ represents a substituted or unsubstituted phenylene group, wherein Ar³ represents a substituted or unsubstituted naphthyl group, a substituted or unsubstituted phenanthryl group, or a substituted or unsubstituted triphenylenyl group, wherein Ar² represents a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group, wherein α² represents either a substituted or unsubstituted phenylene group or a substituted or unsubstituted biphenyldiyl group, wherein in the case where R¹, R², and Ar³ have substituents, the subtituents are separately an alkyl group having 1 to 12 carbon atoms, an unsubstituted phenyl group, an unsubstituted biphenyl group, an unsubstituted naphthyl group, an unsubstituted phenanthryl group, or an unsubstituted triphenyl group, and wherein in the case where α³ has a substituent, the substituent of α³ is an alkyl group having 1 to 12 carbon atoms.

12. A light-emitting element comprising the carbazole compound according to claim 11.

13. A light-emitting device comprising the light-emitting element according to claim 12.

14. A lighting device comprising the light-emitting element according to claim 12.

15. An electronic device comprising the light-emitting element according to claim 12.

16. A carbazole compound represented by General Formula (I2):

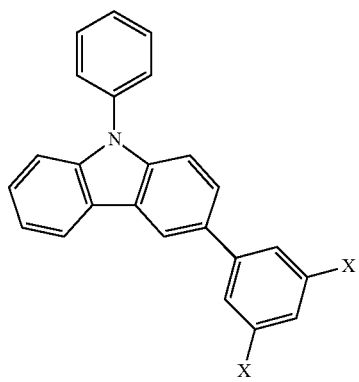

(I2)

wherein X represents chlorine, bromine, or iodine.

17. The carbazole compound according to claim 1, wherein the carbazole compound is represented by Structural Formula (102) or Structural formula (105):

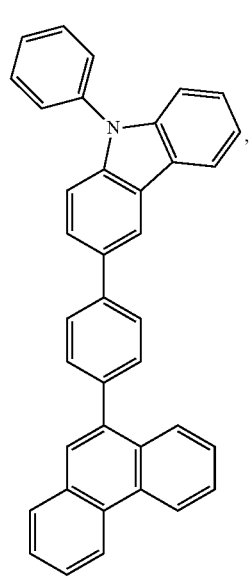

(102)

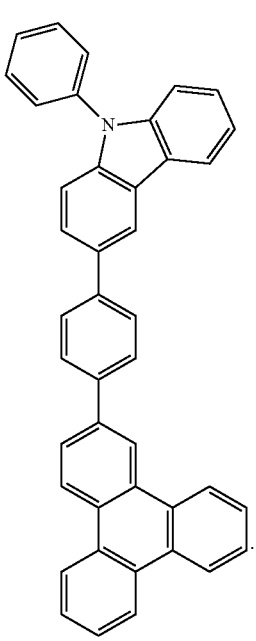

(105)

18. The carbazole compound according to claim 1, wherein the carbazloe compound is represented by Structural Formula (100), Structural Formula (108), Structural Formula (111), or Structural Formula (120):
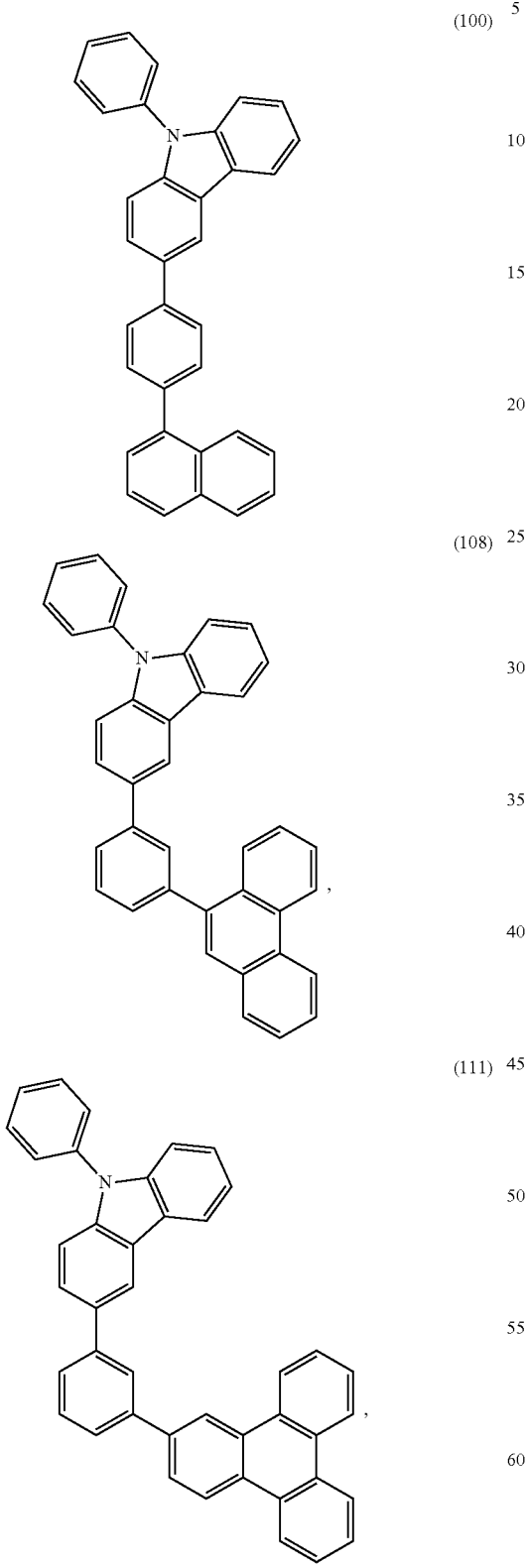
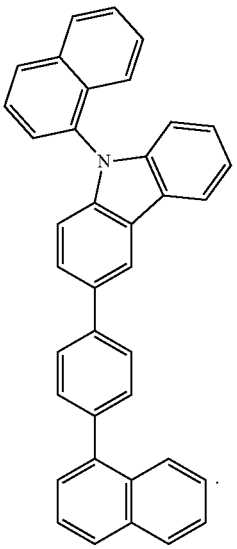
19. The carbazole compound according to claim 1, the wherein carbazloe compound is represented by Structural Formula (112):
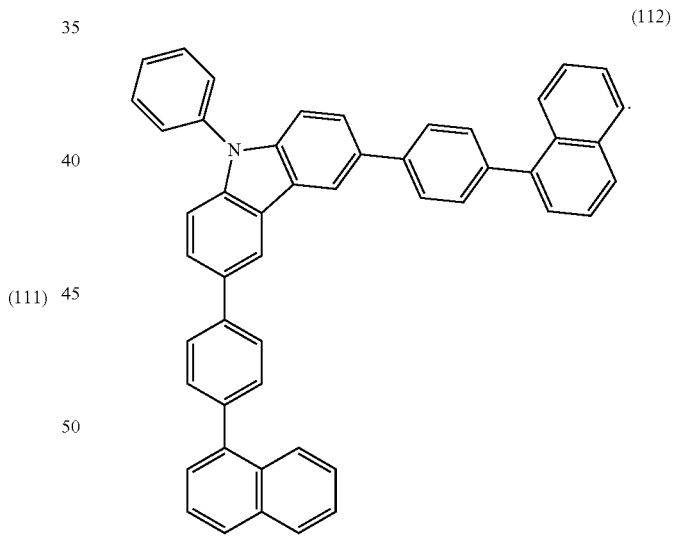
* * * * *

UNITED STATES PATENT AND TRADEMARK OFFICE
CERTIFICATE OF CORRECTION

PATENT NO. : 8,614,334 B2
APPLICATION NO. : 13/241313
DATED : December 24, 2013
INVENTOR(S) : Harue Osaka et al.

It is certified that error appears in the above-identified patent and that said Letters Patent is hereby corrected as shown below:

In the Claims

Column 145, line 45, "phenanthrylgroup" should read --phenanthryl group--.

Column 146, line 20, "biphenylgroup" should read --biphenyl group--.

Column 146, line 28, "subtituents" should read --substituents--.

Column 148, line 48, "(Ar-5) Structural" should read --(Ar-5), Structural--.

Column 148, line 48, "(Ar-6Structural" should read --(Ar-6), Structural--.

Column 149, line 67, "14), Structural" should read --14) or Structural--.

Column 151, line 29, "subtituents" should read --substituents--.

Column 152, line 3, "formula" should read --Formula--.

Column 153, line 2, "carbazloe" should read --carbazole--.

Column 154, line 30, "carbazloe" should read --carbazole--.

Column 60, lines 65-66, "poly(-vinyltriphenylamine)" should read --poly(4-vinyltriphenylamine)--.

Column 62, line 63, "fluoranthene-3,10-d iamine" should read --fluoranthene-3,10-diamine--.

Column 63, line 7, "trifluoro methyl" should read --trifluoromethyl--.

Column 63, line 36, "abbreviation [Ir(mppr-Me)$_2$(acac)])," should read --abbreviation: [Ir(mppr-Me)$_2$(acac)]),--.

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,614,334 B2                                   Page 1 of 1
APPLICATION NO.    : 13/241313
DATED              : December 24, 2013
INVENTOR(S)        : Harue Osaka et al.

It is certified that error appears in the above-identified patent and that said Letters Patent is hereby corrected as shown below:

In the Specification

Column 97, lines 33-67, the formula should appear as follows:

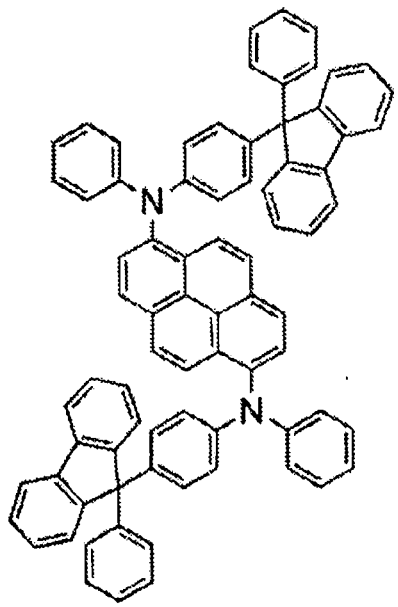

1,6FLPAPrn

Signed and Sealed this
Seventh Day of October, 2014

Michelle K. Lee
*Deputy Director of the United States Patent and Trademark Office*